US008193372B2

(12) United States Patent
Dousson et al.

(10) Patent No.: US 8,193,372 B2
(45) Date of Patent: Jun. 5, 2012

(54) PHOSPHOTHIOPHENE AND PHOSPHOTHIAZOLE HCV POLYMERASE INHIBITORS

(75) Inventors: Cyril Dousson, Canet (FR); Claire Pierra, Montarnaud (FR); Jean-Francois Griffon, Teyran (FR); Frederic Leroy, Montarnaud (FR); Jean-Laurent Paparin, Vendemian (FR); David Dukhan, St Gely du Fresc (FR); Dominique Surleraux, Wauthier Braine (BE)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 91 days.

(21) Appl. No.: 12/716,278

(22) Filed: Mar. 3, 2010

(65) Prior Publication Data

US 2010/0233123 A1   Sep. 16, 2010

Related U.S. Application Data

(60) Provisional application No. 61/157,211, filed on Mar. 4, 2009.

(51) Int. Cl.
*C07D 333/36* (2006.01)
*C07D 277/20* (2006.01)
*C07F 9/02* (2006.01)
*A61K 31/519* (2006.01)
*A61K 31/425* (2006.01)
*A61K 31/38* (2006.01)

(52) U.S. Cl. ......... 549/6; 544/244; 548/202; 514/259.3; 514/365; 514/447

(58) Field of Classification Search .......................... None
See application file for complete search history.

(56) References Cited

U.S. PATENT DOCUMENTS

| | | | |
|---|---|---|---|
| 5,654,297 | A | 8/1997 | Albright et al. |
| 5,696,112 | A | 12/1997 | Albright et al. |
| 5,994,563 | A | 11/1999 | Beers et al. |
| 6,117,873 | A | 9/2000 | Acklin et al. |
| 6,965,033 | B2 | 11/2005 | Jiang et al. |
| 7,396,599 | B2 | 7/2008 | Lyu et al. |
| 7,405,231 | B2 | 7/2008 | Bossenmaier et al. |
| 7,514,448 | B2 | 4/2009 | Pierard et al. |
| 2005/0038248 | A1 | 2/2005 | Henderson et al. |
| 2007/0004682 | A1 | 1/2007 | Biju |

FOREIGN PATENT DOCUMENTS

| | | |
|---|---|---|
| EP | 640592 | 3/1995 |
| EP | 1813620 A1 | 8/2007 |
| WO | WO 9508550 | 3/1995 |
| WO | WO 9701556 | 1/1997 |
| WO | WO 9701558 | 1/1997 |
| WO | WO 9748409 | 12/1997 |
| WO | WO 2006004984 | 1/2006 |
| WO | WO 2006/054182 A2 | 5/2006 |
| WO | WO 2008/005565 A2 | 1/2008 |

OTHER PUBLICATIONS

Dominguez et al. Journal of Agricultural and Food Chemistry (2008) 56 (10), 3721-3731.*
Font et al. Journal of Agricultural and Food Chemistry (2008) 56(18), 8451-8460.*
Stephanie T. Shi et al. "In Vitro Resistance Study of AG-021541, a Novel Nonnucleoside Inhibitor of the Hepatitis C Virus RNA-Dependent RNA Polymerase", Antimicrobial Agents and Chemotherapy, 2008, p. 675-683, vol. 52, issue 2.
Anita Y.Mhowe"Molecular Mechanism of a Thumb Domain Hepatitis C Virus Nonnucleoside RNA-Dependent RNA Polymerase Inhibitor", Antimicrobial Agents and Chemotherapy, 2006, p. 4103-4113, vol. 50, issue 12.
Gerbier P et al., "An organometallic route to sinc phosphonates and their intercalates", Journal of Materials Chemistry, 1999, vol. 9, No. 10, p. 2559-2565.
Arbuzov B A et al., "Synthesis of esters of phosphonic acids containg heterocyclic radicals. I. Synthesis of esters of phosphonic acids with a thiazole radical", Zhurnal O Bshchei Khimii, Izdatel'Stvo Nauka, Sankt-Peterburgskoe Otdetenie, Russiam Federation, 1951, vol. 21, p. 1869-1872.
C4b is English translation of C4 reference.
Lee Chull Bom et al., "Insights into Long-Range Structural Effects on the stereochemistry of Aldol Condensations: A Practical Total Synethesis of Desoxyepothilone F", Journal of the American Chemical Society, 2001, vol. 123, No. 22, p. 5249-7863.
Lampin Jean P et al., "Metallation of thienylphosphines. Application to the synethesis of new condensed heterocyclic phosphorus compounds", Journal of Organometallic Chemistry, 1974, vol. 71, No. 2, p. 239-255.
Allen David W et al., "The Chemistry of Heteroarylphosphorus Compounds. Part 11. The Effects of 3-Furyl and 3-Thienyl Substituents at Phosphorus on the Rate and Course of Alkaline Hydrolysis of phosphonium salts and on the Decomposition of Phosphonium Batines", Journal of the Chemical Society, 1978, No. 6, p. 675-677.
International Search Report and Written Opinion dated Sep. 24, 2010.

* cited by examiner

*Primary Examiner* — Kamal Saeed
*Assistant Examiner* — Nyeemah A Grazier
(74) *Attorney, Agent, or Firm* — Jones Day

(57) ABSTRACT

Provided herein are phosphothiophene and phosphothiazole compounds, for example, of any of Formulae I, IA, IIA, IIIA, IVA, VA, VIA, VIIA, IB, IIB, IIIB, IVB, VB, VIB and VIIB disclosed herein, pharmaceutical compositions comprising the compounds, and processes of preparation thereof. Also provided are methods of their use for the treatment of an HCV infection in a host infected with HCV.

29 Claims, No Drawings

PHOSPHOTHIOPHENE AND PHOSPHOTHIAZOLE HCV POLYMERASE INHIBITORS

PRIOR RELATED APPLICATIONS

This application claims the benefit of U.S. Provisional Patent Application No. 61/157,211, filed Mar. 4, 2009, 2009, which is incorporated herein by reference in its entirety.

FIELD

Provided herein are phosphothiophene and phosphothiazole compounds, pharmaceutical compositions comprising the compounds, and processes for their preparation. Also provided are methods of their use for the treatment of an HCV infection in a host in need thereof.

BACKGROUND

Hepatitis C virus (HCV) is known to cause at least 80% of posttransfusion hepatitis and a substantial proportion of sporadic acute hepatitis (Houghton et al., Science 1989, 244, 362-364; Thomas, Curr. Top. Microbiol. Immunol. 2000, 25-41). Preliminary evidence also implicates HCV in many cases of "idiopathic" chronic hepatitis, "cryptogenic" cirrhosis, and probably hepatocellular carcinoma unrelated to other hepatitis viruses, such as hepatitis B virus (Di Besceglie et al., Scientific American, 1999, October, 80-85; Boyer et al., J. Hepatol. 2000, 32, 98-112).

HCV is an enveloped virus containing a positive-sense single-stranded RNA genome of approximately 9.4 kb (Kato et al., Proc. Natl. Acad. Sci. USA 1990, 87, 9524-9528; Kato, Acta Medica Okayama, 2001, 55, 133-159). The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteases, a zinc-dependent metalloproteinase encoded by the NS2-NS3 region and a serine proteases encoded in the NS3 region. These proteases are required for cleavage of specific regions of the precursor polyprotein into mature peptides. The carboxyl half of nonstructural protein 5, NS5B, contains the RNA-dependent RNA polymerase.

Presently, the most effective HCV therapy employs a combination of alpha-interferon and ribavirin, leading to sustained efficacy in about 40% of patients (Poynard et al., Lancet 1998, 352, 1426-1432). Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load (Manns et al, Lancet 2001, 358, 958-965; Fried et al., N. Engl. J. Med. 2002, 347, 975-982; Hadziyannis et al., Ann. Intern. Med. 2004, 140, 346-355). Furthermore, research shows that using pegylated interferon and ribavirin to treat patients with HCV can cause significant side effects, such as alopecia, anorexia, depression, fatigue, myalgia, nausea and prunitus (Ward et al., American Family Physician. 2005, Vol. 72, No. 4; Al-Huthail, The Saudi Journal of Gastroenterology. 2006, Vol. 12, No. 2, 59-67). Severe weight loss is also reported as a side effect in the interferon-based therapy in combination with ribavirin (Bani-Sadr et al., Journal of Viral Hepatitis. 2008, 15(4): 255-260). Thus, there is a clear and unmet need to develop effective therapeutics for treatment of HCV infection.

SUMMARY OF THE DISCLOSURE

Provided herein are phosphothiophene and phosphothiazole compounds, pharmaceutical compositions comprising the compounds, and processes for their preparation. Also provided are methods for using the compounds for the treatment of a host infected with HCV.

In one aspect, provided herein is a phosphothiophene or phosphothiazole compound of Formula I:

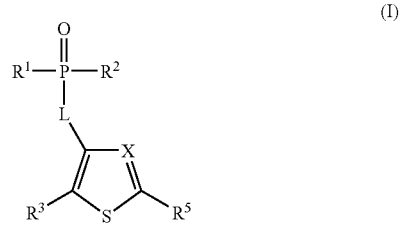

(I)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein each of $R^1$ and $R^2$ is independently —$OR^6$, —$NR^{14}R^{15}$, alkyl, alkenyl, alkynyl, aryl, aralkyl, alkaryl, cycloalkyl, heterocyclyl or heteroaryl;

$R^3$ is H, —$C(O)R^7$, —$C(O)OR^8$, —$C(O)NR^9R^{10}$, —$C(=NR^{11})R^{12}$, —$P(O)(OR^6)_2$ or —$C(O)NHSO_2R^{21}$;

X is N or $CR^4$;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$ or —$SO_2R^{18}$ or $R^4$ and $R^5$ together with the two carbon atoms to which they are attached form a ring (e.g., 5-, 6- or 7-membered ring);

L is a bond or any divalent group such as O, S, $NR^{16}$ or $CR^{19}R^{20}$; and each of $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene), or cycloalkyl-alkylene. In some embodiments, each of alkyl, aryl, arylalkyl, alkaryl, heteroaryl, alkenyl, alkynyl, cycloalkyl, heterocyclyl, alkyl-cycloalkylene or cycloalkyl-alkylene is optionally substituted.

In some embodiments, the phosphothiophene compound disclosed herein has Formula IA:

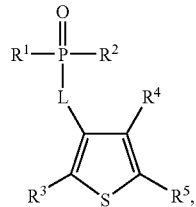
(IA)

or a single enantiomer, a mixture of an enantiomeric pair, an individual diastereomer, a mixture of diastereomers, or a tautomeric form thereof; or a pharmaceutically acceptable salt, solvate, or prodrug thereof, wherein $R^1$, $R^2$, $R^3$, $R^4$, $R^5$ and L are as defined herein.

In some embodiments, the phosphothiazole compound disclosed herein has Formula IB:

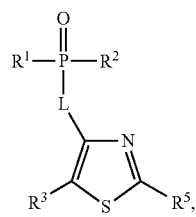
(IB)

or a single enantiomer, a mixture of an enantiomeric pair, an individual diastereomer, a mixture of diastereomers, or a tautomeric form thereof; or a pharmaceutically acceptable salt, solvate, or prodrug thereof, wherein $R^1$, $R^2$, $R^3$, $R^5$ and L are as defined herein.

In certain embodiments, the phosphothiophene compound disclosed herein has Formula IIA, IIIA, IVA, VA, VIA or VIIA:

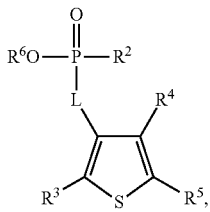
(IIA)

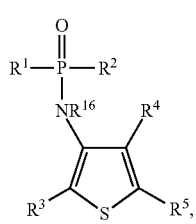
(IIIA)

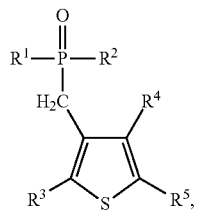
(IVA)

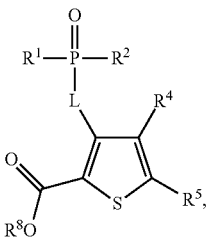
(VA)

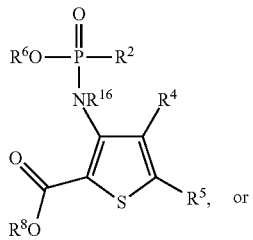
(VIA), or

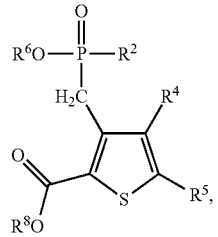
(VIIA)

where $R^1$, $R^2$, $R^3$, $R^4$, $R^5$, $R^6$, $R^8$, $R^{16}$ and L are as defined herein.

In some embodiments, the phosphothiazole compound has formula IIB, IIIB, IVB, VB, VIB or VIIB:

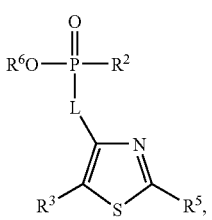
(IIB)

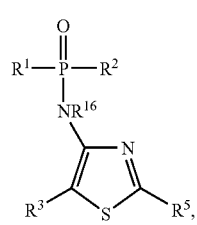
(IIIB)

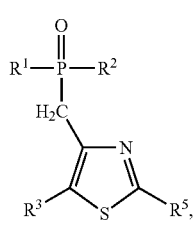
(IVB)

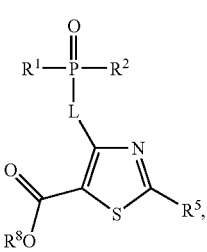
(VB)

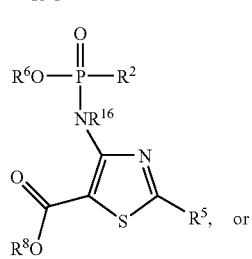
(VIB)

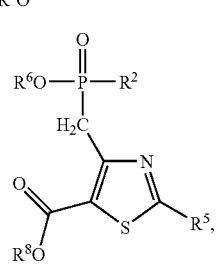
(VIIB)

where $R^1$, $R^2$, $R^3$, $R^5$, $R^6$, $R^8$, $R^{16}$ and L are as defined herein.

In certain embodiments, $R^1$ of Formula I, IA, IIIA, IVA or VA is alkyl, alkoxy, hydroxy, or aryl. In some embodiments, $R^1$ of Formula I, IA, IIIA, IVA or VA is methyl, ethyl, methoxy, ethoxy, or hydroxy.

In some embodiments, $R^2$ of Formula I, IA, IIA, IIIA, IVA, VA, VIA, VIIA, IB, IIB, IIIB, IVB, VB, VIB or VIIB is cycloalkyl, aryl or heteroaryl and wherein each cycloalkyl, aryl or heteroaryl is optionally substituted.

In certain embodiments, $R^3$ of Formula I, IA, IIA, IIIA, IVA, IB, IIB, IIIB or IVB is —C(O)$R^7$, —C(O)O$R^8$, —C(O)NR$^9$R$^{10}$ or —C(=NR$^{11}$)R$^{12}$. In some embodiments, $R^3$ of Formula IA, IIA, IIIA, IVA, IB, IIB, IIIB or IVB is —C(O)OH or —C(O)OCH$_3$.

In some embodiments, $R^4$ of Formula I, IA, IIA, IIIA, IVA, VA, VIA or VIIA is hydrogen, alkenyl, alkynyl, halogen, aryl, heteroaryl or a combination thereof.

In certain embodiments, $R^5$ of Formula Formula I, IA, IIA, IIIA, IVA, VA, VIA, VIIA, IB, IIB, IIIB, IVB, VB, VIB or VIIB is alkyl, alkenyl, alkynyl, aryl, heteroaryl or a combination thereof.

In some embodiments, $R^6$ of Formula I, IA, IB, IIA, IIIA, IVA, VA, VIA, VIIA, IIB, IIIB, VB, VIB or VIIB is H, methyl, ethyl, n-propyl, iso-propyl, n-butyl, iso-butyl or tert-butyl.

In certain embodiments, $R^{16}$ of Formula I, IA, IB, IIA, IIIA, VA, VIA, IIB, IIIB, VB or VIB is H, methyl, ethyl, n-propyl, iso-propyl, n-butyl, iso-butyl, tert-butyl, cycloalkyl or heterocyclyl.

In some embodiments, $R^8$ of Formula I, IA, IB, IIA, IIIA, IVA, VA, VIA, VIIA, IIB, IIIB, IVB, VB, VIB or VIIB is H, methyl, ethyl, n-propyl, iso-propyl, n-butyl, iso-butyl or tert-butyl.

Also provided herein is a pharmaceutical composition comprising a phosphothiophene compound disclosed herein, e.g., the phosphothiophene compound of Formula IA, IIA, IIIA, IVA, VA, VIA, or VIIA, or a phosphothiazole compound disclosed herein, e.g., the phosphothiazole compound of Formula IB, IIB, IIIB, IVB, VB, VIB or VIIB, including a single enantiomer, a mixture of an enantiomeric pair, an individual diastereomer, a mixture of diastereomers, or a tautomeric form thereof or a pharmaceutically acceptable salt, solvate, or prodrug thereof in combination with one or more pharmaceutically acceptable diluents, excipients or carriers.

Further provided herein is a method for treating or preventing an HCV infection, which comprises administering to a subject infected with HCV a therapeutically effective amount of a phosphothiophene compound disclosed herein, e.g., the phosphothiophene compound of Formula IA, IIA, IIIA, IVA, VA, VIA, or VIIA, or a phosphothiazole compound disclosed herein, e.g., the phosphothiazole compound of Formula IB, IIB, IIIB, IVB, VB, VIB or VIIB, including a single enantiomer, a mixture of an enantiomeric pair, an individual diastereomer, a mixture of diastereomers, or a tautomeric form thereof thereof or a pharmaceutically acceptable salt, solvate, or prodrug thereof.

Additionally provided herein is a method for treating, preventing, or ameliorating one or more symptoms of a liver disease or disorder associated with an HCV infection, comprising administering to a subject having the disease or disorder a therapeutically effective amount of a phosphothiophene compound disclosed herein, e.g., the phosphothiophene compound of Formula IA, IIA, IIIA, IVA, VA, VIA, or VIIA, or a phosphothiazole compound disclosed herein, e.g., the phosphothiazole compound of Formula IB, IIB, IIIB, IVB, VB, VIB or VIIB, including a single enantiomer, a mixture of an enantiomeric pair, an individual diastereomer, a mixture of diastereomers, or a tautomeric form thereof thereof or a pharmaceutically acceptable salt, solvate, or prodrug thereof.

Provided herein is a method for inhibiting replication of a virus in a host, which comprises contacting the host with a therapeutically effective amount of a phosphothiophene compound disclosed herein, e.g., the phosphothiophene compound of Formula IA, IIA, IIIA, IVA, VA, VIA, or VIIA, or a phosphothiazole compound disclosed herein, e.g., the phosphothiazole compound of Formula IB, IIB, IIIB, IVB, VB, VIB or VIIB, including a single enantiomer, a mixture of an enantiomeric pair, an individual diastereomer, a mixture of diastereomers, or a tautomeric form thereof; or a pharmaceutically acceptable salt, solvate, or prodrug thereof.

Provided herein is a method for inhibiting replication of a virus in a cell, which comprises contacting the cell with a therapeutically effective amount of a phosphothiophene compound disclosed herein, e.g., the phosphothiophene compound of Formula IA, IIA, IIIA, IVA, VA, VIA, or VIIA, or a phosphothiazole compound disclosed herein, e.g., the phosphothiazole compound of Formula IB, IIB, IIIB, IVB, VB, VIB or VIIB, including a single enantiomer, a mixture of an enantiomeric pair, an individual diastereomer, a mixture of diastereomers, or a tautomeric form thereof; or a pharmaceutically acceptable salt, solvate, or prodrug thereof.

Provided herein is a method for inhibiting replication of a virus, which comprises contacting the virus with a therapeutically effective amount of a phosphothiophene compound disclosed herein, e.g., the phosphothiophene compound of Formula IA, IIA, IIIA, IVA, VA, VIA, or VIIA, or a phosphothiazole compound disclosed herein, e.g., the phosphothiazole compound of Formula IB, IIB, IIIB, IVB, VB, VIB or VIIB, including a single enantiomer, a mixture of an enantiomeric pair, an individual diastereomer, a mixture of diastereomers, or a tautomeric form thereof; or a pharmaceutically acceptable salt, solvate, or prodrug thereof.

Provided herein is a method for inhibiting the activity of a polymerase, which comprises contacting the polymerase with a phosphothiophene compound disclosed herein, e.g., the phosphothiophene compound of Formula IA, IIA, IIIA, IVA, VA, VIA, or VIIA, or a phosphothiazole compound disclosed herein, e.g., the phosphothiazole compound of Formula IB, IIB, IIIB, IVB, VB, VIB or VIIB, including a single enantiomer, a mixture of an enantiomeric pair, an individual diastereomer, a mixture of diastereomers, or a tautomeric form thereof; or a pharmaceutically acceptable salt, solvate, or prodrug thereof.

Provided herein is a phosphothiophene or phosphothiazole compound disclosed herein or a pharmaceutical composition disclosed herein for use in therapy.

Provided herein is a phosphothiophene or phosphothiazole compound disclosed herein or a pharmaceutical composition disclosed herein for use in treating or preventing an HCV infection.

Provided herein is use of a phosphothiophene or phosphothiazole compound disclosed herein or a pharmaceutical composition disclosed herein in the manufacture of a medicament for treating or preventing an HCV infection.

Provided herein is use of a phosphothiophene or phosphothiazole compound disclosed herein or a pharmaceutical composition disclosed herein in the manufacture of a medicament for treating, preventing, or ameliorating one or more symptoms of a liver disease or disorder associated with an HCV infection.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The term "host" refers to a unicellular or multicellular organism in which a virus can replicate, including, but not limited to, a cell, cell line, and animal, such as human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disease; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The term "$IC_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "release controlling excipient" refers to an excipient whose primary function is to modify the duration or place of release of an active substance from a dosage form as compared with a conventional immediate release dosage form.

The term "nonrelease controlling excipient" refers to an excipient whose primary function do not include modifying the duration or place of release of an active substance from a dosage form as compared with a conventional immediate release dosage form.

The term "alkyl" refers to a linear or branched saturated monovalent hydrocarbon radical. The term "alkyl" encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl may be substituted.

The term "alkylene" refers to a linear or branched saturated divalent hydrocarbon radical, wherein the alkylene may optionally be substituted. The term "alkylene" encompasses both linear and branched alkylene, unless otherwise specified. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_{2-6}$ alkylene refers to a linear saturated divalent hydrocarbon radical of 2 to 6 carbon atoms or a branched saturated divalent hydrocarbon radical of 3 to 6 carbon atoms.

The term "alkenyl" refers to a linear or branched monovalent hydrocarbon radical, which contains one or more carbon-carbon double bonds. The alkenyl may be optionally substituted, e.g., as described herein. The term "alkenyl" also embraces radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propenyl, allyl, propenyl, butenyl, and 4-methylbutenyl.

The term "alkenylene" refers to a linear or branched divalent hydrocarbon radical, which contains one or more carbon-carbon double bonds. The alkenylene may be optionally substituted, e.g., as described herein. Similarly, the term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, propenylene, allylene, propenylene, butenylene, and 4-methylbutenylene.

The term "alkynyl" refers to a linear or branched monovalent hydrocarbon radical, which contains one or more carbon-carbon triple bonds. The alkynyl may be optionally substituted, e.g., as described herein. The term "alkynyl" encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "alkynylene" refers to a linear or branched divalent hydrocarbon radical, which contains one or more carbon-carbon triple bonds. The alkynylene may be optionally substituted, e.g., as described herein. The term "alkynylene" encompasses both linear and branched alkynylene, unless otherwise specified. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene (—C≡C—) and propargylene (—CH$_2$C≡C—). For example, $C_{2-6}$ alkynyl refers to a linear unsaturated divalent hydrocarbon radical of 2 to 6 carbon atoms or a branched unsaturated divalent hydrocarbon radical of 3 to 6 carbon atoms.

The term "cycloalkyl" refers to a cyclic saturated bridged or non-bridged monovalent hydrocarbon radical, which may be optionally substituted, e.g., as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

The term "cycloalkylene" refers to a cyclic saturated bridged or non-bridged divalent hydrocarbon radical, which may be optionally substituted, e.g., as described herein. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene, cyclobutylene, cyclopentylene, cyclohexylene, cycloheptylene, decalinylene, and adamantylene.

The term "aryl" refers to a monocyclic or multicyclic monovalent aromatic group. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). All such aryl groups may also be optionally substituted, e.g., as described herein.

The term "arylene" refers to a monocyclic or multicyclic divalent aromatic group. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydro-naphthylene (tetralinyl). All such aryl groups may also be optionally substituted, e.g., as described herein.

In some embodiments, the term "aralkyl" or "arylalkyl" includes an alkyl group with an aryl substituent. In certain embodiments, the term "aralkyl" or "arylalkyl" refers to

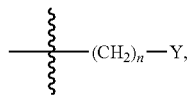

wherein Y is aryl and n is an integer from 1 to 20. In some embodiments, n is an integer from 1 to 10. In some embodiments, n is an integer from 1-5. In some embodiments, n is an integer from 1-3. In some embodiments, n is 1. In some embodiments, n is 2. In some embodiments, n is 3.

In some embodiments, the term "alkaryl" or "alkylaryl" includes an aryl group with an alkyl substituent. In certain embodiments, the term "alkaryl" or "alkylaryl" refers to

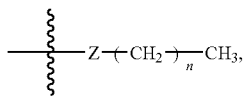

wherein Z is arylene and n is an integer from 0 to 20. In some embodiments, n is an integer from 0 to 10. In some embodiments, n is an integer from 0-5. In some embodiments, n is an integer from 0-3. In some embodiments, n is 0. In some embodiments, n is 1. In some embodiments, n is 2.

The term "heteroaryl" refers to a monocyclic or multicyclic aromatic group, wherein at least one ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. All such heteroaryl groups may also be optionally substituted, e.g., as described herein.

The term "heterocyclyl" or "heterocyclic" refers to a monocyclic or multicyclic non-aromatic ring system, wherein one or more of the ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Examples of heterocyclyl groups include, but are not limited to, pyrrolidinyl, piperidinyl, 2-oxopyrrolidinyl, 2-oxopiperidinyl, morpholinyl, piperazinyl, tetrahydropyranyl, and thiomorpholinyl. All such heterocyclic groups may also be optionally substituted, e.g., as described herein.

The term "alkoxy" refers to an —OR radical, wherein R is, for example, alkyl, alkenyl, alkynyl, cycloalkyl, aryl, heteroaryl, or heterocyclyl, each as defined herein. Examples of alkoxy groups include, but are not limited to, methoxy, ethoxy, propoxy, n-propoxy, 2-propoxy, n-butoxy, isobutoxy, tert-butoxy, cyclohexyloxy, phenoxy, benzoxy, and 2-naphthyloxy.

The term "acyl" refers to a —C(O)R radical, wherein R is, for example, alkyl, alkenyl, alkynyl, cycloalkyl, aryl, heteroaryl, or heterocyclyl, each as defined herein. Examples of acyl groups include, but are not limited to, acetyl, propionyl, butanoyl, isobutanoyl, pentanoyl, hexanoyl, heptanoyl, octanoyl, nonanoyl, decanoyl, dodecanoyl, tetradecanoyl, hexadecanoyl, octadecanoyl, eicosanoyl, docosanoyl, myristoleoyl, palmitoleoyl, oleoyl, linoleoyl, arachidonoyl, benzoyl, pyridinylcarbonyl, and furoyl.

The term "halogen", "halide" or "halo" refers to fluorine, chlorine, bromine, or iodine.

The term "substituted" or "optionally substituted" is intended to mean that a group, such as an alkyl, alkylene, alkenyl, alkenylene, alkynyl, alkynylene, cycloalkyl, cycloalkylene, aryl, arylene, heteroaryl, or heterocyclyl group, may be substituted with one or more substituents independently selected from, e.g., halo, cyano, nitro, —$SR^a$, —$S(O)R^a$, —$S(O)_2R^a$, —$R^a$, —$C(O)R^a$, —$C(O)OR^a$, —$C(O)NR^bR^c$, —$C(NR^a)NR^bR^c$, —$OR^a$, —$OC(O)R^a$, —$OC(O)OR^a$, —$OC(O)NR^bR^c$, —$OC(=NR^a)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^b$, —$NR^aC(O)OR^b$, —$NR^aC(O)NR^bR^c$, —$NR^aC(=NR^d)NR^bR^c$, —$NR^aS(O)R^b$, —$NR^aS(O)_2R^b$, —$NR^aS(O)R^bR^c$, or —$NR^aS(O)_2R^bR^c$; wherein $R^a$, $R^b$, $R^c$, and $R^d$ are each independently, e.g., hydrogen, alkyl, alkenyl, alkynyl, cycloalkyl, aryl, heteroaryl, or heterocyclyl, each optionally substituted, e.g., as described herein; or $R^b$ and $R^c$ together with the N atom to which they are attached form heterocyclyl or heteroaryl, each optionally substituted, e.g., as described herein. The group can be substituted with any described moiety, including, but not limited to, one or more moieties selected from the group consisting of halogen (fluoro, chloro, bromo, or iodo), hydroxy, amino, alkylamino (e.g., monoalkylamino, dialkylamino, or trialkylamino), arylamino (e.g., monoarylamino, diarylamino, or triarylamino), alkoxy, aryloxy, nitro, cyano, sulfonic acid, sulfate, phosphonic acid, phosphate, or phosphonate, either unprotected or protected as necessary, as known to those skilled in the art, for example, as taught in Greene, et al., *Protective Groups in Organic Synthesis*, John Wiley and Sons, Second Edition, 1991. As used herein, all groups that can be substituted in some embodiments are "optionally substituted," unless otherwise specified.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, or no less than about 94% no less than about 95%, no less than about 96%, no less than about 97%, no less than about 98%, no less than about 99%, or no less than about 99.5%, no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

Compounds

Provided herein are phosphorus-containing heterocyclic compounds (e.g., phosphothiophene compounds, phosphothiazole compounds and phosphopyrazole compounds) useful for the treatment of HCV infection, which, in some embodiments, can have activity as HCV polymerase inhibitors. Also provided herein are pharmaceutical compositions that comprise the compounds, methods of manufacture of the compounds, and methods of using compounds for the treatment of HCV infection in a host in need of treatment.

In some embodiments, provided herein is a compound according to any of Formulae I, IA, IIA, IIIA, IVA, VA, VIA, VIIA, IB, IIB, IIIB, IVB, VB, VIB, VIIB and X as described below, or a single enantiomer, a mixture of an enantiomeric pair, an individual diastereomer, or a mixture of diastereomers thereof or a pharmaceutically acceptable salt, solvate, or prodrug thereof.

In one aspect, provided herein is a phosphorus-containing heterocyclic compounds of Formula XX:

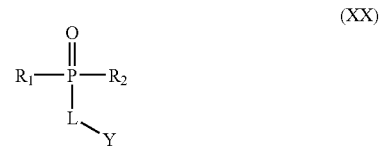

(XX)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein each of $R^1$ and $R^2$ is independently —$OR^6$, —$NR^{14}R^{15}$, alkyl, alkenyl, alkynyl, aryl, aralkyl, alkaryl, cycloalkyl, heterocyclyl or heteroaryl;

L is a bond or any divalent group such as O, S, $NR^{16}$ or $CR^{19}R^{20}$;

each of $R^6$, $R^{16}$, $R^{19}$ and $R^{20}$ is as defined herein; and

Y is aryl, heterocyclyl or heteroaryl.

In some embodiments, Y is heteroaryl. In further embodiments, Y is furyl, thienyl, pyrrolyl, indolyl, indolizinyl, isoindolyl, pyrazolyl, imidazolyl, thiazolyl, thiadiazolyl, benzothiazolyl, 1,2,4-triazolyl, 1,2,3-triazolyl, indazolyl, benzotriazolyl, benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, and a combination thereof. In some embodiments, Y includes any combination of heteroaryl groups and aryl groups joined together either by a bond (as in bicarbazolyl or phenyl-8aH-imidazo[1,2-a]pyridine) or by a linking group (as in 1,6-di(10H-10-phenothiazinyl)hexane). The linking group may include an alkyl group, an alkenyl group, an alkyne group, O, S, O=S=O, an amino group, an aromatic group, a heterocyclic group, and combinations thereof. Furthermore, the linking group may comprise at least one heteroatom such as O, S, Si, and N.

In certain embodiments of Formula XX, Y has:

(XXI)

wherein A is $CR^a$, N, $NR^b$, O or S;

B is $CR^c$, N, $NR^d$, O or S;

C is $CR^e$, N, $NR^f$, O or S;

D is $CR^g$, N, $NR^h$, O or S, with the proviso that at least one of A, B, C or D is N, $NR^b$, $NR^d$, $NR^f$, $NR^h$, O or S;

each of $R^a$, $R^b$, $R^c$, $R^d$, $R^e$, $R^f$, $R^g$ and $R^h$ is independently H, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$, —$SO_2R^{18}$—C(O) or $NSO_2R^{21}$; and each of $R^6$, $R^7$, $R^8$, $R^9$, $R^{10}$, $R^{11}$, $R^{12}$, $R^{13}$, $R^{14}$, $R^{15}$, $R^{17}$, $R^{18}$ and $R^{21}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene), or cycloalkyl-alkylene. In some embodiments, each alkyl, aryl, arylalkyl, alkaryl, heteroaryl, alkenyl, alkynyl, cycloalkyl, heterocyclyl, alkyl-cycloalkylene or cycloalkyl-alkylene is optionally substituted.

In further embodiments, Y has formula XXIA, XXIB:

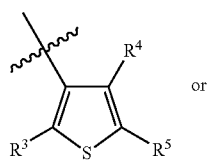

(XXIA)

or

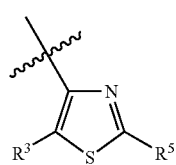

(XXIB)

wherein each $R^3$ is independently H, —$C(O)R^7$, —$C(O)OR^8$, —$C(O)NR^9R^{10}$, —$C(=NR^{11})R^{12}$, —$P(O)(OR^6)_2$ or —$C(O)NHSO_2R^{21}$;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$ or —$SO_2R^{18}$ or $R^4$ and $R^5$ together with the two carbon atoms to which they are attached form a ring (e.g., 5-, 6- or 7-membered ring); and each of $R^6$, $R^7$, $R^8$, $R^9$, $R^{10}$, $R^{11}$, $R^{12}$, $R^{13}$, $R^{14}$, $R^{15}$, $R^{17}$, $R^{18}$ and $R^{21}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene), or cycloalkyl-alkylene. In some embodiments, each alkyl, aryl, arylalkyl, alkaryl, heteroaryl, alkenyl, alkynyl, cycloalkyl, heterocyclyl, alkyl-cycloalkylene or cycloalkyl-alkylene is optionally substituted.

In one aspect, provided herein is a phosphothiophene or phosphothiazole compound of Formula I:

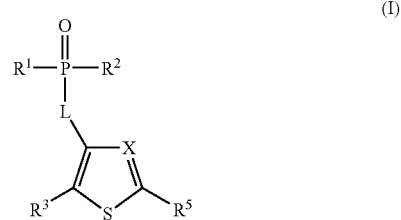

(I)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein each of $R^1$ and $R^2$ is independently —$OR^6$, —$NR^{14}R^{15}$, alkyl, alkenyl, alkynyl, aryl, aralkyl, alkaryl, cycloalkyl, heterocyclyl or heteroaryl;

$R^3$ is H, —$C(O)R^7$, —$C(O)OR^8$, —$C(O)NR^9R^{10}$, —$C(=NR^{11})R^{12}$, —$P(O)(OR^6)_2$ or —$C(O)NHSO_2R^{21}$;

X is N or $CR^4$;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$ or —$SO_2R^{18}$ or $R^4$ and $R^5$ together with the two carbon atoms to which they are attached form a ring (e.g., 5-, 6- or 7-membered ring);

L is a bond or any divalent group such as O, S, $NR^{16}$ or $CR^{19}R^{20}$; and each of $R^6$, $R^7$, $R^8$, $R^9$, $R^{10}$; $R^{11}$; $R^{12}$; $R^{13}$; $R^{14}$; $R^{15}$; $R^{16}$; $R^{17}$; $R^{18}$; $R^{19}$; $R^{20}$ and $R^{21}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene), or cycloalkyl-alkylene. In some embodiments, each alkyl, aryl, arylalkyl, alkaryl, heteroaryl, alkenyl, alkynyl, cycloalkyl, heterocyclyl, alkyl-cycloalkylene or cycloalkyl-alkylene is optionally substituted.

In some embodiments, X of formula I is $CR^4$ wherein $R^4$ is as defined herein. In some embodiments, the compound has formula IA:

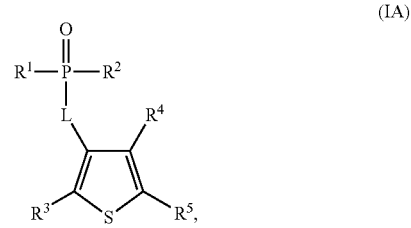

(IA)

or a single enantiomer, a mixture of an enantiomeric pair, an individual diastereomer, a mixture of diastereomers, or a tautomeric form thereof; or a pharmaceutically acceptable salt, solvate, or prodrug thereof, wherein $R^1$, $R^2$, $R^3$, $R^4$, $R^5$ and L are as defined herein.

In certain embodiments, X of formula I is N. In some embodiments, the compound has formula IB:

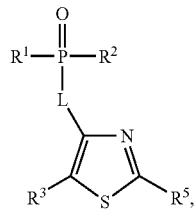

(IB)

or a single enantiomer, a mixture of an enantiomeric pair, an individual diastereomer, a mixture of diastereomers, or a tautomeric form thereof; or a pharmaceutically acceptable salt, solvate, or prodrug thereof, wherein $R^1$, $R^2$, $R^3$, $R^4$, $R^5$ and L are as defined herein In some embodiments, provided herein is a compound of Formula IIA:

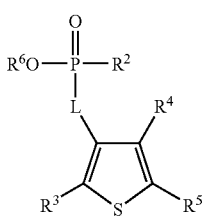

(IIA)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein $R^2$ is —$OR^6$, —$R^{14}R^{15}$, alkyl, alkenyl, alkynyl, aryl, aralkyl, alkaryl, cycloalkyl, heterocyclyl or heteroaryl;

$R^3$ is H, —$C(O)R^7$, —$C(O)OR^8$, —$C(O)NR^9R^{10}$, —$C(=NR^{11})R^{12}$, —$P(O)(OR^6)_2$ or —$C(O)NHSO_2R^{21}$;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$, or —$SO_2R^{18}$ or $R^4$ and $R^5$ together with the two carbon atoms to which they are attached form a ring (e.g., 5-, 6- or 7-membered ring);

L is a bond or any divalent group such as O, S, $NR^{16}$ or $CR^{19}R^{20}$; and each of $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene) or cycloalkyl-alkylene.

In some embodiments, provided herein is a compound of Formula IIIA:

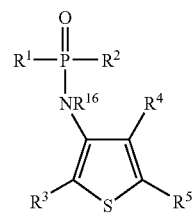

(IIIA)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein each of $R^1$ and $R^2$ is independently —$OR^6$, —$NR^{14}R^{15}$, alkyl, alkenyl, alkynyl, aryl, aralkyl, alkaryl, cycloalkyl, heterocyclyl or heteroaryl;

$R^3$ is H, —$C(O)R^7$, —$C(O)OR^8$, —$C(O)NR^9R^{10}$, —$C(=NR^{11})R^{12}$, —$P(O)(OR^6)_2$ or —$C(O)NHSO_2R^{21}$;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$, or —$SO_2R^{18}$ or $R^4$ and $R^5$ together with the two carbon atoms to which they are attached form a ring (e.g., 5-, 6- or 7-membered ring); and each of $R^6$, $R^7$, $R^8$, $R^9$, $R^{10}$, $R^{11}$, $R^{12}$, $R^{13}$, $R^{14}$, $R^{15}$, $R^{17}$, $R^{18}$, $R^{19}$, $R^{20}$ and $R^{21}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene) or cycloalkyl-alkylene.

In some embodiments, provided herein is a compound of Formula IVA:

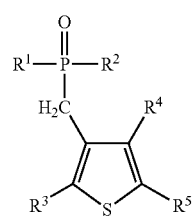

(IVA)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein each of $R^1$ and $R^2$ is independently —$OR^6$, —$NR^{14}R^{15}$, alkyl, alkenyl, alkynyl, aryl, aralkyl, alkaryl, cycloalkyl, heterocyclyl or heteroaryl;

$R^3$ is H, —$C(O)R^7$, —$C(O)OR^8$, —$C(O)NR^9R^{10}$, —$C(=NR^{11})R^{12}$, —$P(O)(OR^6)_2$ or —$C(O)NHSO_2R^{21}$;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$, or —$SO_2R^{18}$ or $R^4$ and $R^5$ together with the two carbon atoms to which they are attached form a ring (e.g., 5-, 6- or 7-membered ring); and each of $R^6$, $R^7$, $R^8$, $R^9$, $R^{10}$, $R^{11}$, $R^{12}$, $R^{13}$, $R^{14}$, $R^{15}$, $R^{17}$, $R^{18}$, $R^{19}$, $R^{20}$ and $R^{21}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene) or cycloalkyl-alkylene.

In some embodiments, provided herein is a compound of Formula VA:

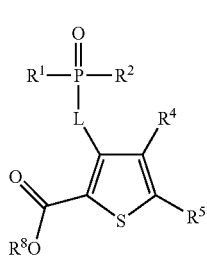

(VA)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein each of $R^1$ and $R^2$ is independently —$OR^6$, —$NR^{14}R^{15}$, alkyl, alkenyl, alkynyl, aryl, aralkyl, alkaryl, cycloalkyl, heterocyclyl or heteroaryl;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$, or —$SO_2R^{18}$, or $R^4$ and $R^5$ together with the two carbon atoms to which they are attached form a ring (e.g., 5-, 6- or 7-membered ring);

L is a bond or any divalent group such as O, S, $NR^{16}$ or $CR^{19}R^{20}$; and each of $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene), or cycloalkyl-alkylene.

In some embodiments, provided herein is a compound of Formula VIA:

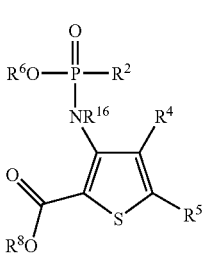

(VIA)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein $R^2$ is —$OR^6$, —$NR^{14}R^{15}$, alkyl, alkenyl, alkynyl, aryl; aralkyl, alkaryl, cycloalkyl, heterocyclyl or heteroaryl;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$, or —$SO_2R^{18}$, or $R^4$ and $R^5$ together with the two carbon atoms to which they are attached form a ring (e.g., 5-, 6- or 7-membered ring); and each of $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene), or cycloalkyl-alkylene.

In some embodiments, provided herein is a compound of Formula VIIA:

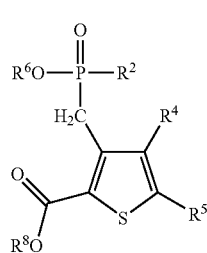

(VIIA)

or a single enantiomer, a mixture of diastereomers, or a tautomeric form thereof; or a pharmaceutically acceptable salt, solvate, or prodrug thereof;

$R^2$ is —$OR^6$, —$NR^{14}R^{15}$, alkyl, alkenyl, alkynyl, aryl, aralkyl, alkaryl, cycloalkyl, heterocyclyl or heteroaryl;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$ or —$SO_2R^{18}$, or $R^4$ and $R^5$ together with the two carbon atoms to which they are attached form a ring (e.g., 5-, 6- or 7-membered ring); and each of $R^6$, $R^7$, $R^8$, $R^9$, $R^{10}$, $R^{11}$, $R^{12}$, $R^{13}$, $R^{14}$, $R^{15}$, $R^{17}$, $R^{18}$ and $R^{19}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene) or cycloalkyl-alkylene.

In some embodiments, provided herein is a compound of Formula IIB:

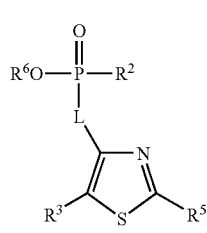

(IIB)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein R² is —OR⁶, —NR¹⁴R¹⁵, alkyl, alkenyl, alkynyl, aryl, aralkyl, alkaryl, cycloalkyl, heterocyclyl or heteroaryl;

R³ is H, —C(O)R⁷, —C(O)OR⁸, —C(O)NR⁹R¹⁰, —C(=NR¹¹)R¹², —P(O)(OR⁶)₂ or —C(O)NHSO₂R²¹;

R⁵ is H, halogen, cyano, azido, alkyl, alkenyl, alkynyl, aryl, aralkyl, alkaryl, cycloalkyl, heterocyclyl, heteroaryl, —OR⁶, —C(O)R⁷, —C(O)OR⁸, —C(O)NR⁹R¹⁰, —C(=NR¹¹)R¹², —NHSO₂R¹³, —NR¹⁴R¹⁵, —SO₃R¹⁷, or —SO₂R¹⁸;

L is a bond or any divalent group such as O, S, NR¹⁶ or CR¹⁹R²⁰; and each of R⁶, R⁷, R⁸, R⁹, R¹⁰, R¹¹, R¹², R¹³, R¹⁴, R¹⁵, R¹⁶, R¹⁷, R¹⁸, R¹⁹, R²⁰ and R²¹ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene) or cycloalkyl-alkylene.

In some embodiments, provided herein is a compound of Formula IIIB:

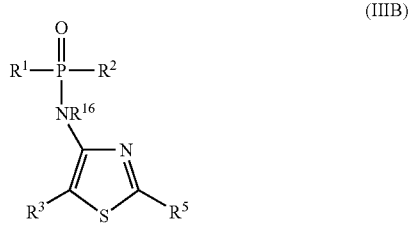

(IIIB)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein each of R¹ and R² is independently —OR⁶, —NR¹⁴R¹⁵, alkyl, alkenyl, alkynyl, aryl, aralkyl, alkaryl, cycloalkyl, heterocyclyl or heteroaryl;

R³ is H, —C(O)R⁷, —C(O)OR⁸, —C(O)NR⁹R¹⁰, —C(=NR¹¹)R¹², —P(O)(OR⁶)₂ or —C(O)NHSO₂R²¹;

R⁵ is H, halogen, cyano, azido, alkyl, alkenyl, alkynyl, aryl, aralkyl, alkaryl, cycloalkyl, heterocyclyl, heteroaryl, —OR⁶, —C(O)R⁷, —C(O)OR⁸, —C(O)NR⁹R¹⁰, —C(=NR¹¹)R¹², —NHSO₂R¹³, —NR¹⁴R¹⁵, —SO₃R¹⁷, or —SO₂R¹⁸; and each of R⁶, R⁷, R⁸, R⁹, R¹⁰, R¹¹, R¹², R¹³, R¹⁴, R¹⁵, R¹⁷, R¹⁸, R¹⁹, R²⁰ and R²¹ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene) or cycloalkyl-alkylene.

In some embodiments, provided herein is a compound of Formula IVB:

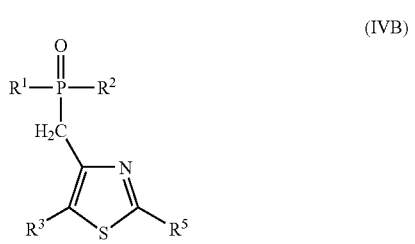

(IVB)

In some embodiments, provided herein is a compound of Formula VB:

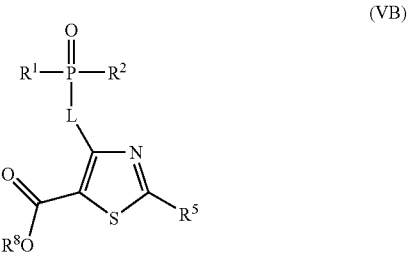

(VB)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein each of R¹ and R² is independently —OR⁶, —NR¹⁴R¹⁵, alkyl, alkenyl, alkynyl, aryl, aralkyl, alkaryl, cycloalkyl, heterocyclyl or heteroaryl;

R⁵ is H, halogen, cyano, azido, alkyl, alkenyl, alkynyl, aryl, aralkyl, alkaryl, cycloalkyl, heterocyclyl, heteroaryl, —OR⁶, —C(O)R⁷, —C(O)OR⁸, —C(O)NR⁹R¹⁰, —C(=NR¹¹)R¹², —NHSO₂R¹³, —NR¹⁴R¹⁵, —SO₃R¹⁷, or —SO₂R¹⁸;

L is a bond or any divalent group such as O, S, NR¹⁶ or CR¹⁹R²⁰; and each of R⁶, R⁷, R⁸, R⁹, R¹⁰, R¹¹, R¹², R¹³, R¹⁴, R¹⁵, R¹⁷, R¹⁸, R¹⁹, and R²⁰ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene), or cycloalkyl-alkylene.

In some embodiments, provided herein is a compound of Formula VIB:

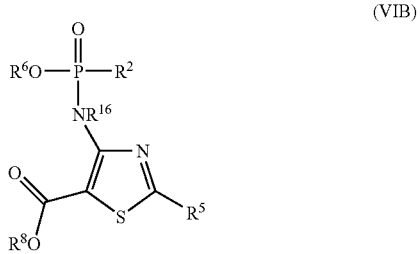

(VIB)

or a single enantiomer, a mixture of an enantiomeric pair, an individual diastereomer, a mixture of diastereomers, or a tautomeric form thereof; or a pharmaceutically acceptable salt, solvate, or prodrug thereof;

wherein $R^2$ is —$OR^6$, —$NR^{14}R^{15}$, alkyl, alkenyl, alkynyl, aryl; aralkyl, alkaryl, cycloalkyl, heterocyclyl or heteroaryl;

$R^5$ is H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$, or —$SO_2R^{18}$; and each of $R^6$, $R^7$, $R^8$, $R^9$, $R^{10}$, $R^{11}$, $R^{12}$, $R^{13}$, $R^{14}$, $R^{15}R^{17}$, and $R^{18}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene), or cycloalkyl-alkylene.

In some embodiments, provided herein is a compound of Formula VIIB:

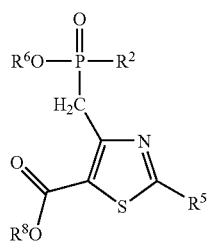

(VIIB)

or a single enantiomer, a mixture of diastereomers, or a tautomeric form thereof; or a pharmaceutically acceptable salt, solvate, or prodrug thereof;

$R^2$ is —$OR^6$, —$NR^{14}R^{15}$, alkyl, alkenyl, alkynyl, aryl, aralkyl, alkaryl, cycloalkyl, heterocyclyl or heteroaryl;

$R^3$ is H, —$C(O)R^7$, —$C(O)OR^8$, —$C(O)NR^9R^{10}$, —$C(=NR^{11})R^{12}$, —$P(O)(OR^6)_2$ or —$C(O)NHSO_2R^{21}$;

$R^5$ is H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$ or —$SO_2R^{18}$; and each of $R^6$, $R^7$, $R^8$, $R^9$, $R^{10}$, $R^{11}$, $R^{12}$, $R^{13}$, $R^{14}$, $R^{15}$, $R^{17}$, $R^{18}$, $R^{19}$, $R^{20}$ and $R^{21}$ is independently hydrogen, alkyl (e.g., $C_{1-6}$ alkyl), alkenyl (e.g., $C_{2-6}$ alkenyl), alkynyl (e.g., $C_{2-6}$ alkynyl), cycloalkyl (e.g., $C_{3-7}$ cycloalkyl), aryl (e.g., $C_{6-14}$ aryl), heteroaryl (e.g., 5-, 6- or 7-membered heteroaryl), heterocyclyl (e.g., 3-7 membered heterocyclyl), alkyl-cycloalkylene (e.g., $C_{1-6}$ alkyl-$C_{3-7}$ cycloalkylene) or cycloalkyl-alkylene.

In certain embodiments according to Formula I, IA, IIA, IIIA, IVA, VA, VIA, VIIA, IB, IIB, IIIB, IVB, VB, VIB, VIIB or XX, each of alkyl, aryl, arylalkyl, alkaryl, heteroaryl, alkenyl, alkynyl, cycloalkyl, heterocyclyl, and alkyl-cycloalkyl is independently unsubstituted. In some embodiments according to Formula I, IA, IIA, IIIA, IVA, VA, VIA, VIIA, IB, IIB, IIIB, IVB, VB, VIB, VIIB or XX, each of alkyl, aryl, arylalkyl, alkaryl, heteroaryl, alkenyl, alkynyl, cycloalkyl, heterocyclyl, and alkyl-cycloalkyl is independently substituted.

In certain embodiments, $R^1$ of Formula IA, IIIA, IVA, VA, IB, IIIB, IVB, VB or XX is alkyl, alkoxy, hydroxy, or aryl, such as phenyl. In further embodiments, $R^1$ of Formula IA, IIIA, IVA, VA, IB, IIIB, IVB, VB or XX is methyl, ethyl, methoxy, ethoxy, or hydroxy.

In certain embodiments, $R^2$ of Formula I, IA, IIA, IIIA, IVA, VA, VIA, VIIA, IB, IIB, IIIB, IVB, VB, VIB, VIIB or XX is

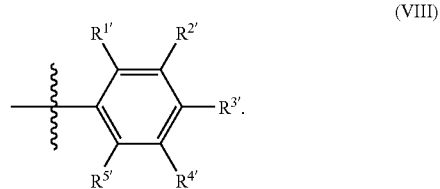

(VIII)

wherein each of $R^{1'}$, $R^{2'}$, $R^{3'}$, $R^{4'}$ and $R^{5'}$ is independently H, halogen, cyano, azido, alkyl, alkenyl, alkynyl, aryl, aralkyl, alkaryl, cycloalkyl, heterocyclyl, heteroaryl, —$OR^6$, —$C(O)R^7$, —$C(O)OR^8$, —$C(O)NR^9R^{10}$, —$C(=NR^{11})R^{12}$, —$NHSO_2R^{13}$, —$NR^{14}R^{15}$, —$SO_3R^{17}$, or —$SO_2R^{18}$, or $R^{1'}$ and $R^{2'}$ or $R^{2'}$ and $R^{3'}$ or $R^{3'}$ and $R^{4'}$ or $R^{4'}$ and $R^{5'}$ together with the two carbon atoms to which they are attached form a ring (e.g., 5-, 6- or 7-membered ring).

In certain embodiments, $R^2$ of Formula I, IA, IIA, IIIA, IVA, VA, VIA, VIIA, IB, IIB, IIIB, IVB, VB, VIB, VIIB VII or XX is cycloalkyl, aryl, or heteroaryl, wherein each cycloalkyl, aryl, or heteroaryl is optionally substituted. In some embodiments, $R^2$ of Formula I, IA, IIA, IIIA, IVA, VA, VIA, VIIA, IB, IIB, IIIB, IVB, VB, VIB, VIIB or XX is:

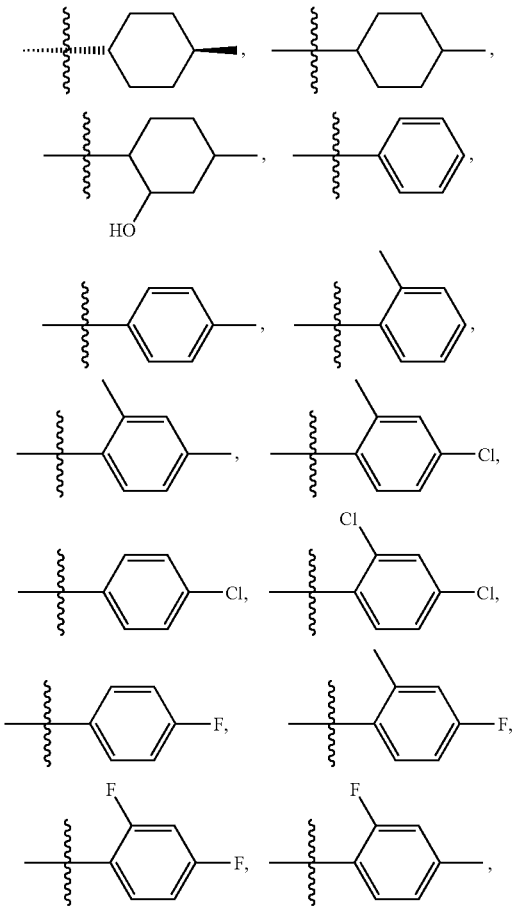

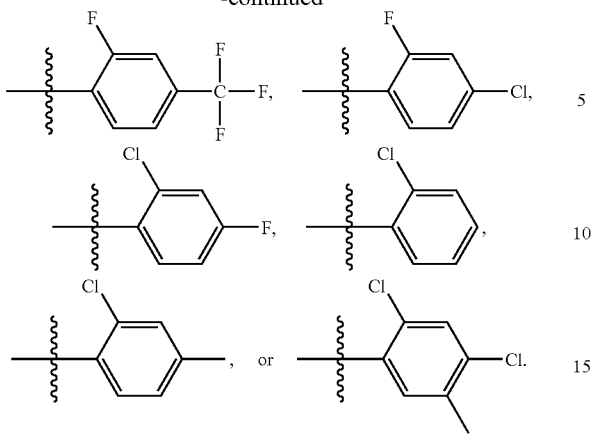

In some embodiments, $R^3$ of Formula I, IA, IIA, IIIA, IVA, IB, IIB, IIIB or IVB is —C(O)$R^7$, —C(O)O$R^8$, —C(O)N$R^9R^{10}$ or —C(=N$R^{11}$)$R^{12}$ wherein each of $R^7$, $R^8$, $R^9$ and $R^{10}$ is as defined herein. In certain embodiments, $R^3$ of Formula I, IA, IIA, IIIA, IVA, IB, IIB, IIIB or IVB is —C(O)OH or —C(O)OCH$_3$.

In some embodiments, $R^4$ of Formula I, IA, IIA, IIIA, IVA, VA, VIA or VIIA is H or halogen.

In certain embodiments according to Formula I, IA, IIA, IIIA, VA or VIA, $R^1$ is O$R^6$; $R^2$ is aryl or cycloalkyl; L is N$R^{16}$; $R^3$ is —C(O)O$R^8$; $R^4$ is H or halogen; $R^5$ is alkyl, aryl, alkynyl, or heterocyclyl; $R^6$ is H or alkyl; $R^{16}$ is H, alkyl, or heterocyclyl; and $R^8$ is H or alkyl.

In certain embodiments according to Formula IVA or VIIA, $R^1$ is O$R^6$; $R^2$ is aryl or cycloalkyl; $R^3$ is —C(O)O$R^8$; $R^4$ is H or halogen; $R^5$ is alkyl, aryl, alkynyl, or heterocyclyl; $R^6$ is H or alkyl; $R^{16}$ is H, alkyl, or heterocyclyl; and $R^8$ is H or alkyl.

In certain embodiments according to Formula I, IB, IIB, IIIB, VB or VIB, $R^1$ is O$R^6$; $R^2$ is aryl or cycloalkyl; L is N$R^{16}$; $R^3$ is —C(O)O$R^8$; $R^5$ is alkyl, aryl, alkynyl, or heterocyclyl; $R^6$ is H or alkyl; $R^{16}$ is H, alkyl, or heterocyclyl; and $R^8$ is H or alkyl.

In certain embodiments according to Formula IVB or VIIB, $R^1$ is O$R^6$; $R^2$ is aryl or cycloalkyl, $R^3$ is —C(O)O$R^8$; $R^5$ is alkyl, aryl, alkynyl, or heterocyclyl; $R^6$ is H or alkyl; $R^{16}$ is H, alkyl, or heterocyclyl; and $R^8$ is H or alkyl.

In certain embodiments, $R^5$ of Formula I, IA, IIA, IIIA, IVA, VA, VIA, VIIA, IB, IIB, IIIB, IVB, VB, VIB, or VIIB is alkyl, alkynyl, alkaryl, aryl, or heteroaryl, wherein each alkynyl, aryl, or heteroaryl is optionally substituted. In further embodiments, $R^5$ of Formula IA, IIA, IIIA, IVA, VA, VIA, VIIA, IB, IIB, IIIB, IVB, VB, VIB, or VIIB is:

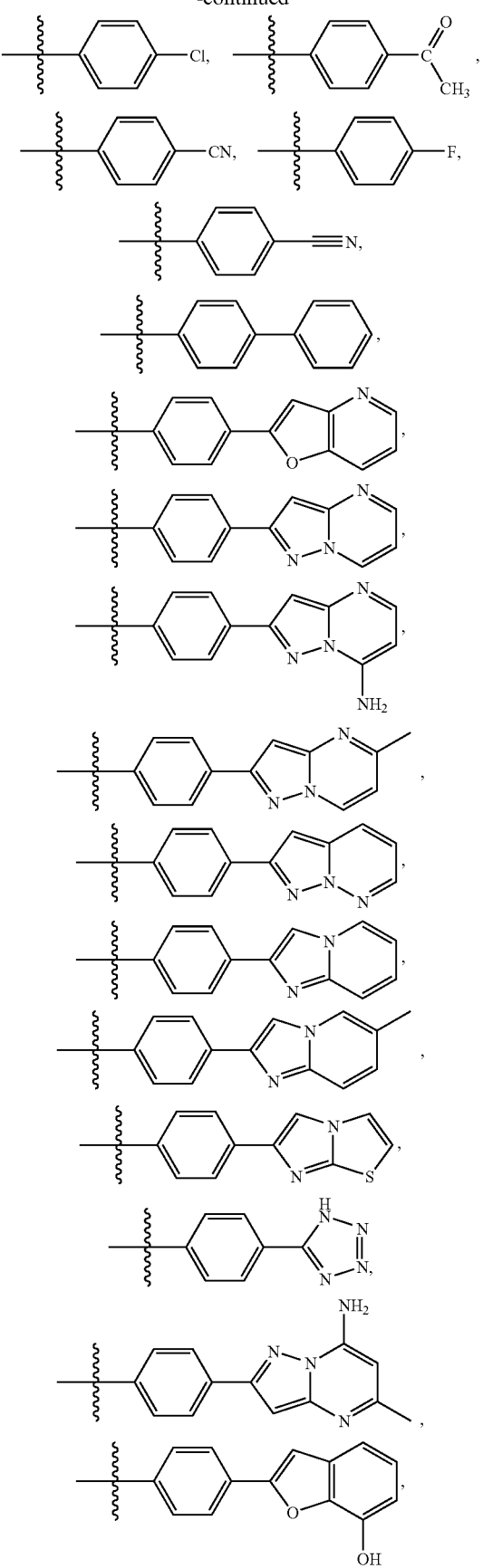

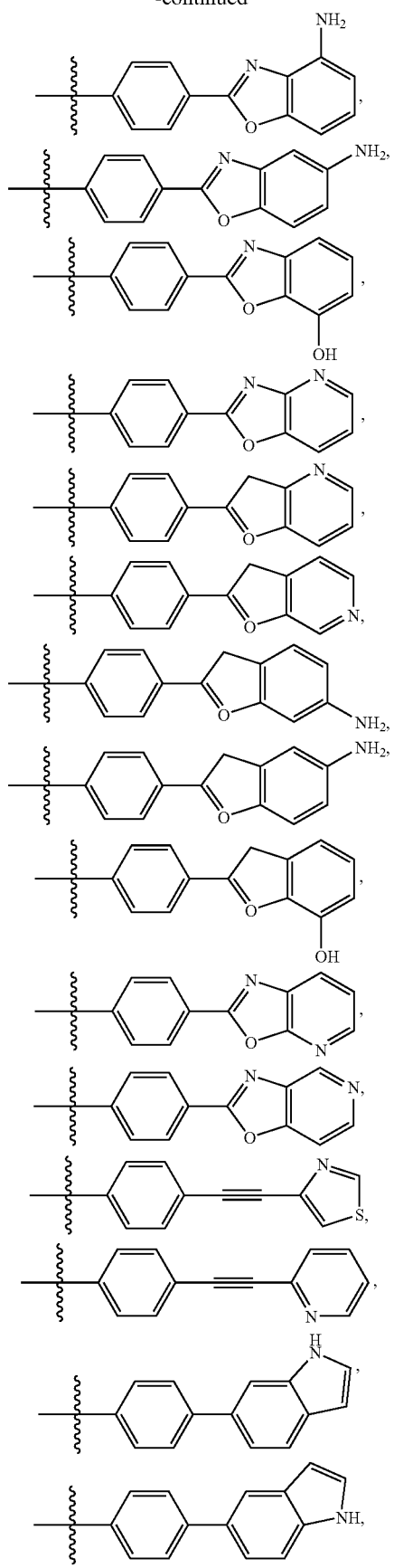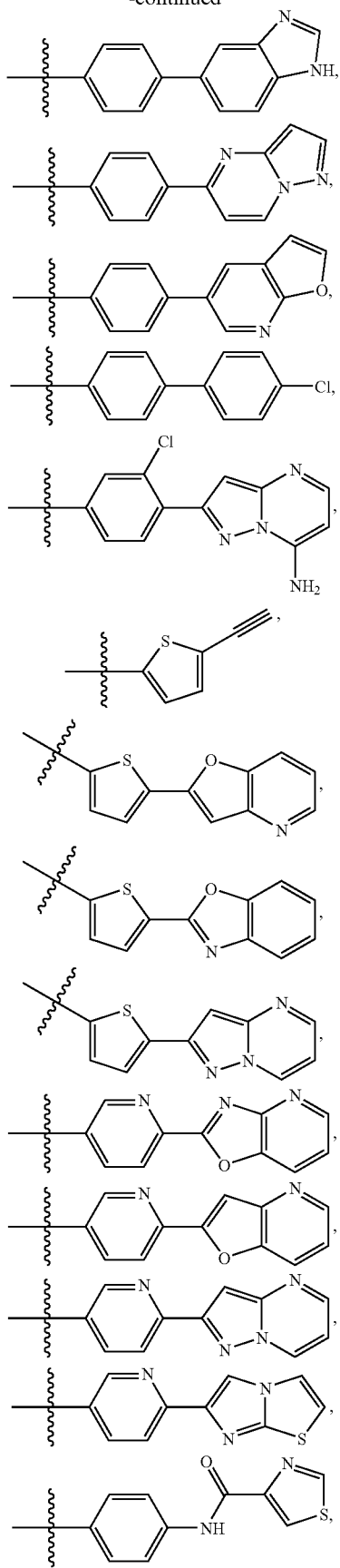

-continued
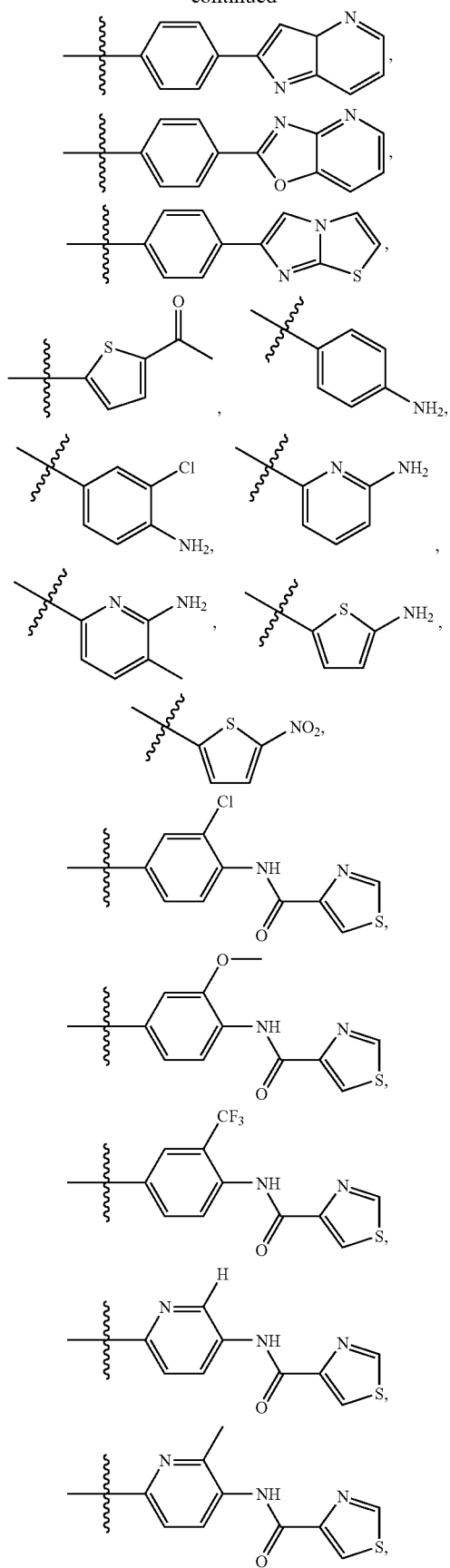
-continued
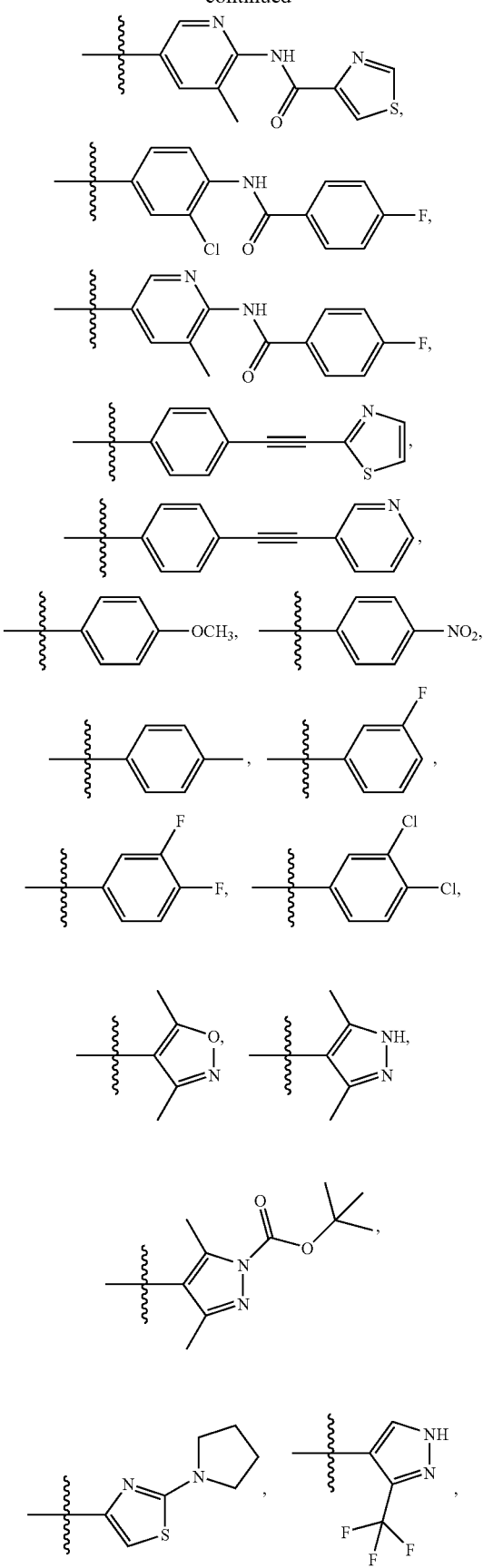

-continued
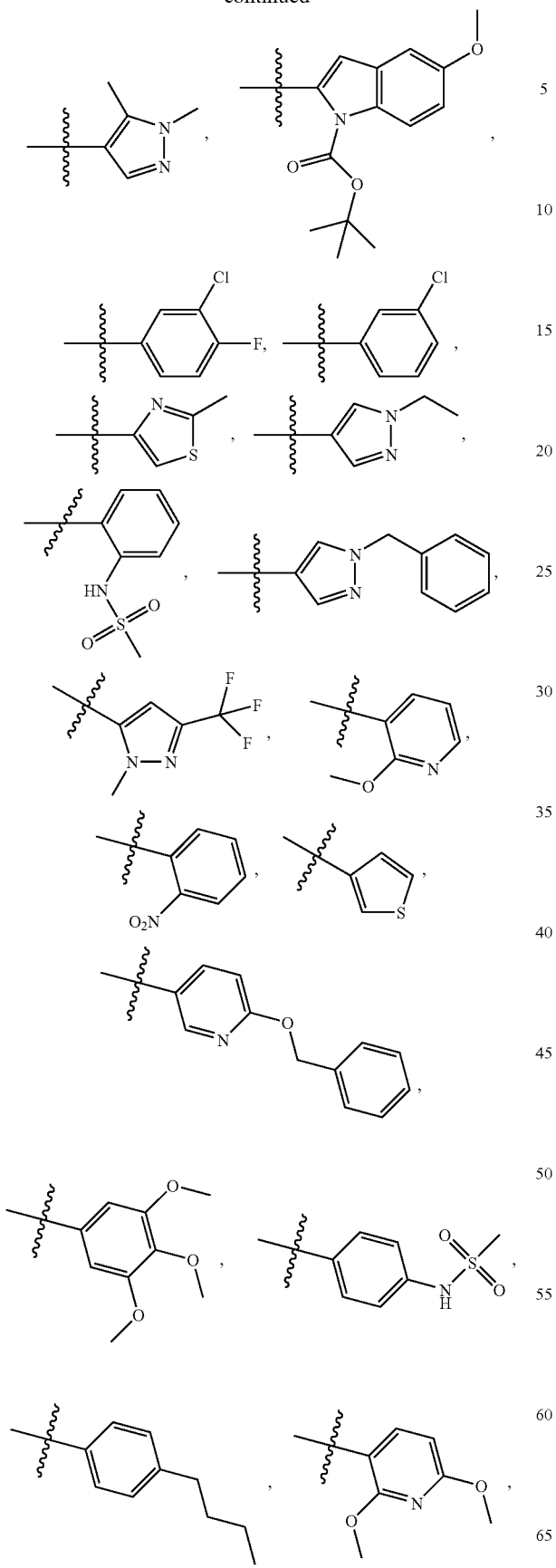
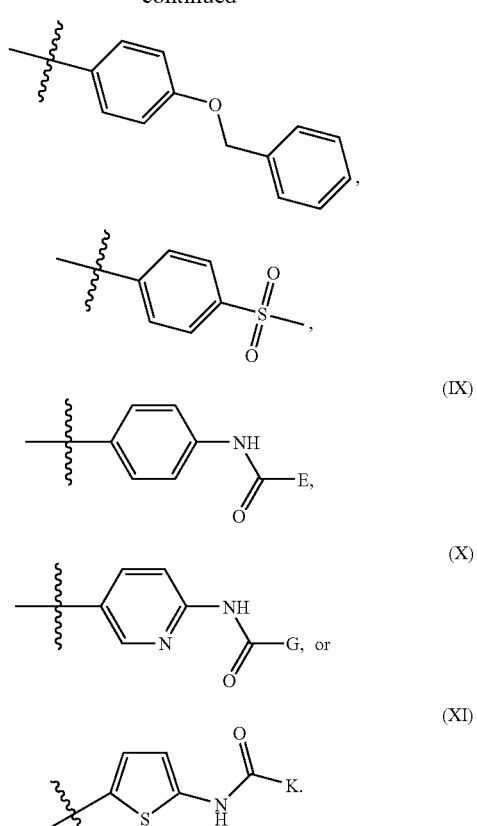
In certain embodiments, E of Formula IX is:
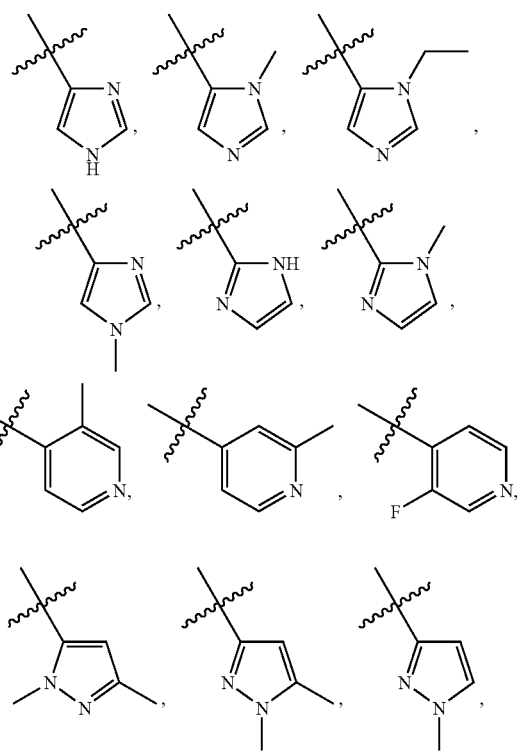

-continued
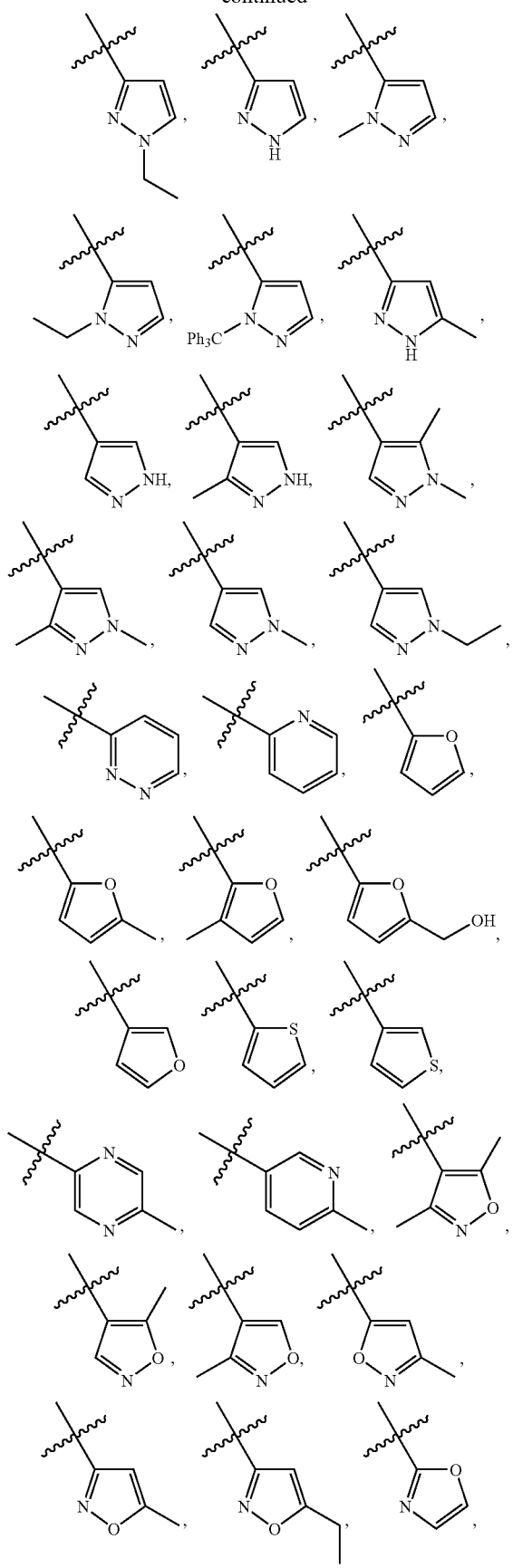
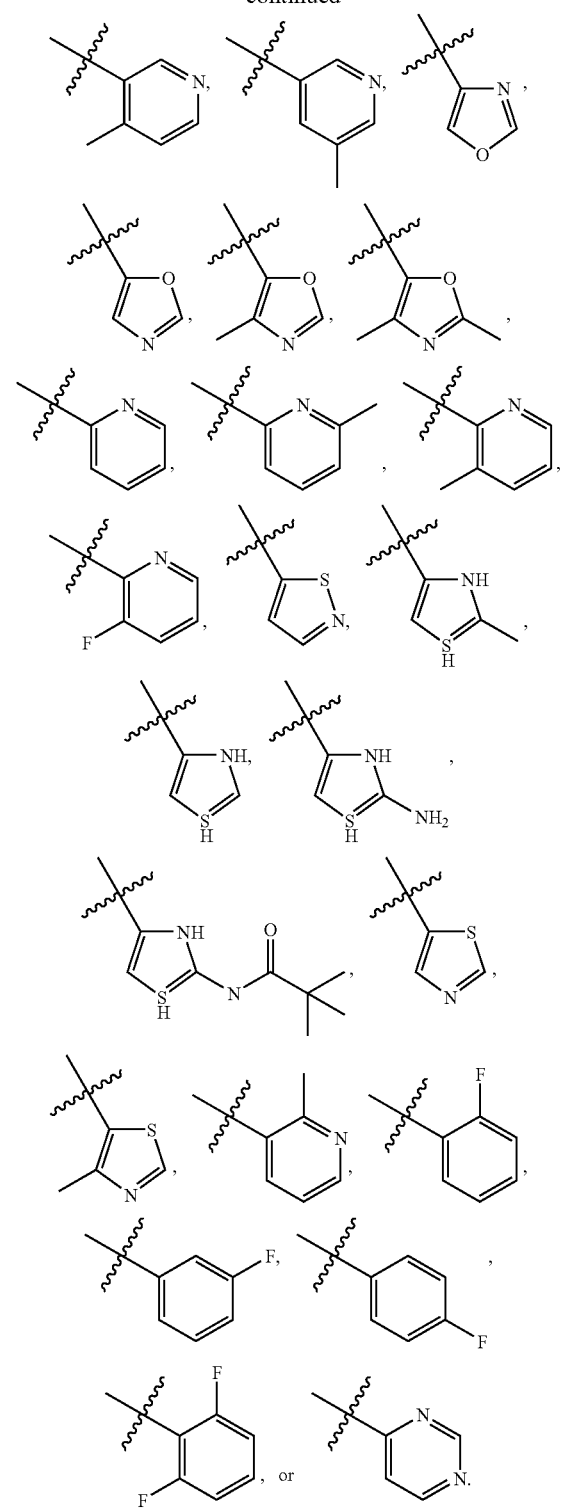
In some embodiments, G of Formula X is:
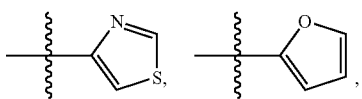

-continued

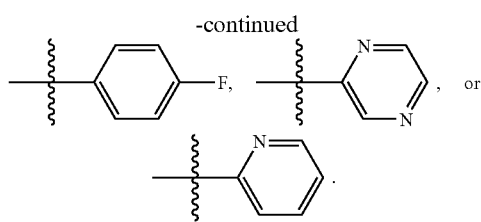

In some embodiments, K of Formula XI is:

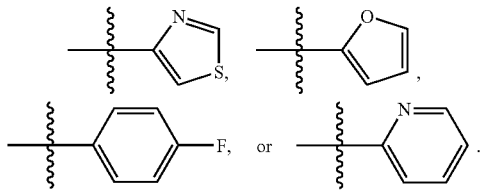

In certain embodiments, $R^6$ of Formula I, IA, IB, IIA, IIIA, IVA, VA, VIA, VIIA, IIB, IIIB, VB, VIB or VIIB is H or alkyl. In further embodiments, $R^6$ of Formula IIA, VIA, VIIA, IIB, VIB, or VIIB is methyl or ethyl.

In certain embodiments, $R^{16}$ of Formula I, IA, IB, IIA, IIIA, VA, VIA, IIB, IIIB, VB or VIB is H, alkyl, heterocyclyl, or cycloalkyl, wherein each alkyl, heterocyclyl, or cycloalkyl is optionally substituted. In some embodiments, $R^{16}$ of Formula IIIA, VIA, IIIB or VIB is methyl, ethyl, isopropyl, tert-butyl or oxanyl. In further embodiments, $R^{16}$ of IIIA, VIA, IIIB or VIB is:

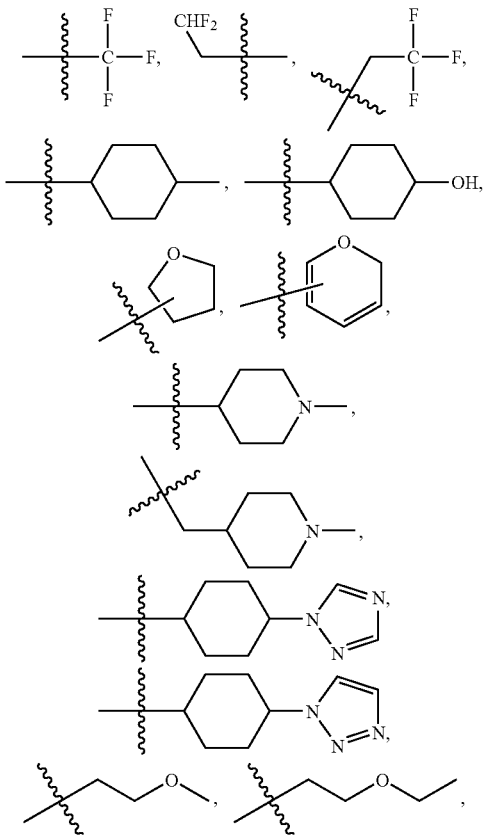

-continued

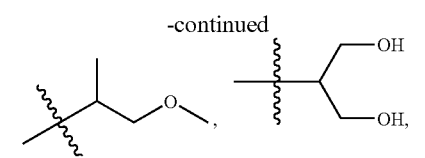

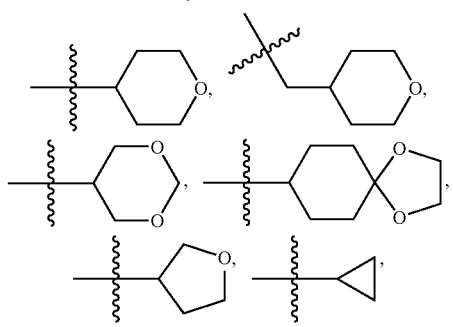

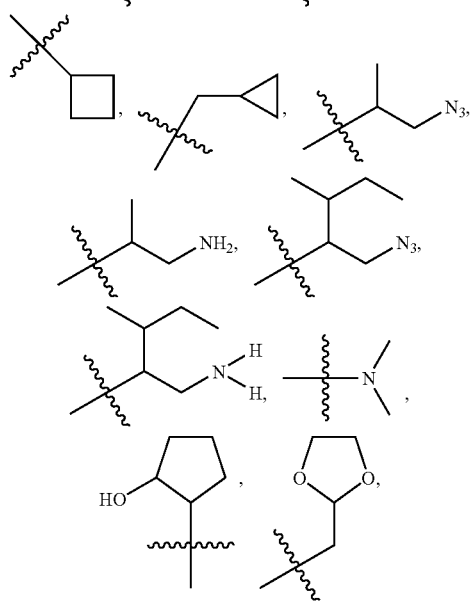

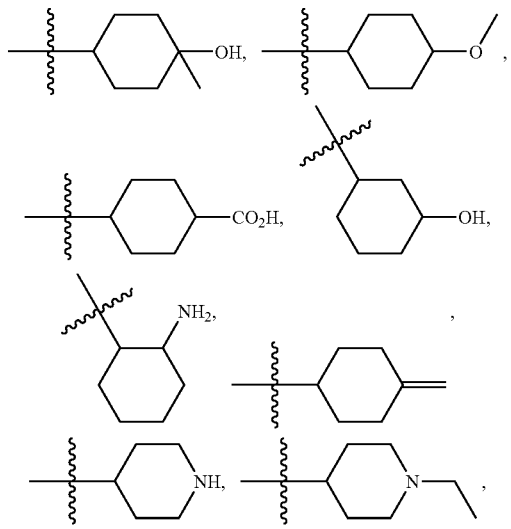

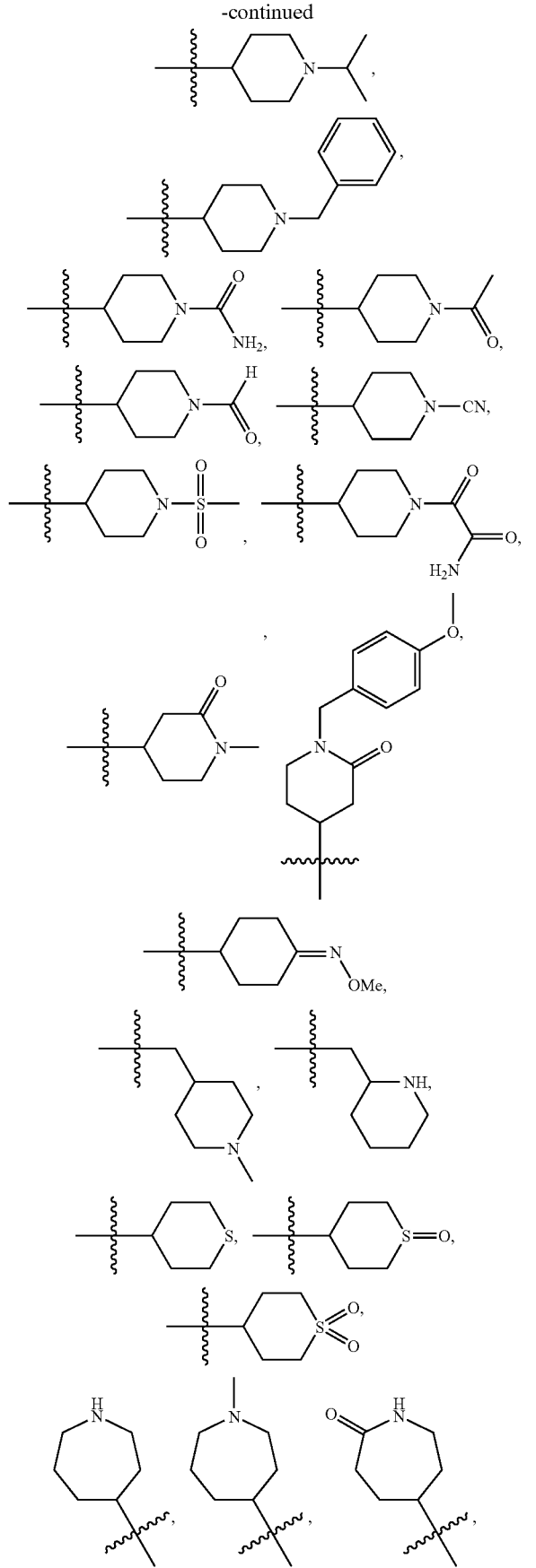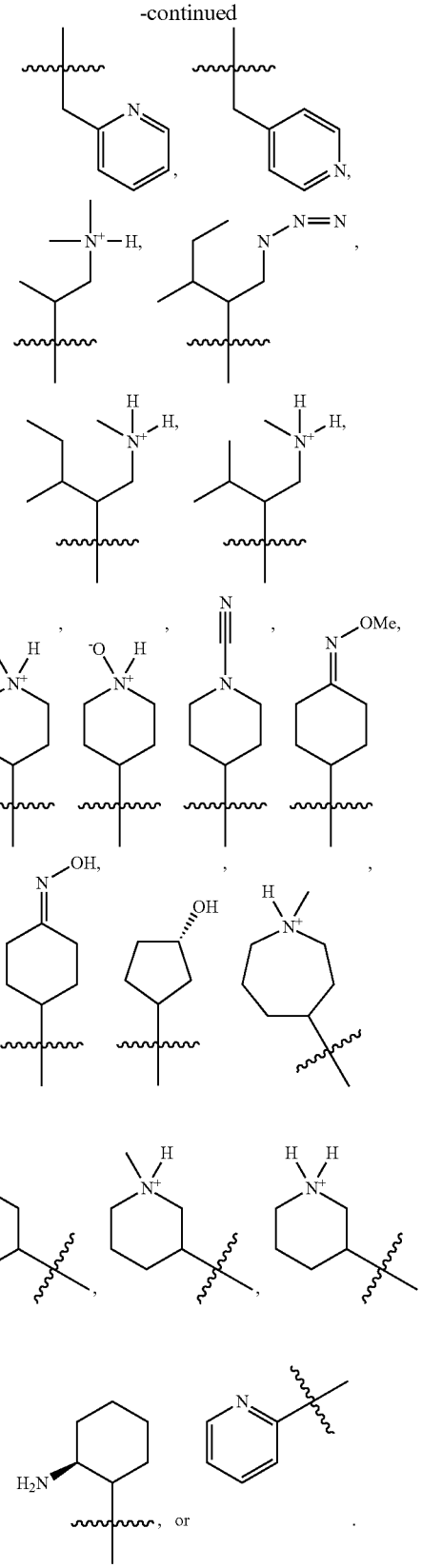
In certain embodiments, L of Formula I, IA, IIA, IIIA, VA, VIA, IB, IIB, IIIB, VB, VIB or XX is $NR^{16}$, O or methylene wherein $R^{16}$ is as defined herein.

In some embodiments, provided herein are compounds 1-201:
(1)
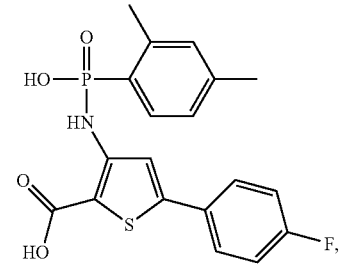
(2)
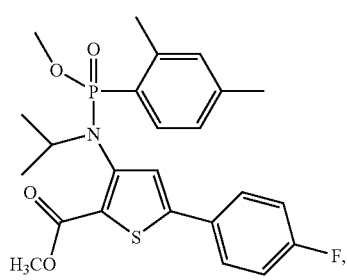
(3)
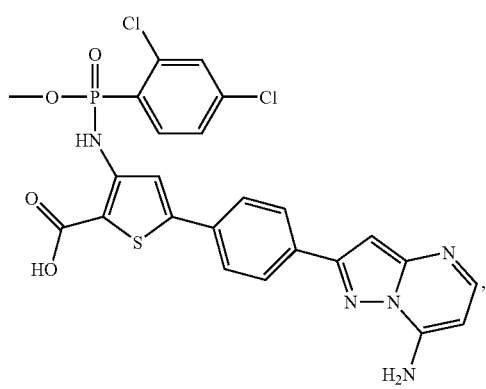
(4)
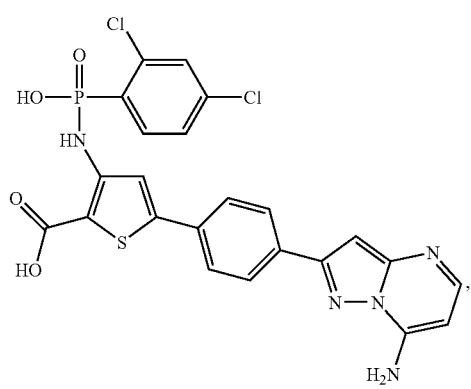
(5)
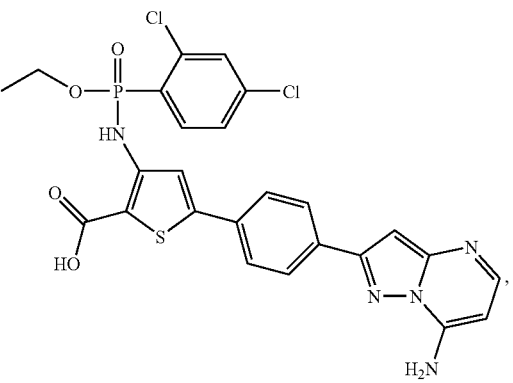
(6)
(7)
(8)
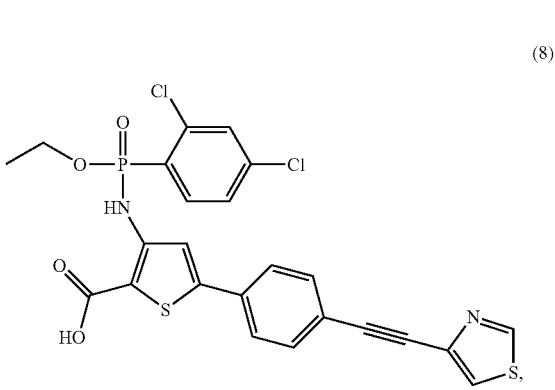

(9)
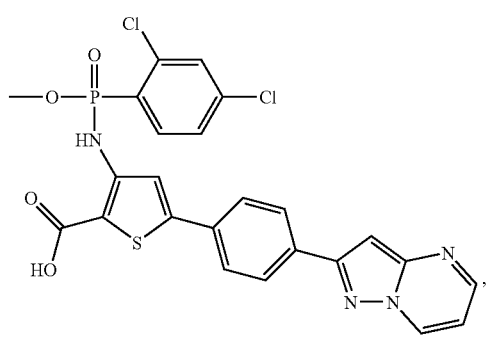
(10)
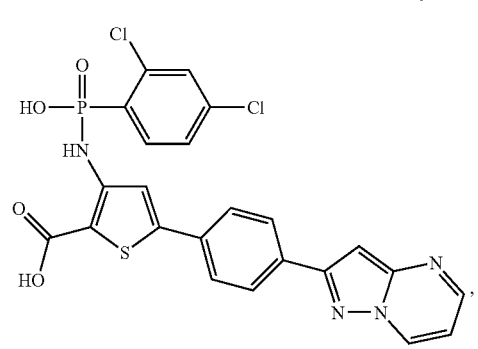
(11)
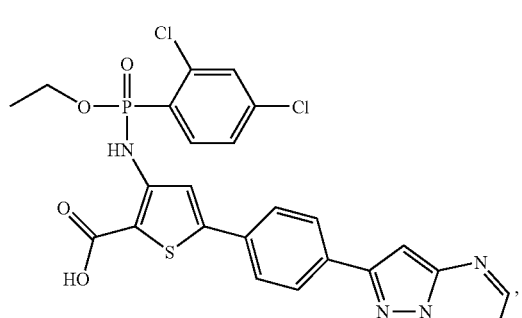
(12)
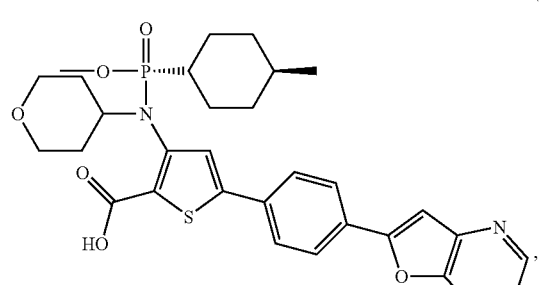
(13)
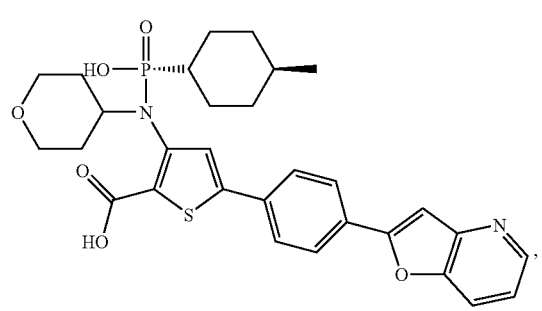
(14)
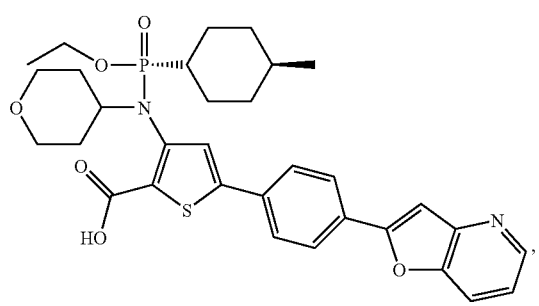
(15)
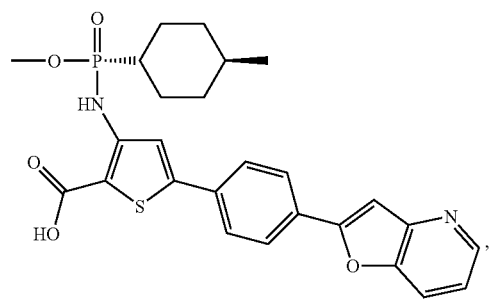
(16)
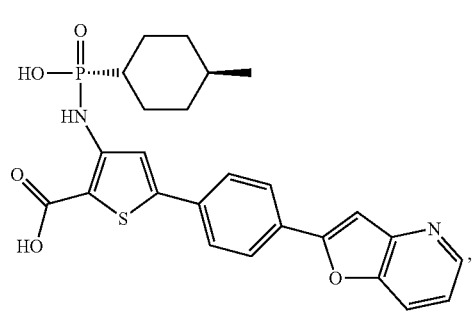
(17)
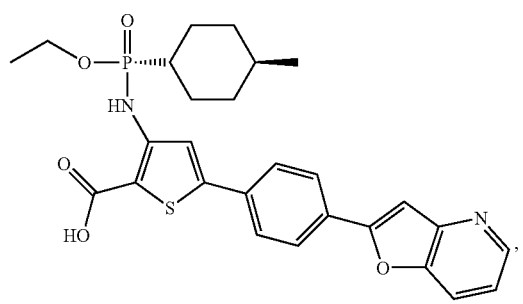
(18)
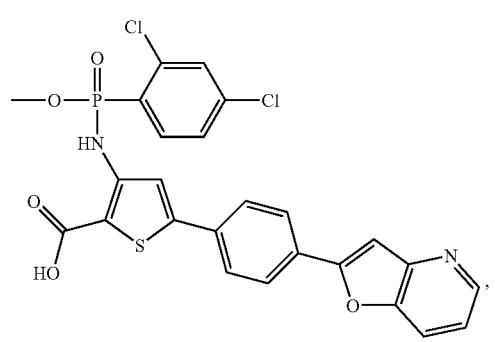

-continued
(19)
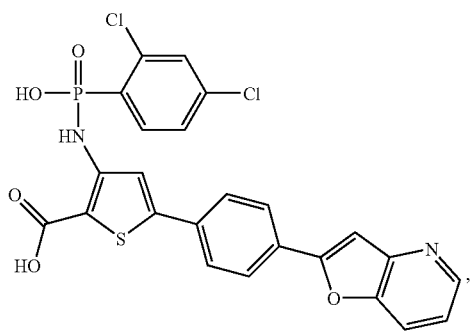
(20)
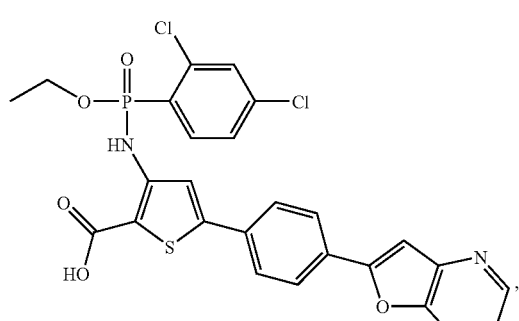
(21)
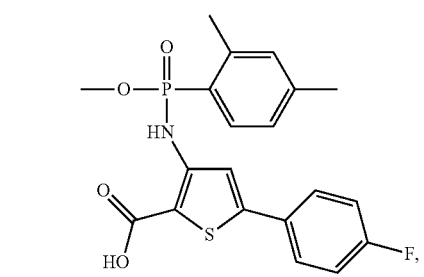
(22)
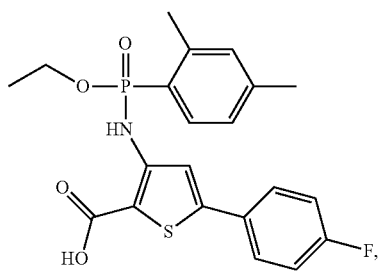
(23)
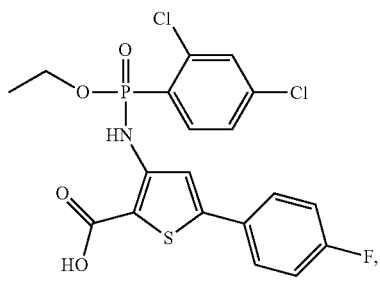
-continued
(24)
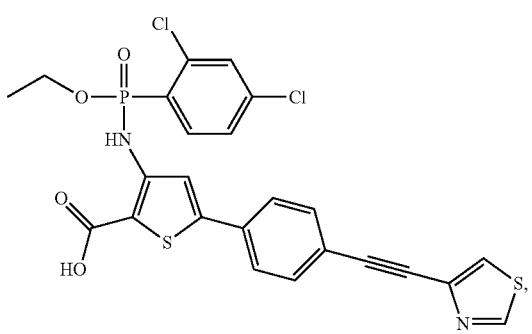
(25)
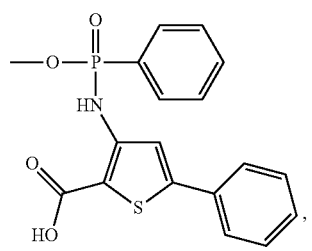
(26)
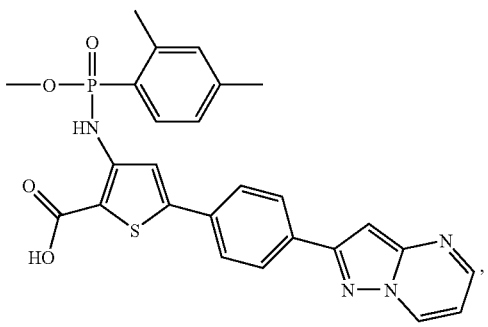
(27)
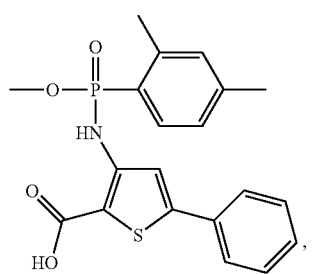
(28)
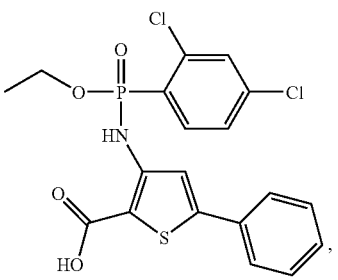

-continued
(29)
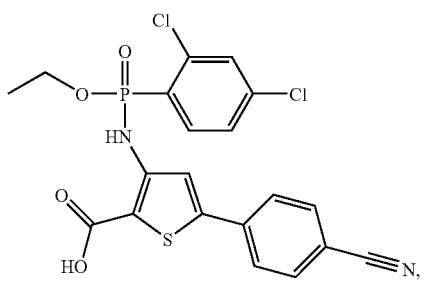
(30)
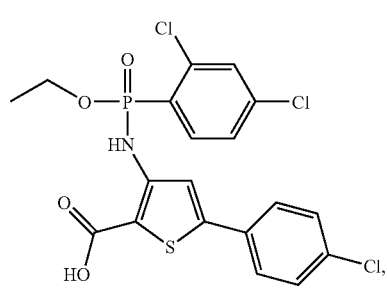
(31)
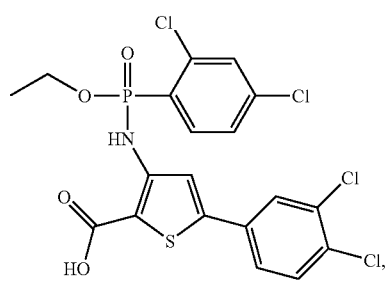
(32)
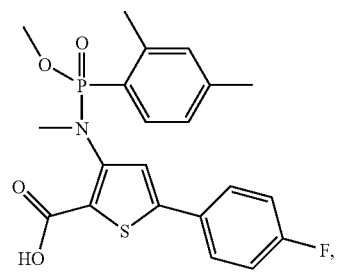
(33)
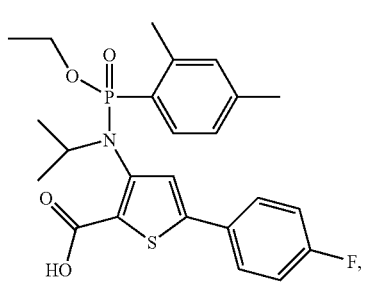
-continued
(34)
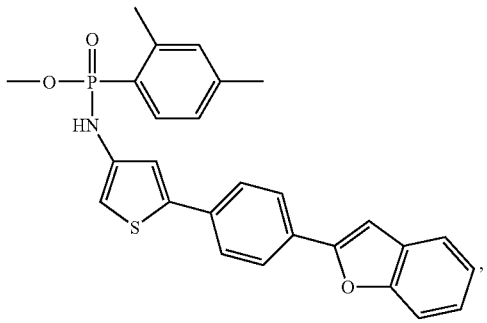
(35)
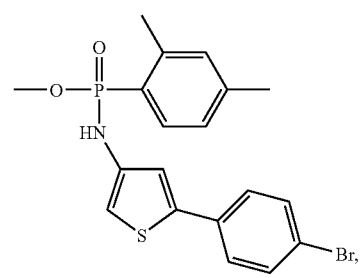
(36)
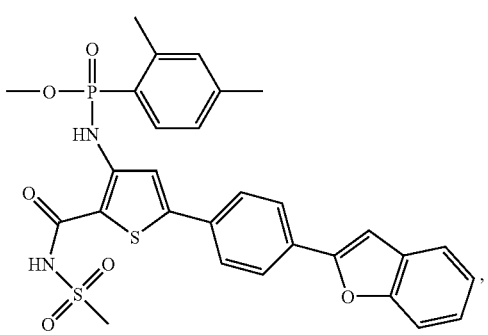
(37)
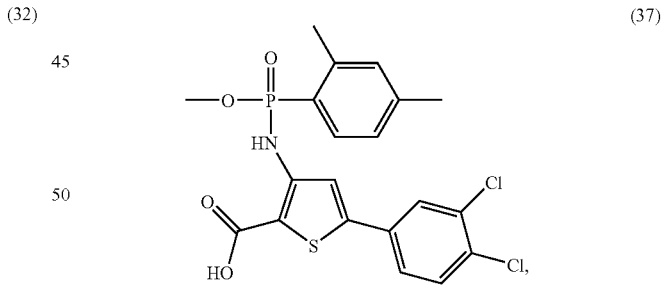
(38)
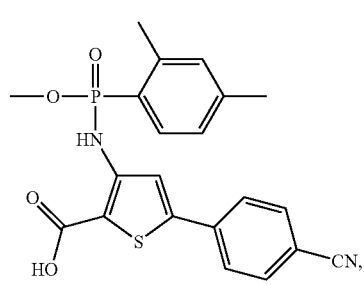

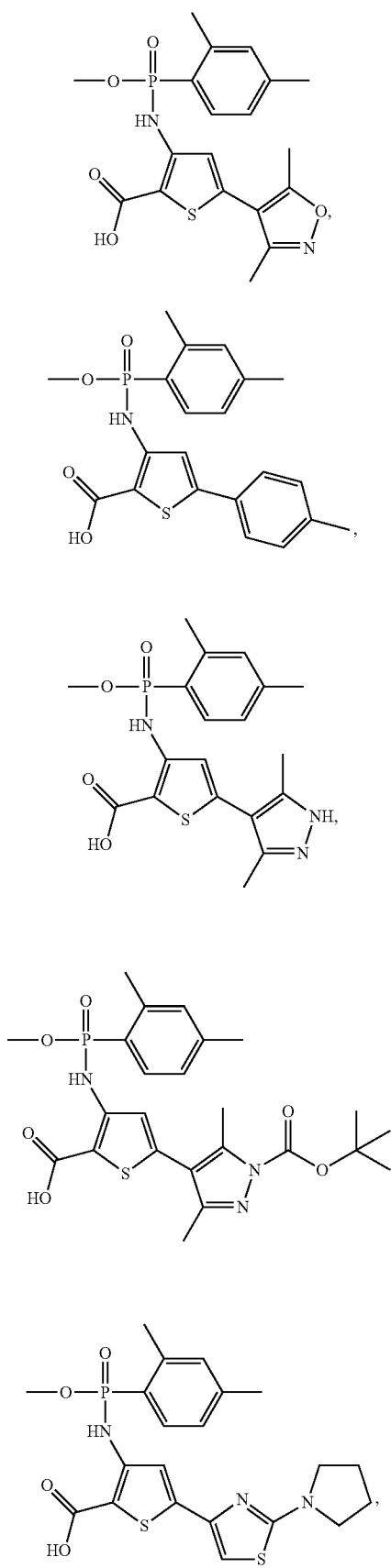
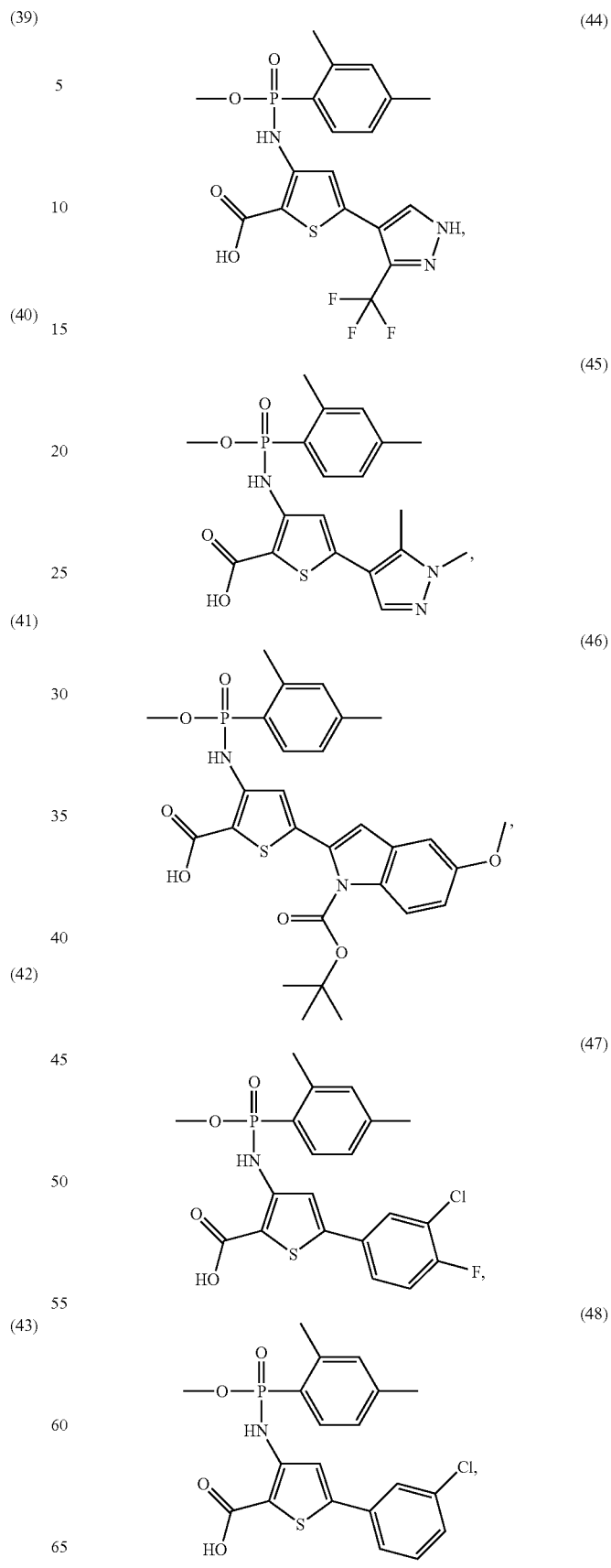

(49)
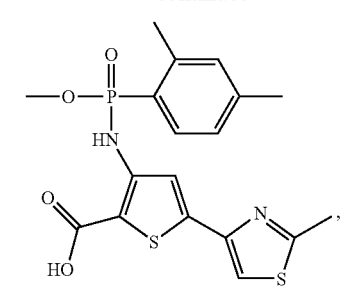
(50)
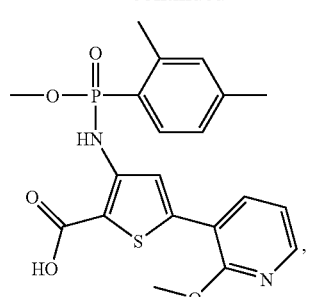
(51)
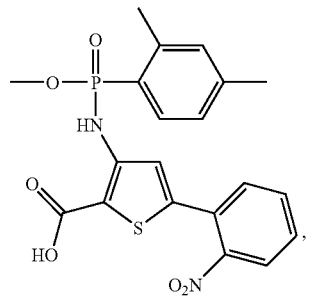
(52)
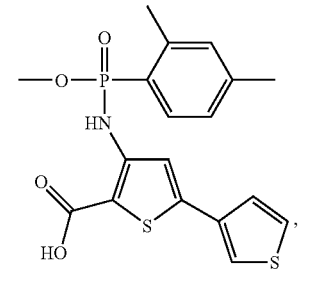
(53)
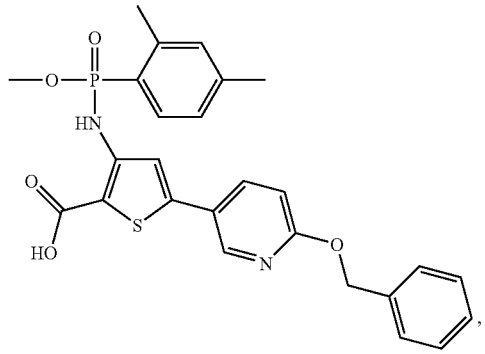
(54)
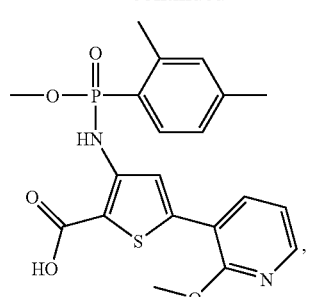
(55)
(56)
(57)
(58)

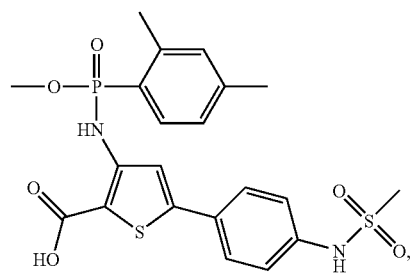
(59)
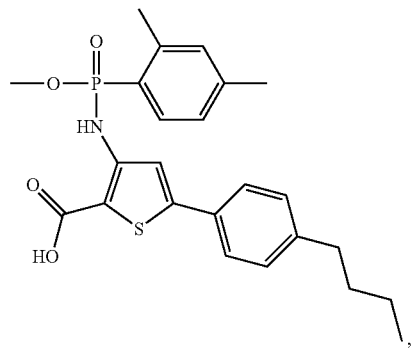
(60)
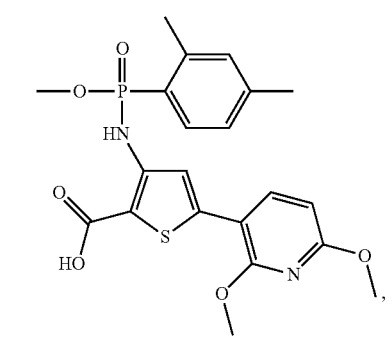
(61)
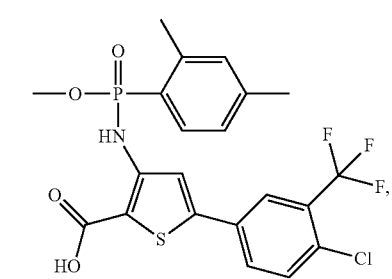
(62)
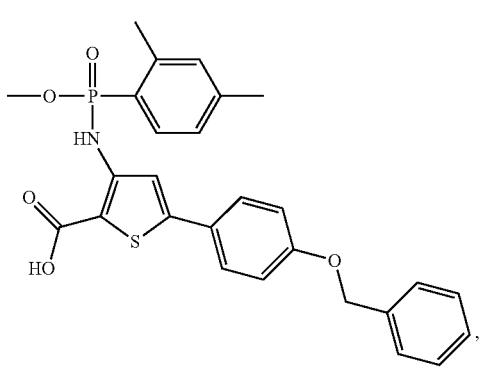
(63)
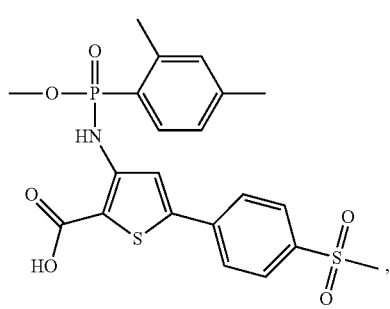
(64)
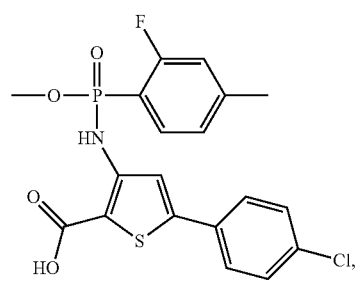
(65)
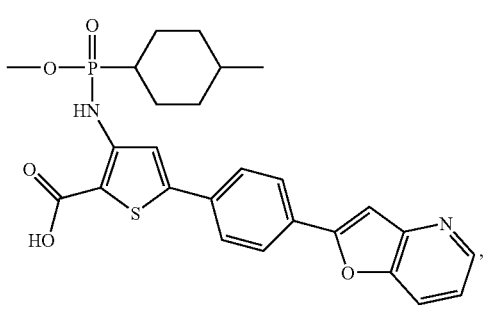
(66)
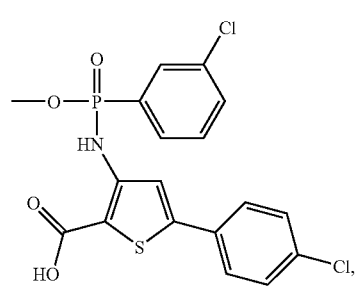
(67)
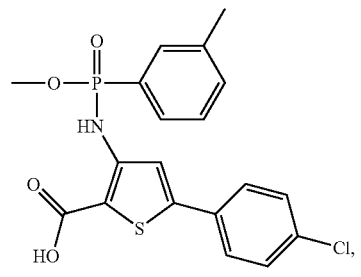
(68)

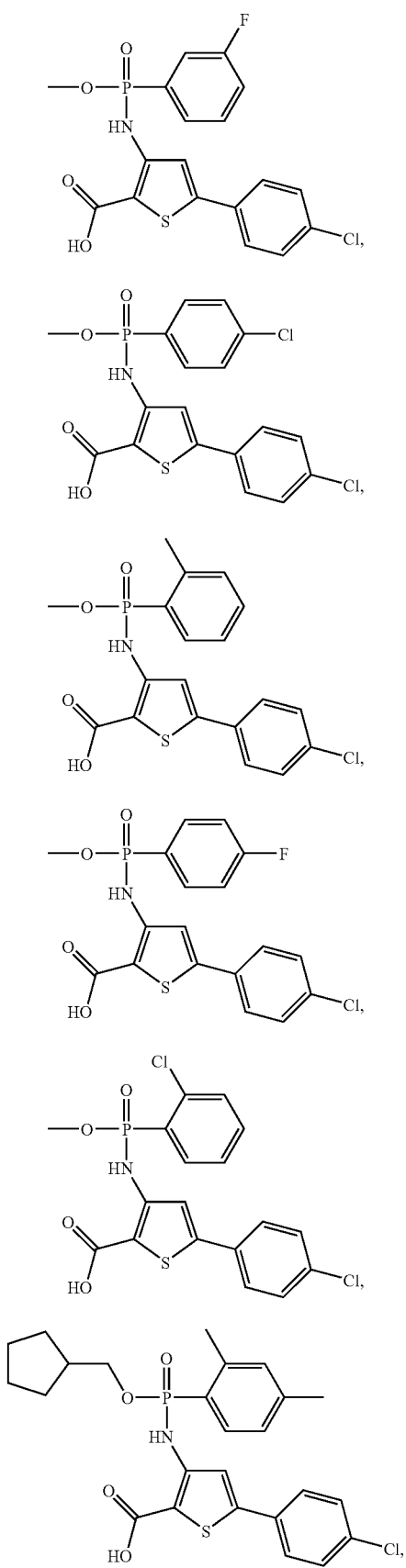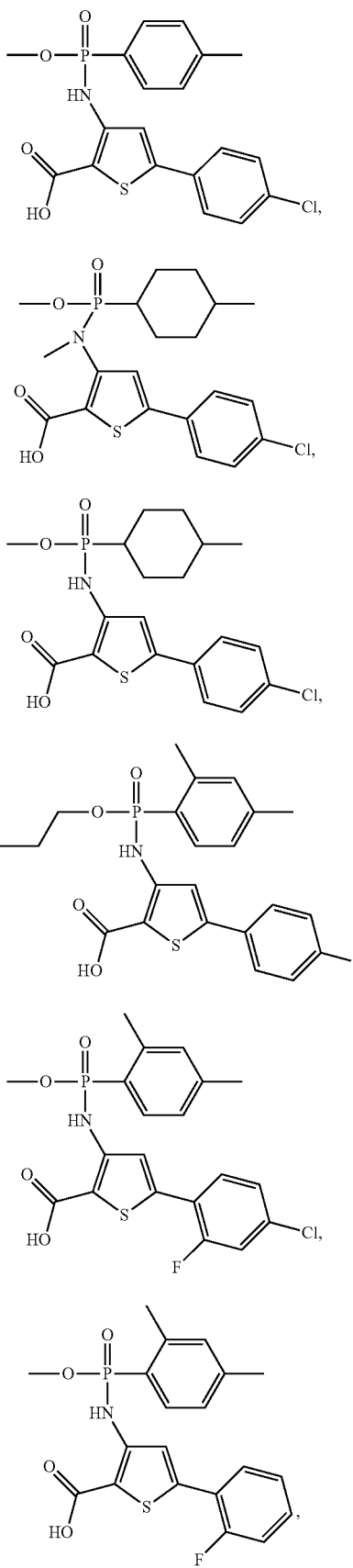

(81)
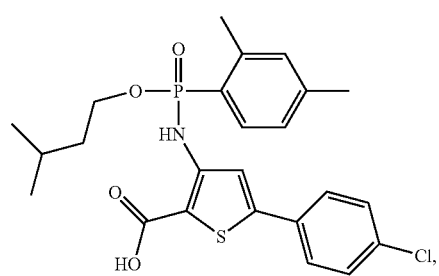
(82)
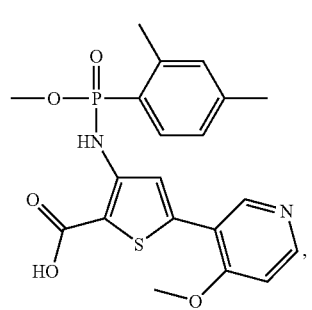
(83)
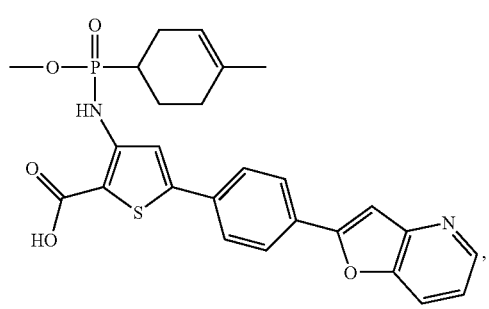
(84)
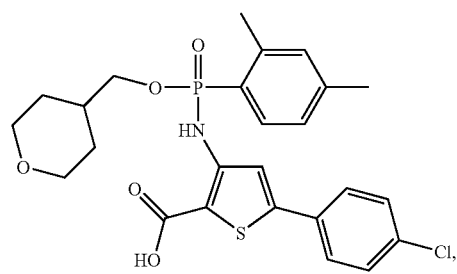
(85)
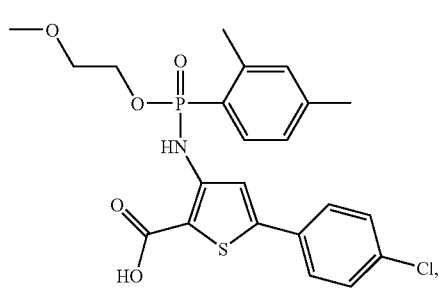
(86)
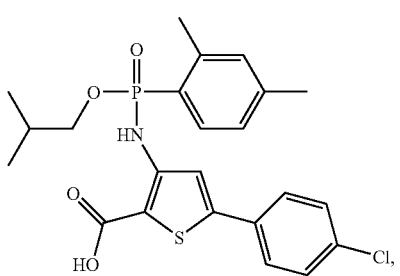
(87)
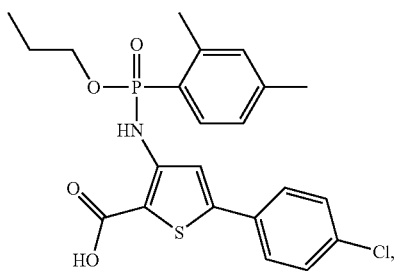
(88)
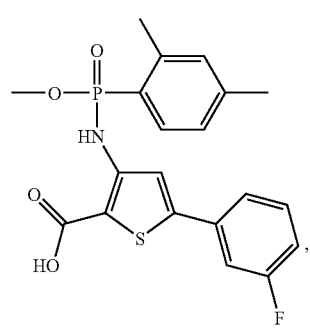
(89)
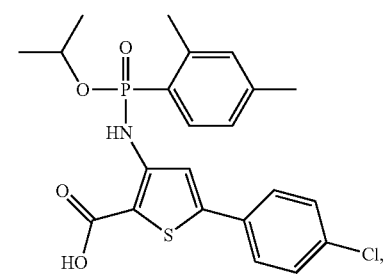
(90)
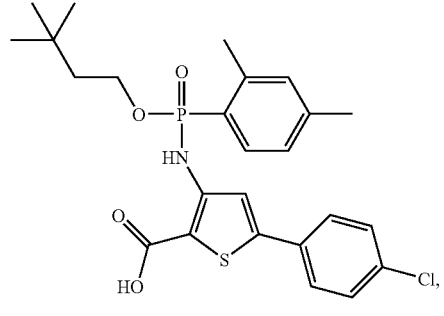

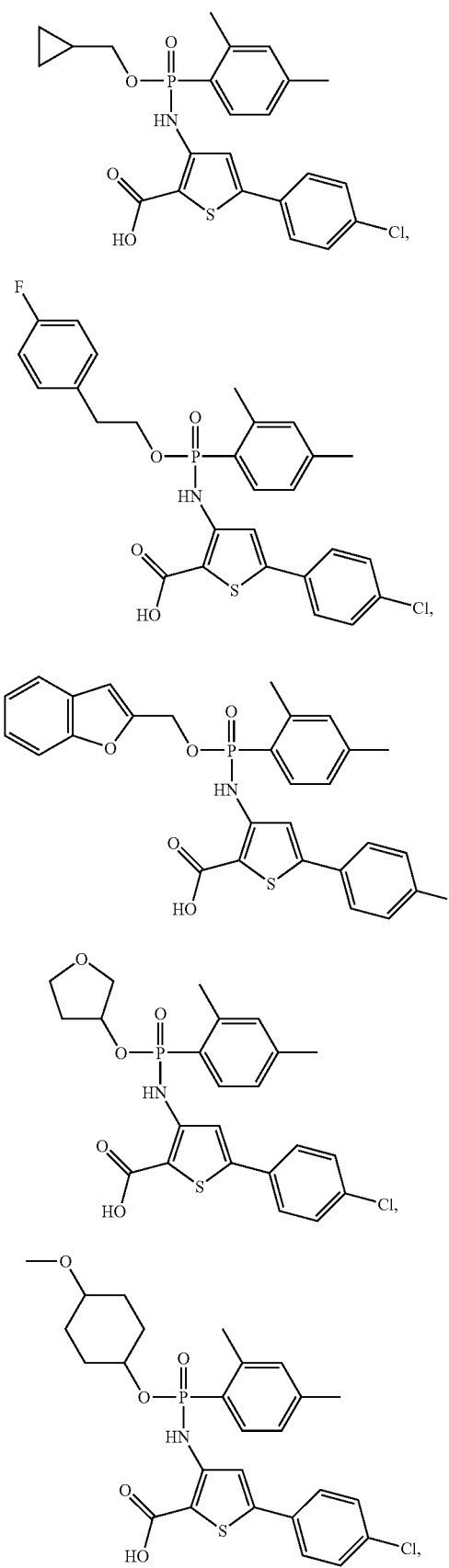
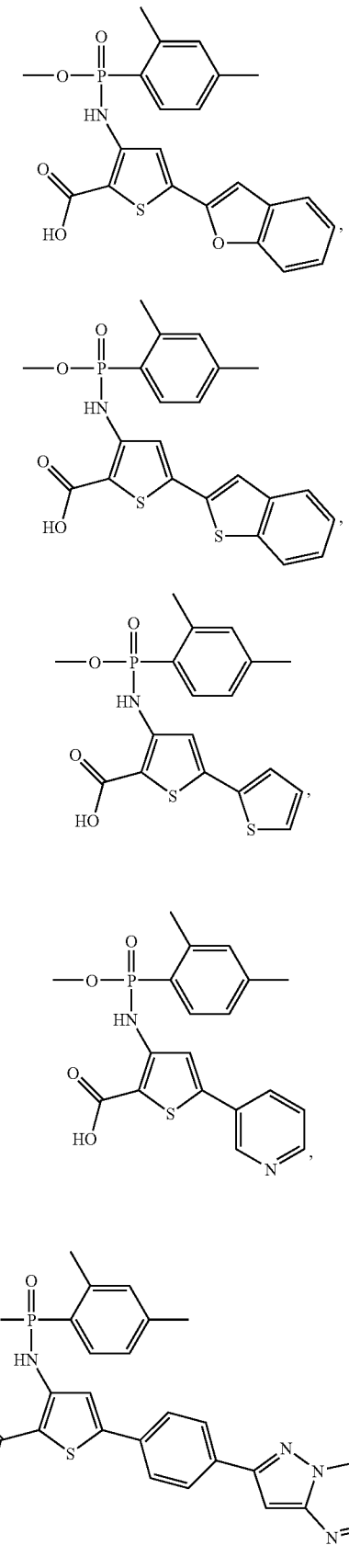

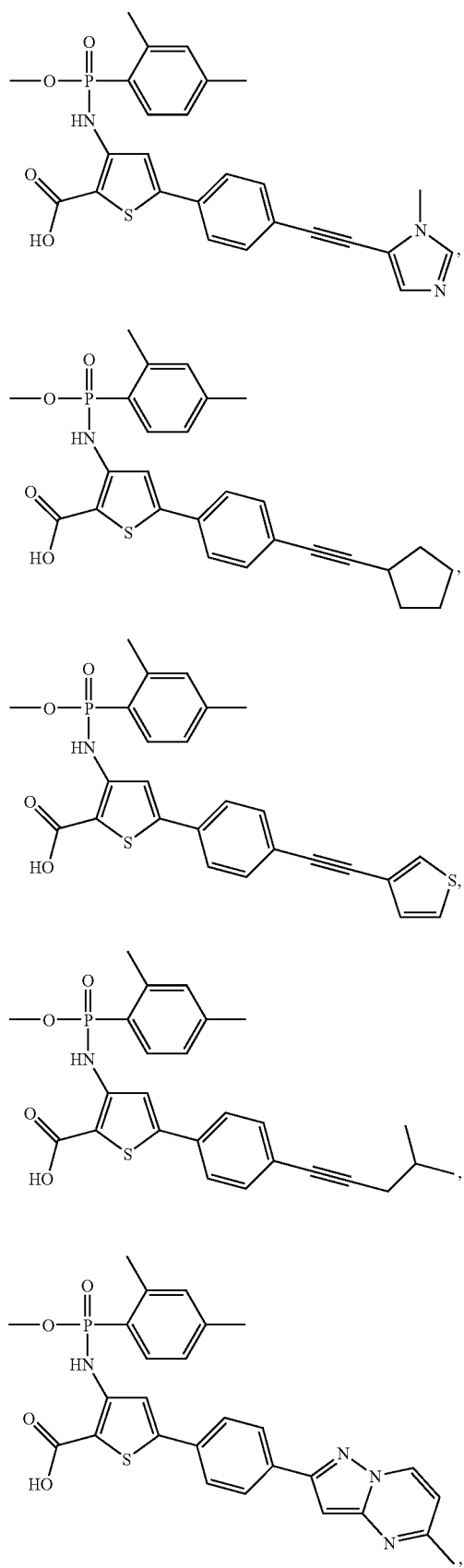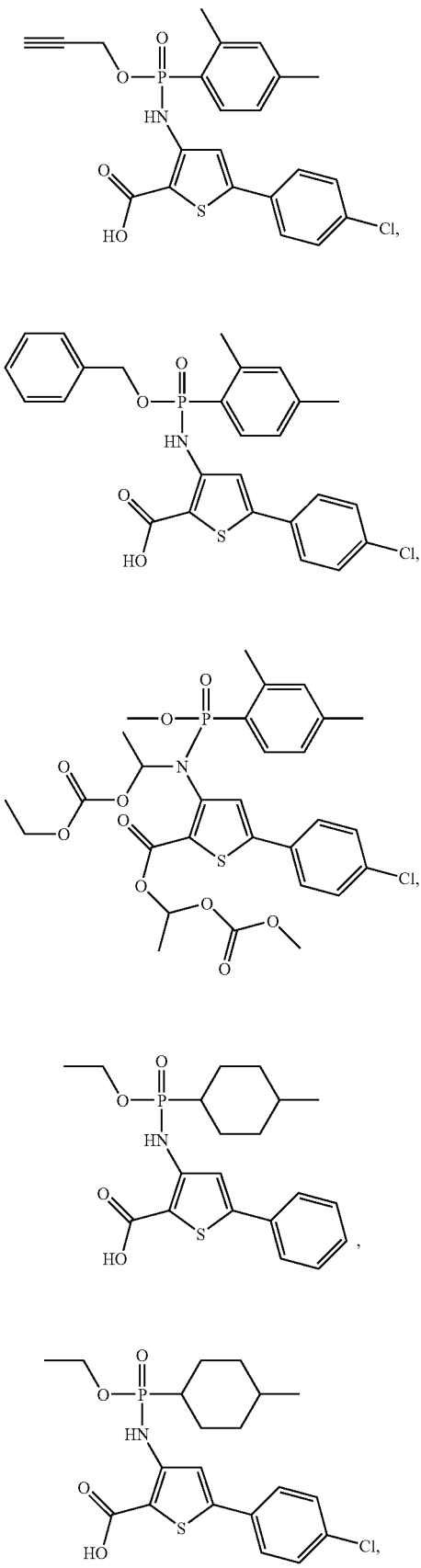

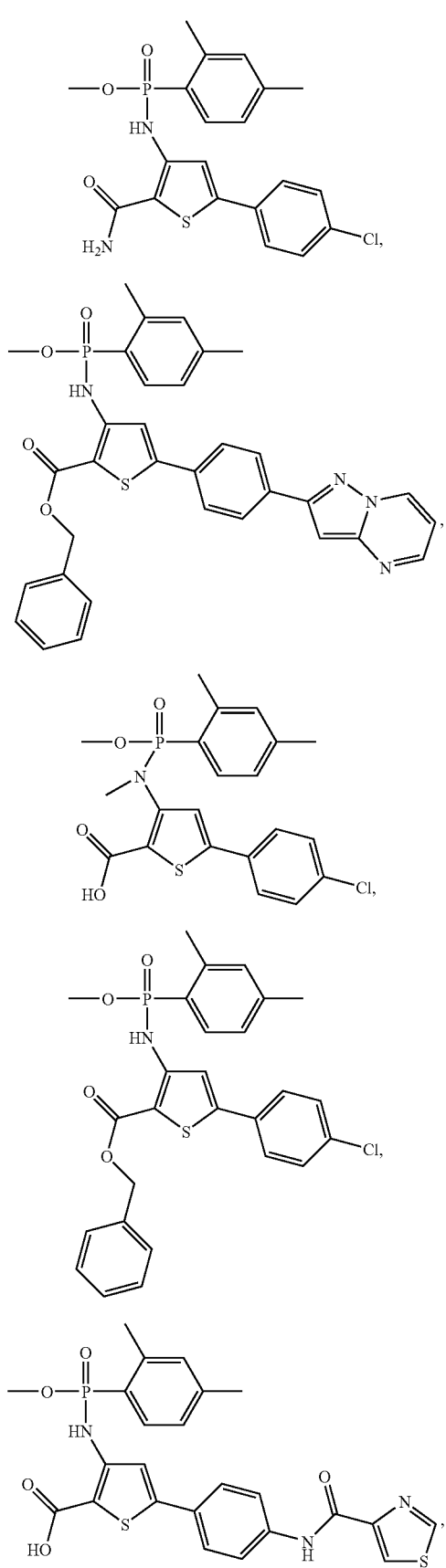
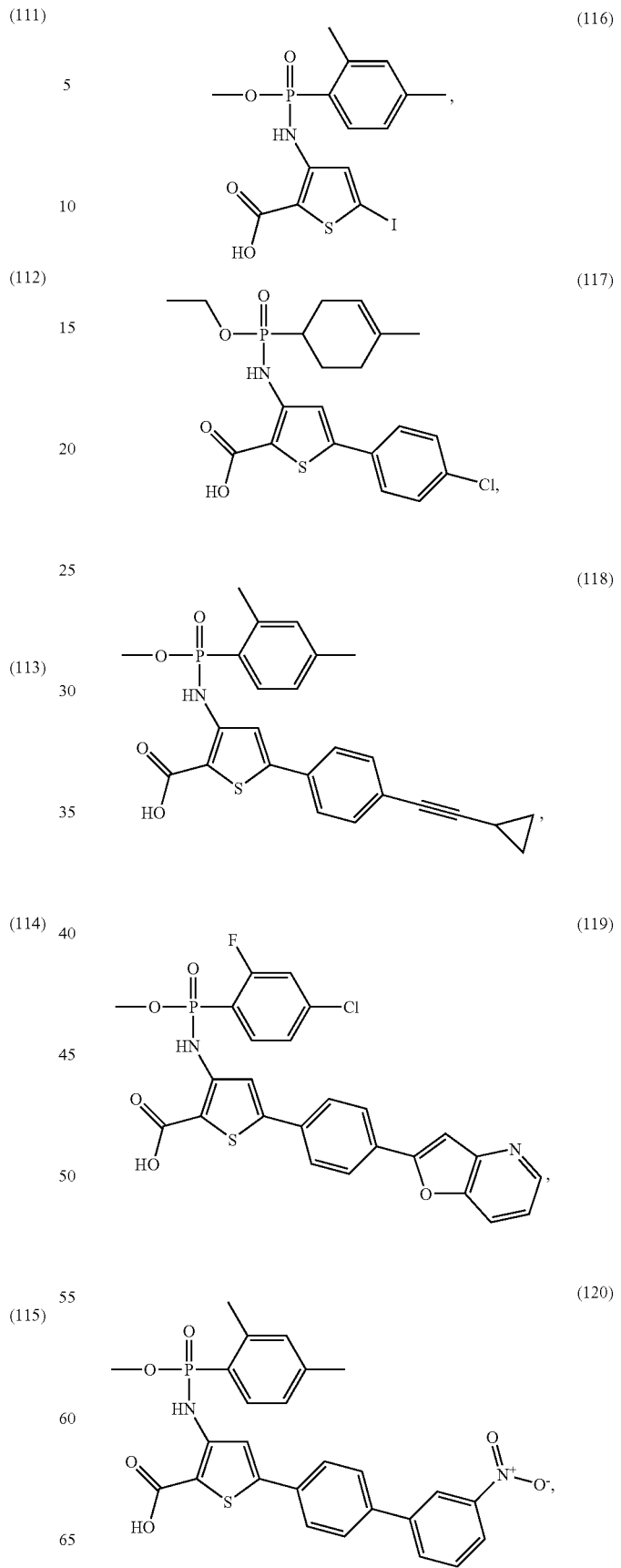

(121)
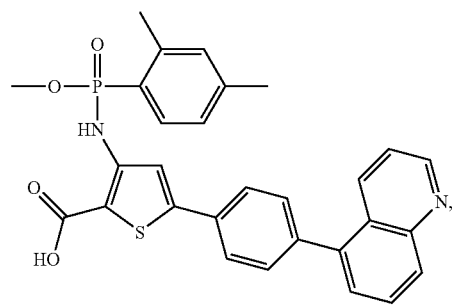
(122)
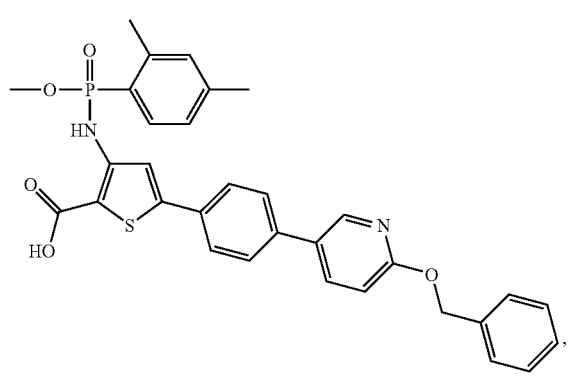
(123)
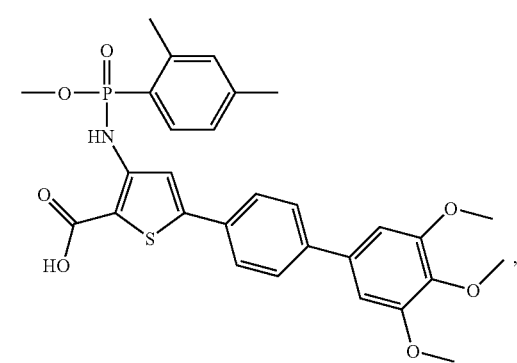
(124)
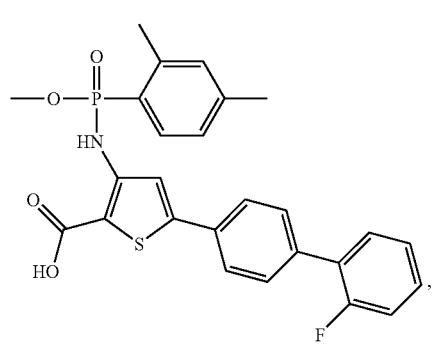
(125)
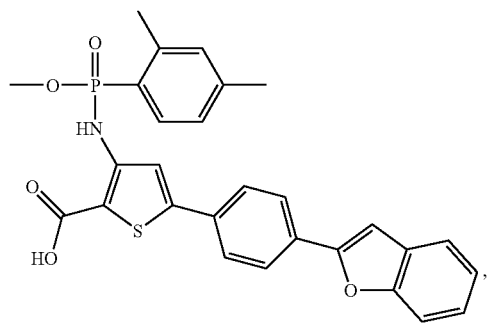
(126)
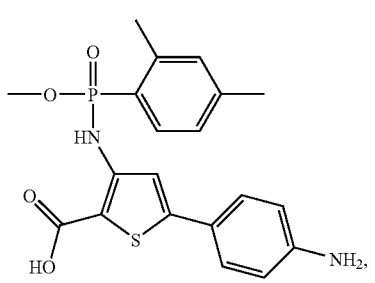
(127)
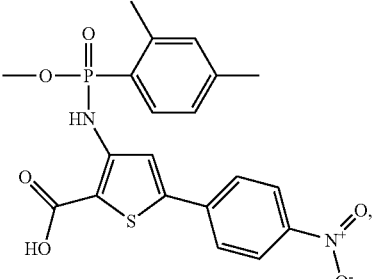
(128)
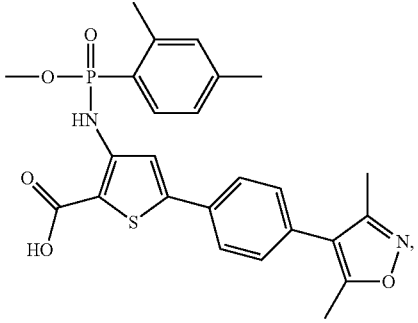
(129)
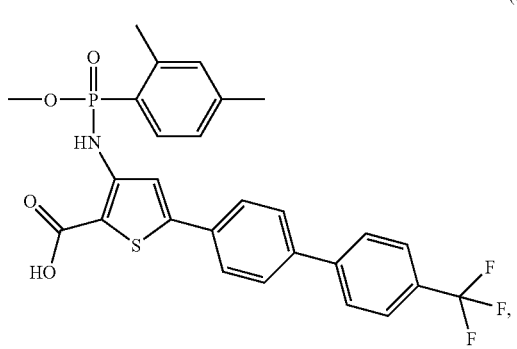

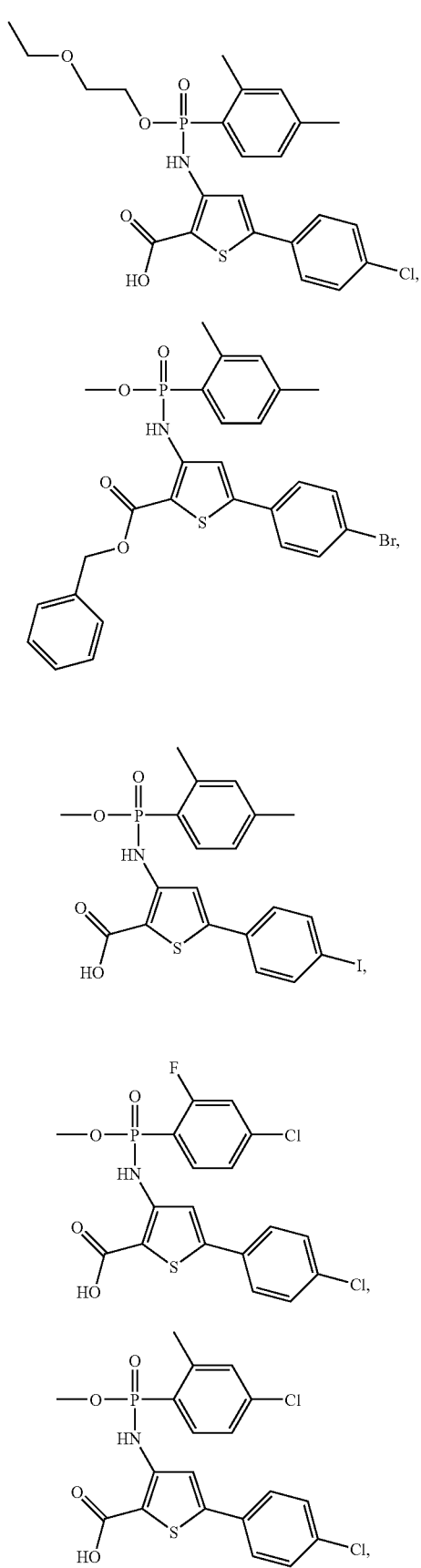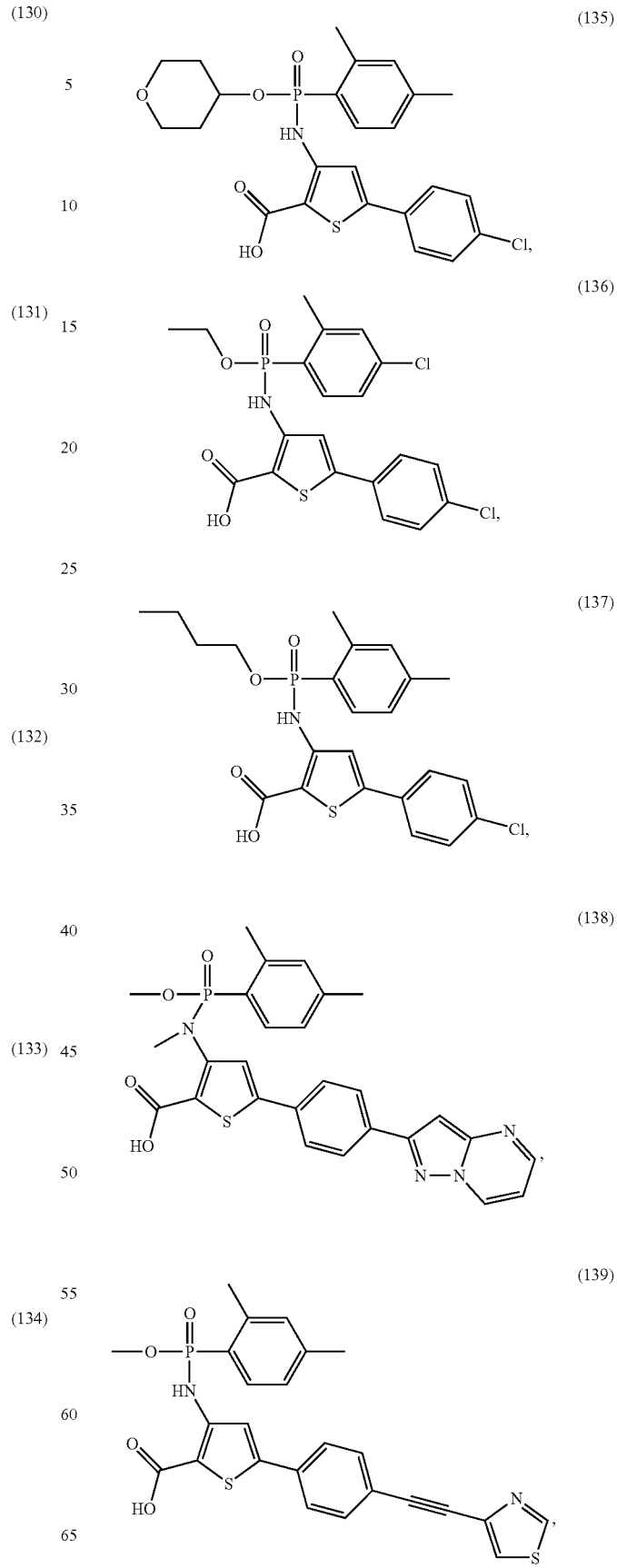

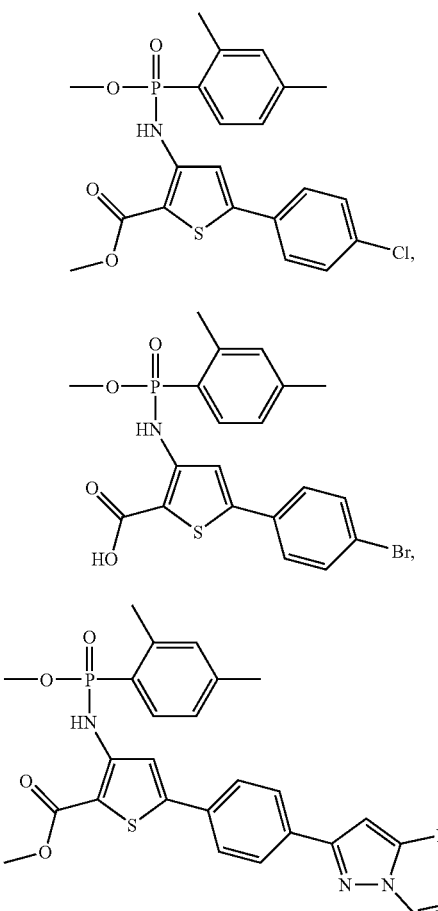
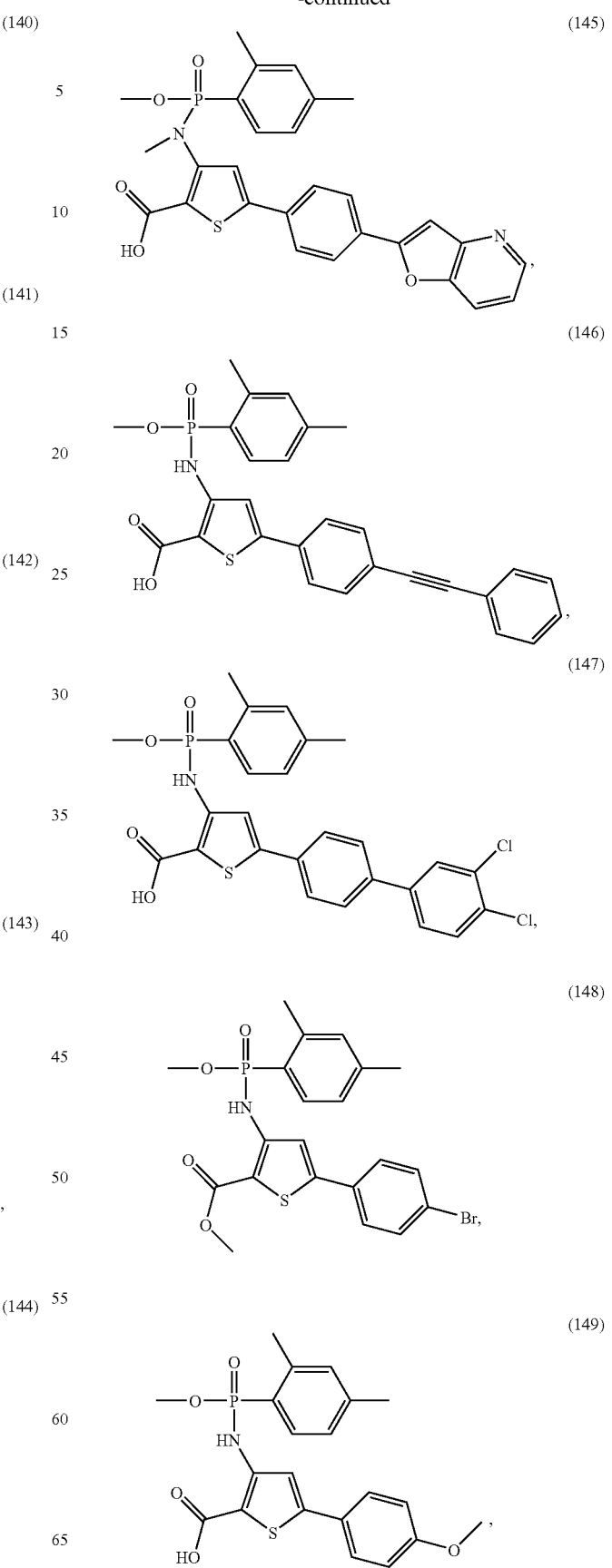

(150)
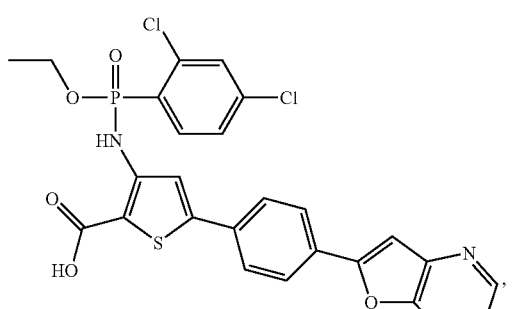
(151)
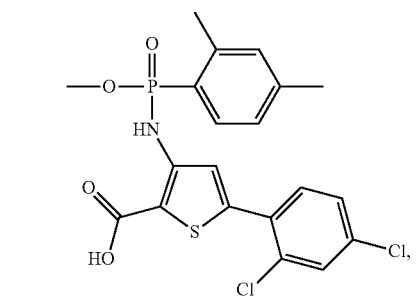
(152)
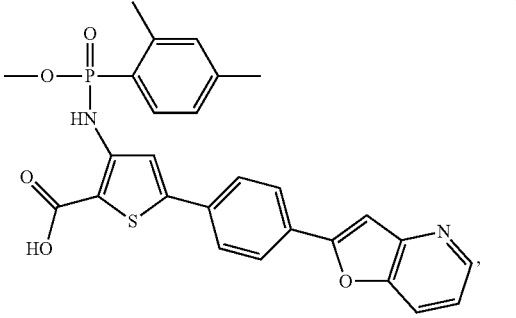
(153)
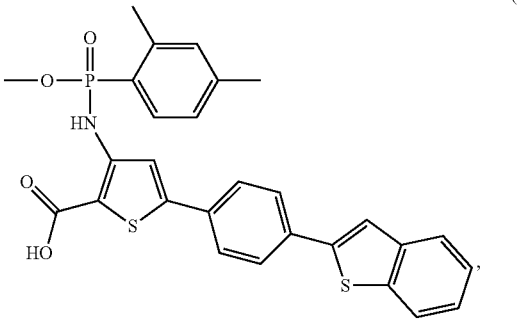
(154)
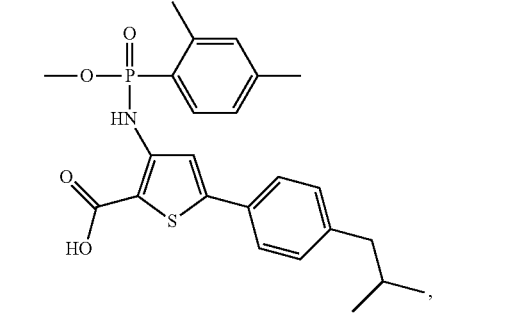
(155)
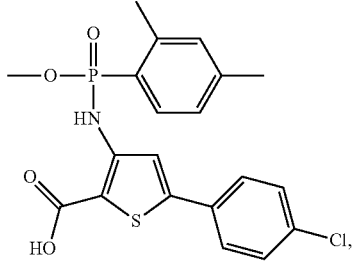
(156)
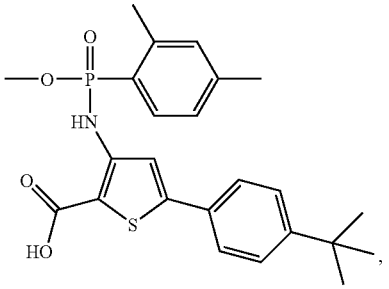
(157)
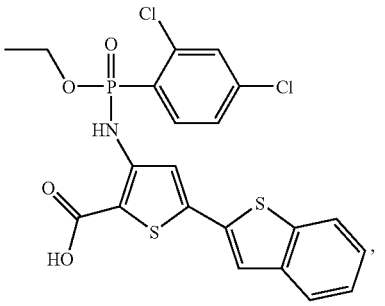
(158)
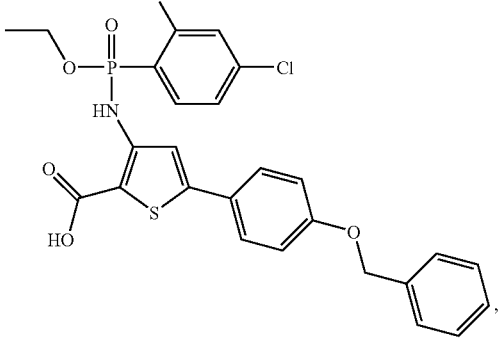
(159)
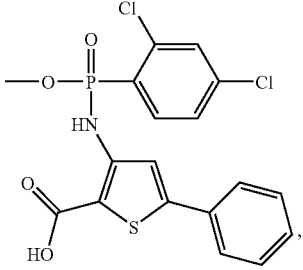

(160)
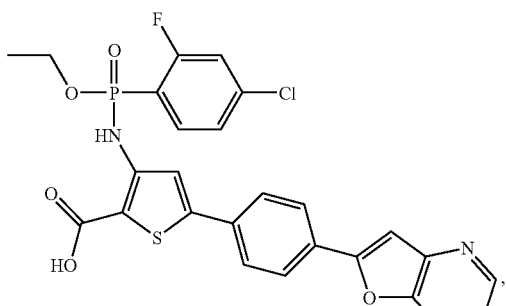
(161)
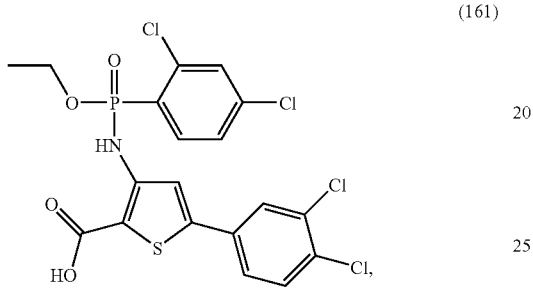
(162)
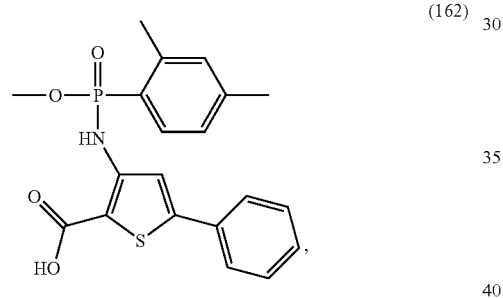
(163)
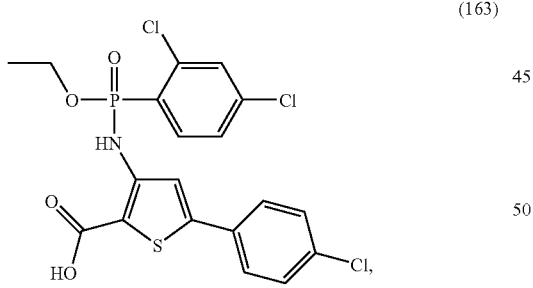
(164)
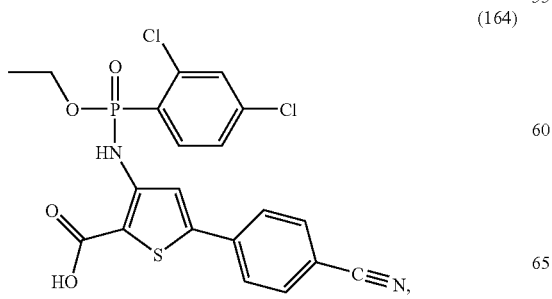
(165)
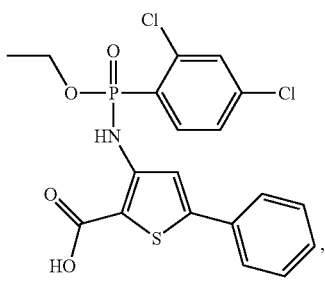
(166)
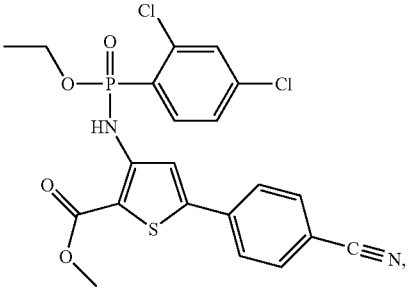
(167)
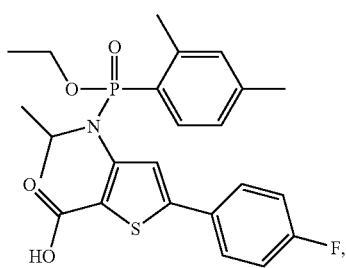
(168)
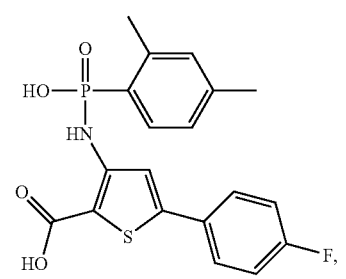
(169)
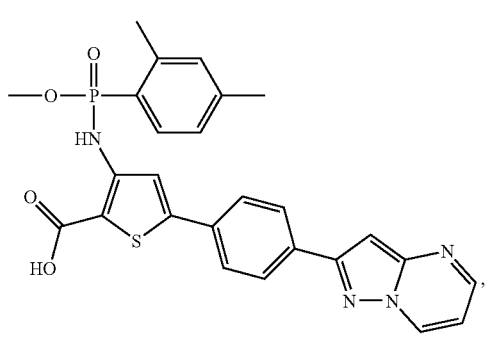

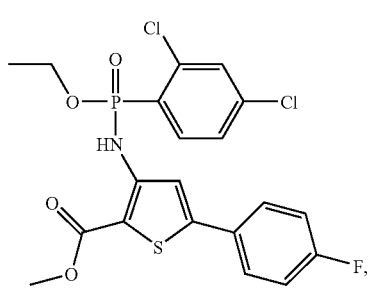
(170)
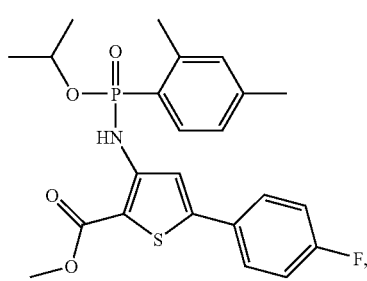
(171)
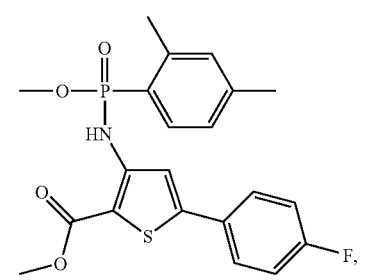
(172)
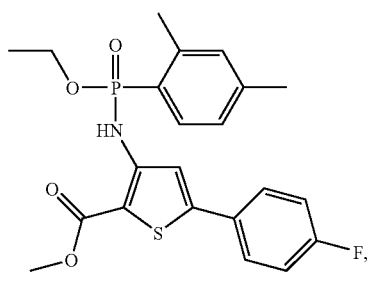
(173)
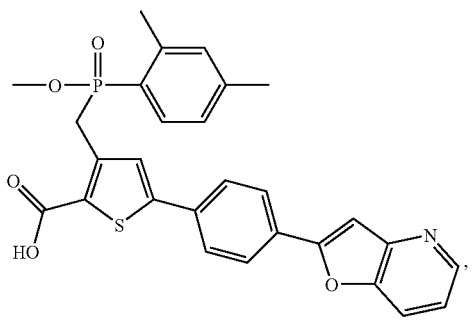
(174)
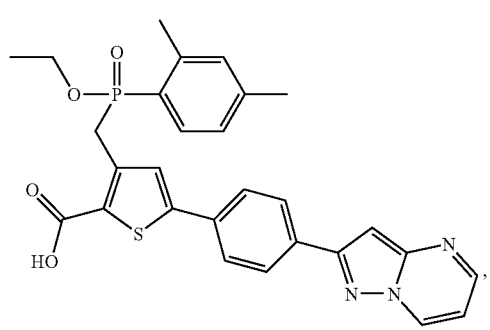
(175)

(176)
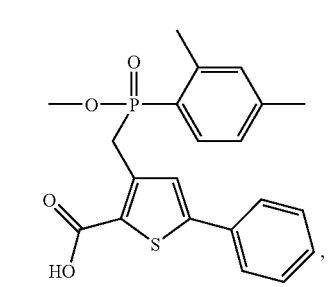
(177)
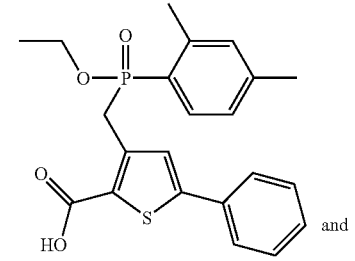
(178)
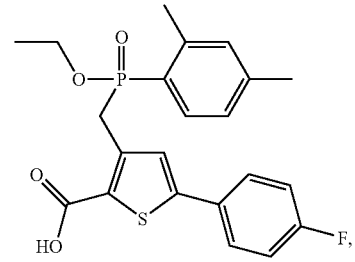
(179)

-continued
(180)
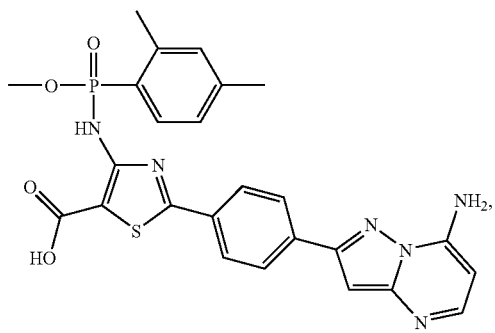
(181)
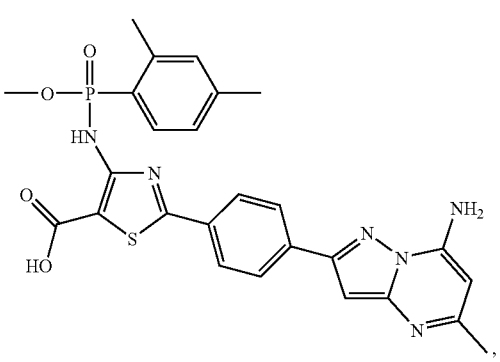
(182)
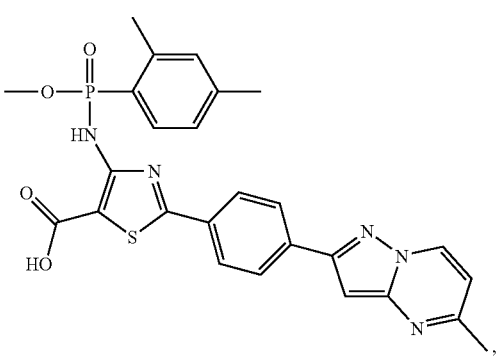
(183)
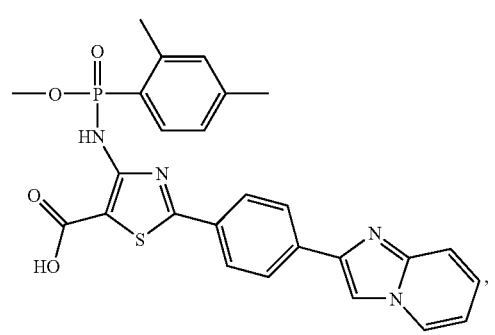
-continued
(184)
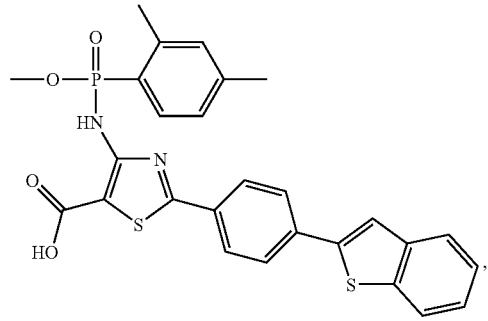
(185)
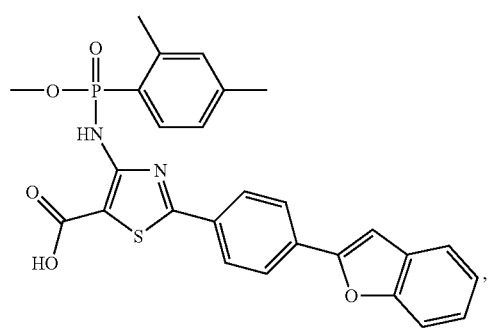
(186)
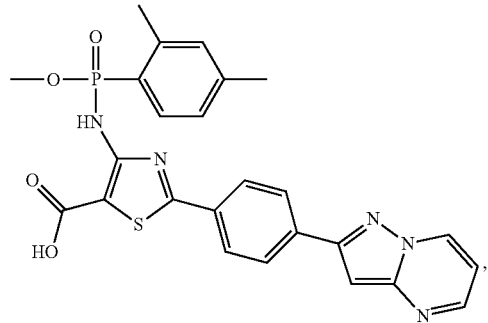
(187)
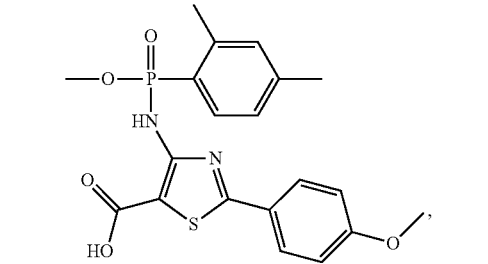
(188)
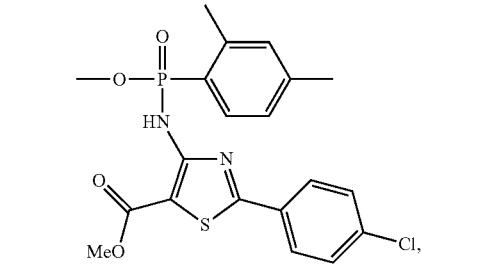

-continued
(189)
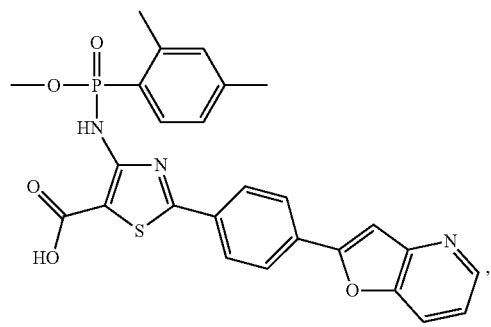
(190)
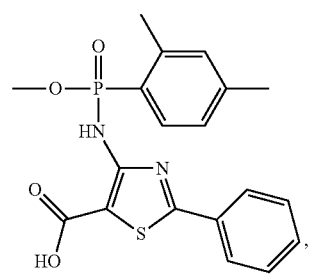
(191)
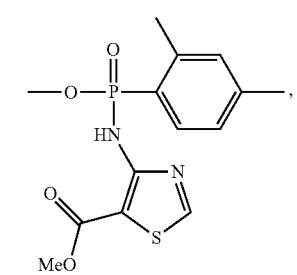
(192)
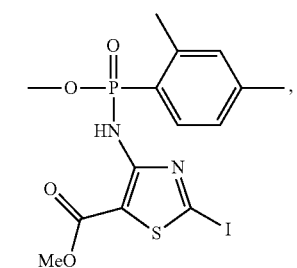
(193)
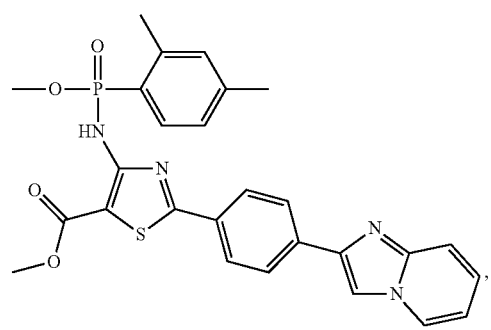
-continued
(194)
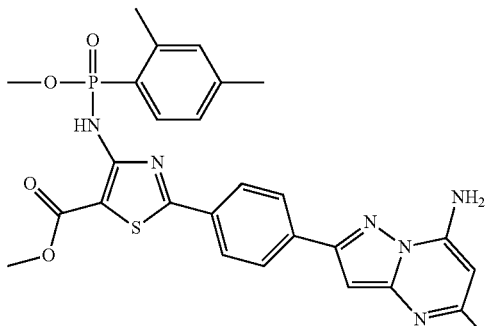
(195)
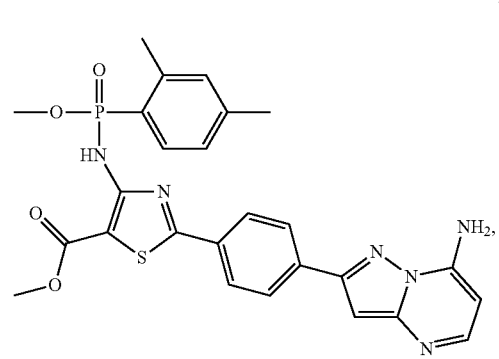
(196)
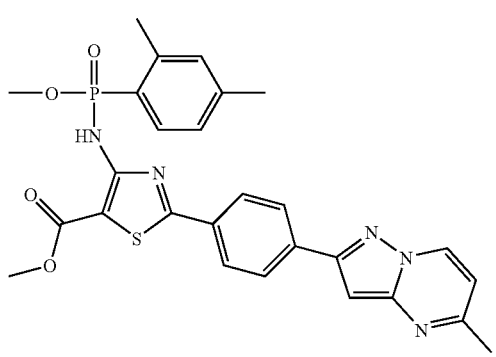
(197)
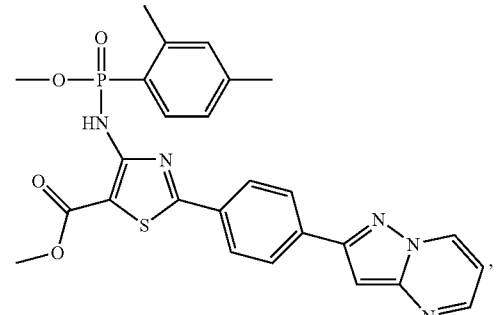
(198)
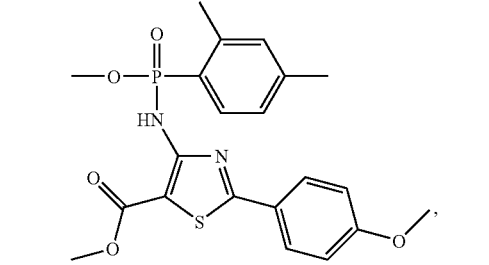

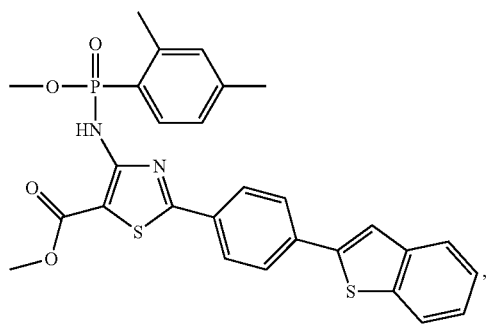
(199)
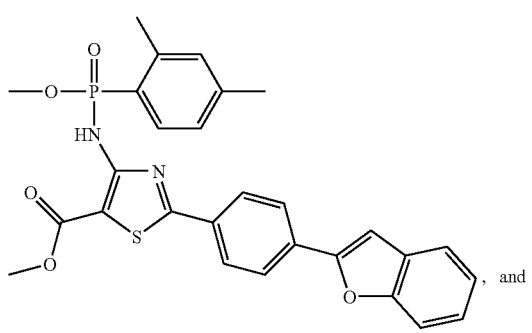
(200), and
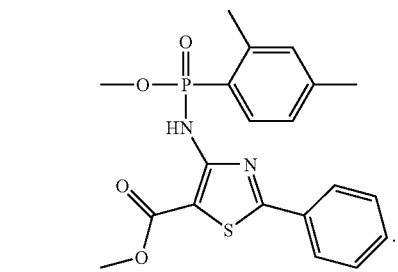
(201).
In certain embodiments, provided herein are the following compounds according to formula IIIA:
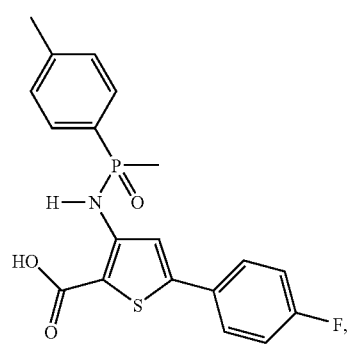
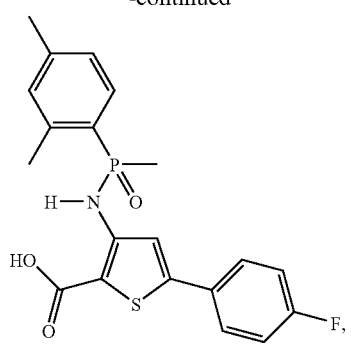
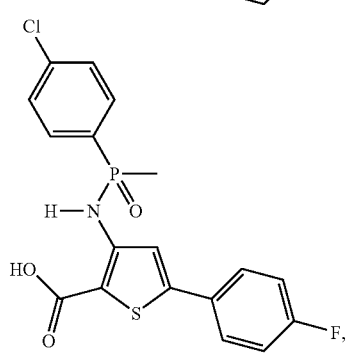
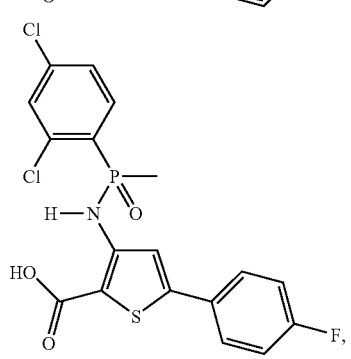
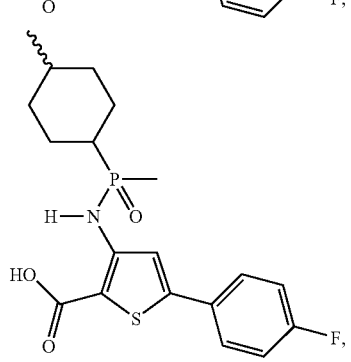
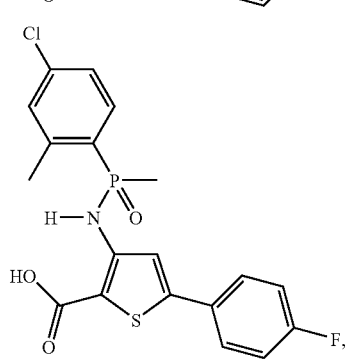

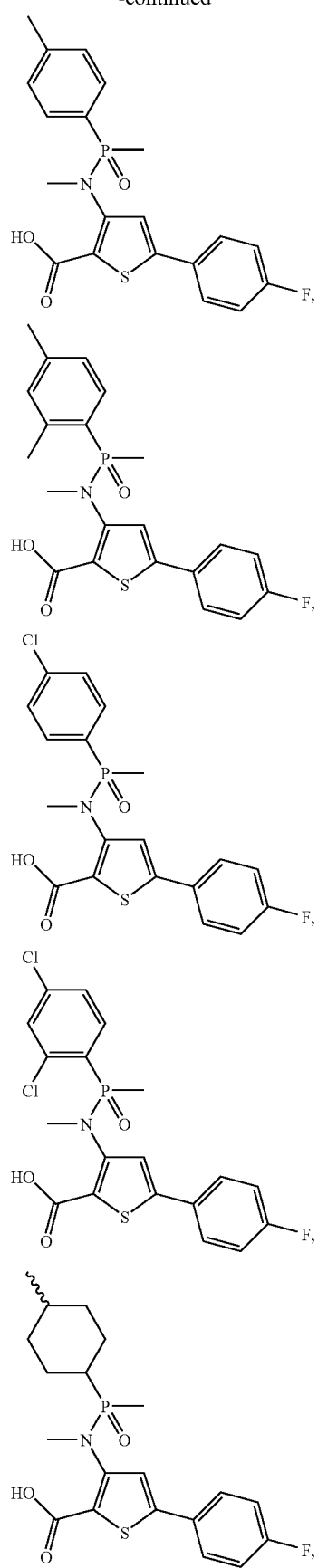
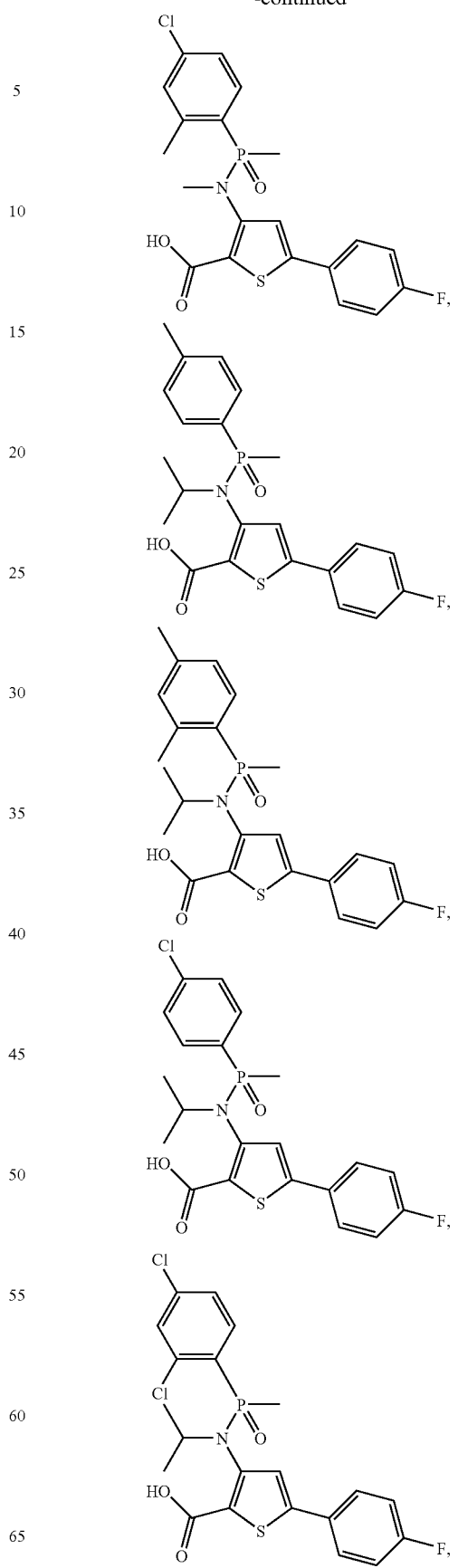

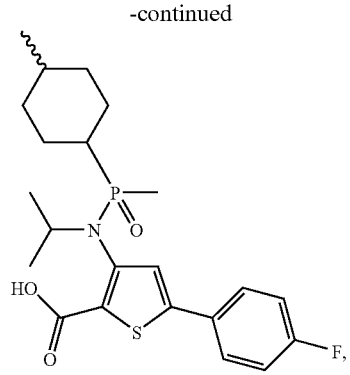
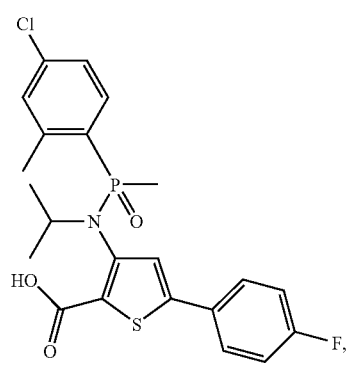
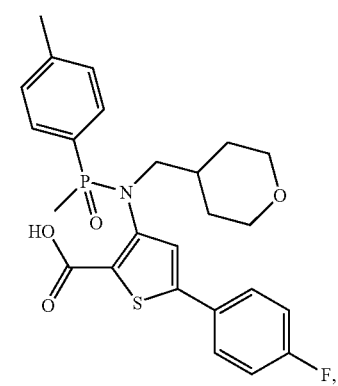
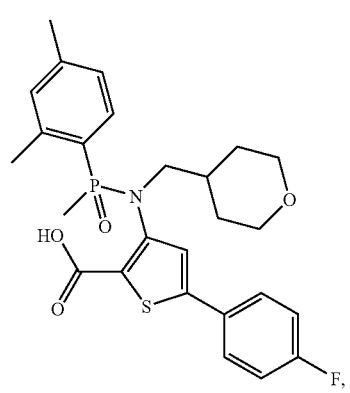
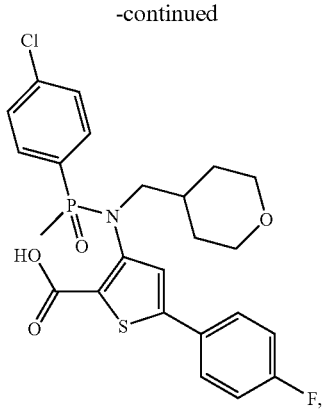
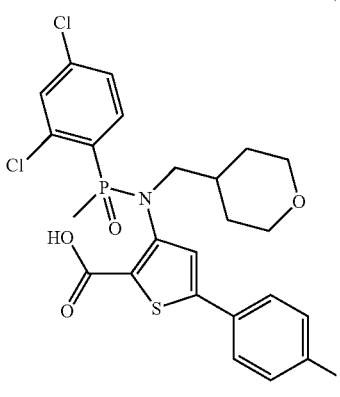
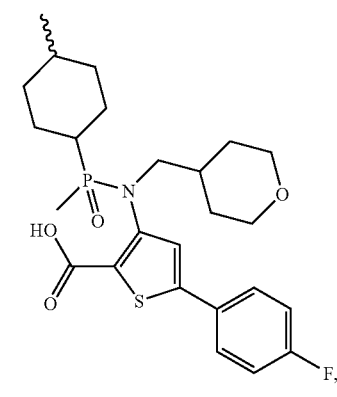
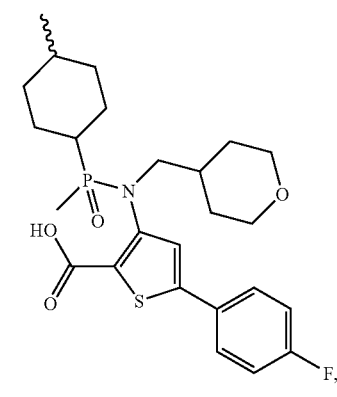

85
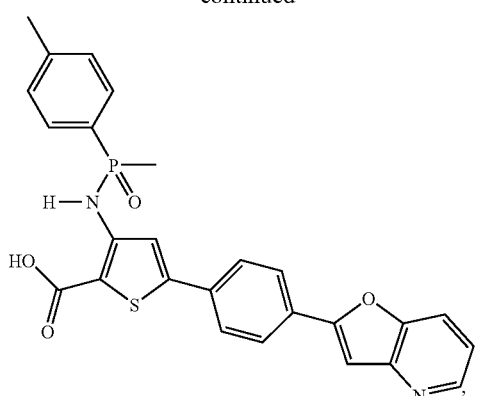
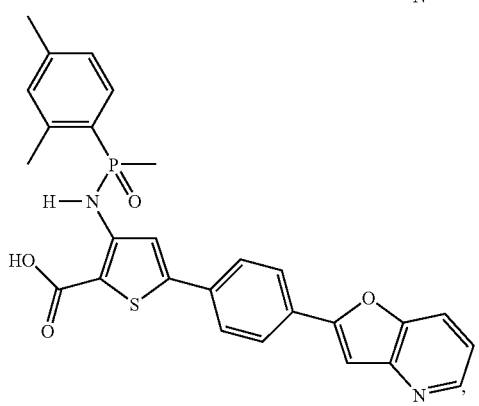
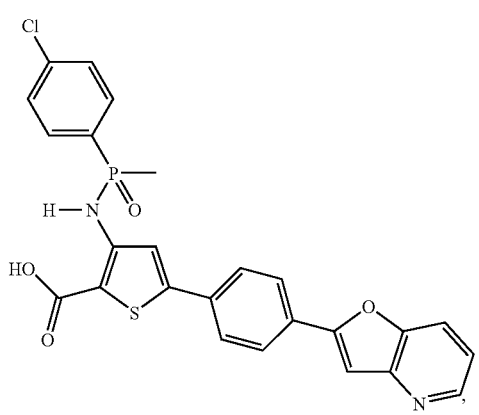
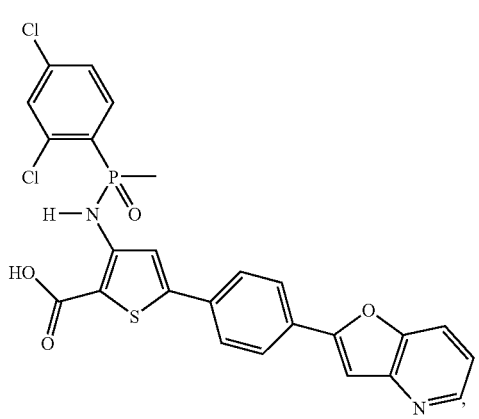
86
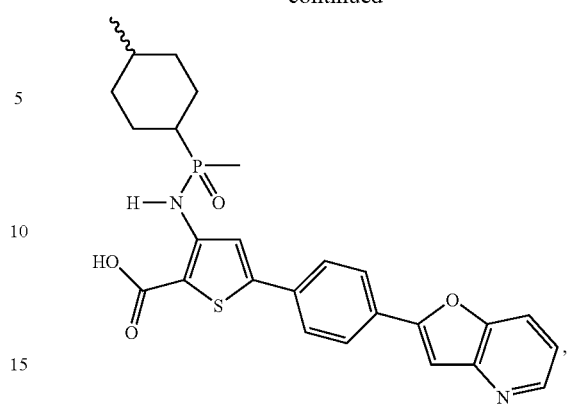
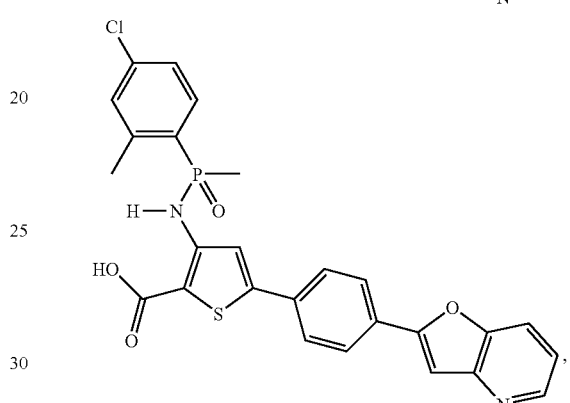
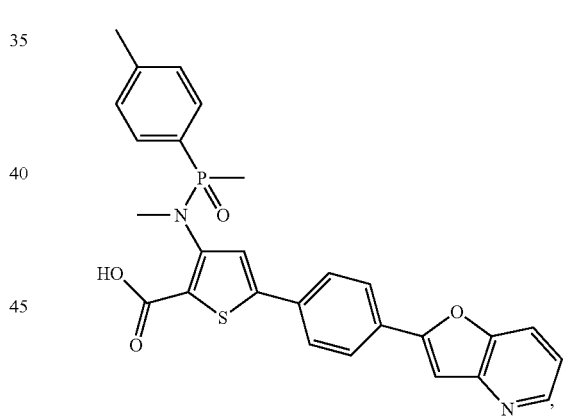
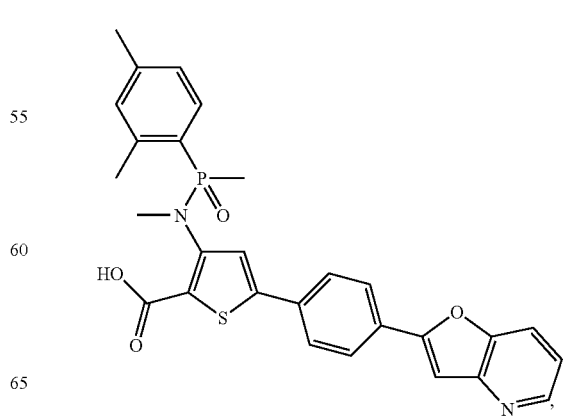

87
-continued
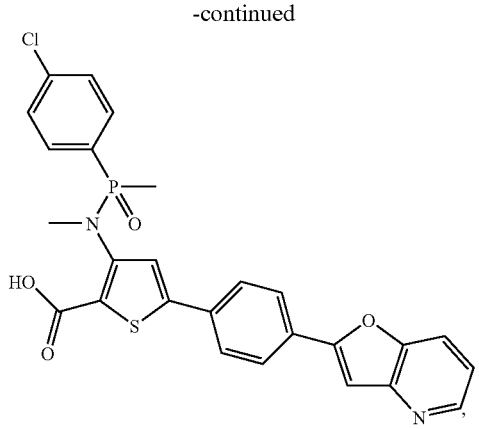
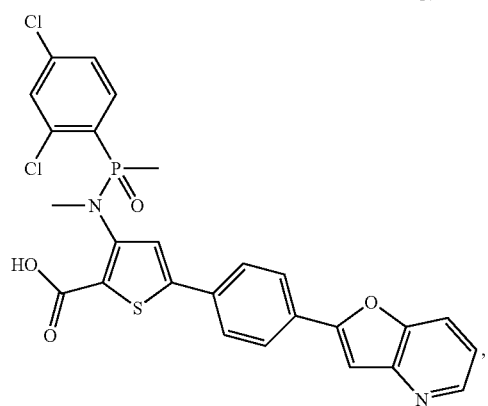
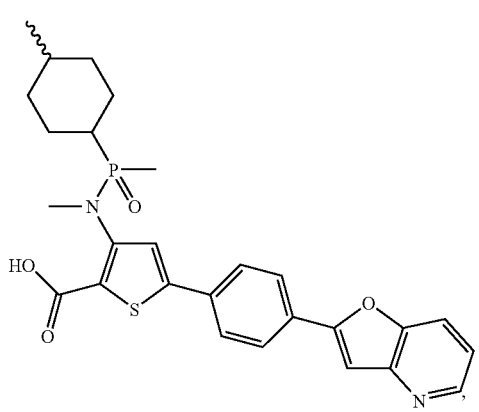
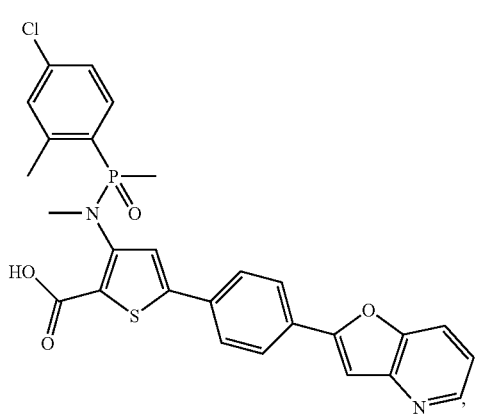
88
-continued
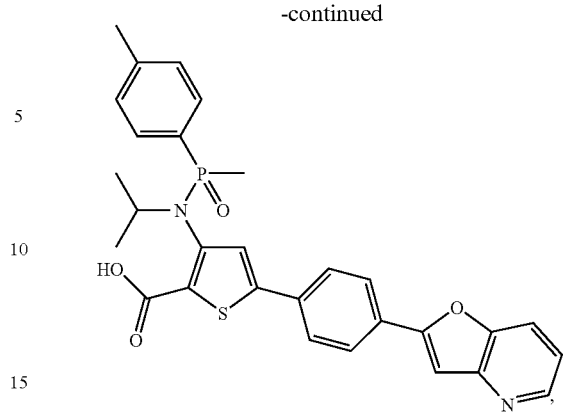
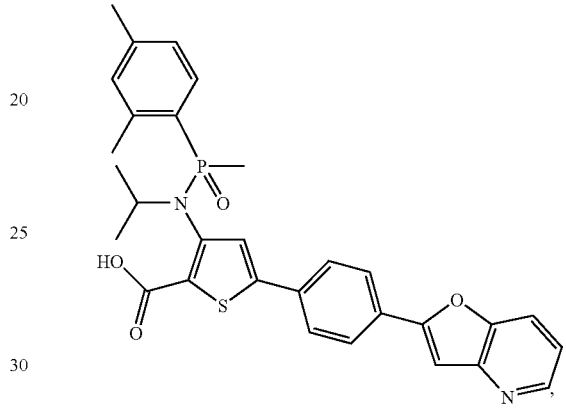

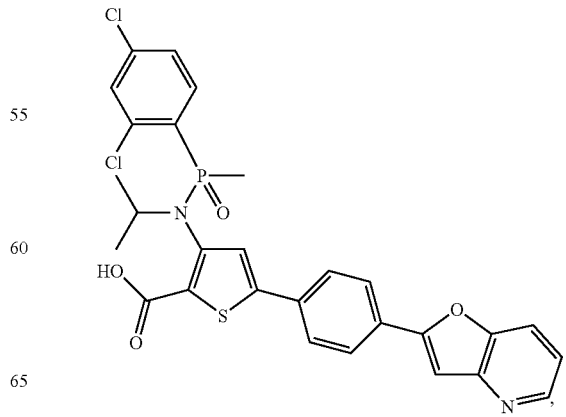

89
-continued
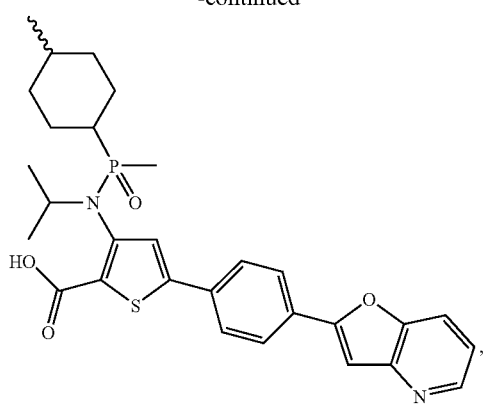
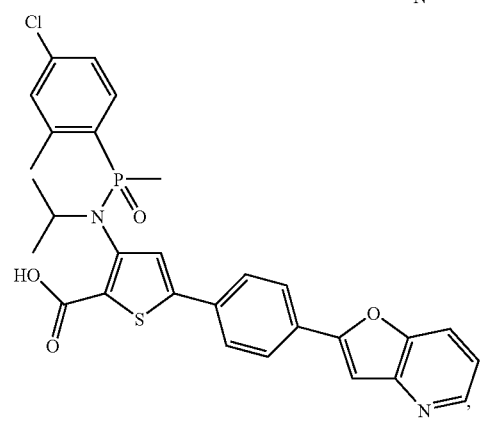
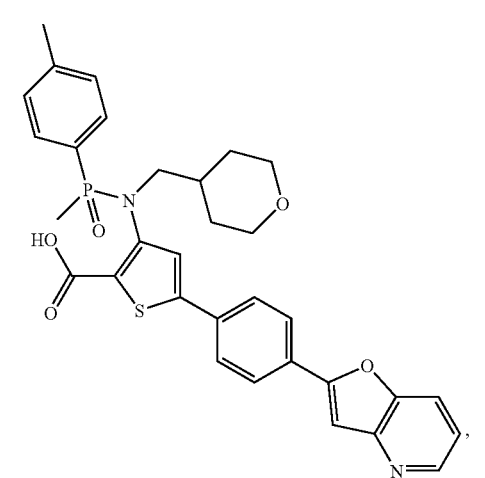
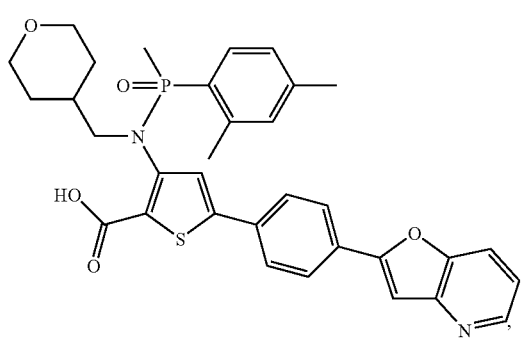
90
-continued
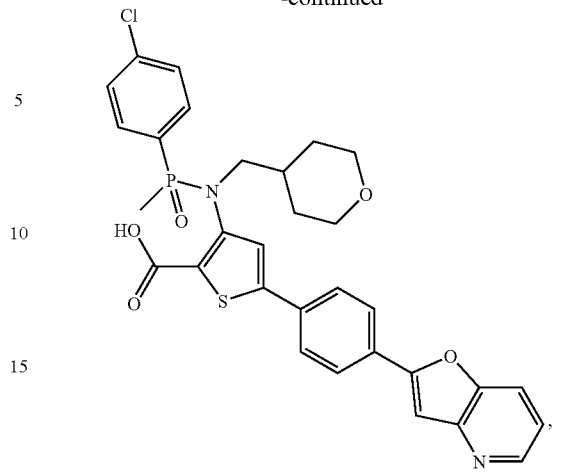
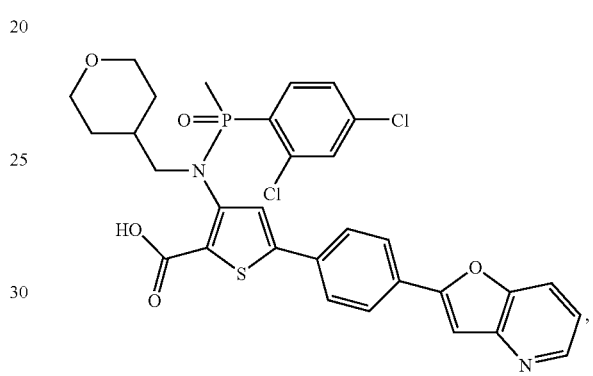
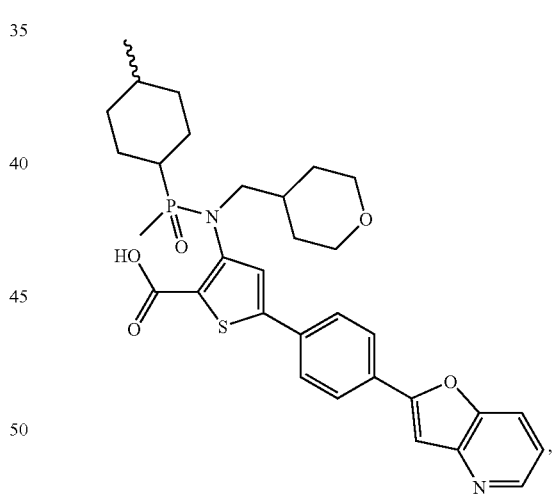
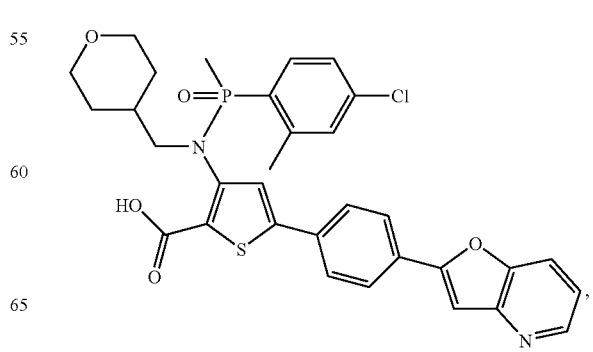

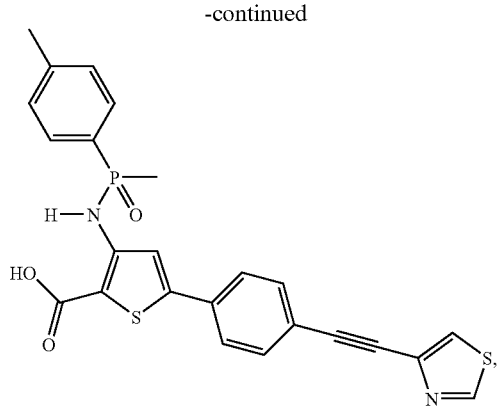
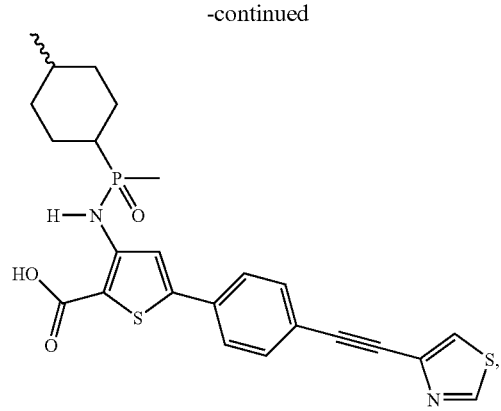
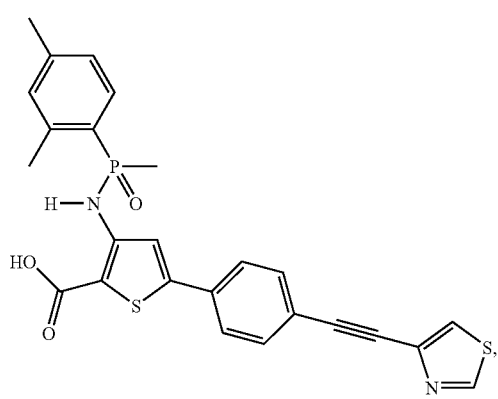
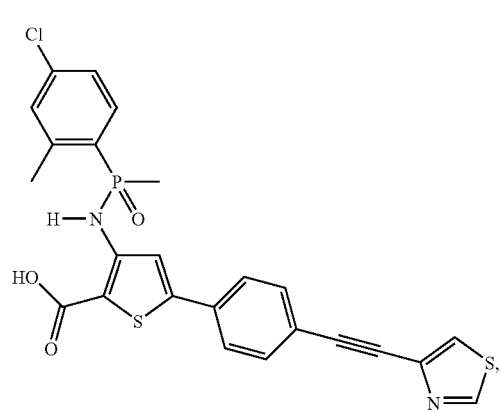
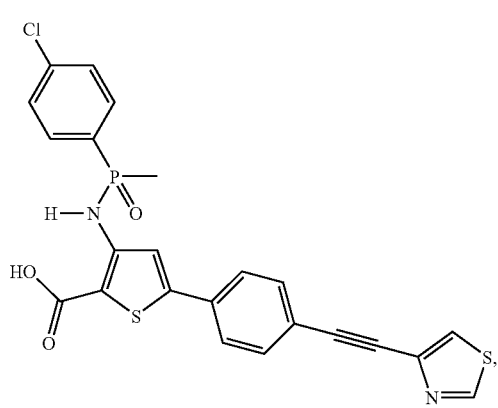
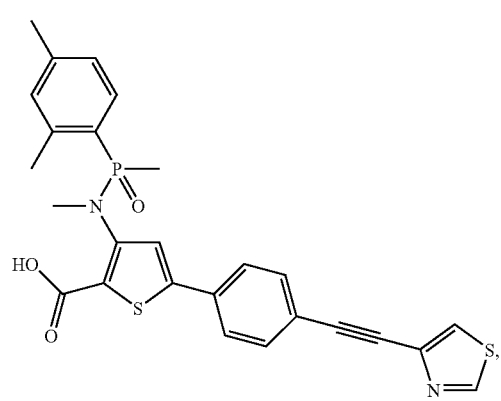

93
-continued
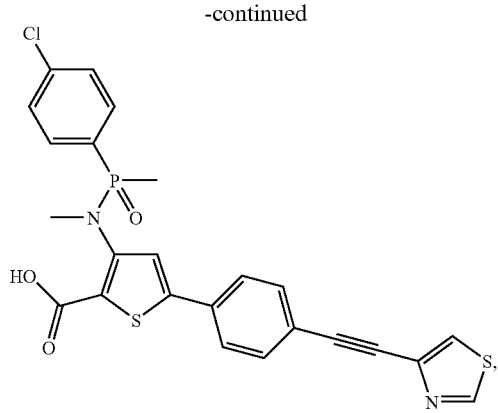
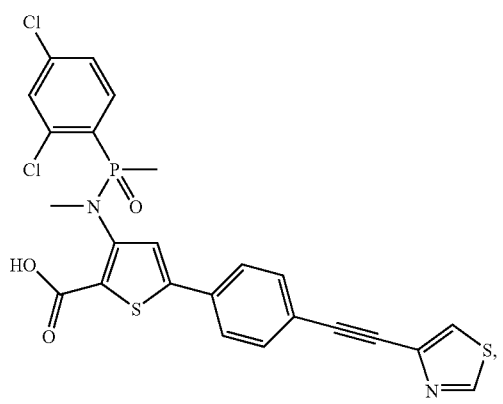
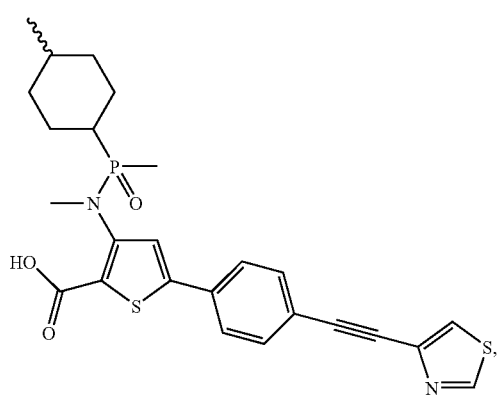
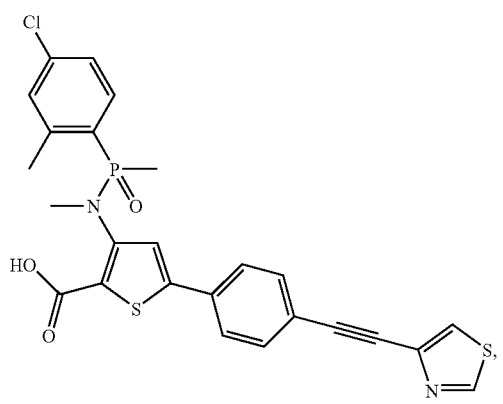
94
-continued
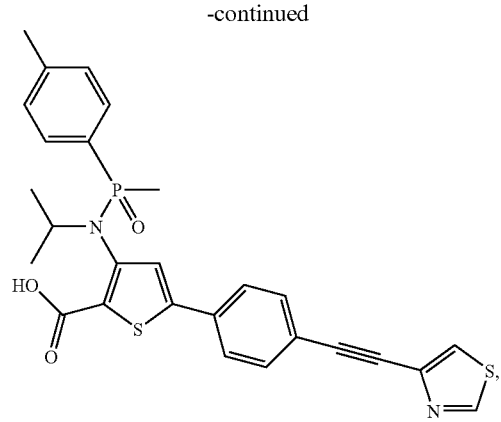
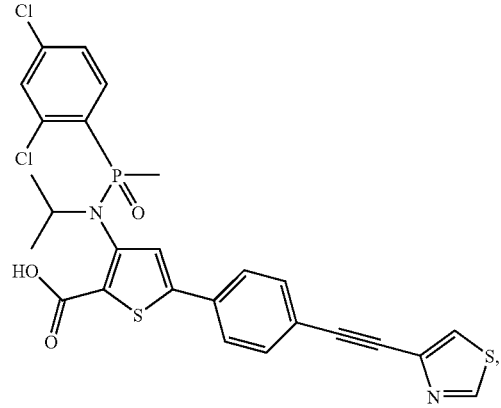

95
-continued
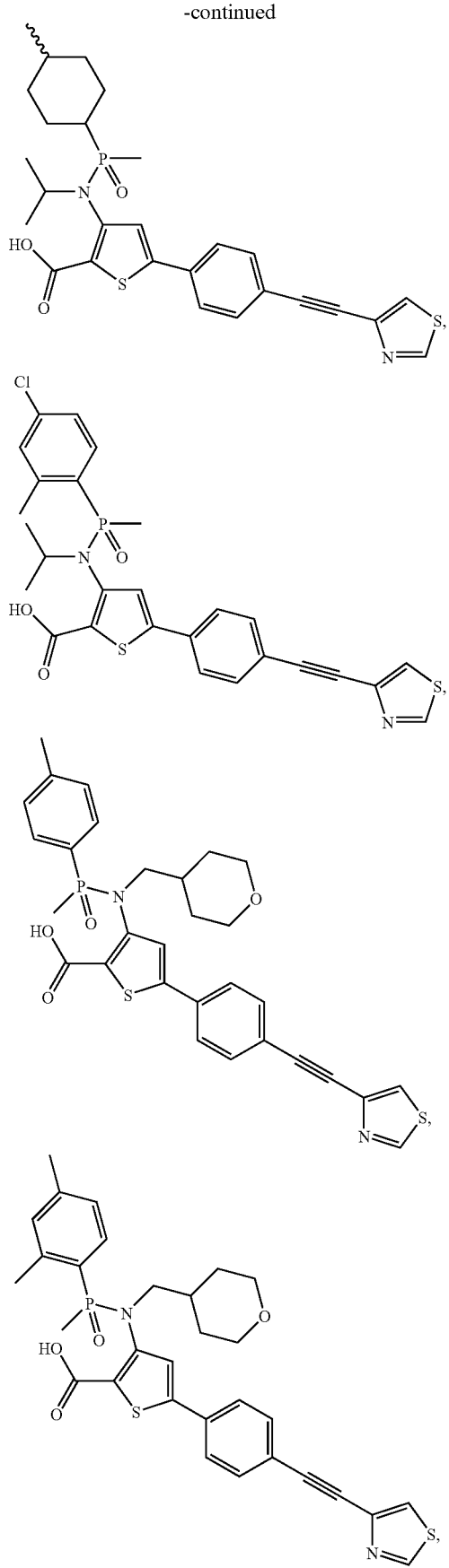
96
-continued
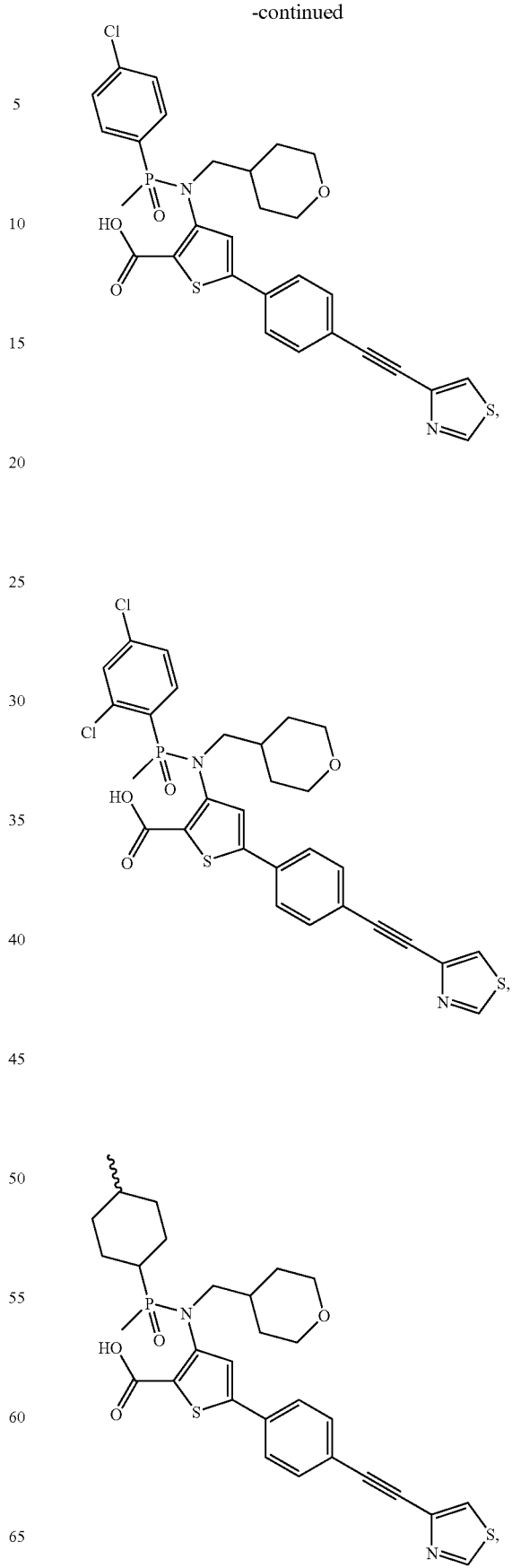

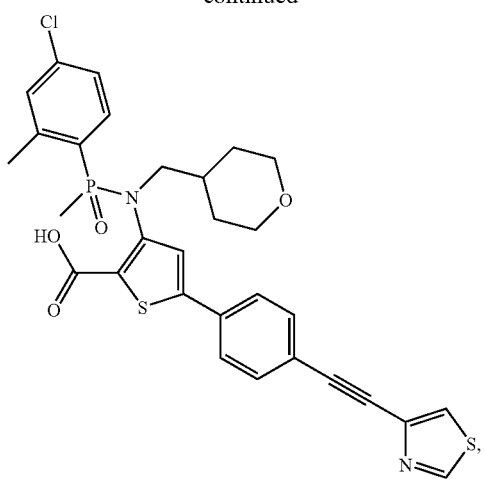
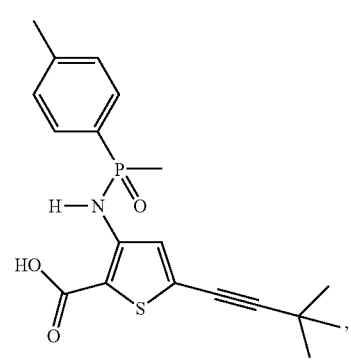
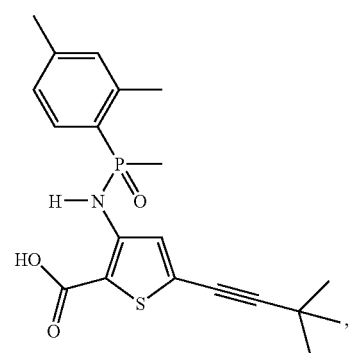
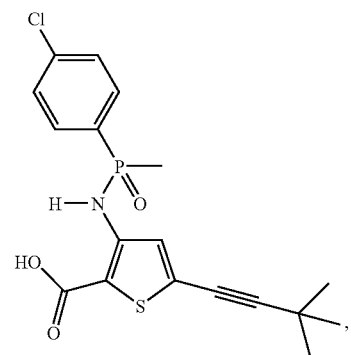
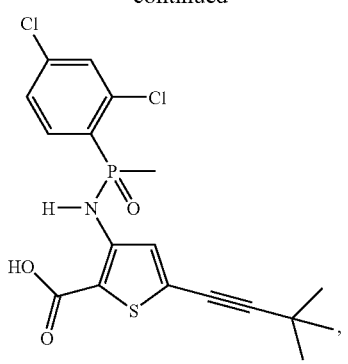
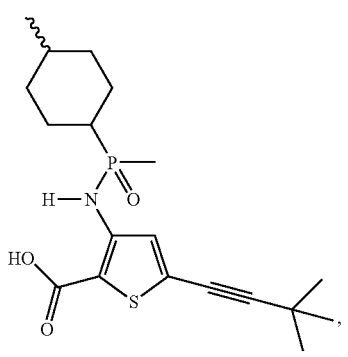
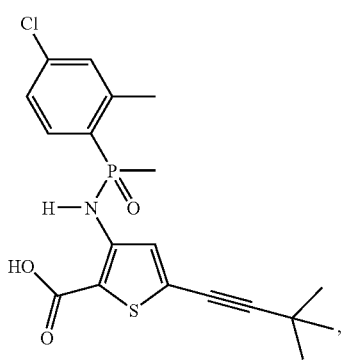
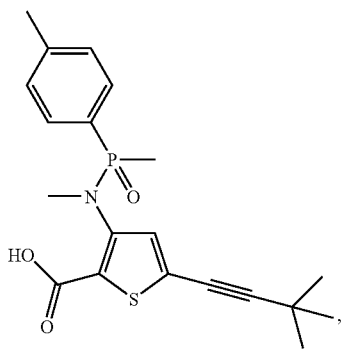

99
-continued
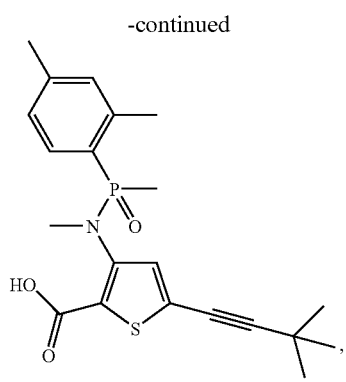
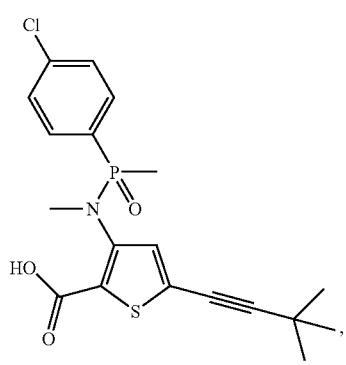
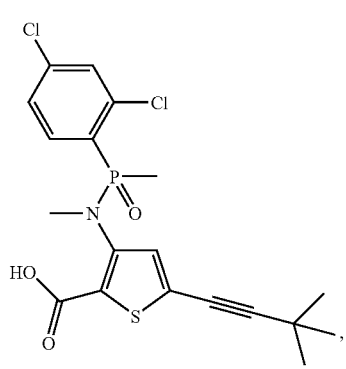
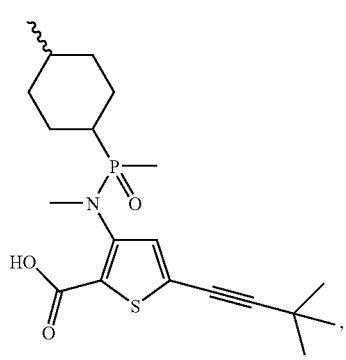
100
-continued
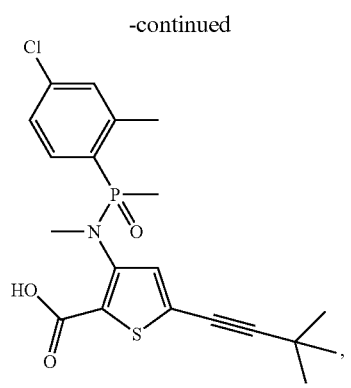
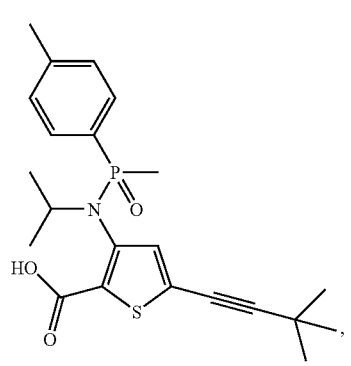
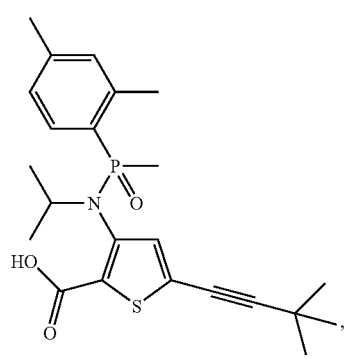
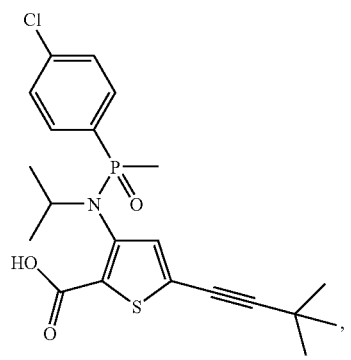

101
-continued
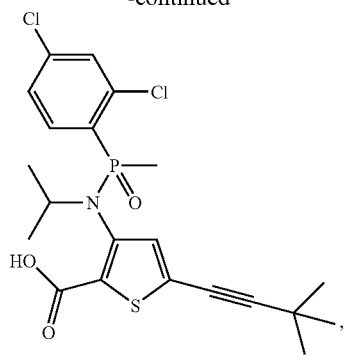
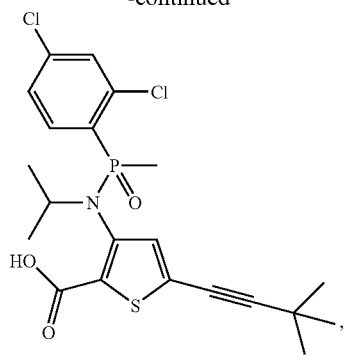
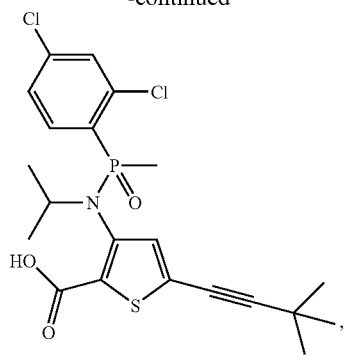
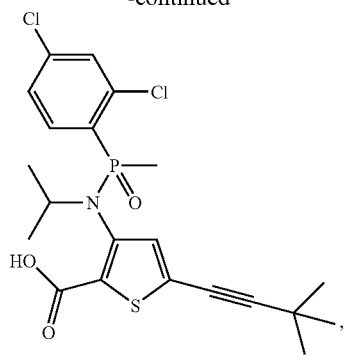
102
-continued
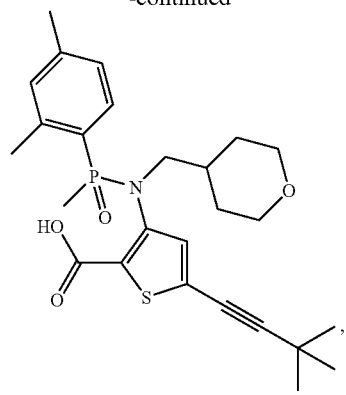
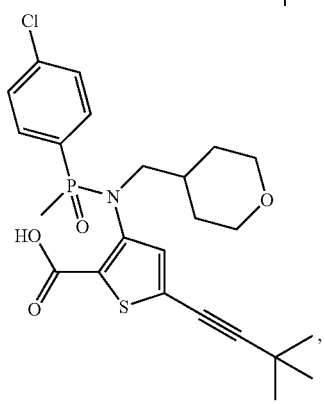
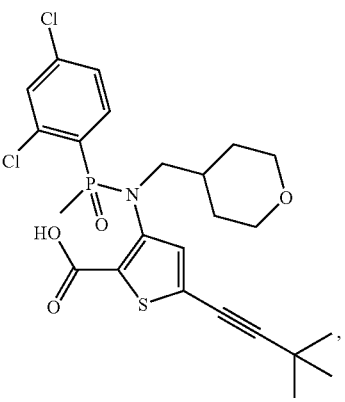
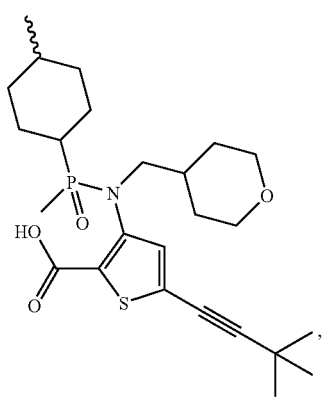

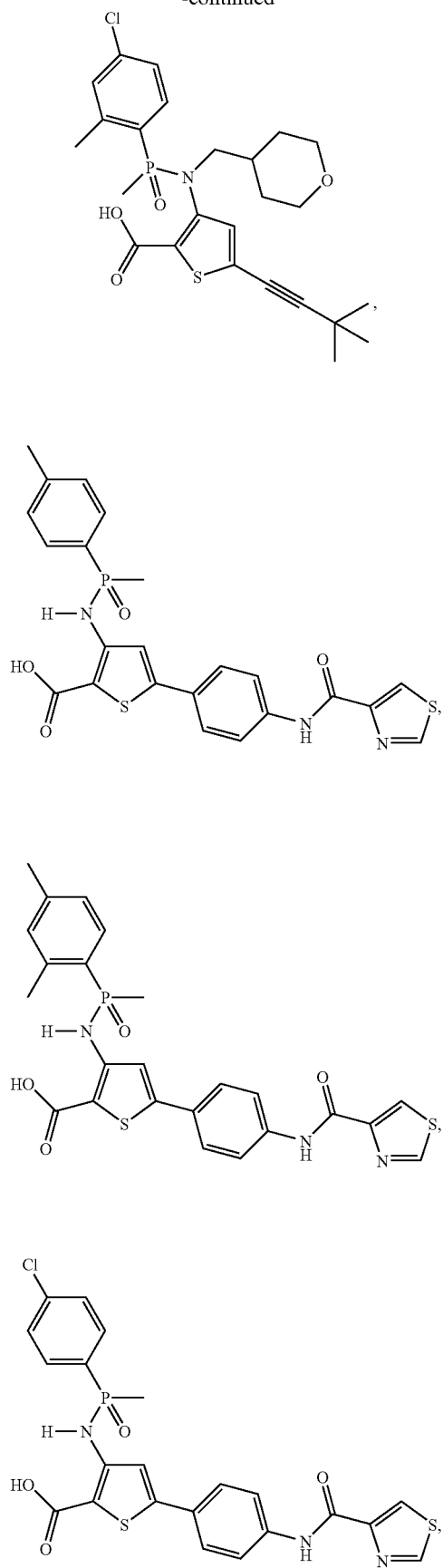

105
-continued
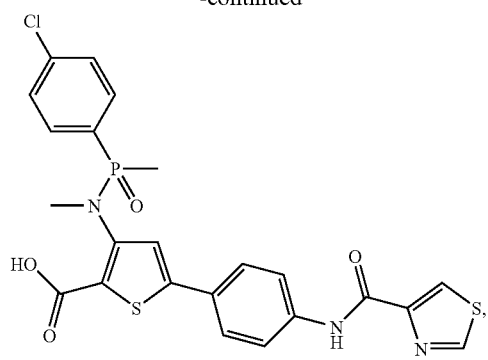
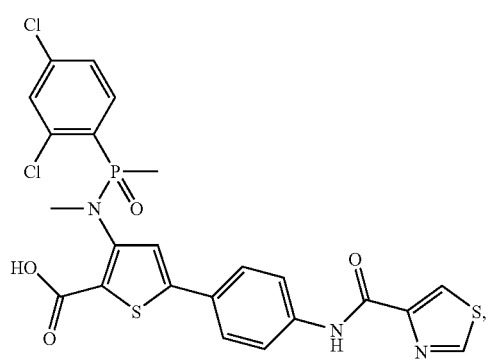
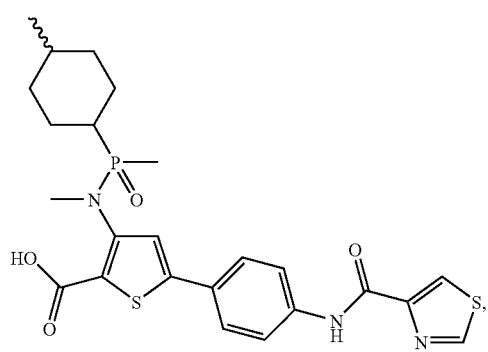
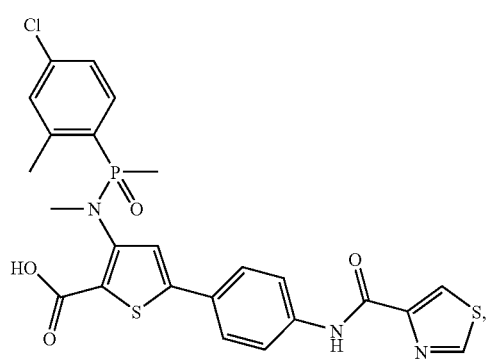
106
-continued
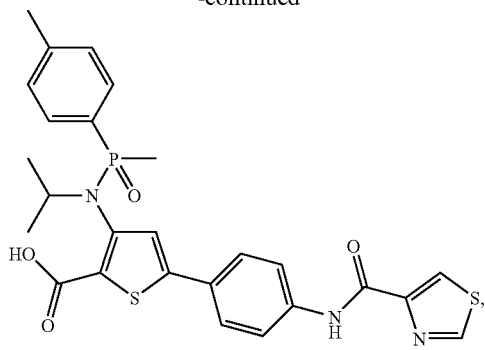
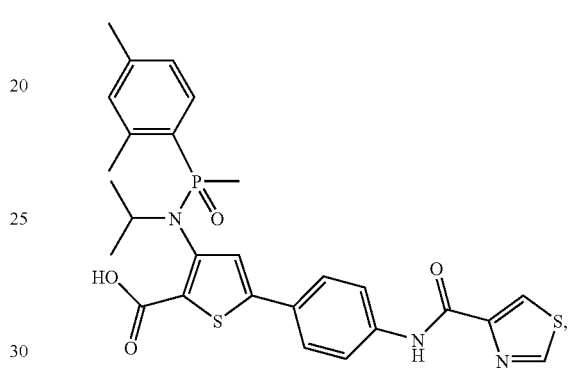
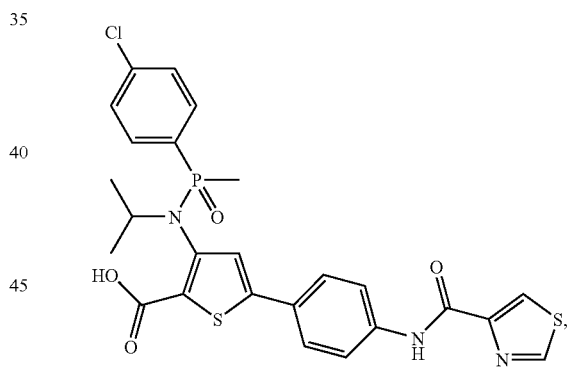
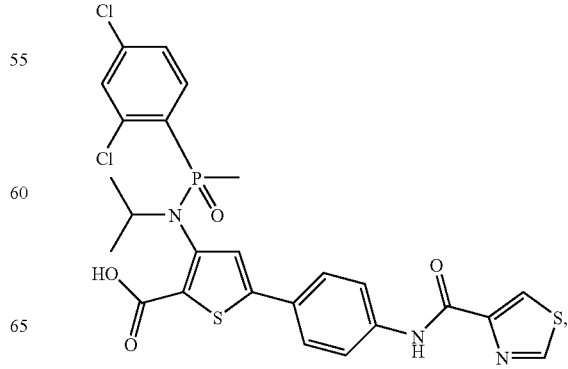

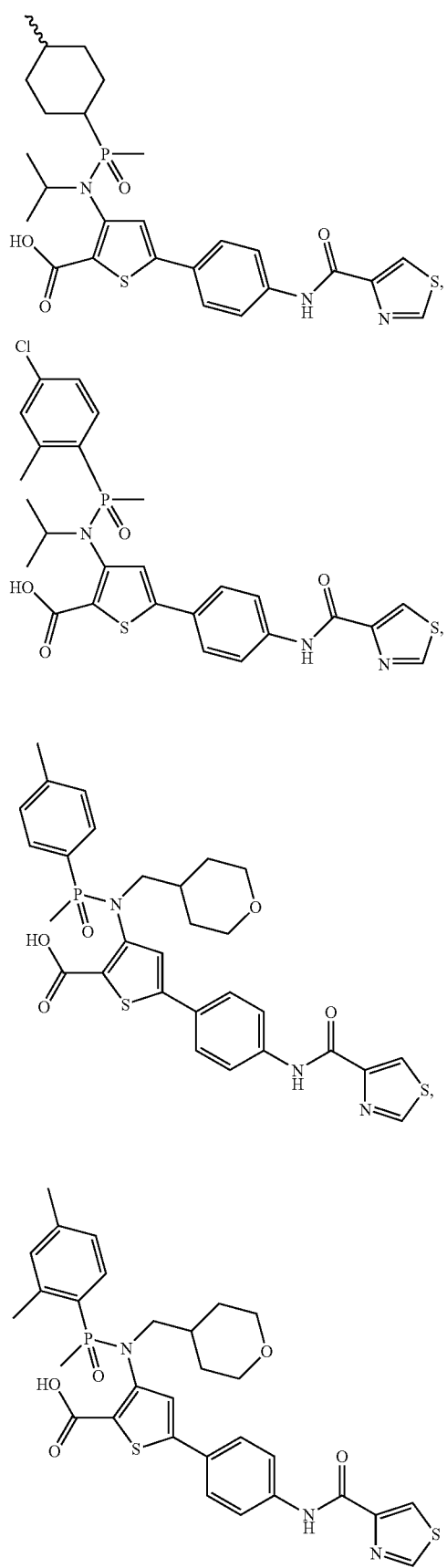
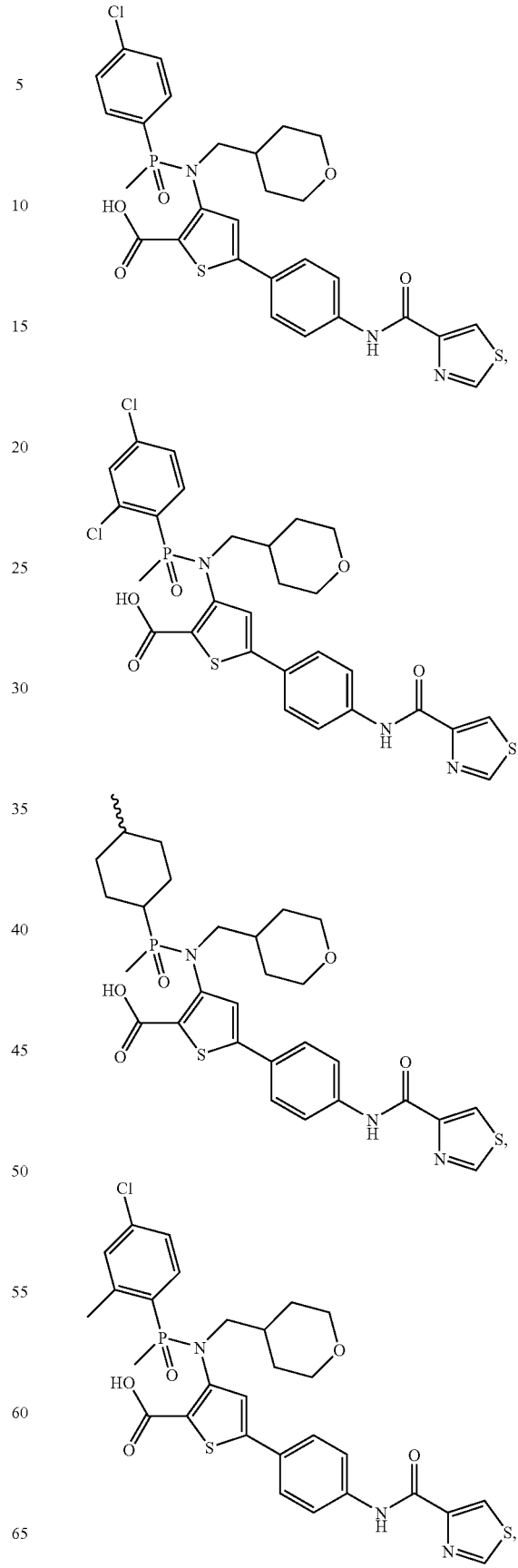

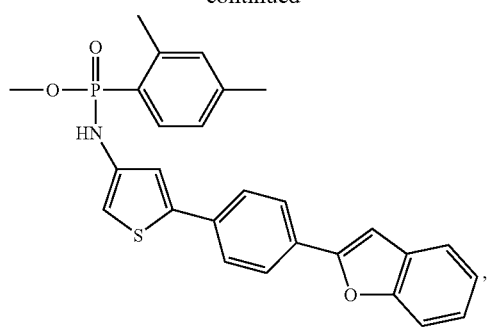
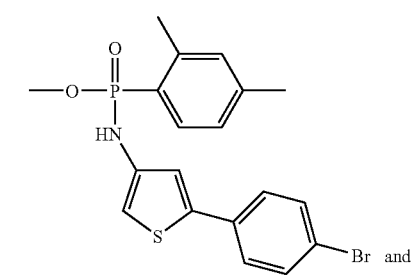
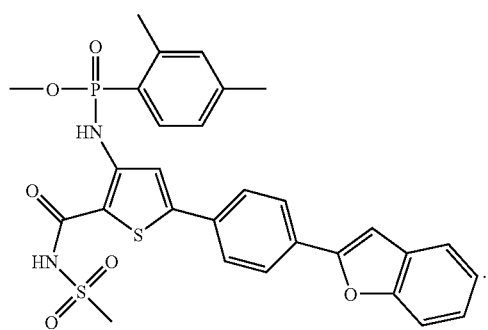
In certain embodiments, provided herein are the following compounds according to formula VIA:
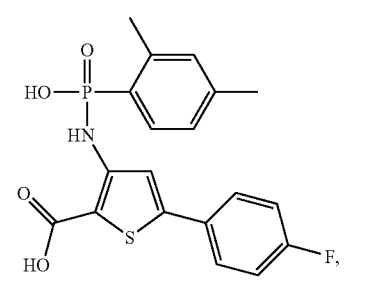
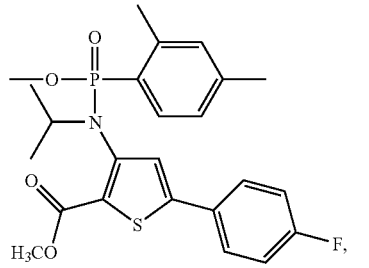
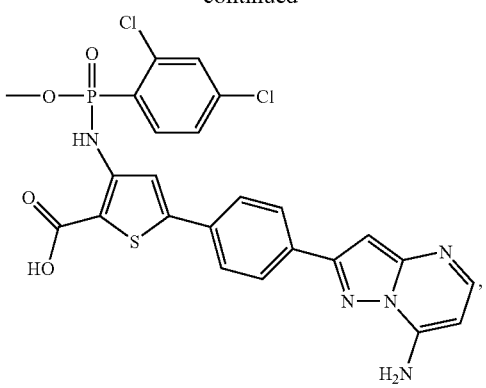
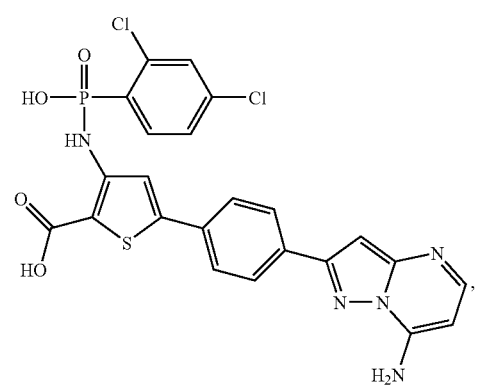
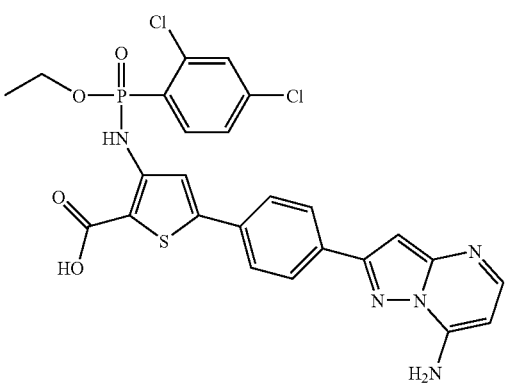
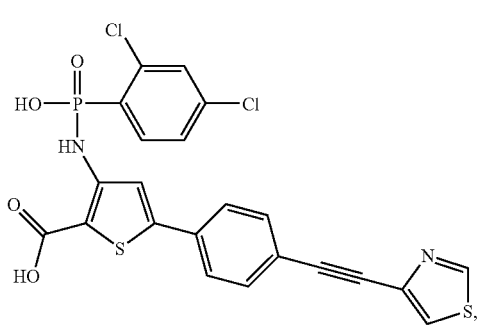

111
-continued
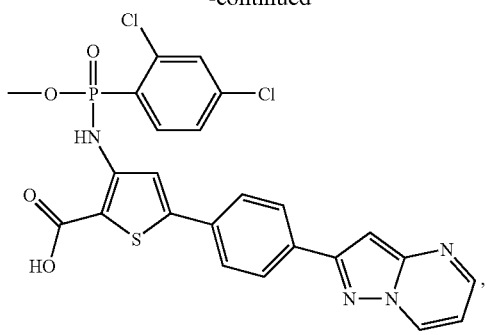
,
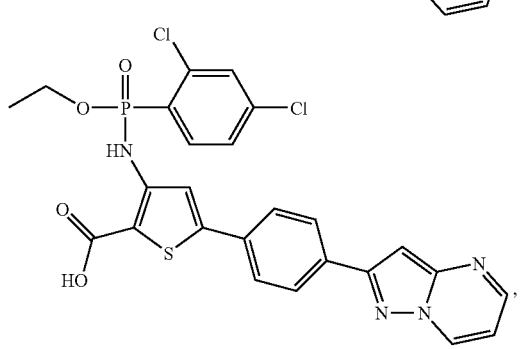
,
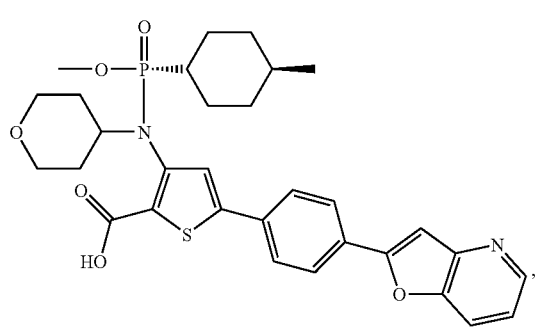
,
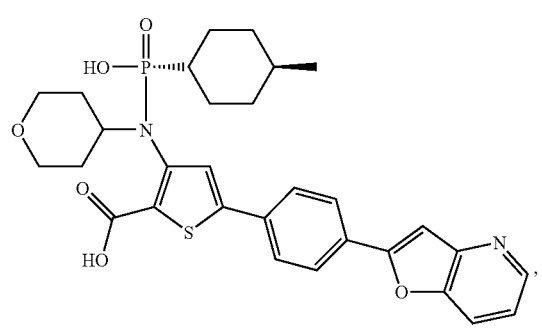
,
112
-continued
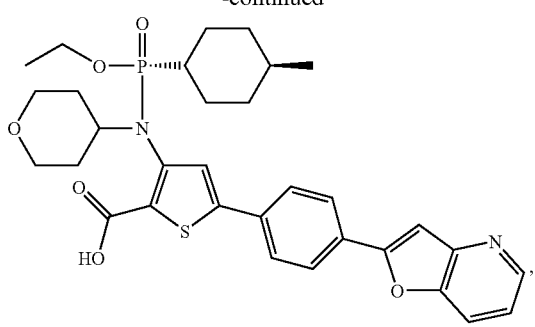
,
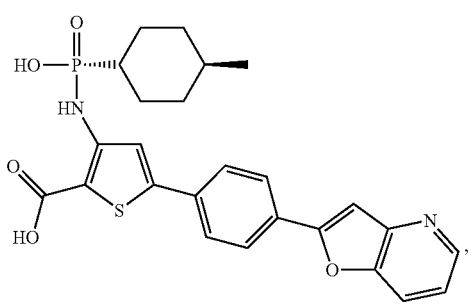
,
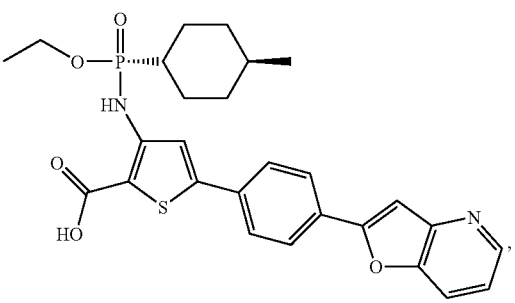
,
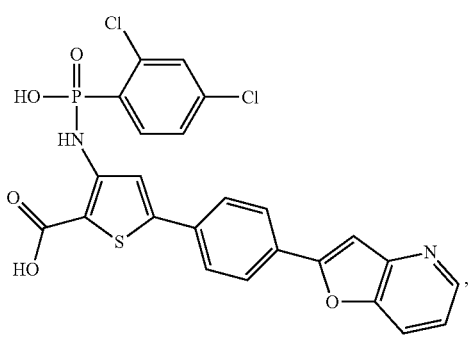
, 113
-continued
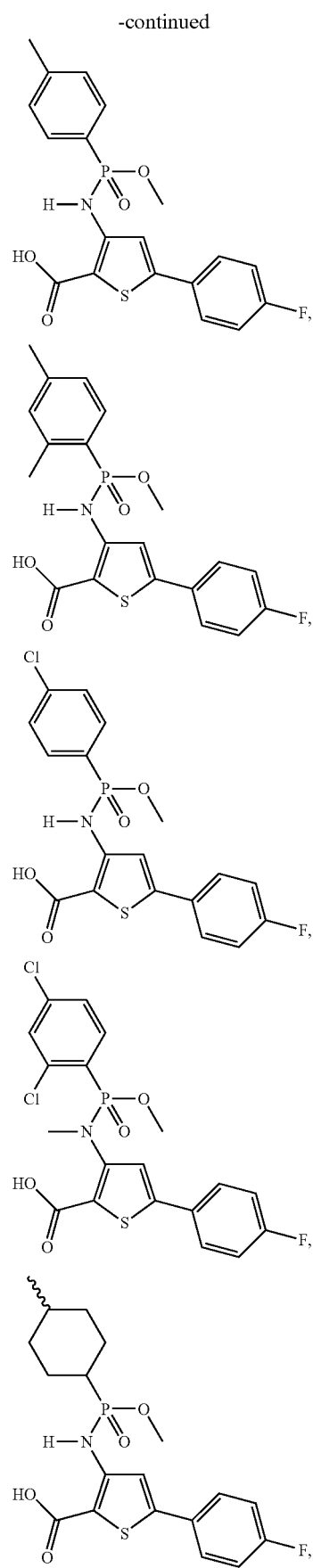
114
-continued
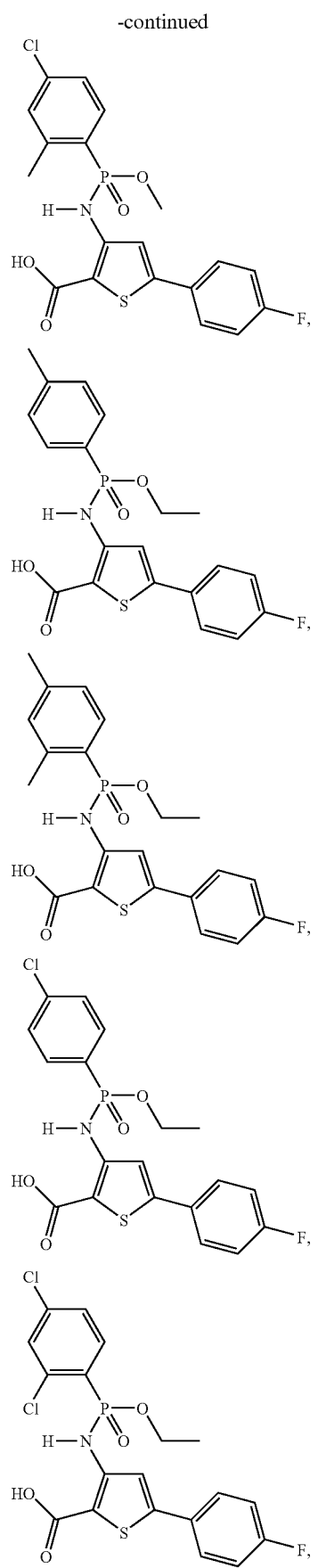

115
-continued
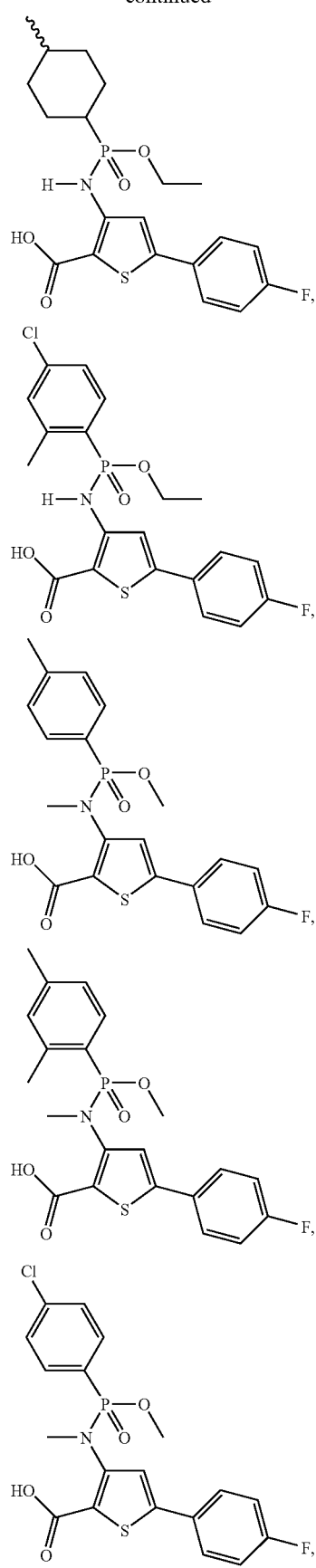
116
-continued
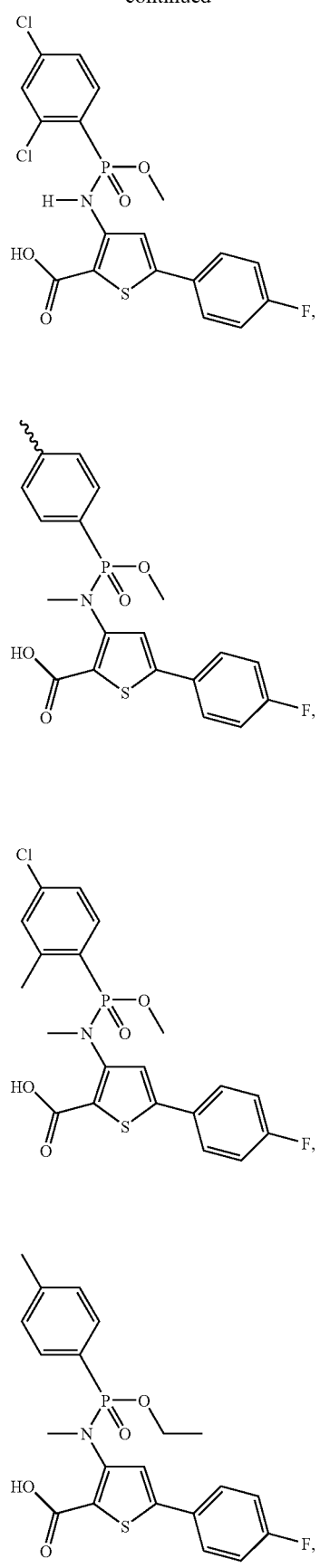

117
-continued
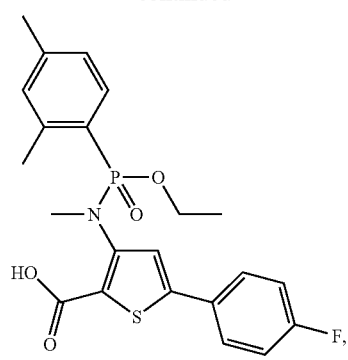
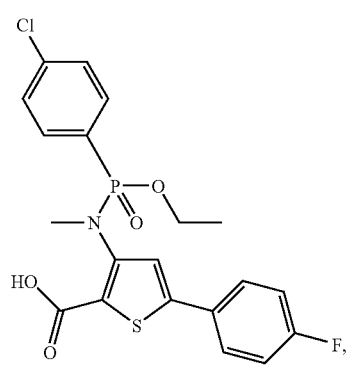
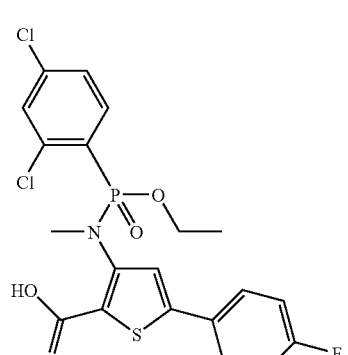
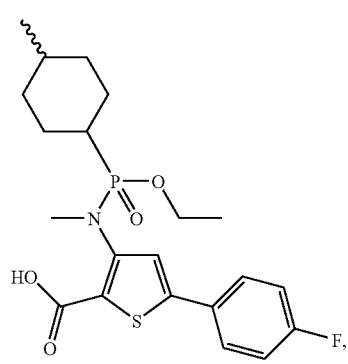
118
-continued
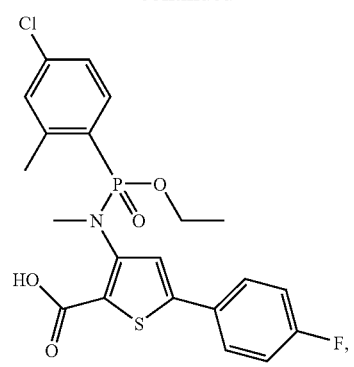
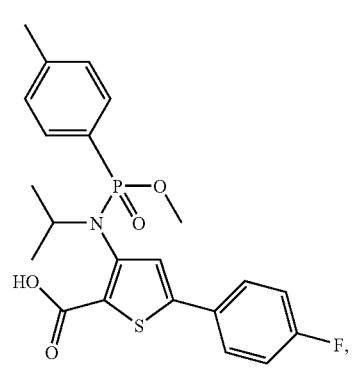
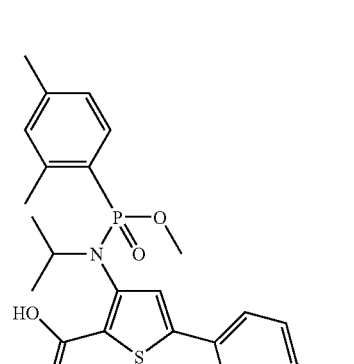
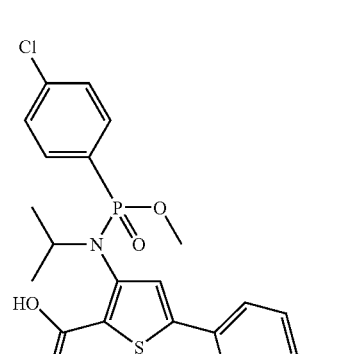

119
-continued
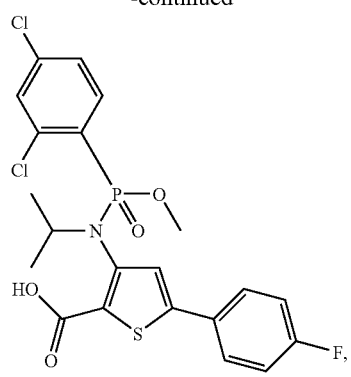
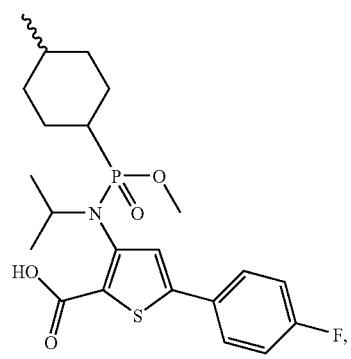
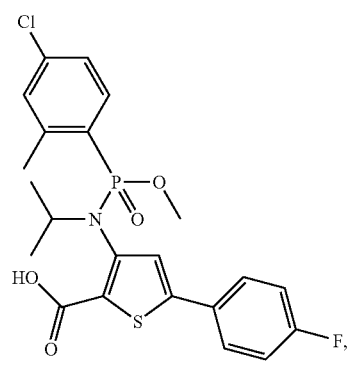
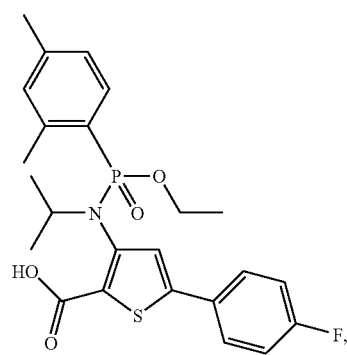
120
-continued
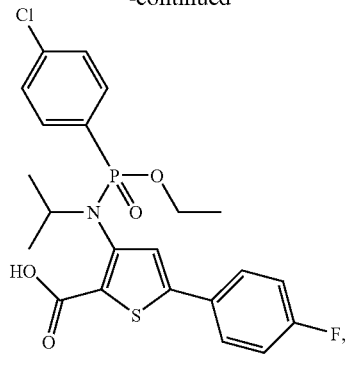
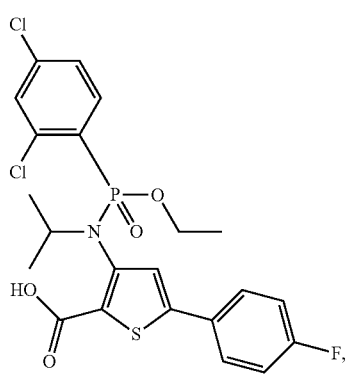
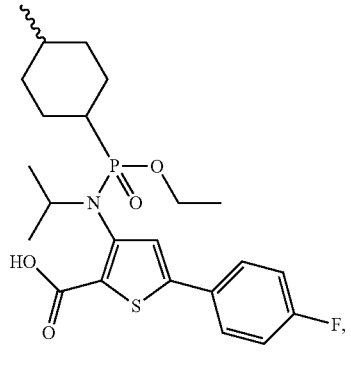
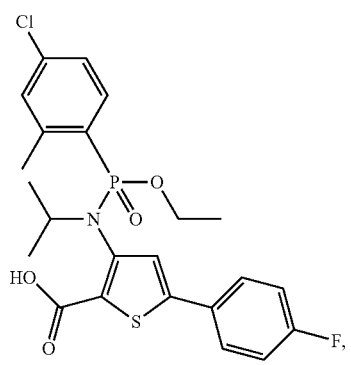

121
-continued
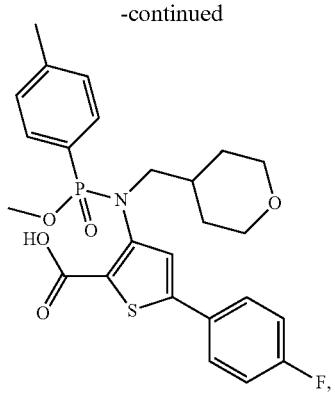
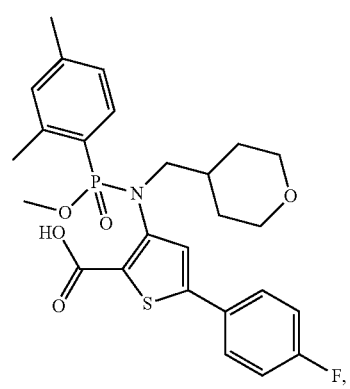
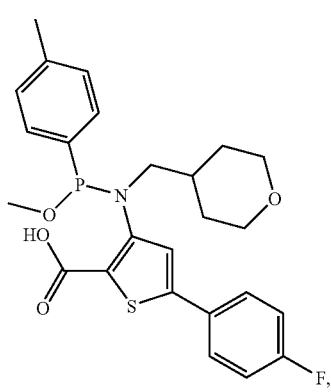
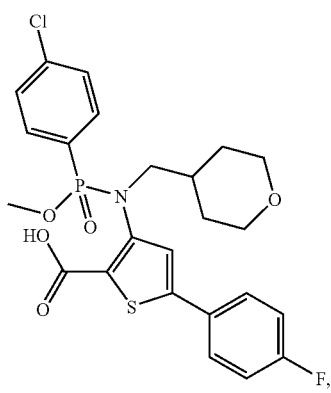
122
-continued
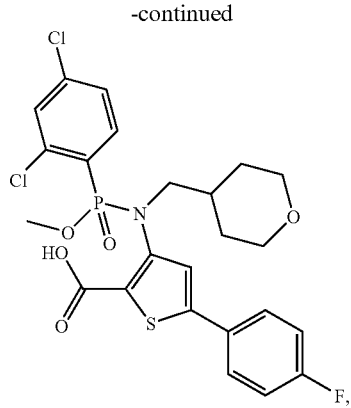
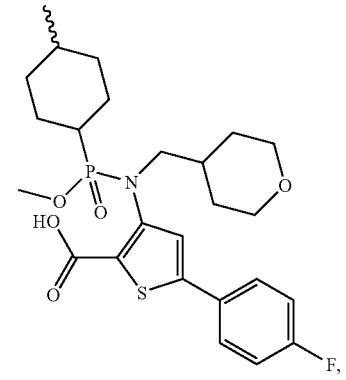
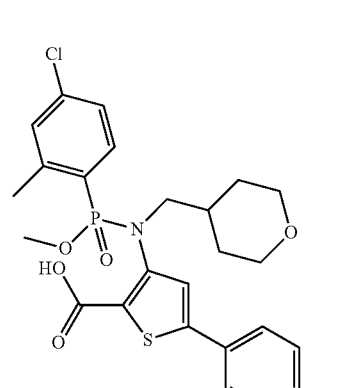
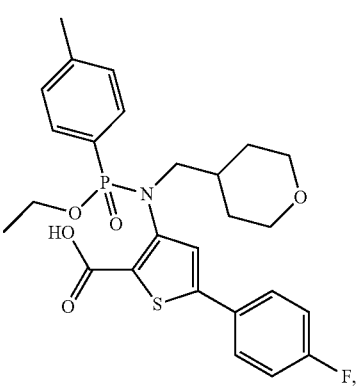

123
-continued
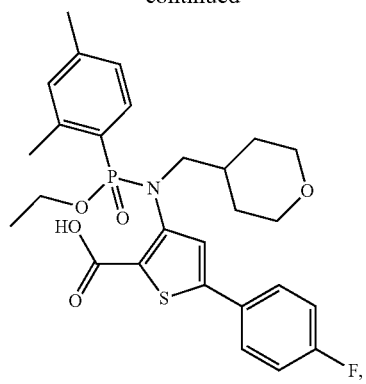
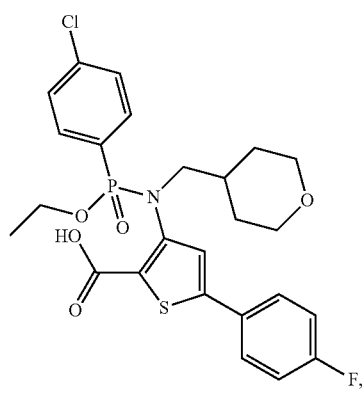
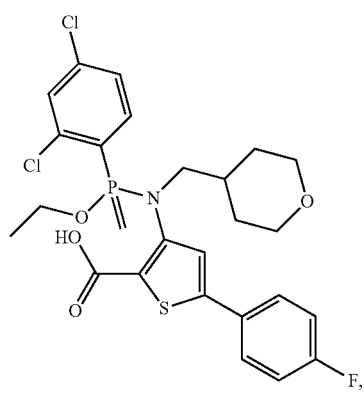
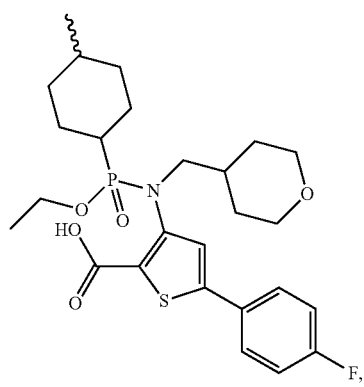
124
-continued
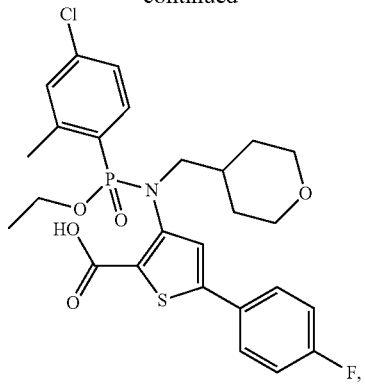
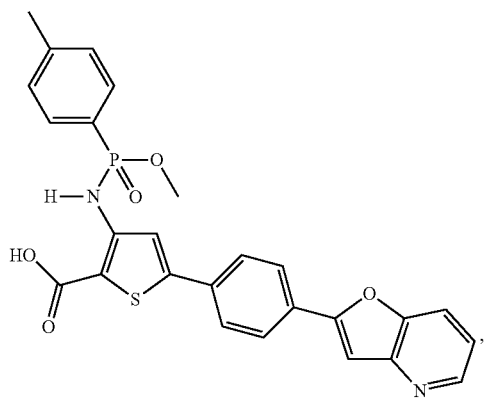
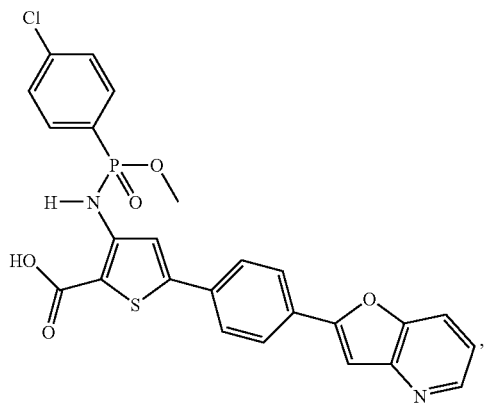

125
-continued
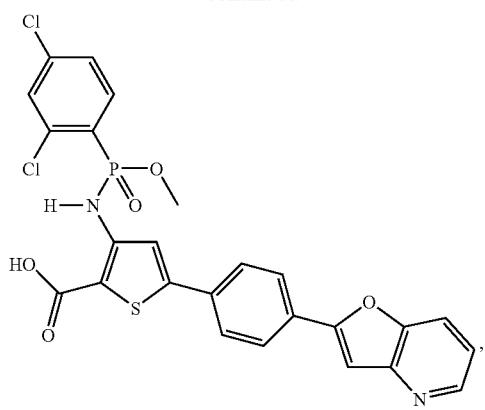
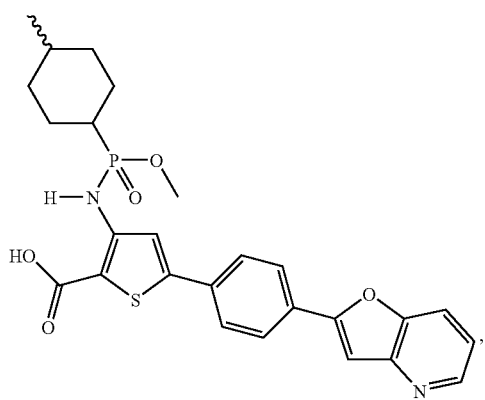
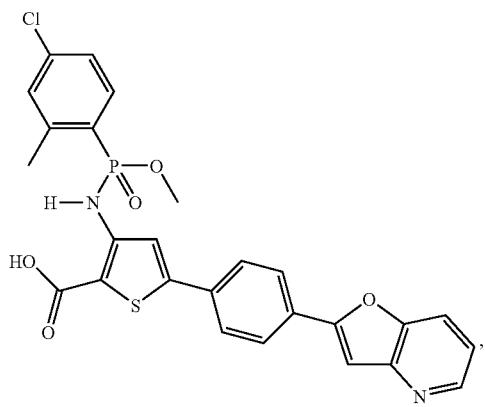
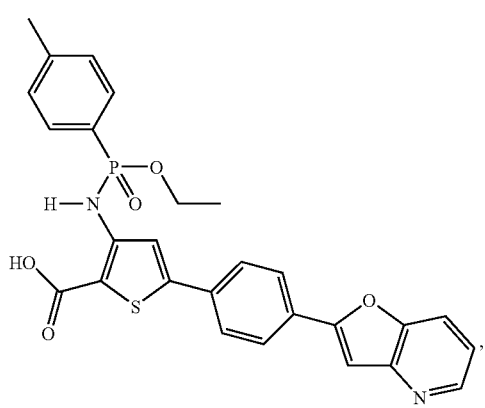
126
-continued
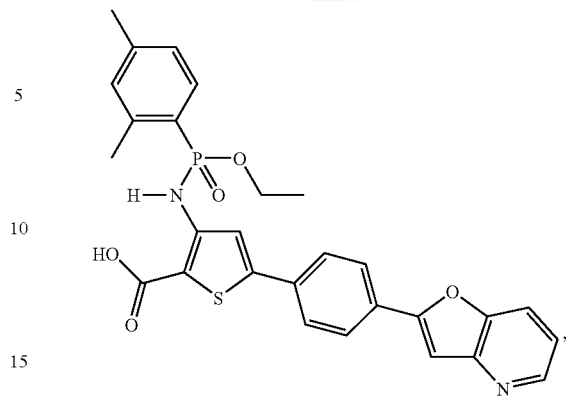
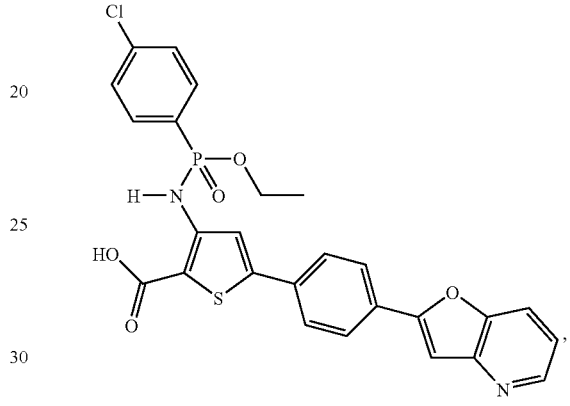
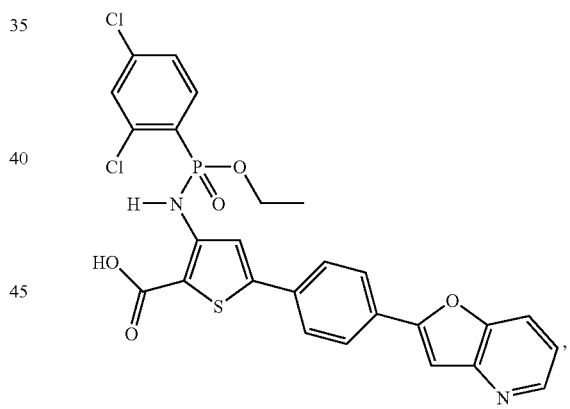
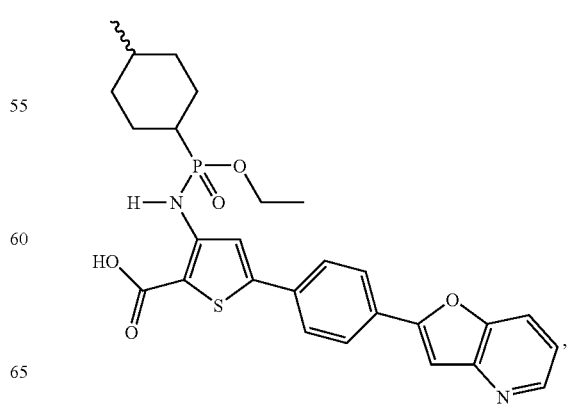

127
-continued
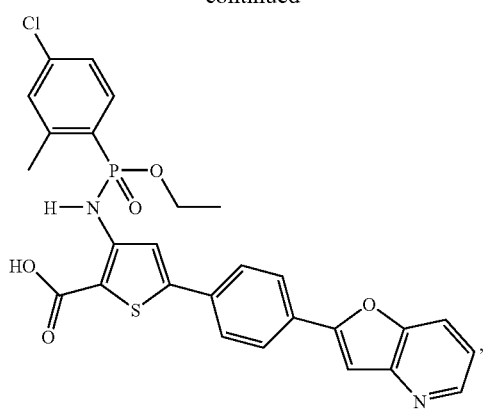
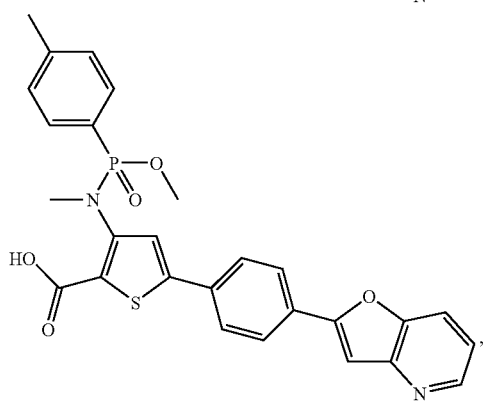
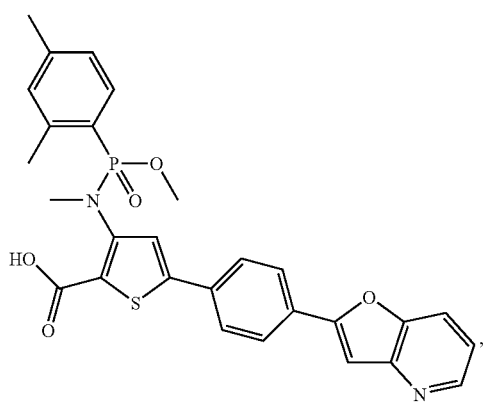
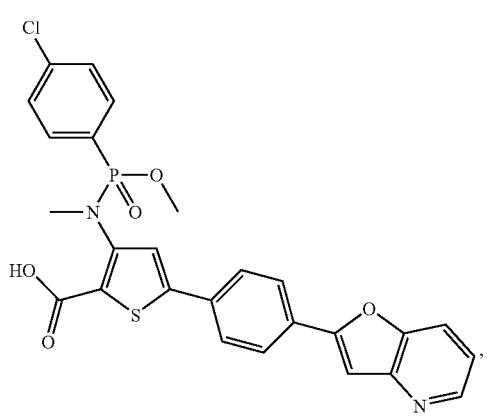
128
-continued
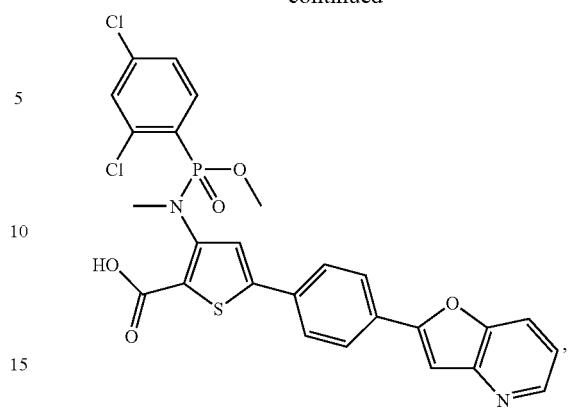
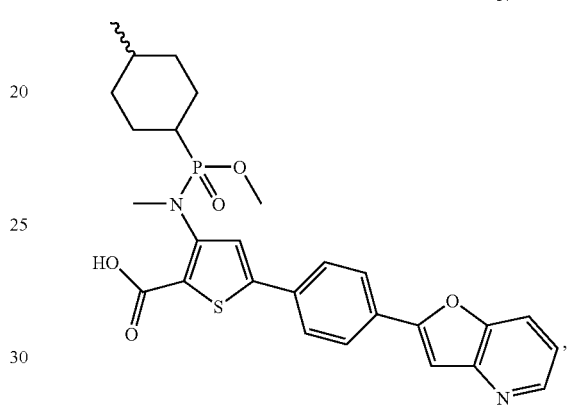
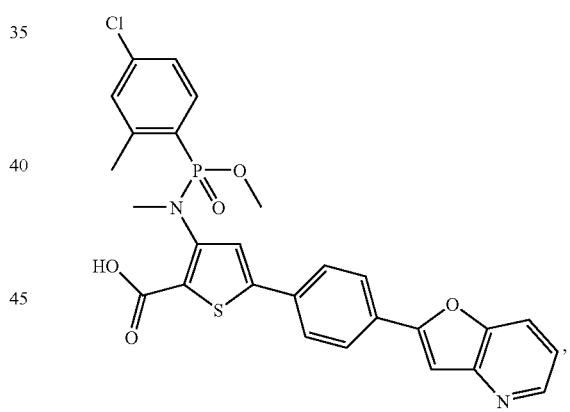
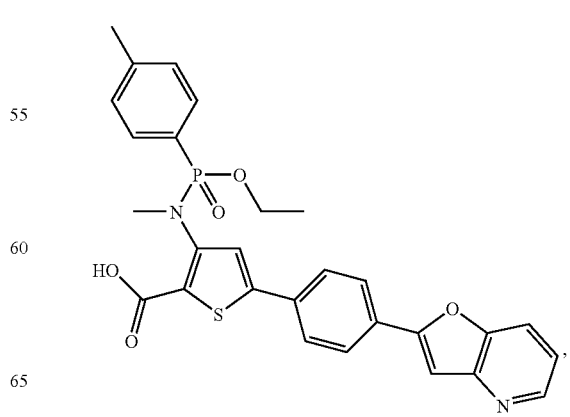

129
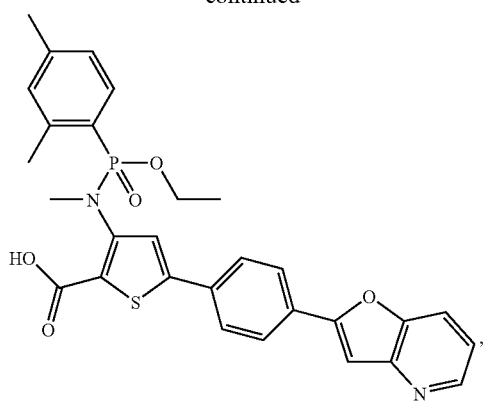
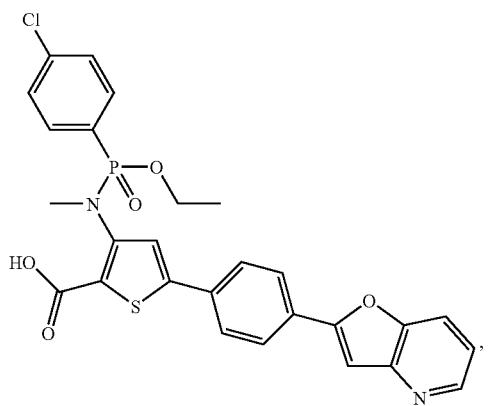
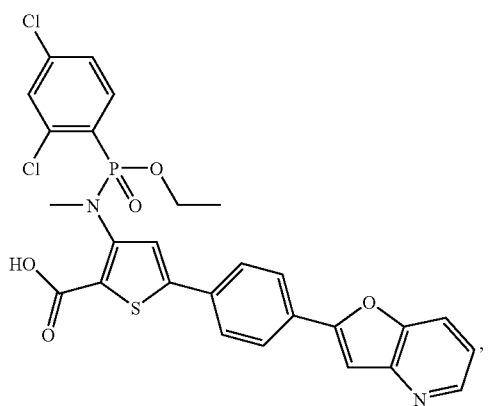
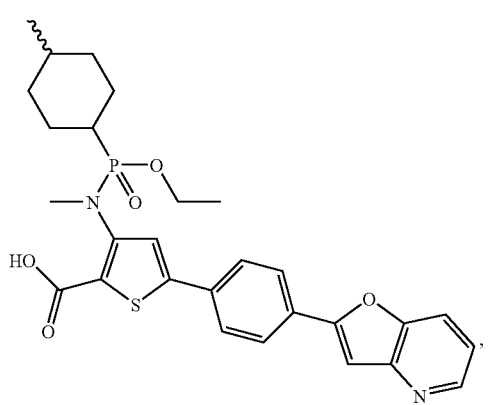
130
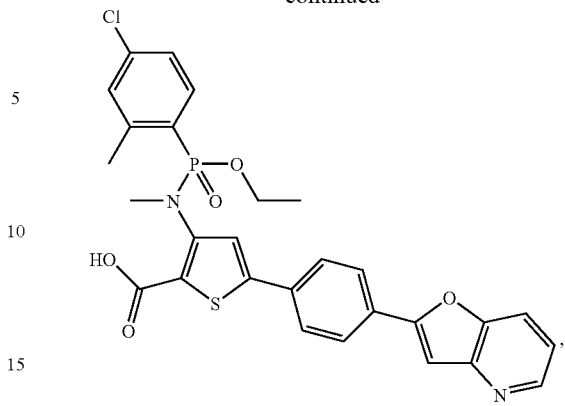
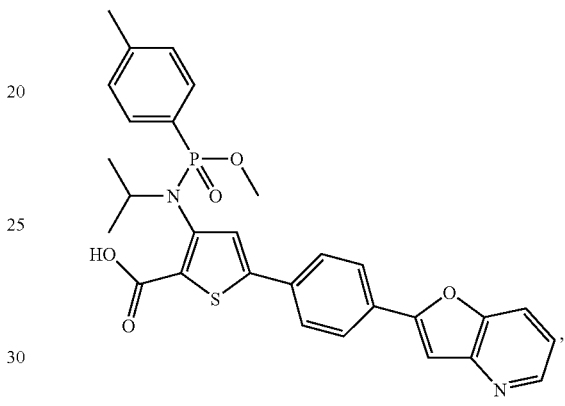
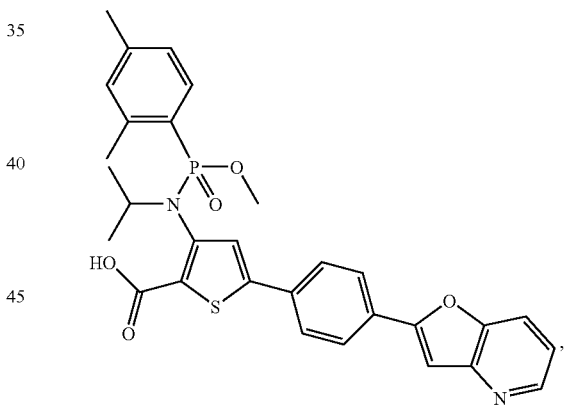
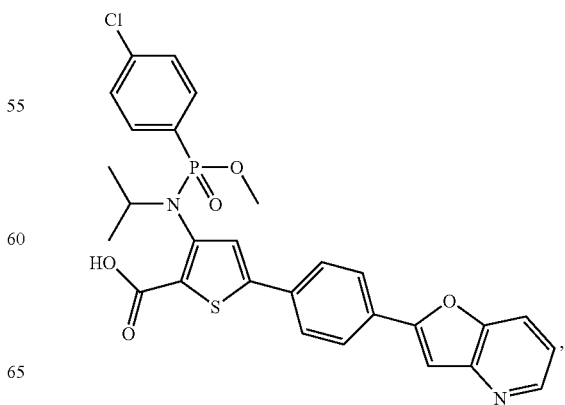

131
-continued
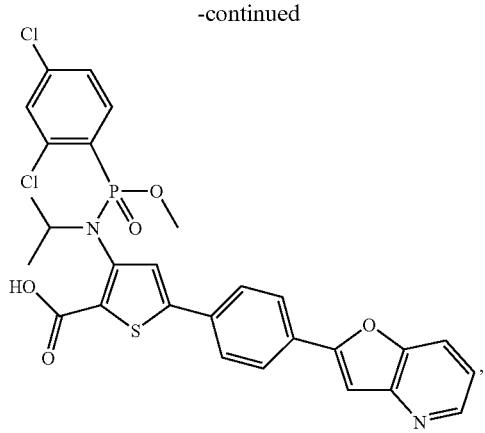
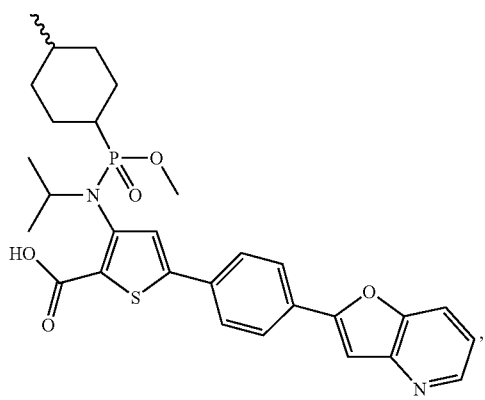
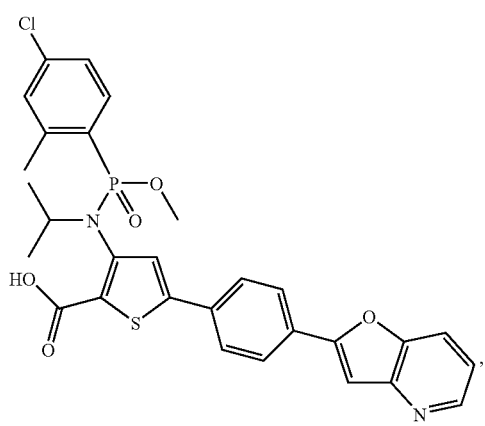
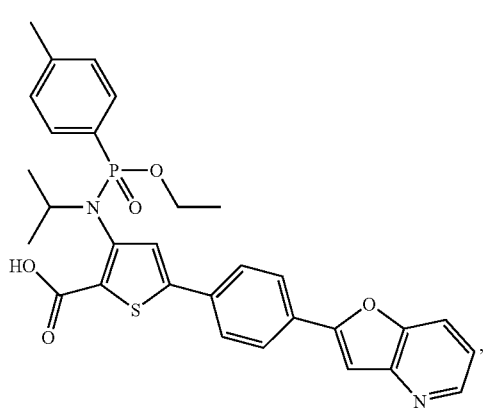
132
-continued
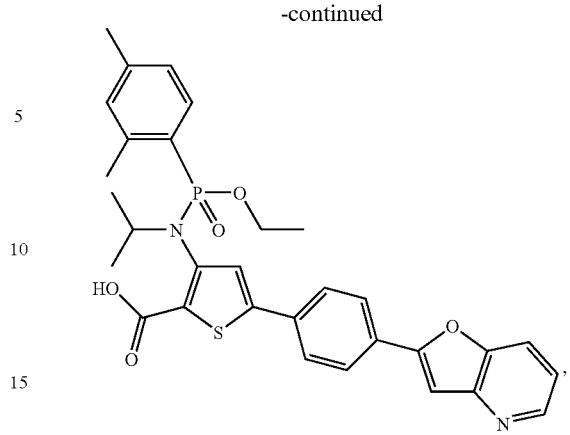
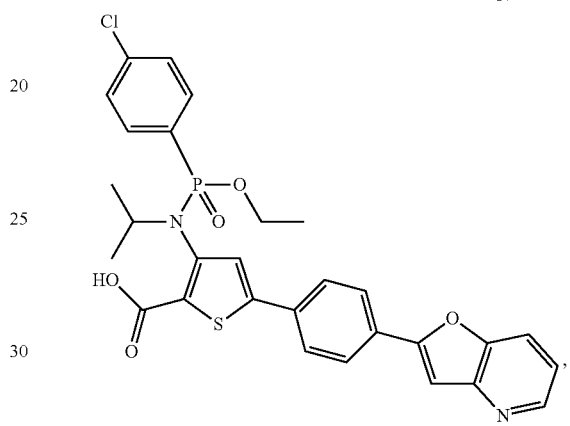
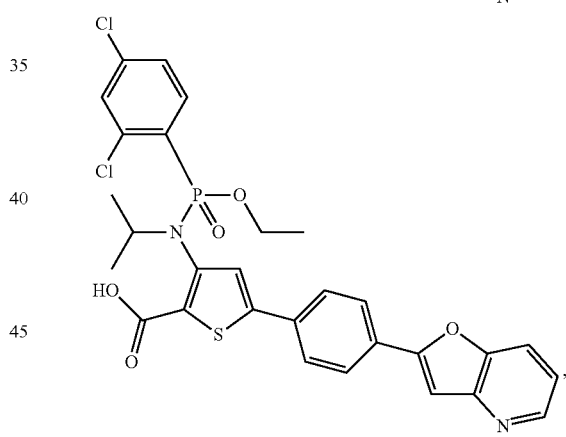
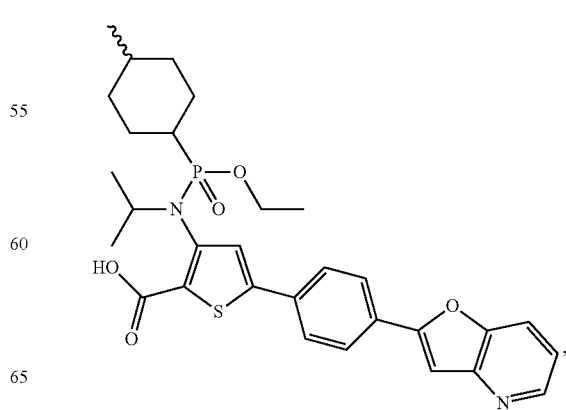

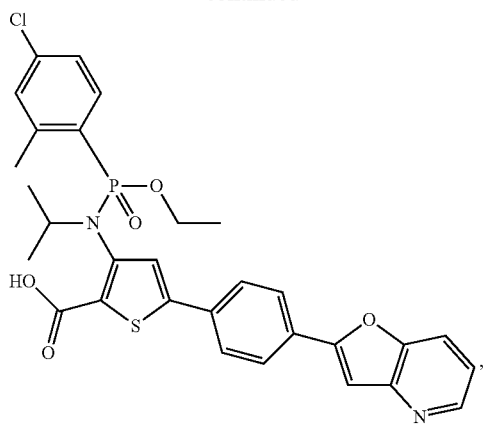
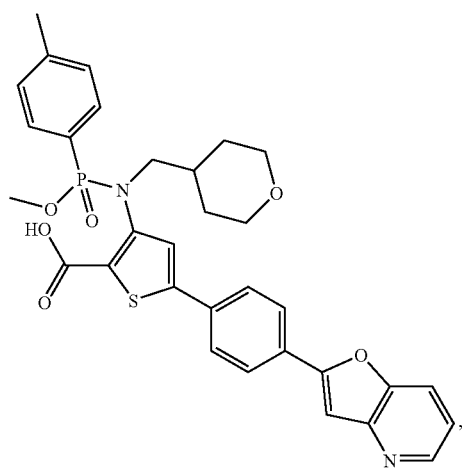
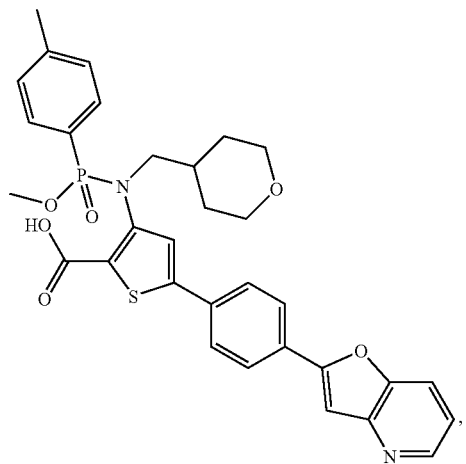
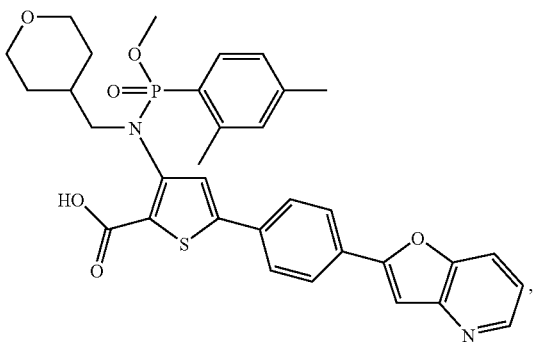
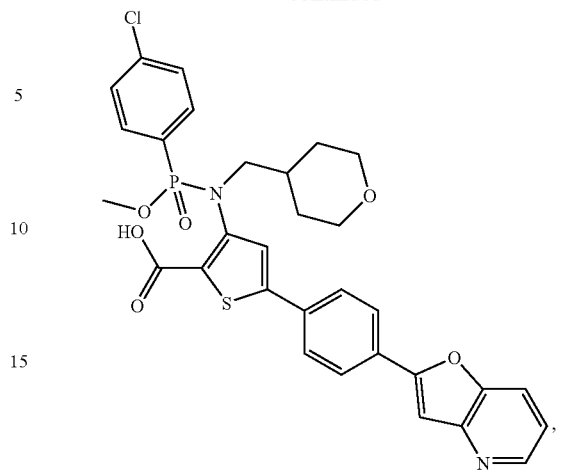
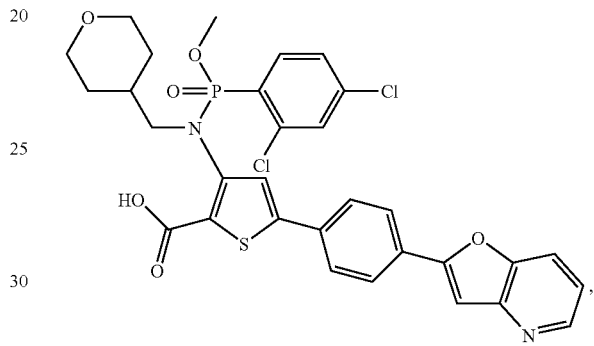
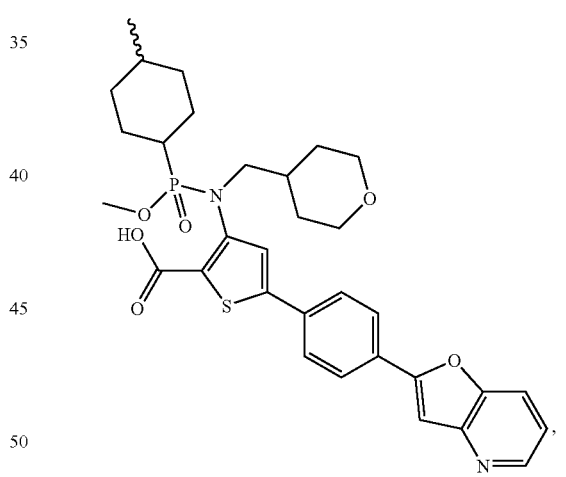
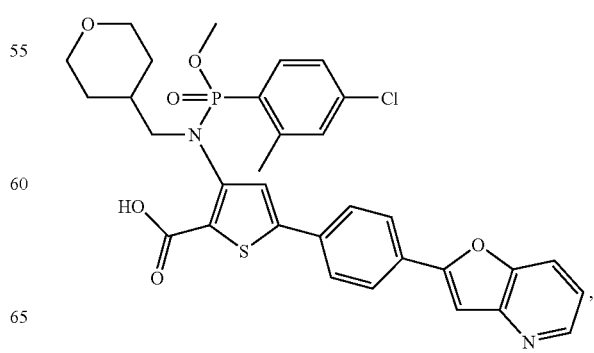

135
-continued
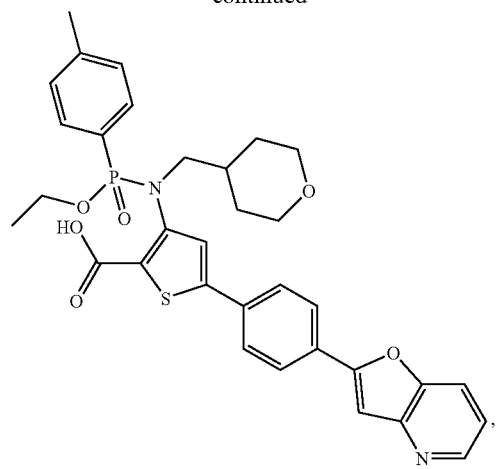
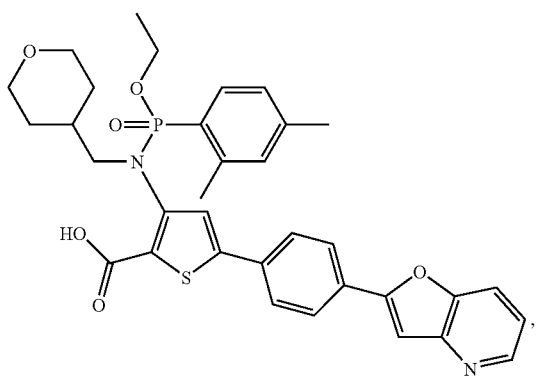
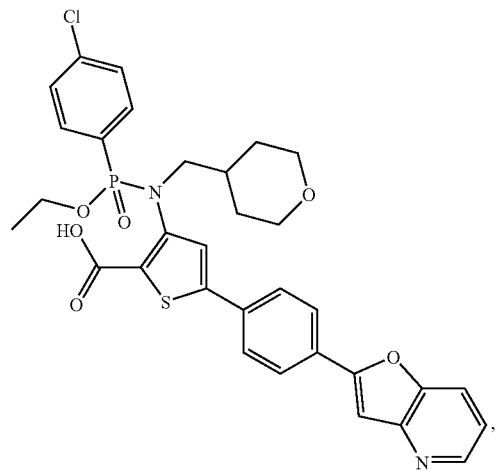
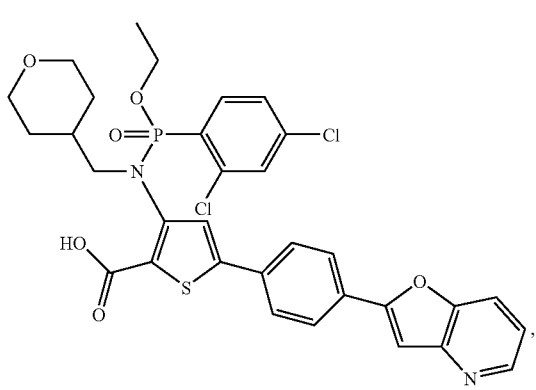
136
-continued
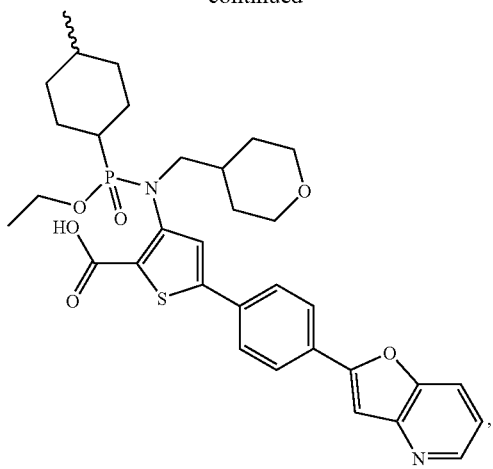
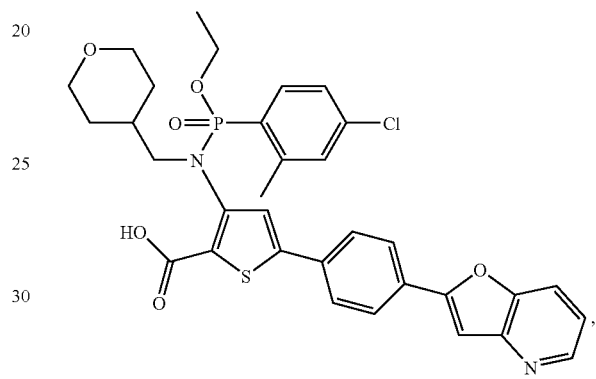
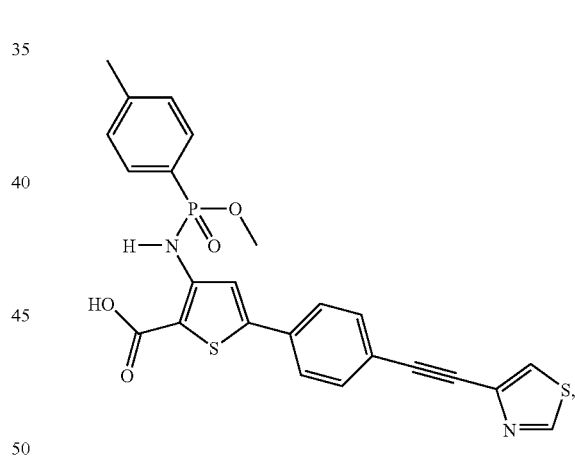
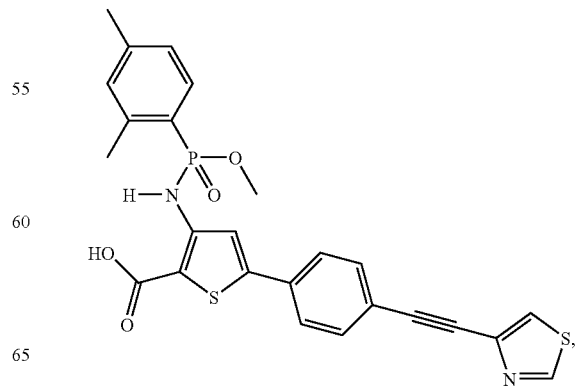

137
-continued
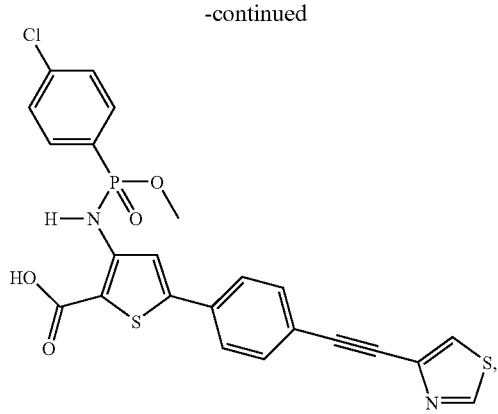
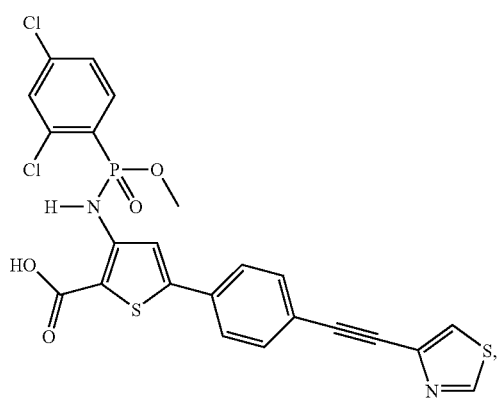
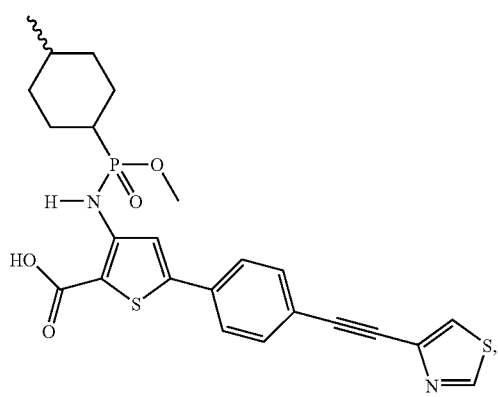
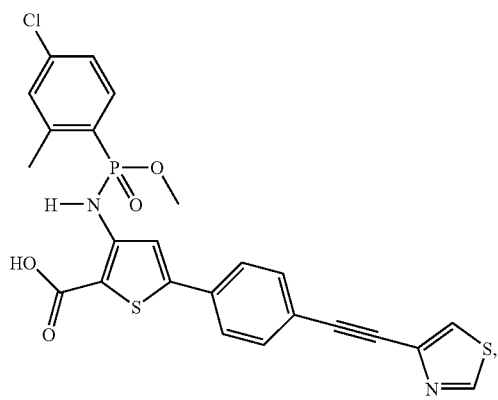
138
-continued
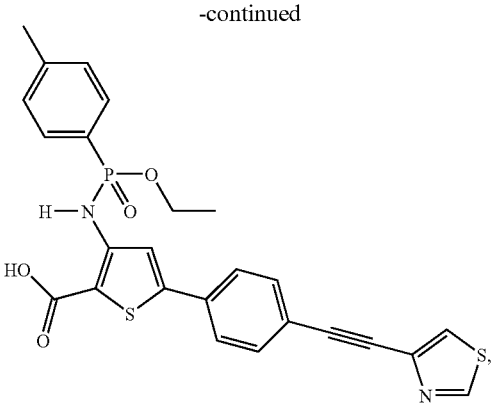
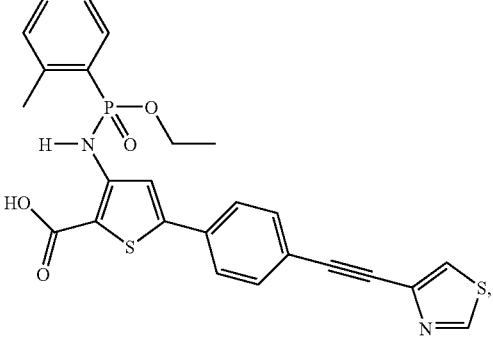
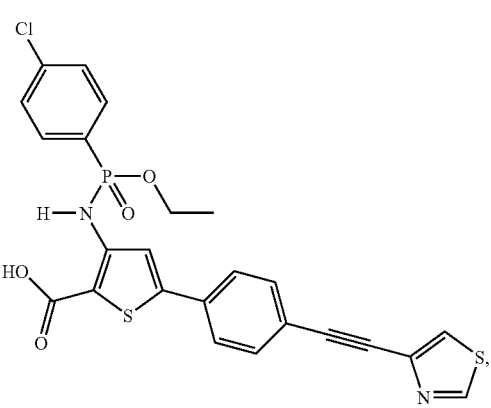
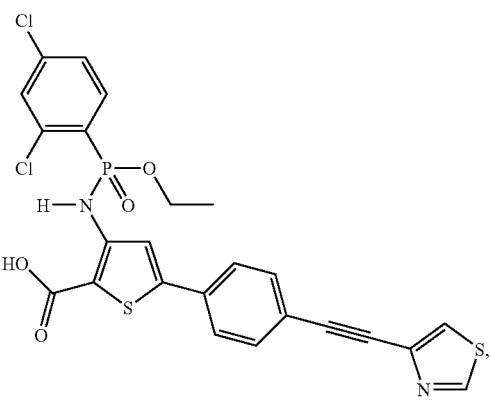

139
-continued
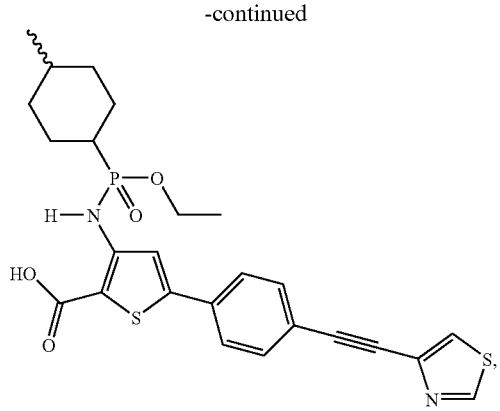
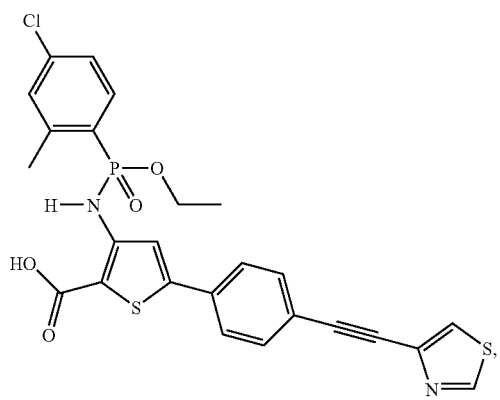
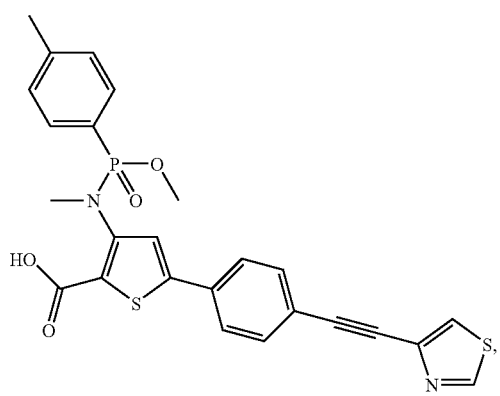
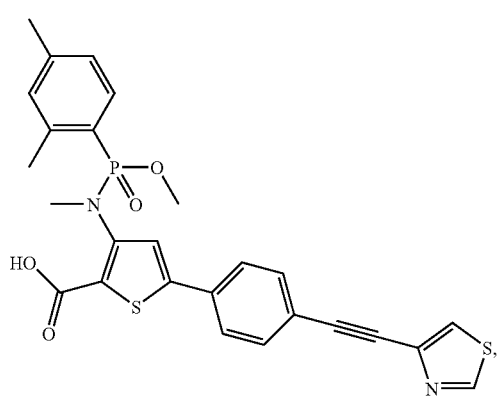
140
-continued
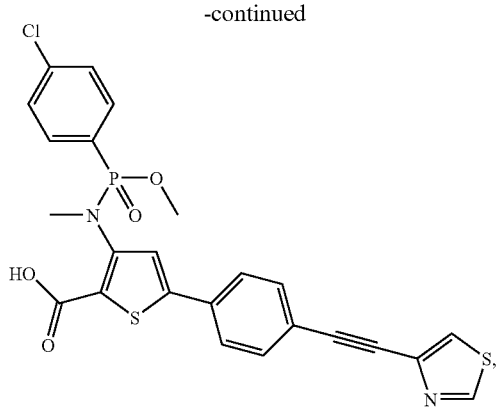
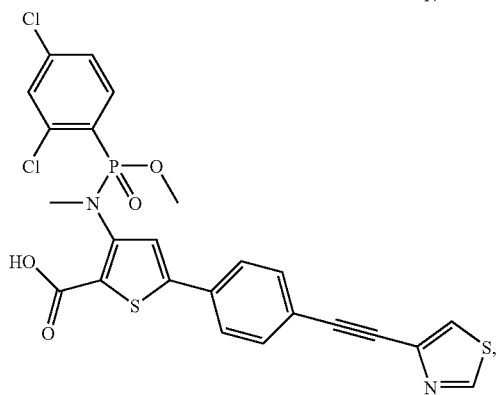

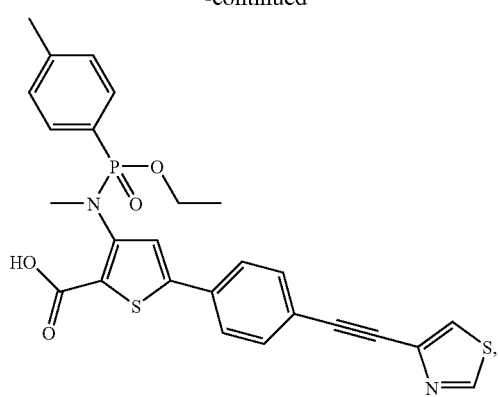
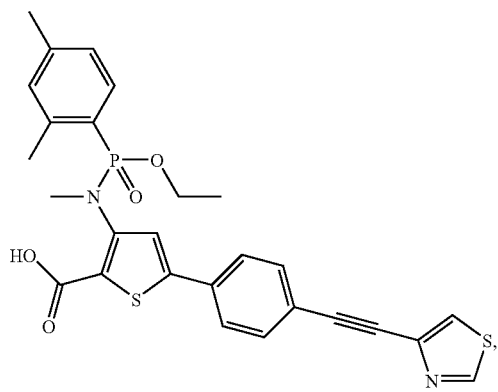
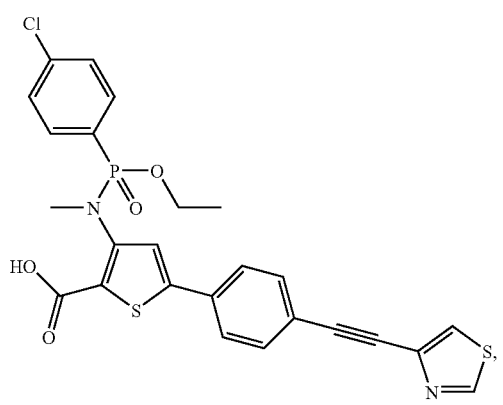
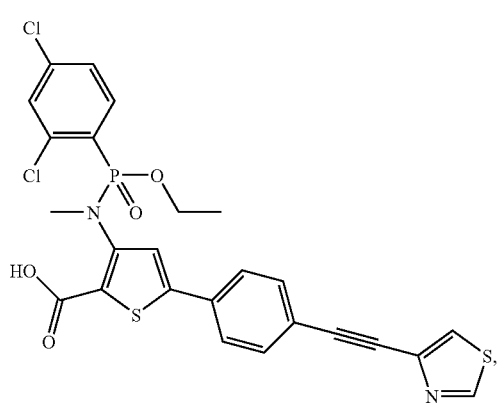
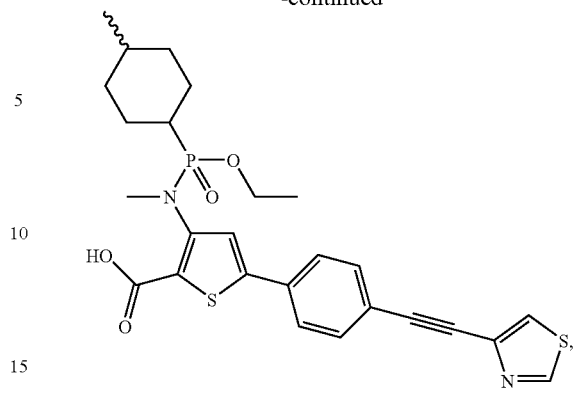
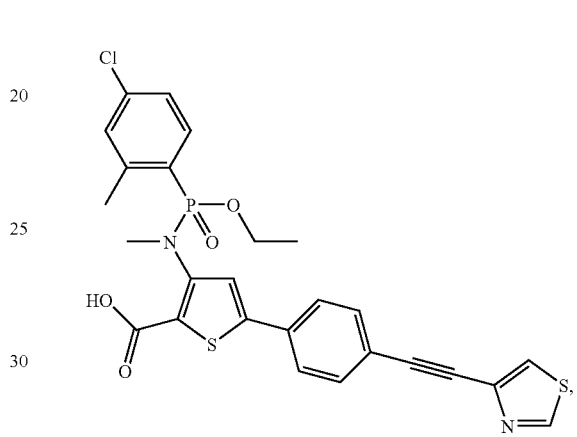

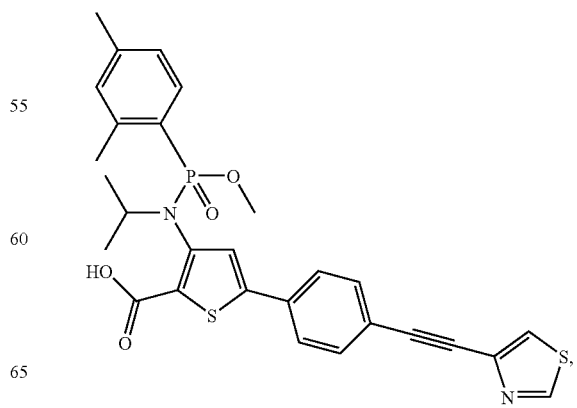

143
-continued
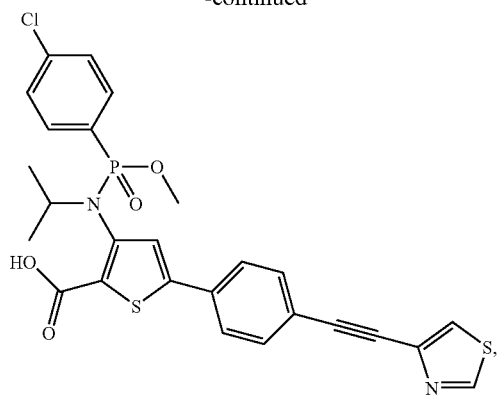
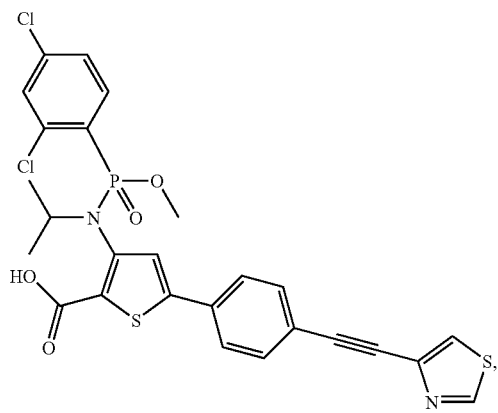
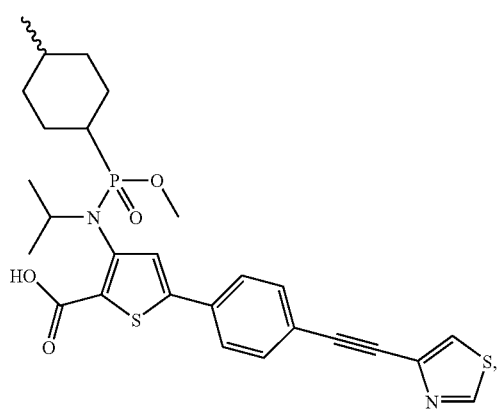
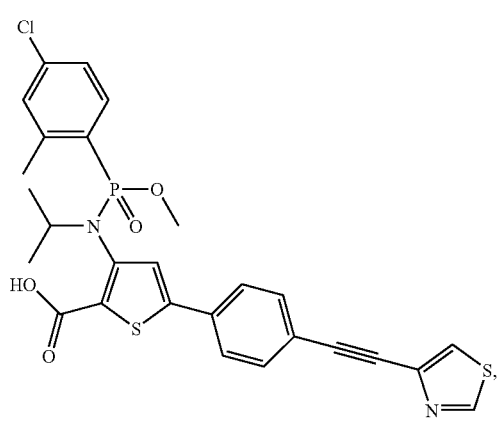
144
-continued
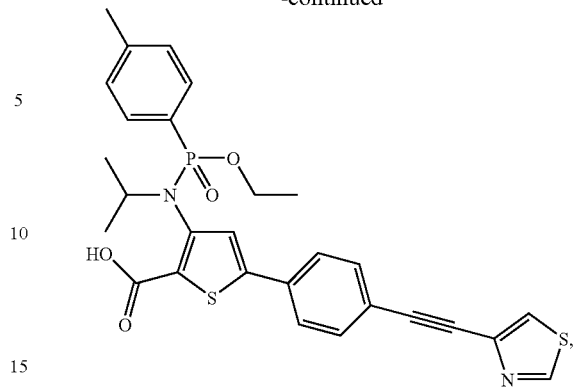
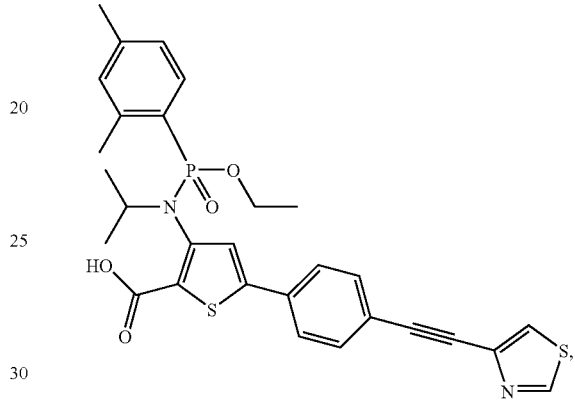
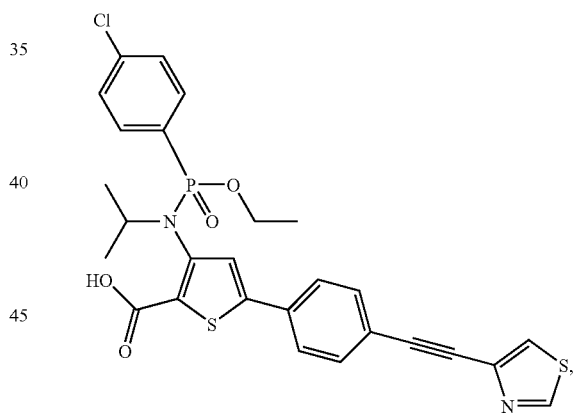
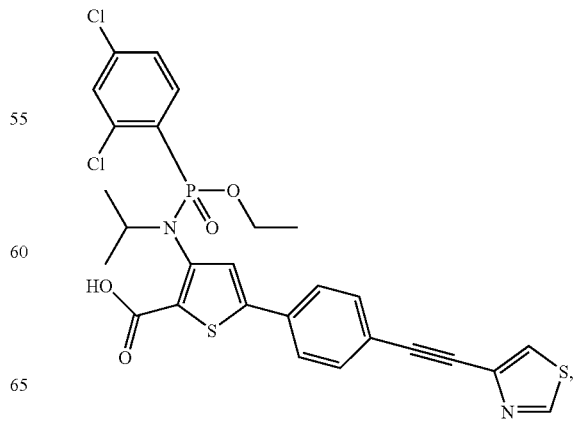

145
-continued
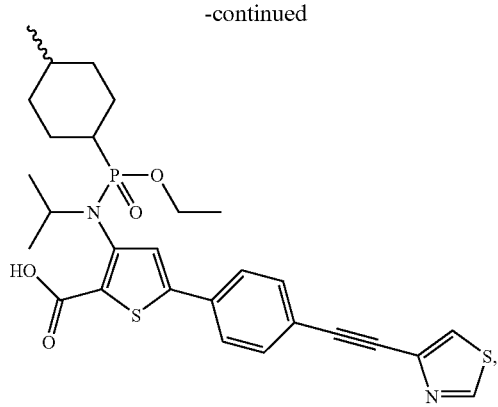
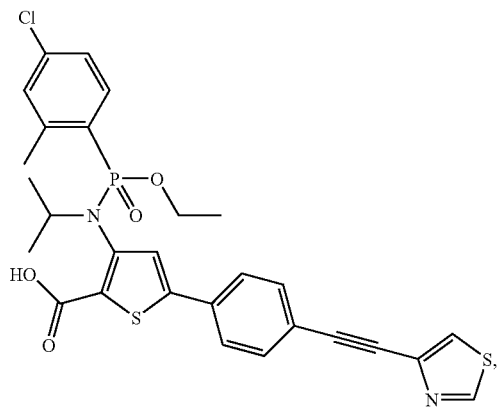
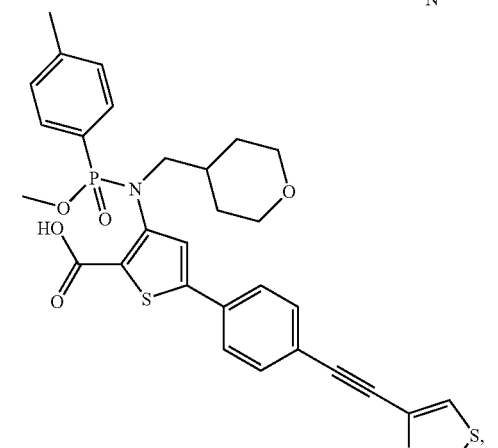
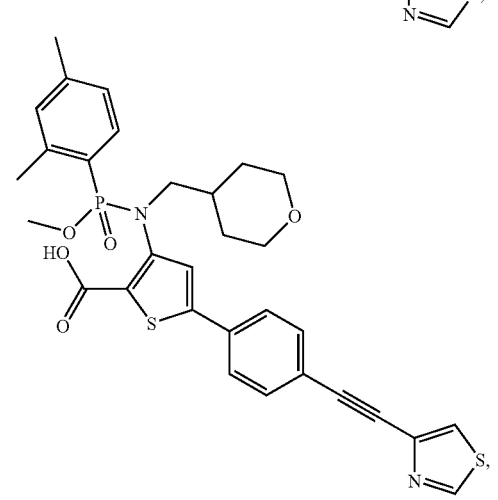
146
-continued
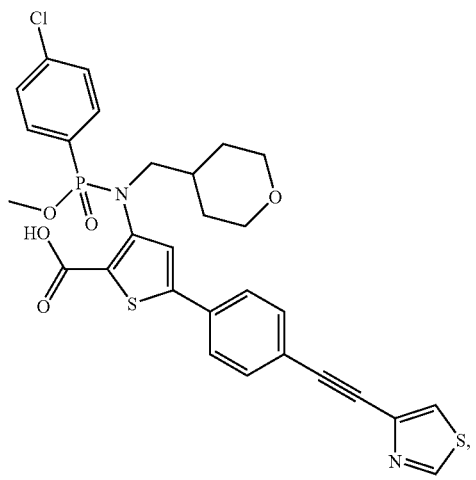
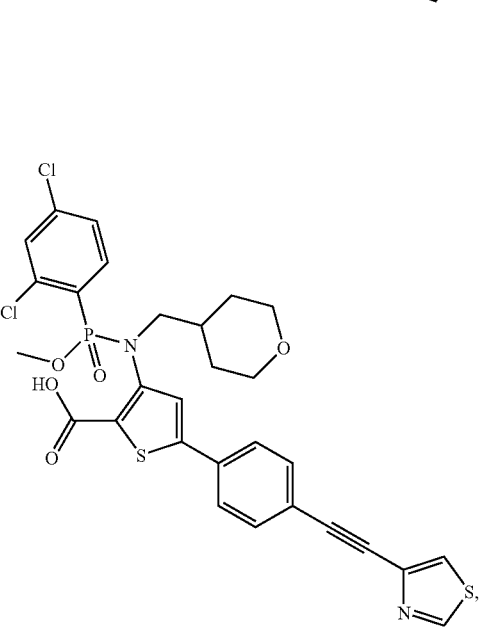
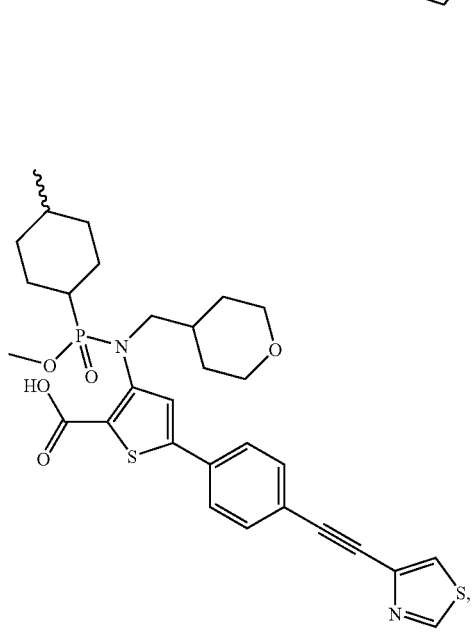

147
-continued
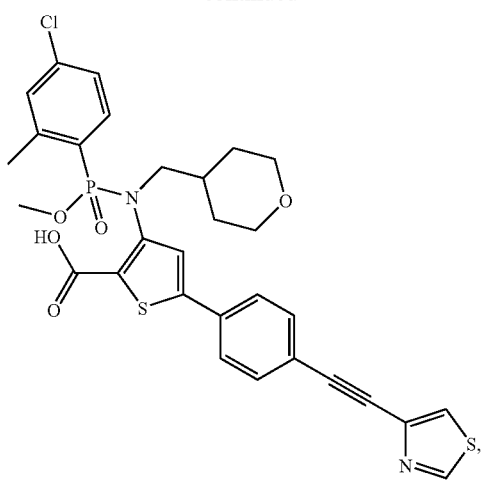
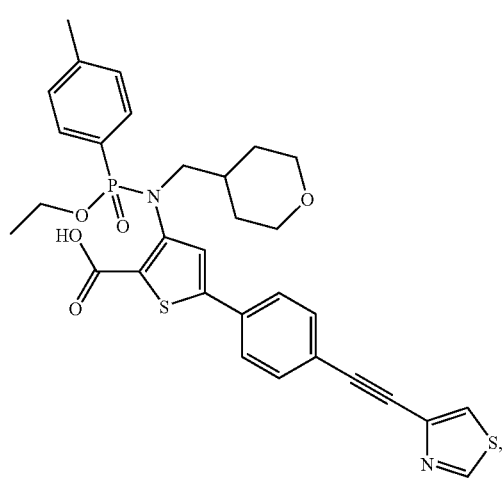
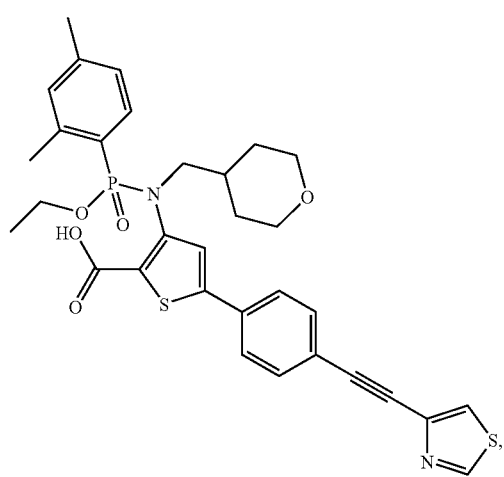
148
-continued
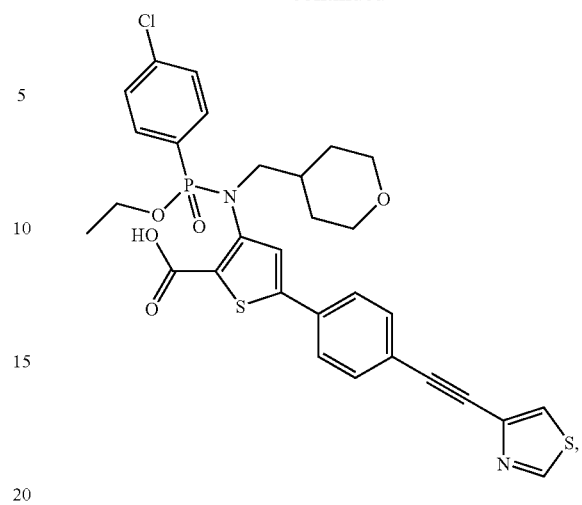
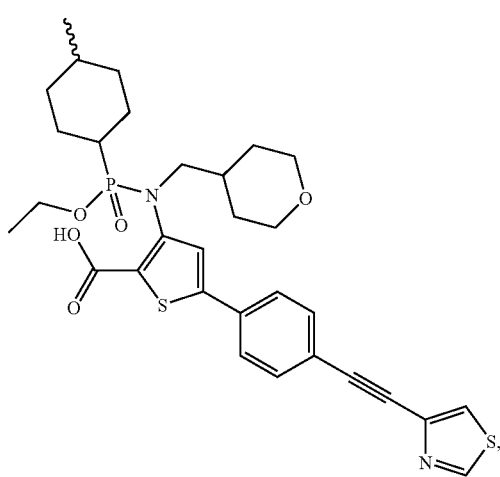

149
-continued
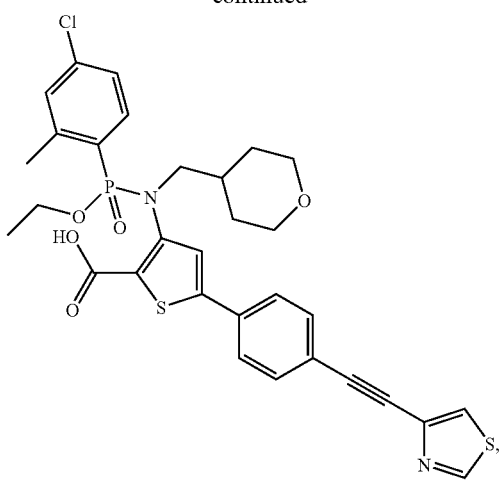
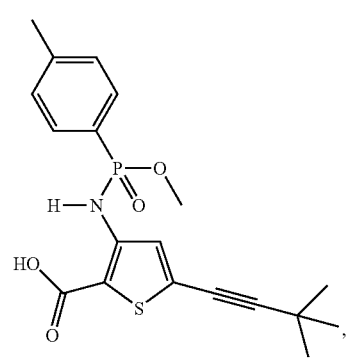
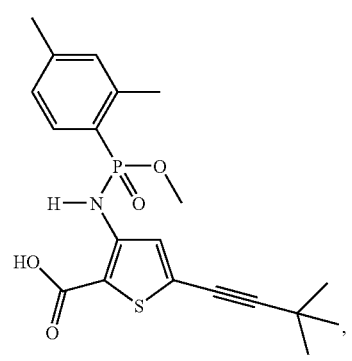
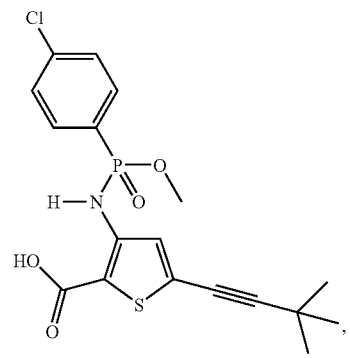
150
-continued
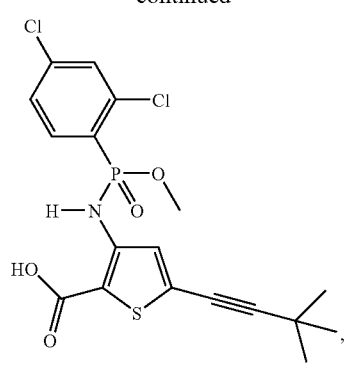
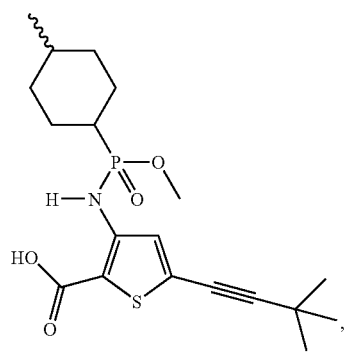
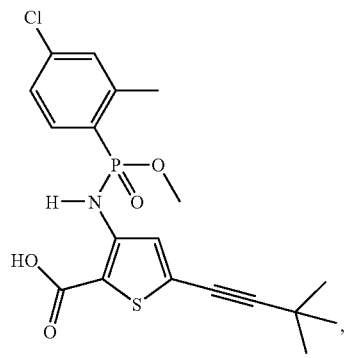
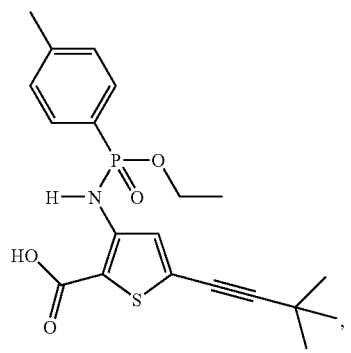

151
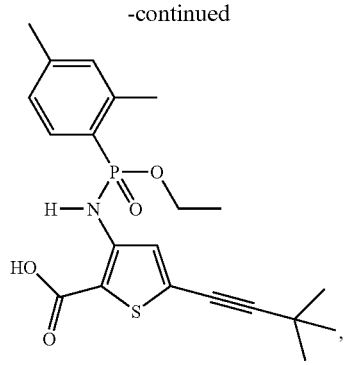
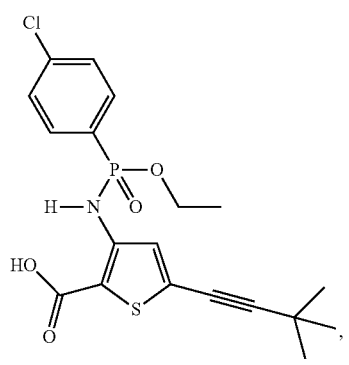
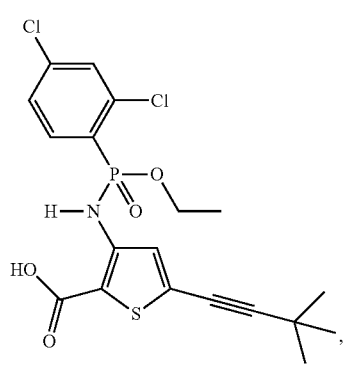
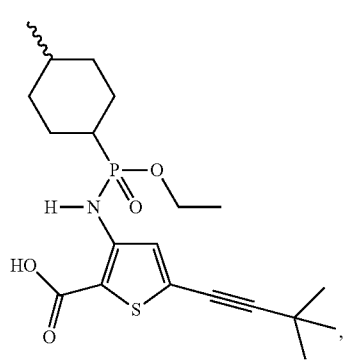
152
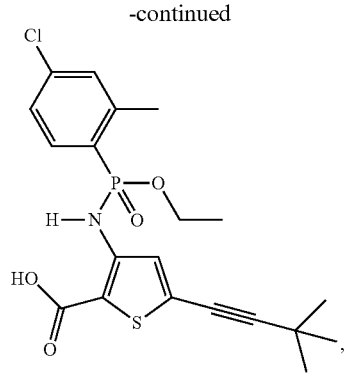
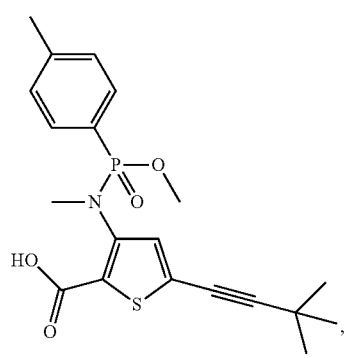
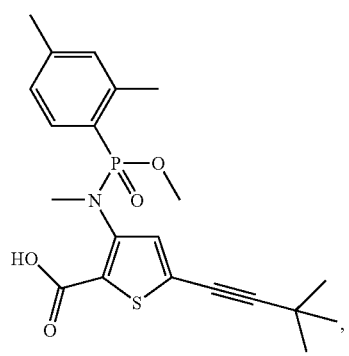
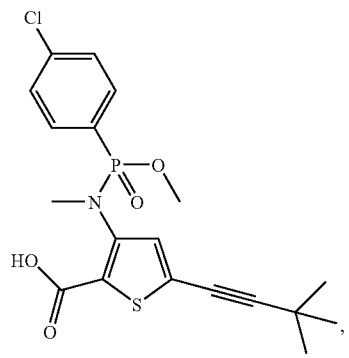

153
-continued
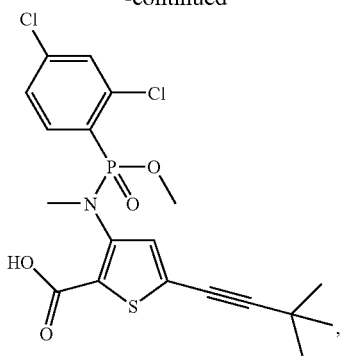
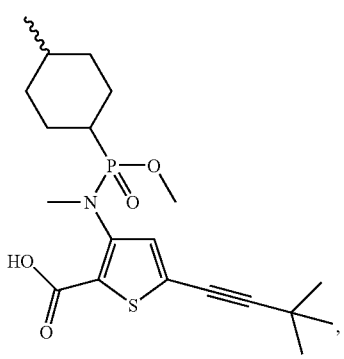
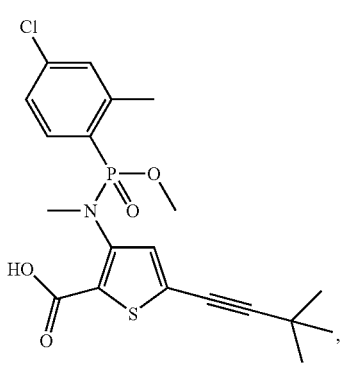
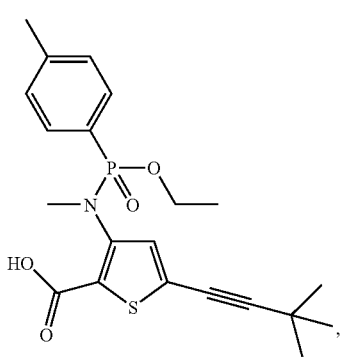
154
-continued
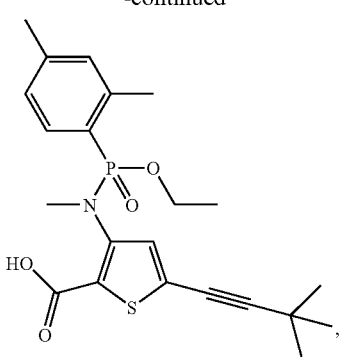
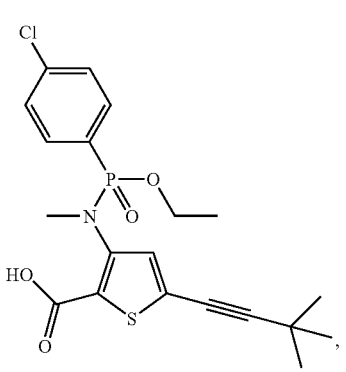
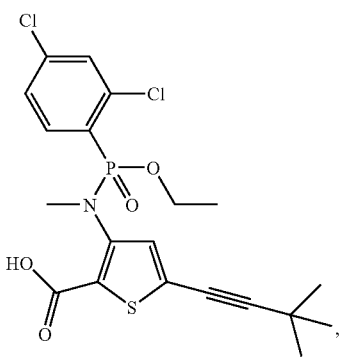
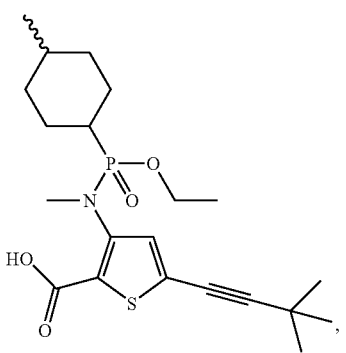

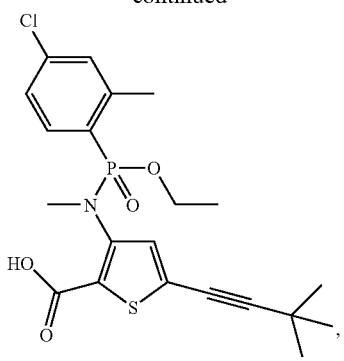
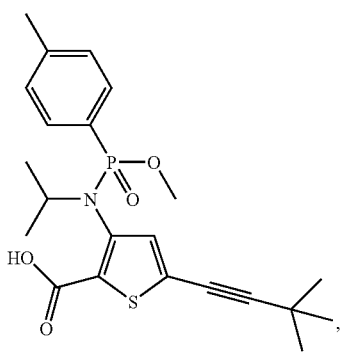
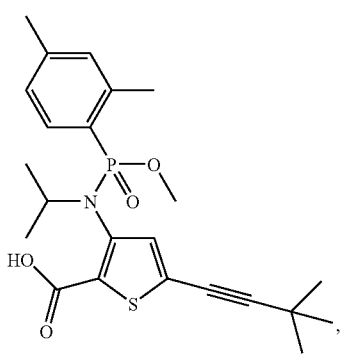
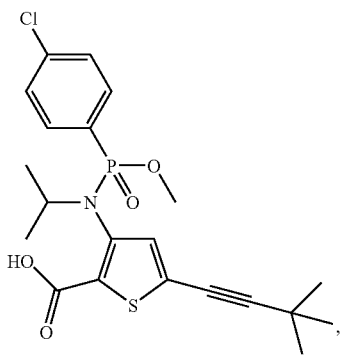
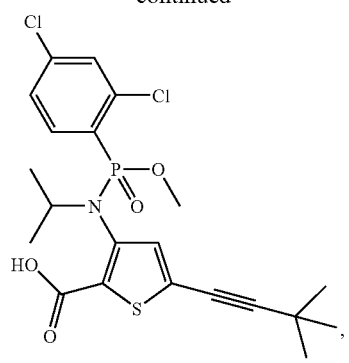
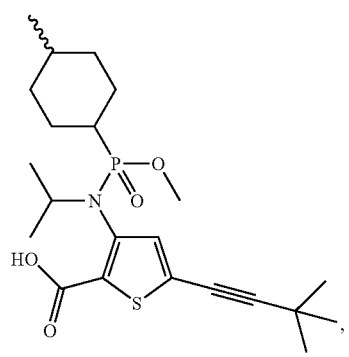
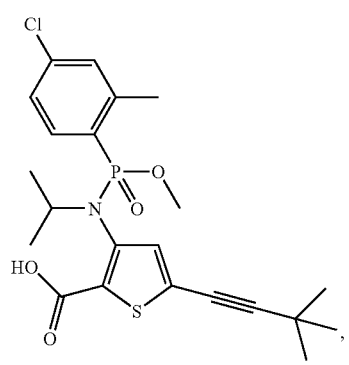
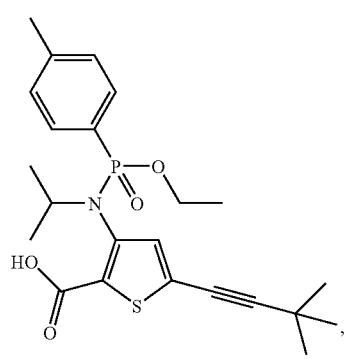

157
-continued
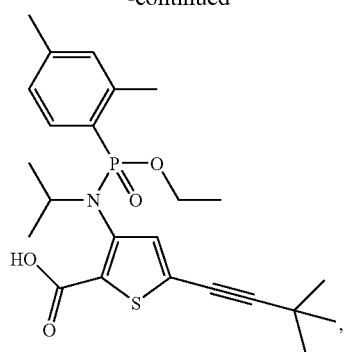
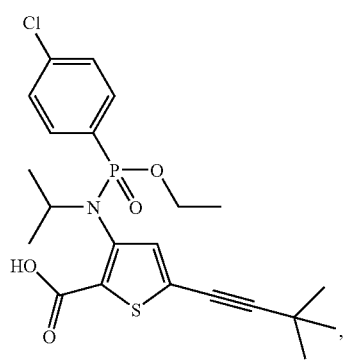
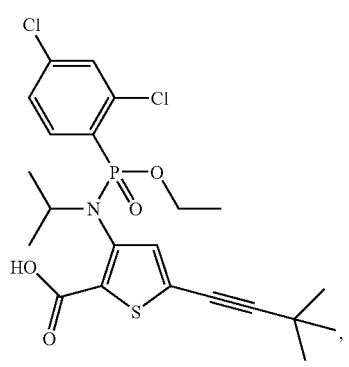
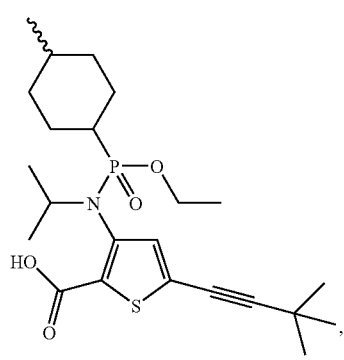
158
-continued
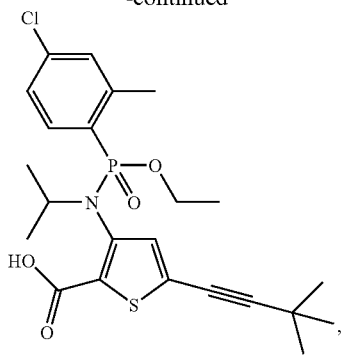
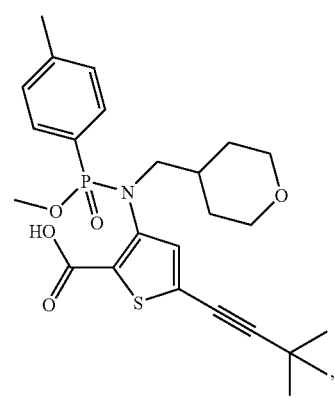
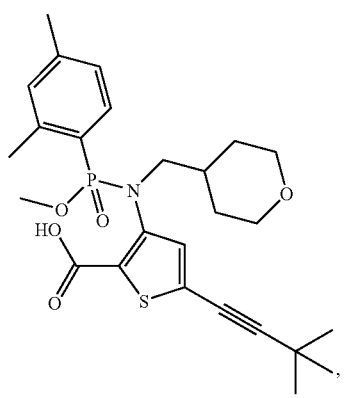
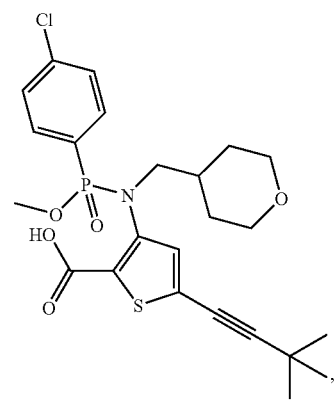

159
-continued
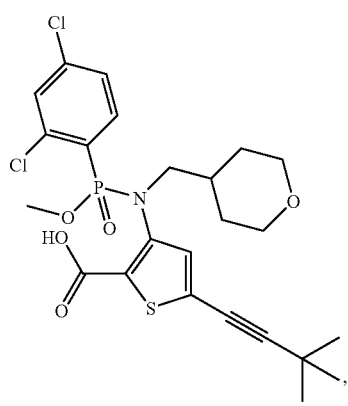
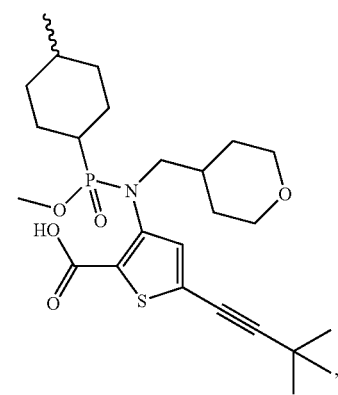
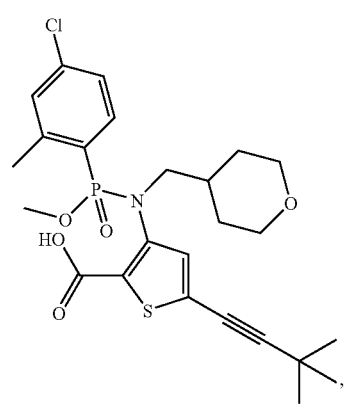
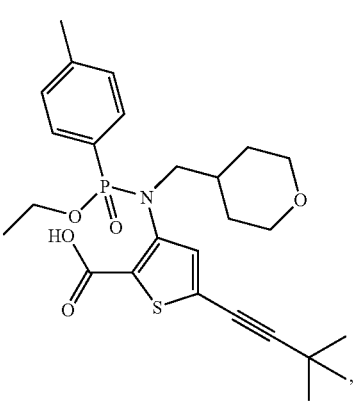
160
-continued
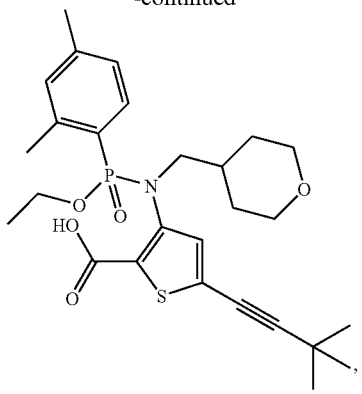
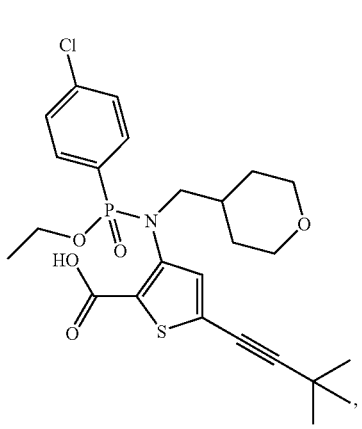
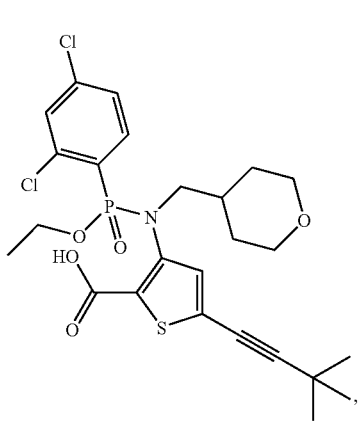
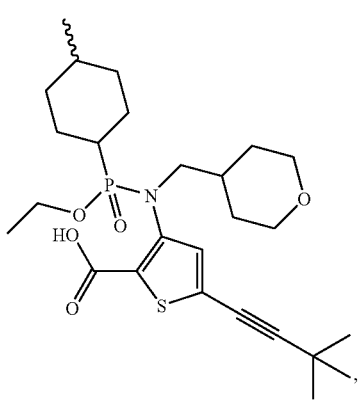

161
-continued
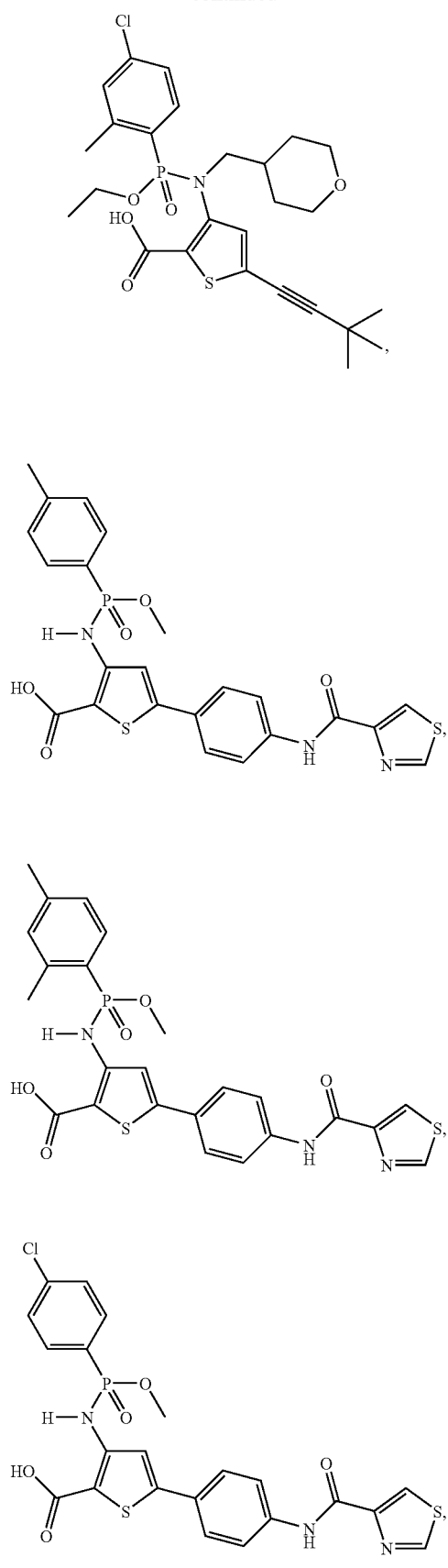
162
-continued
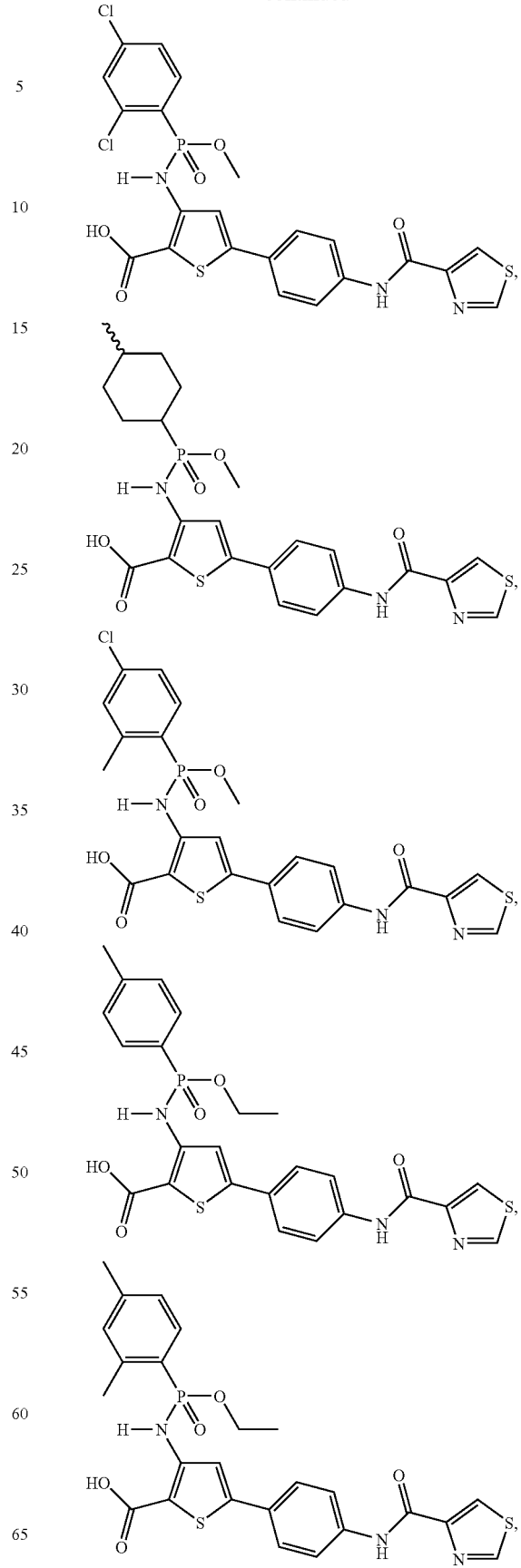

163
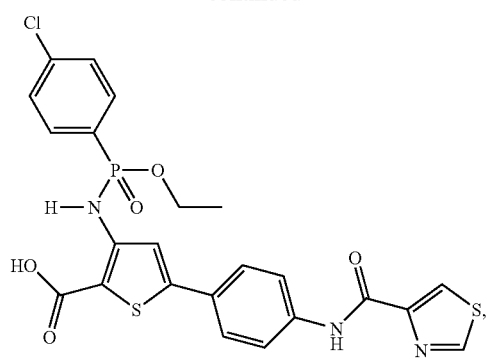
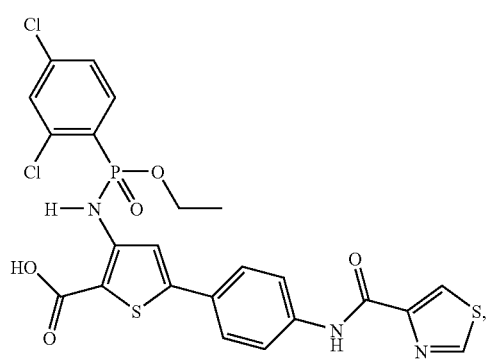
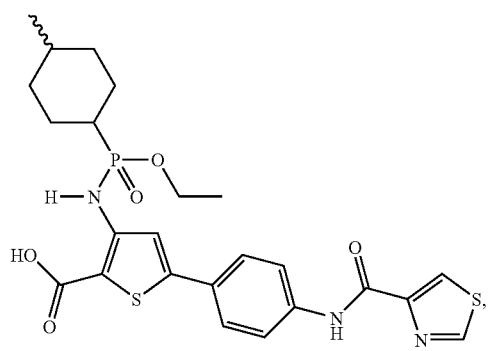
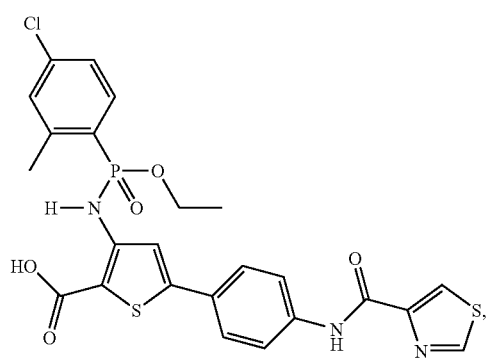
164
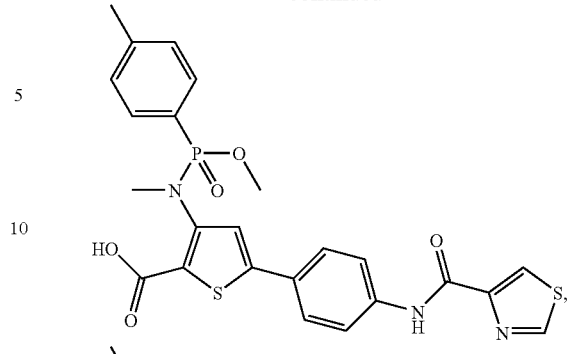
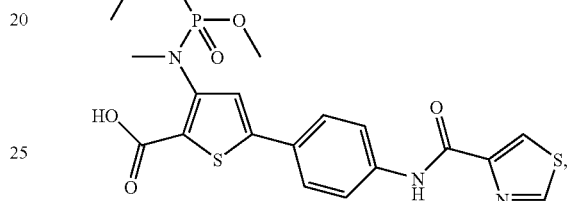
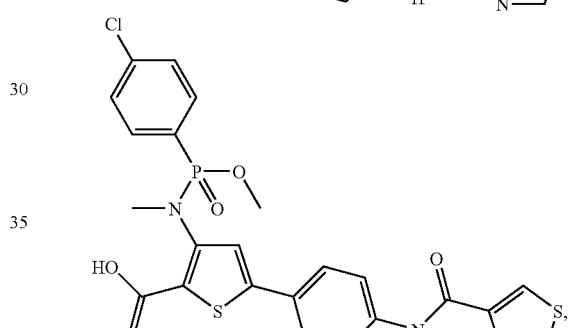
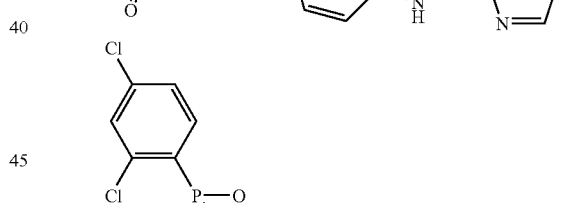
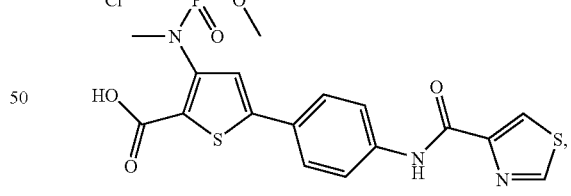
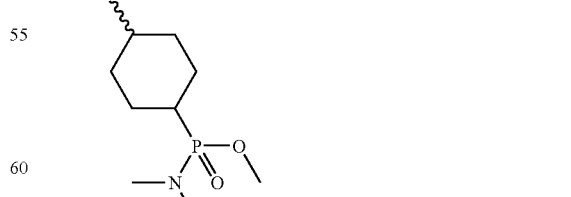
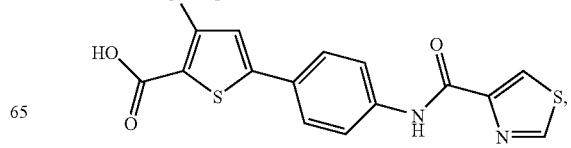

165
-continued
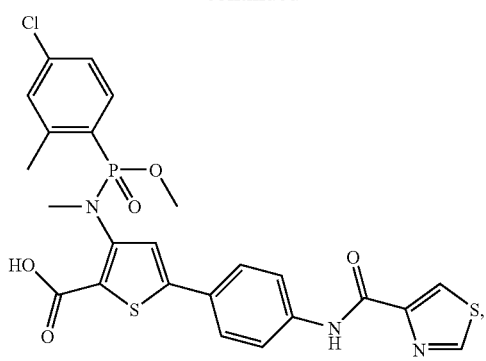
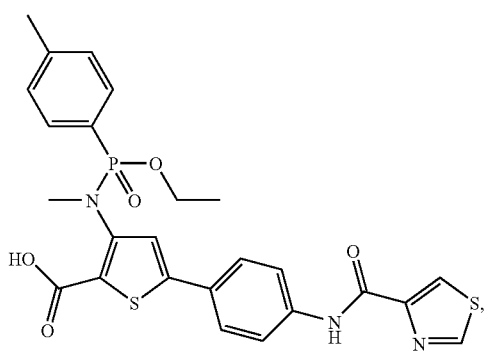
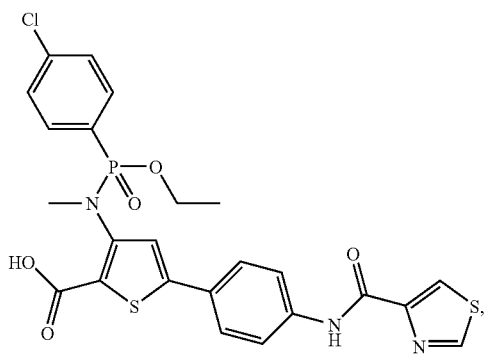
166
-continued
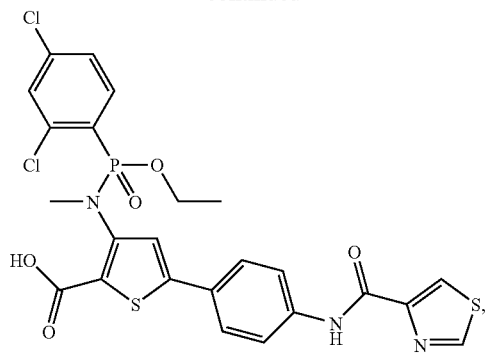
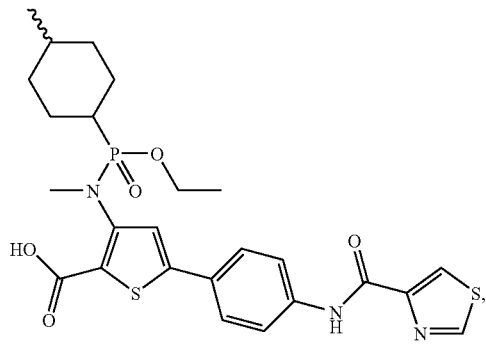
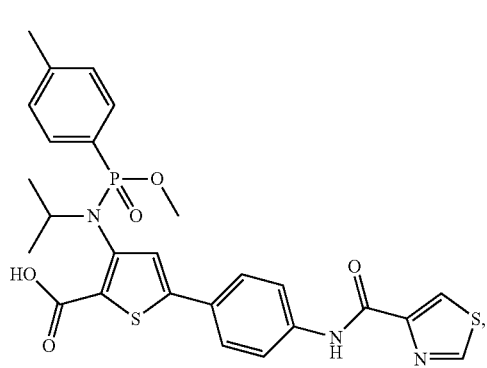

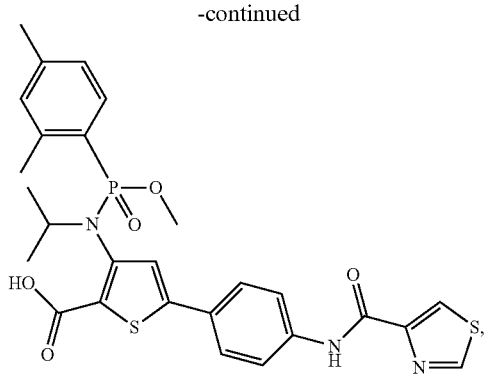
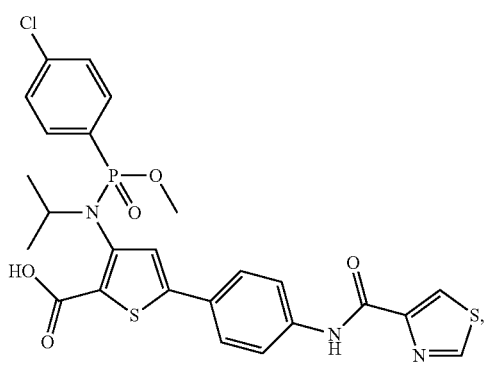
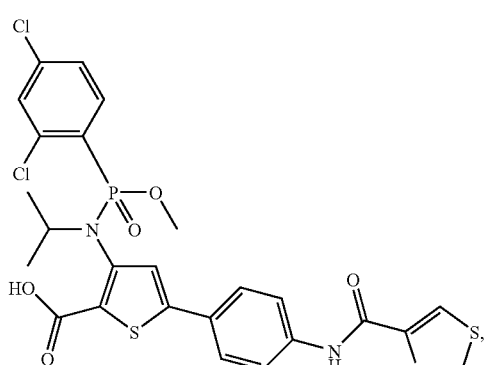
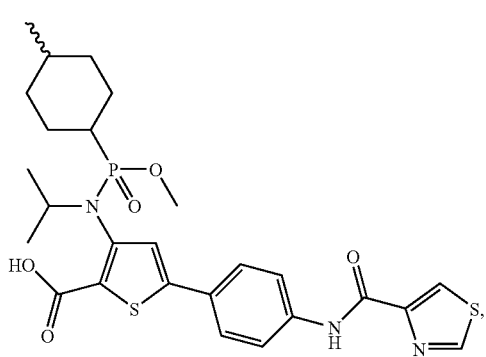
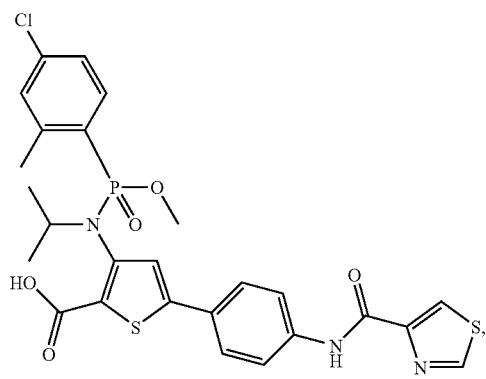
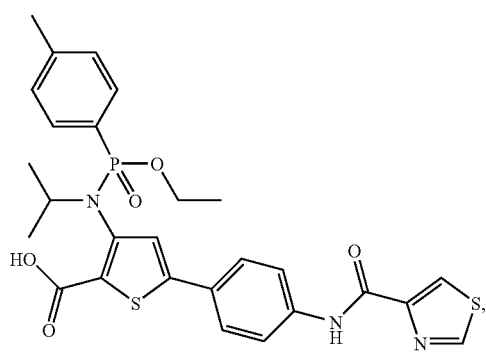
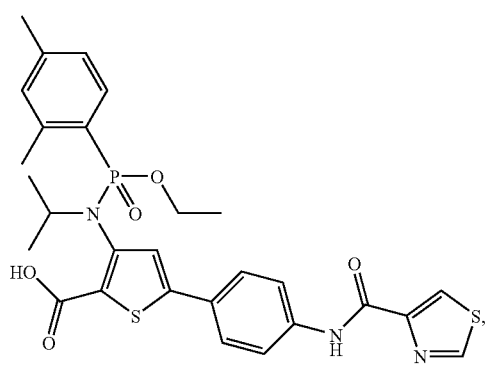
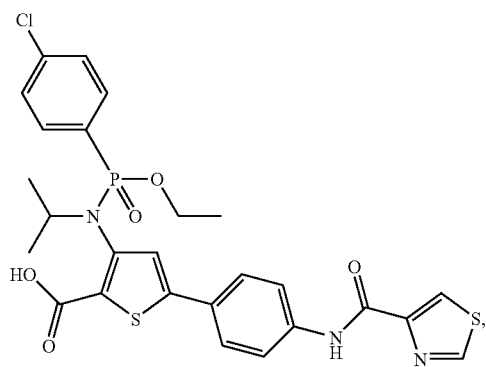

169
-continued
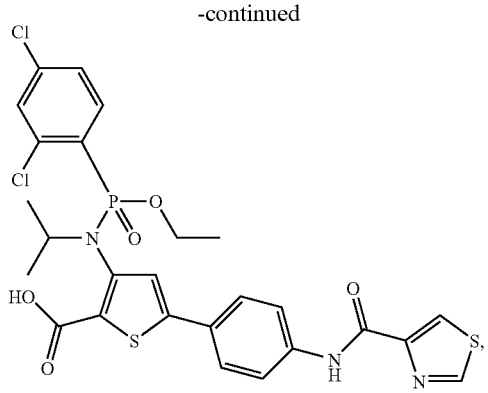
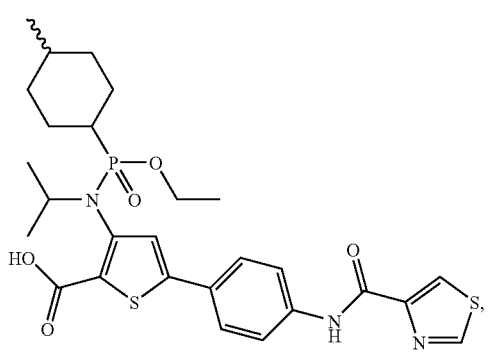
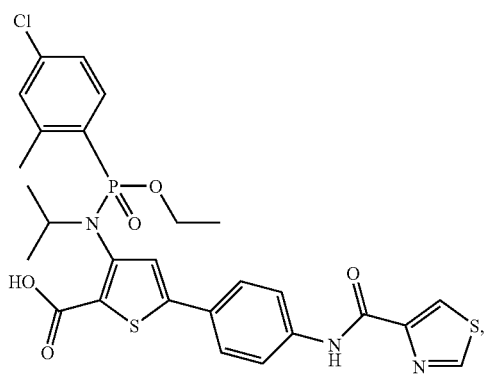
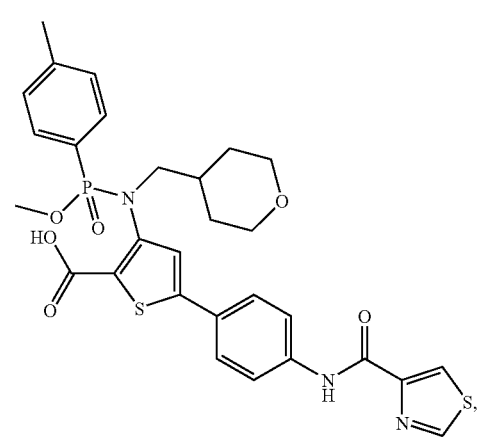
170
-continued
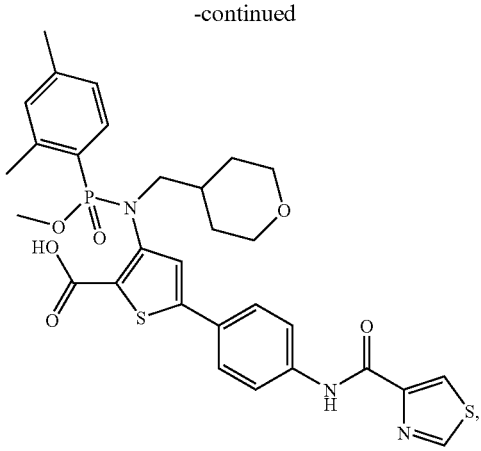
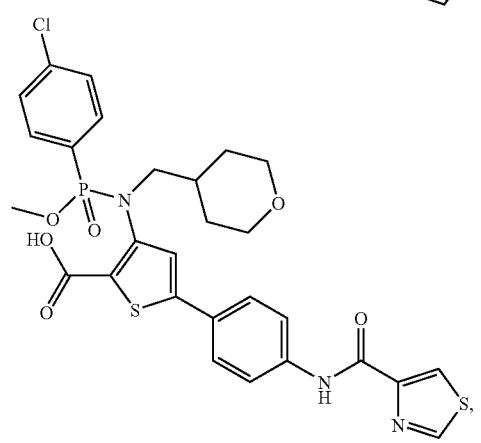
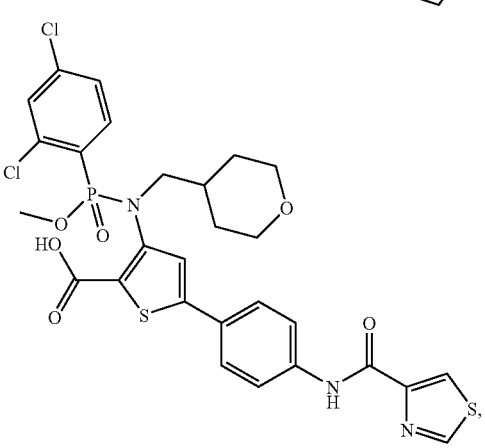
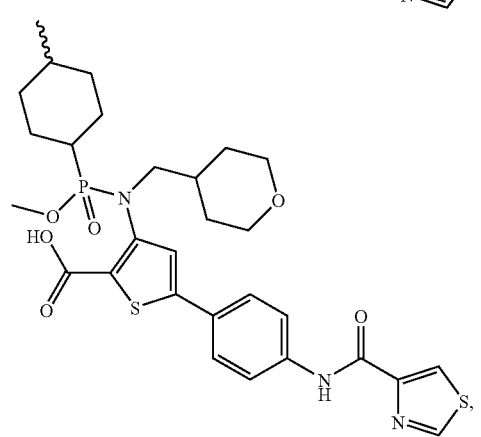

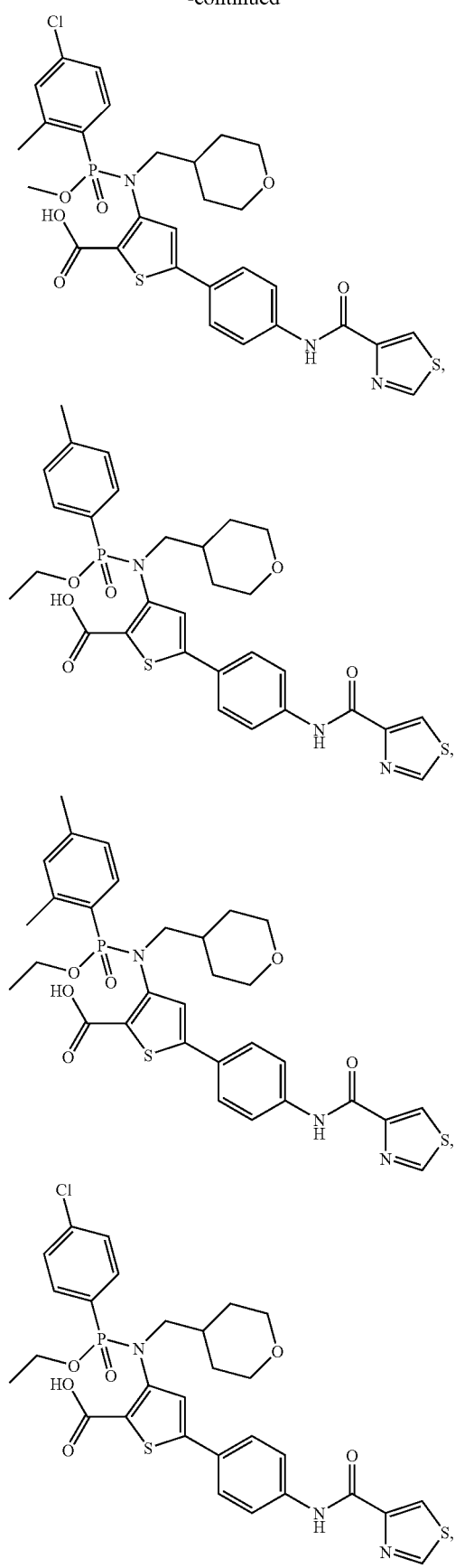
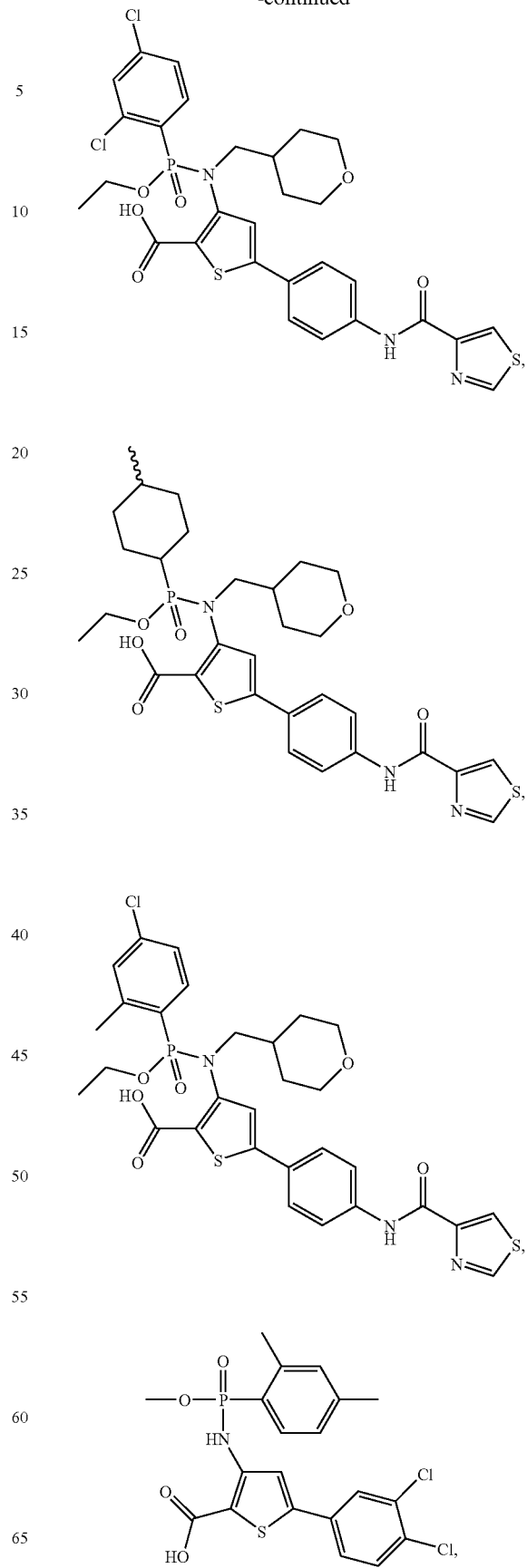

-continued
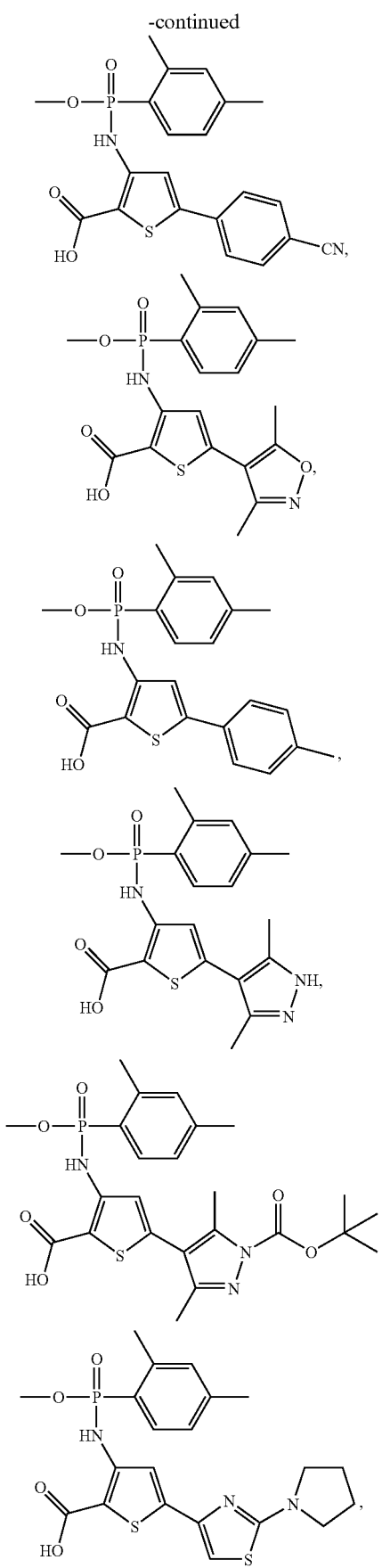
-continued
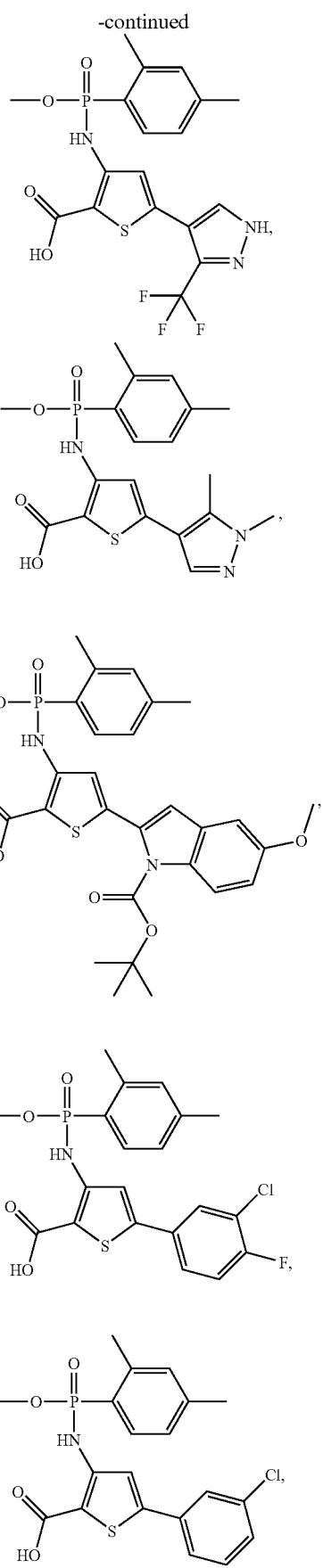

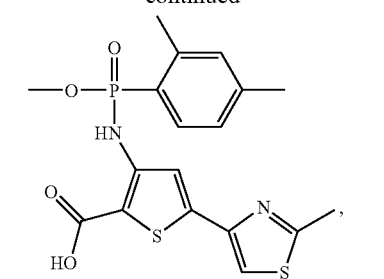
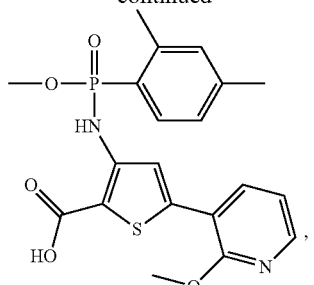
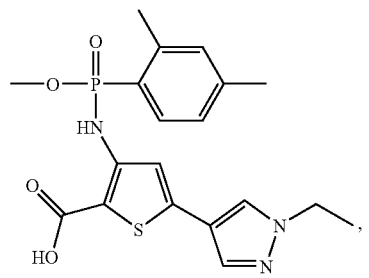
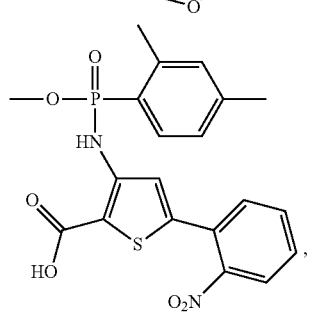
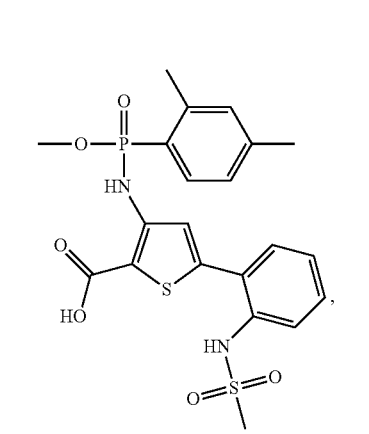
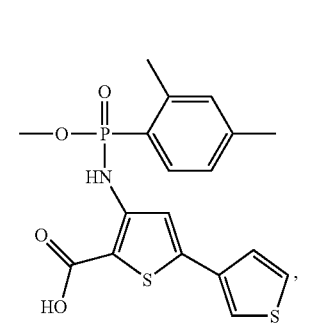
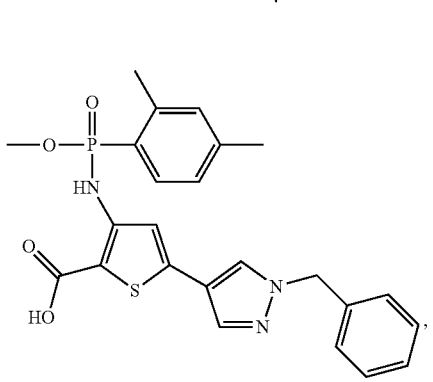
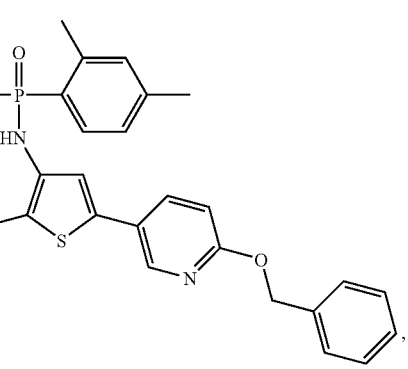
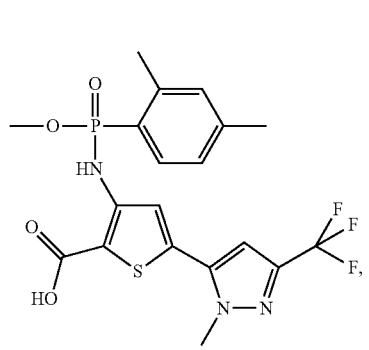
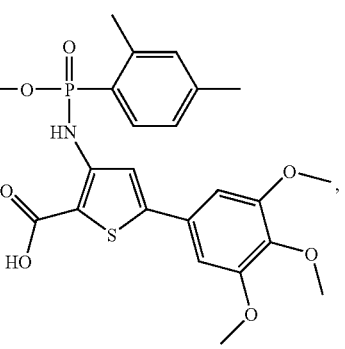

177
-continued
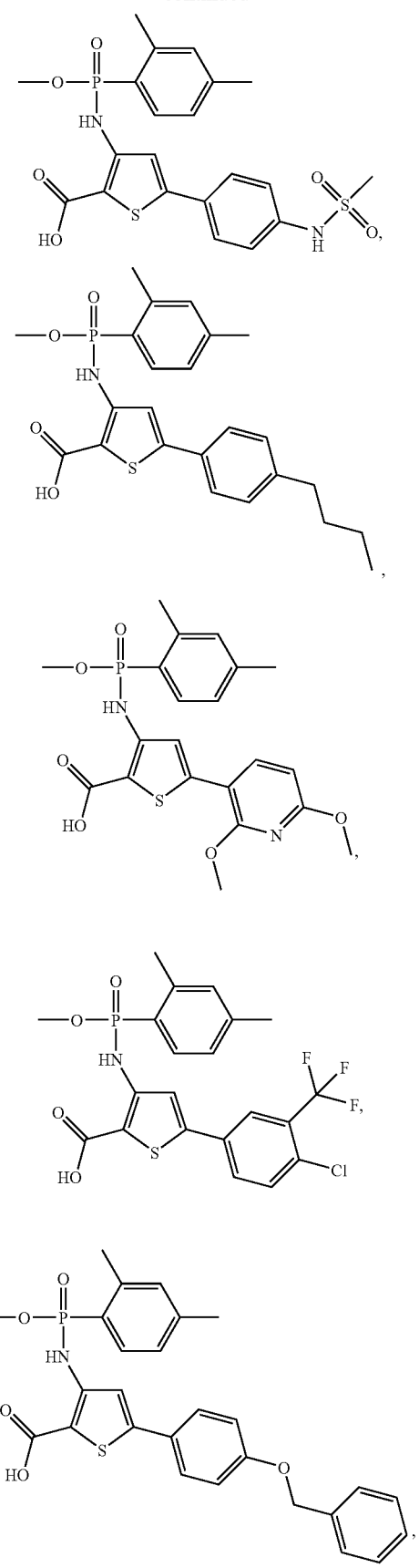
178
-continued
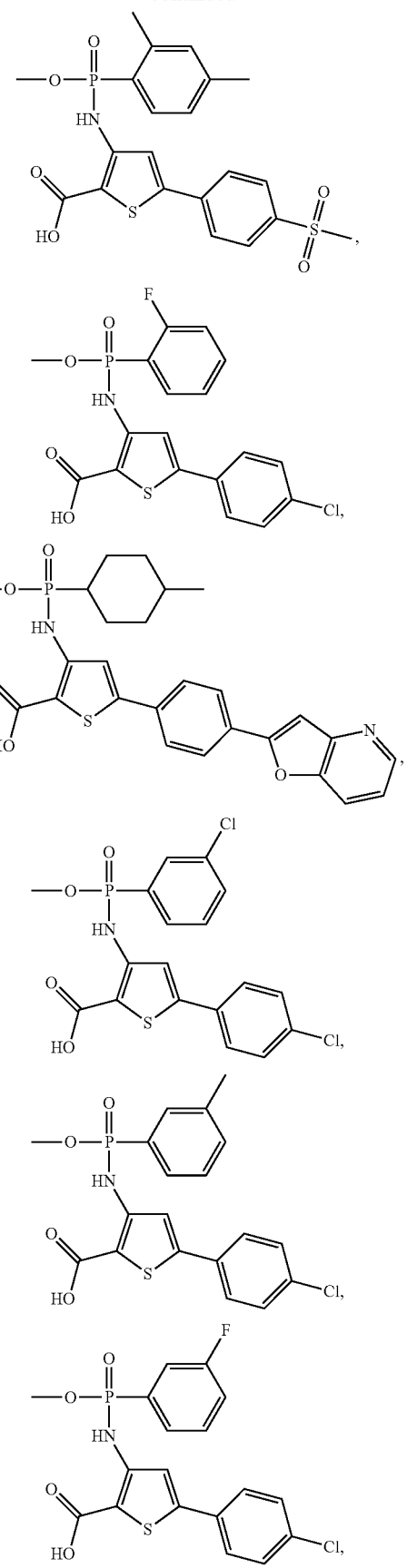

179
-continued
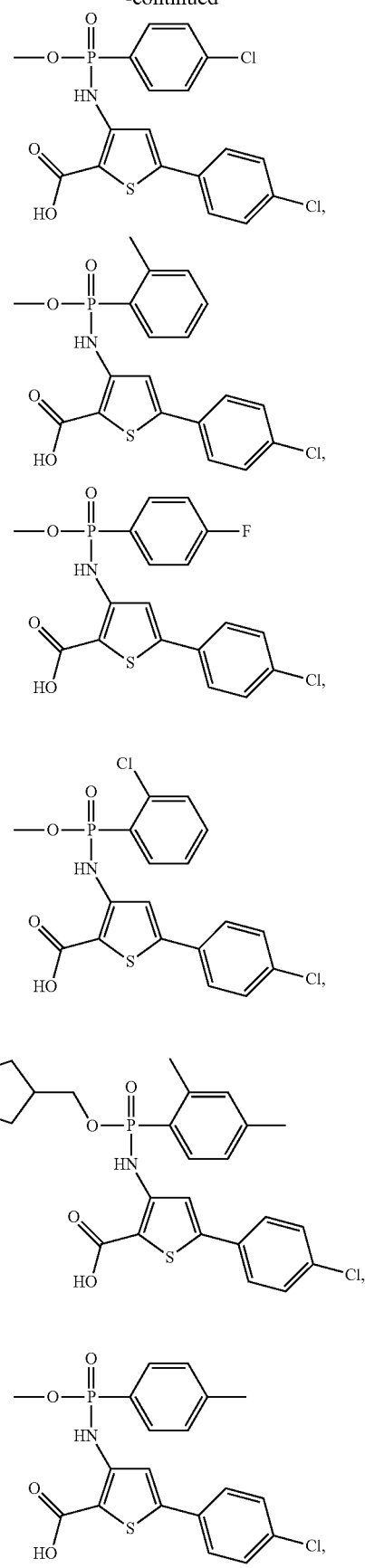
180
-continued
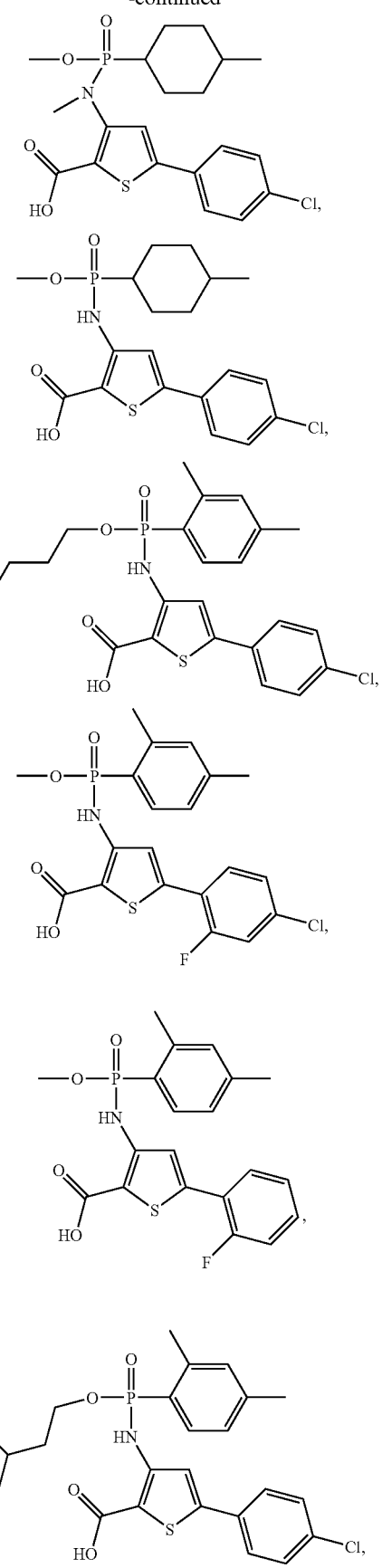

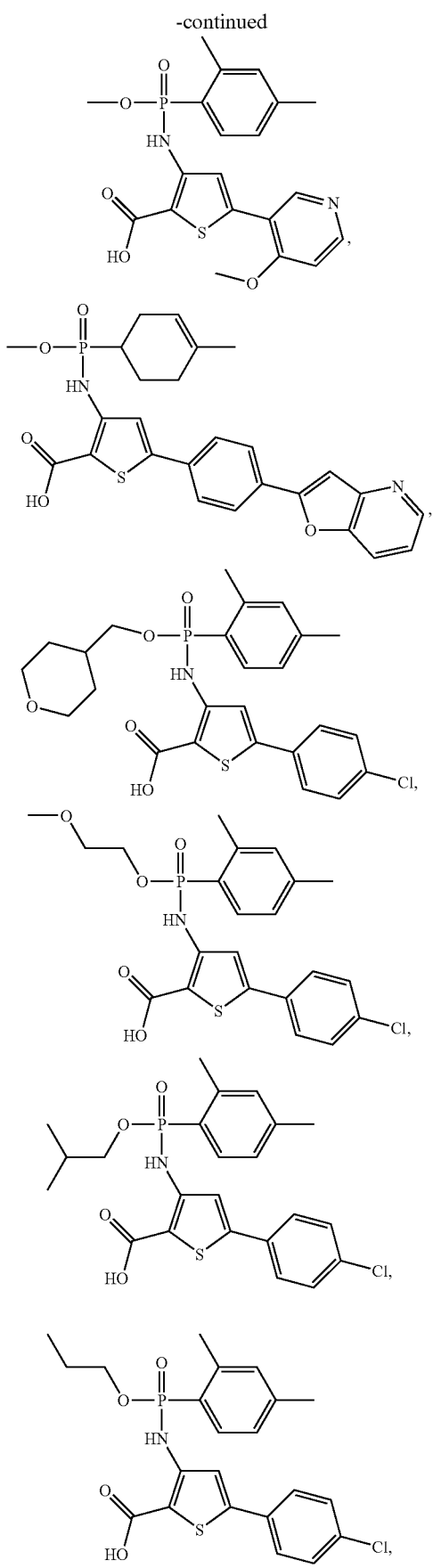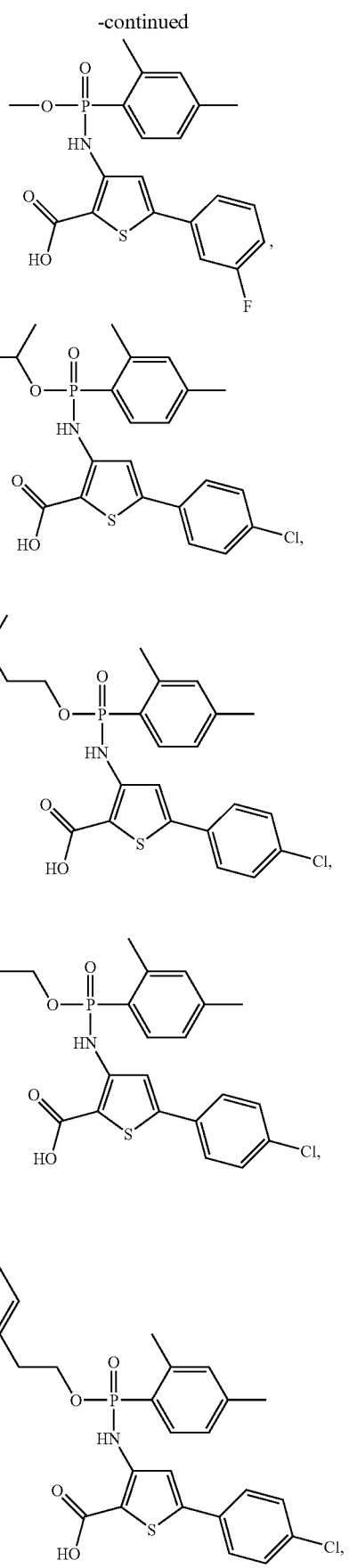

183
-continued
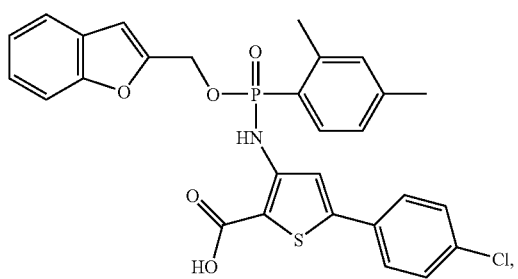
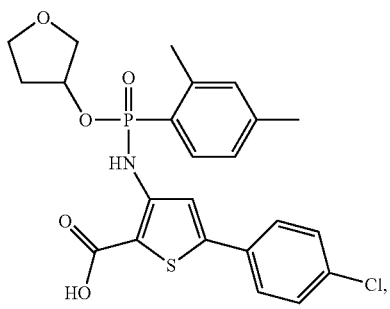
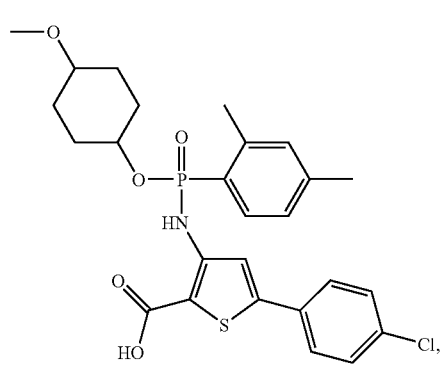
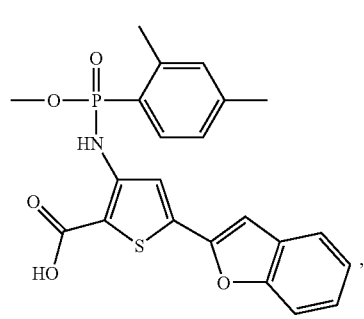
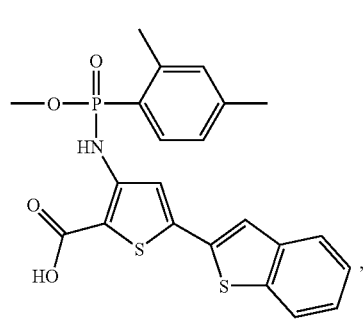
184
-continued
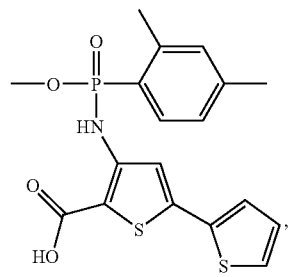
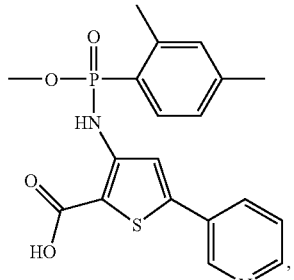
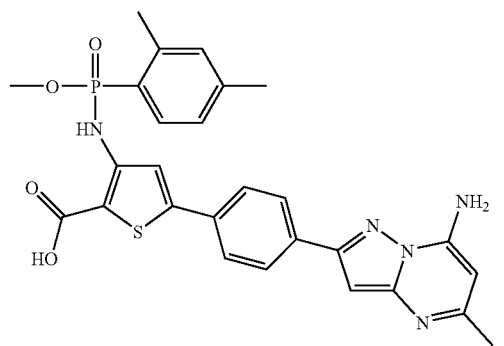
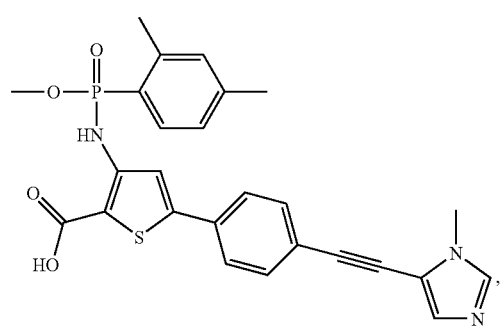
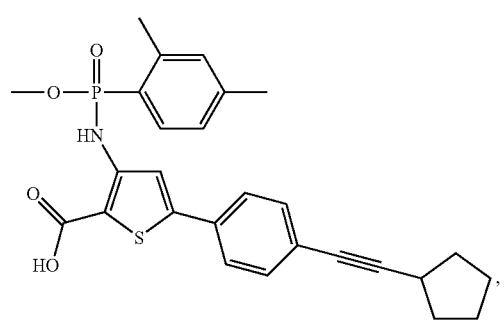

185
-continued
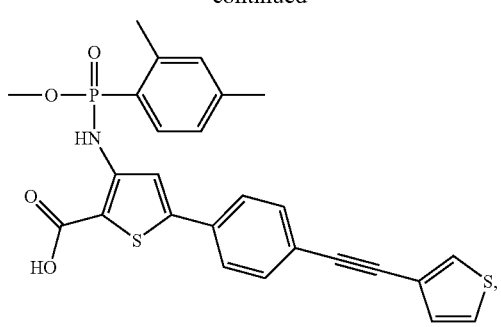
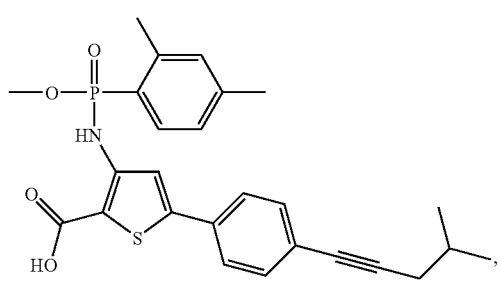
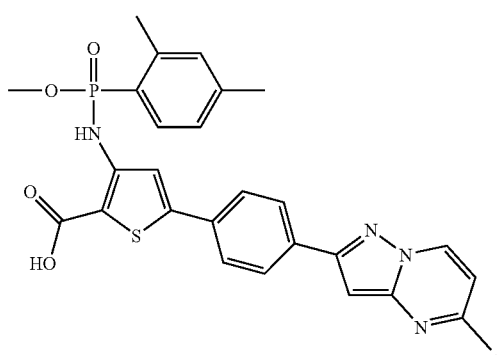
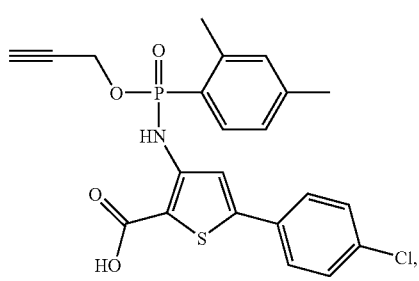
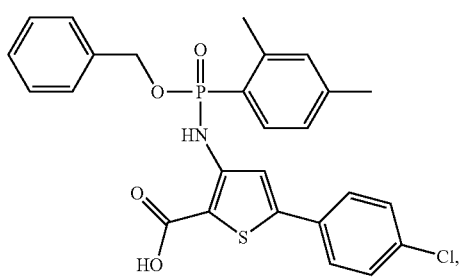
186
-continued
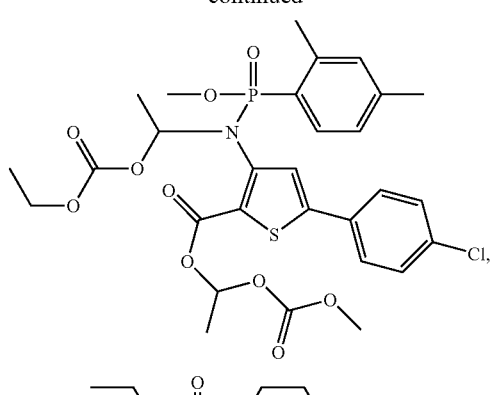
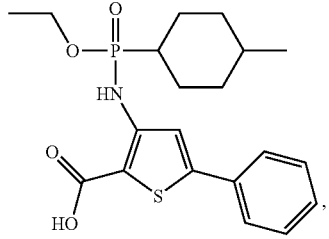
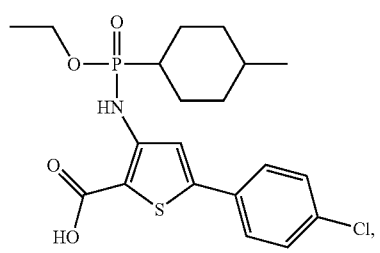
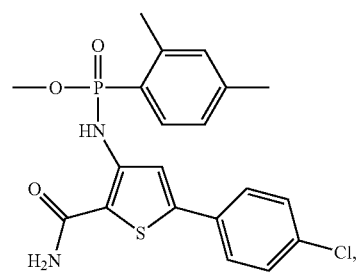
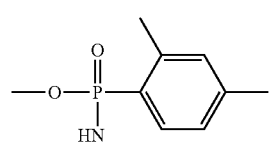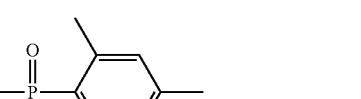
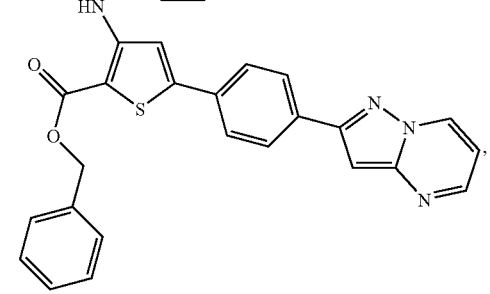

187
-continued
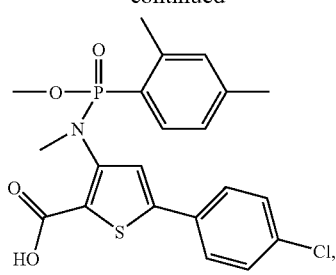
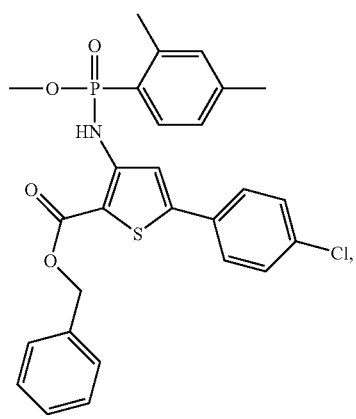
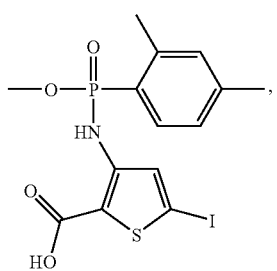
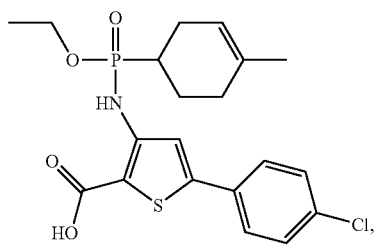
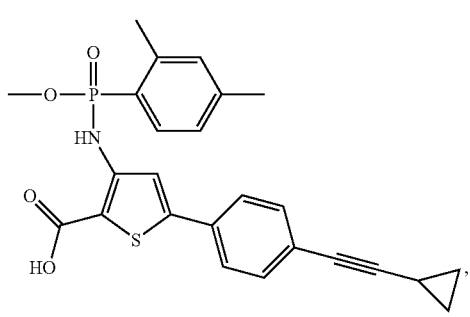
188
-continued
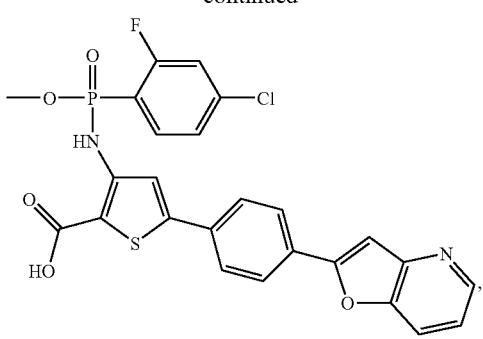
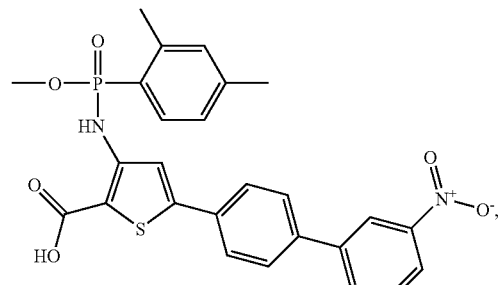
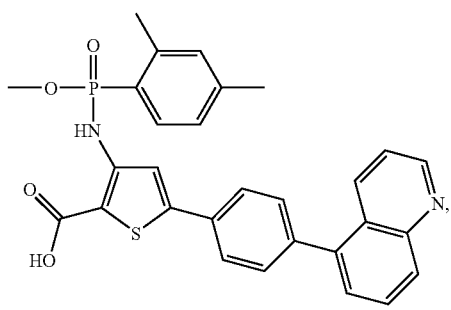
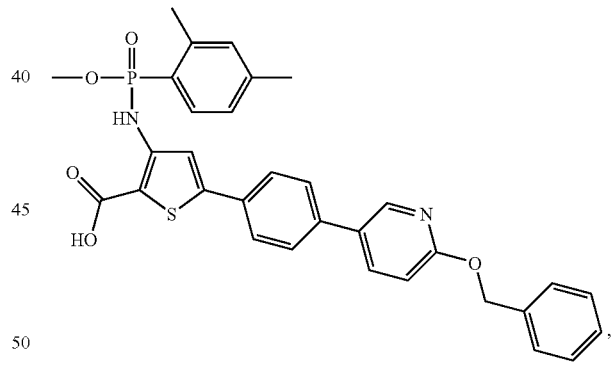
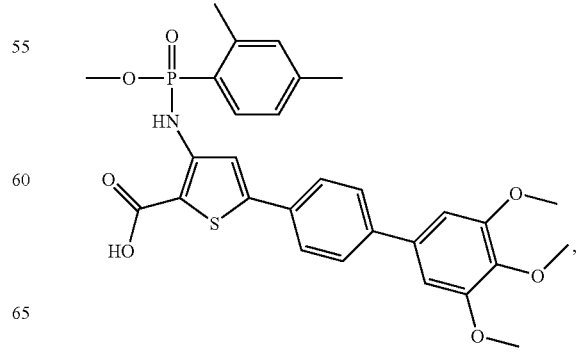

189 -continued
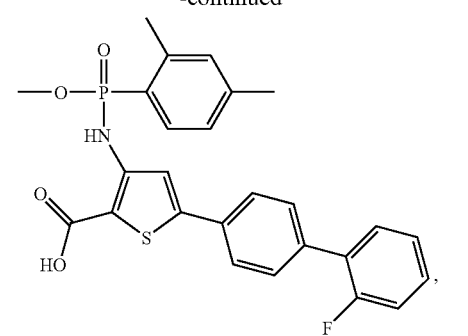
,
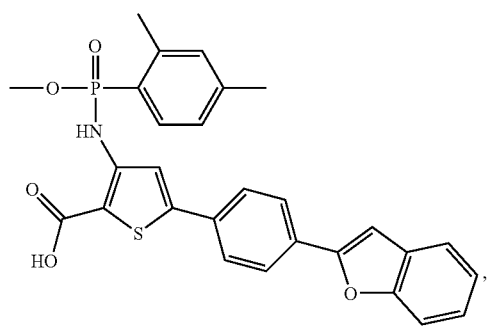
,
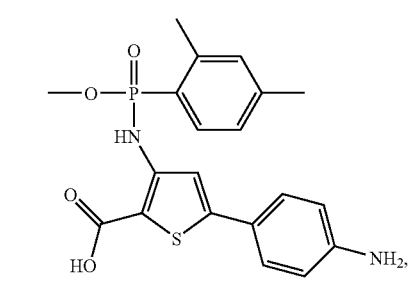
,
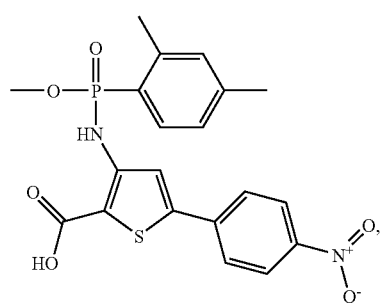
,
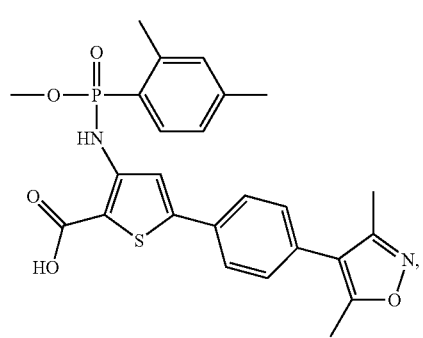
,
190 -continued
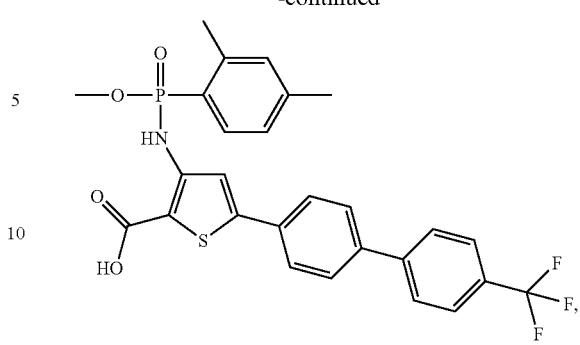
,
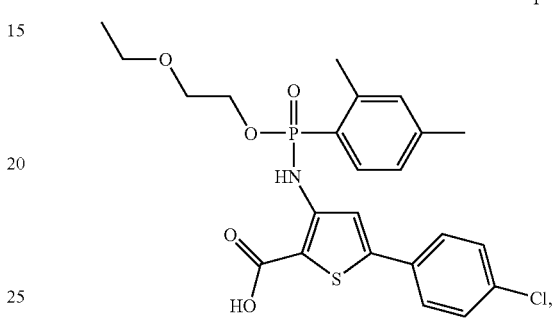
,
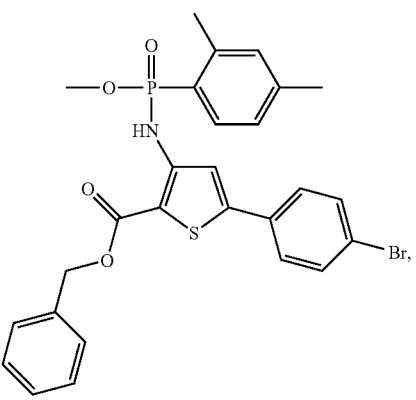
,
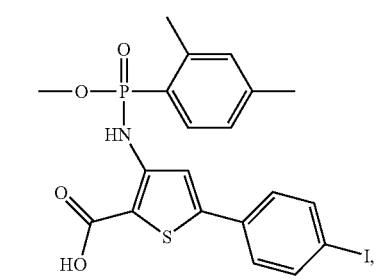
,
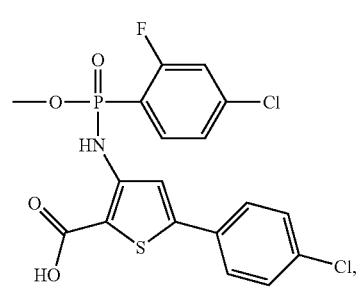
, 191
-continued
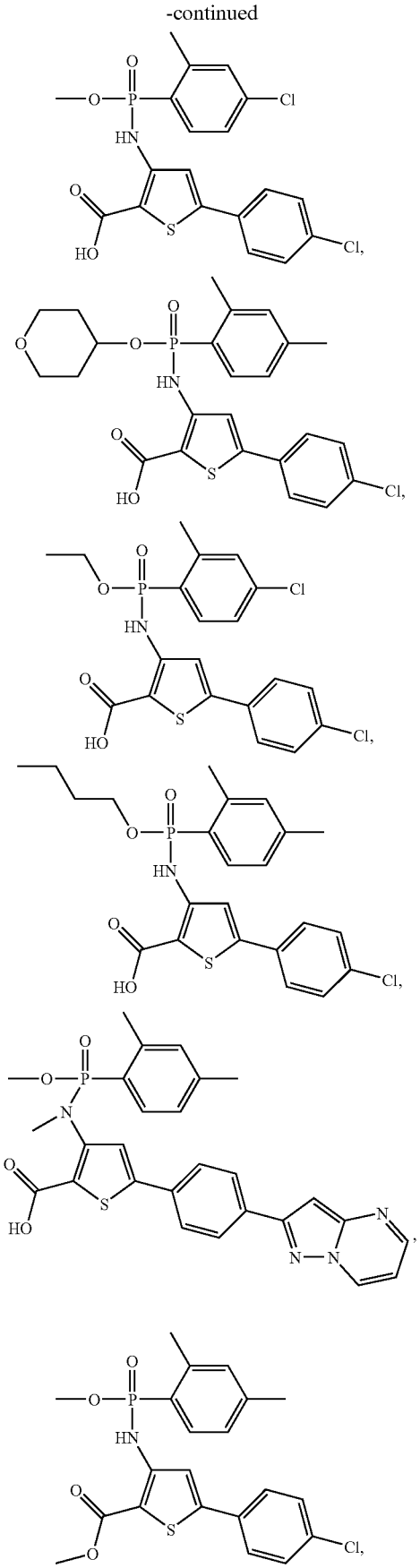
192
-continued
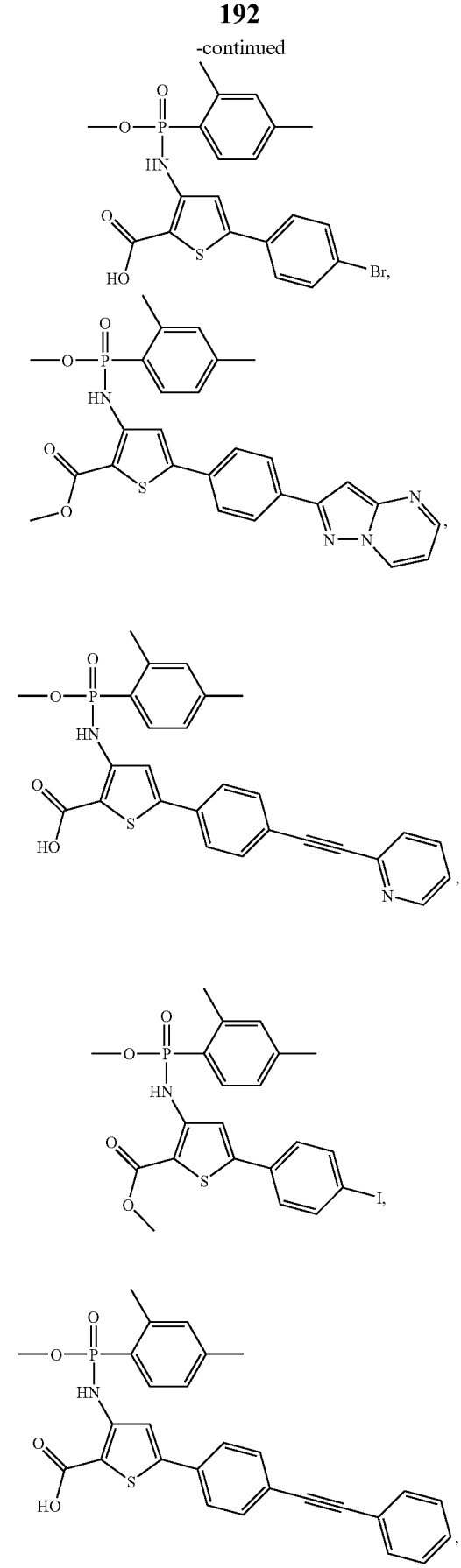

193
-continued
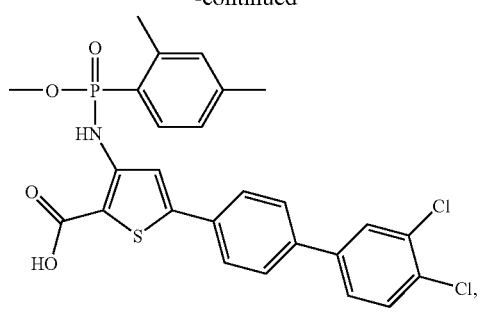
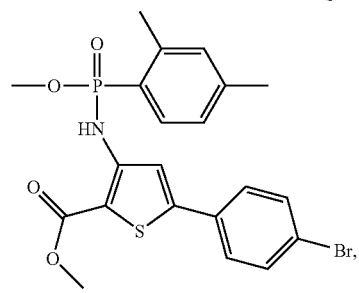
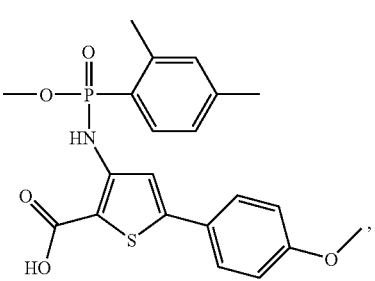
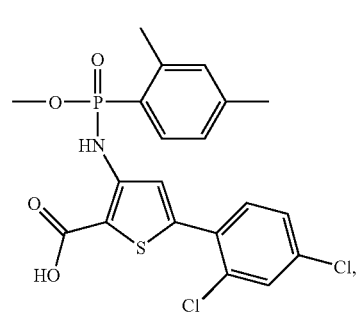
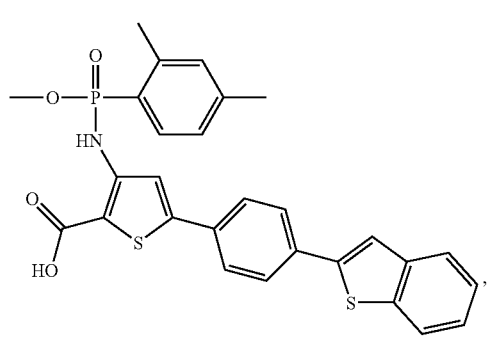
194
-continued
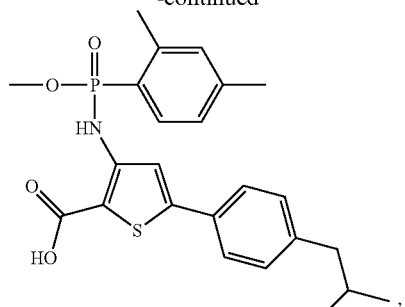
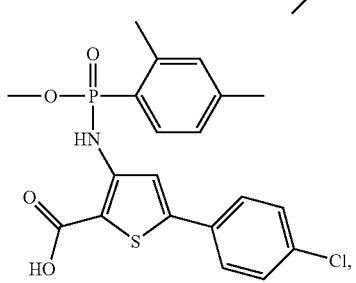
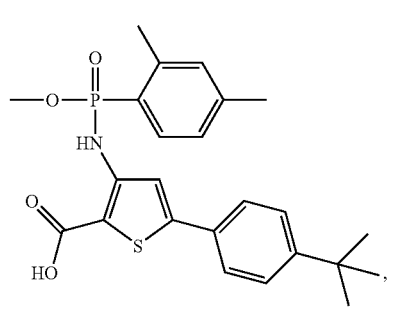
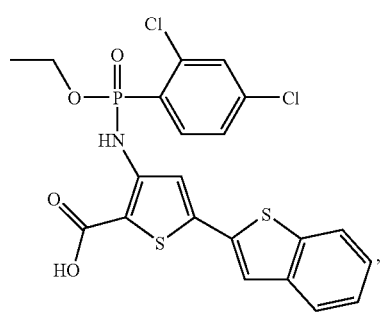
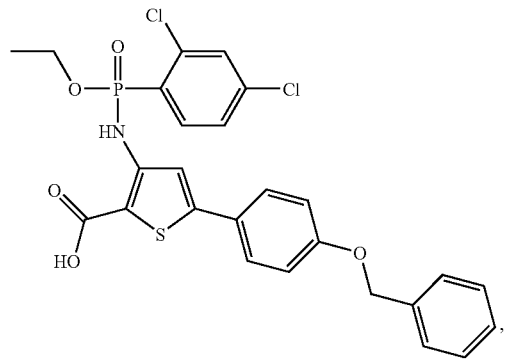

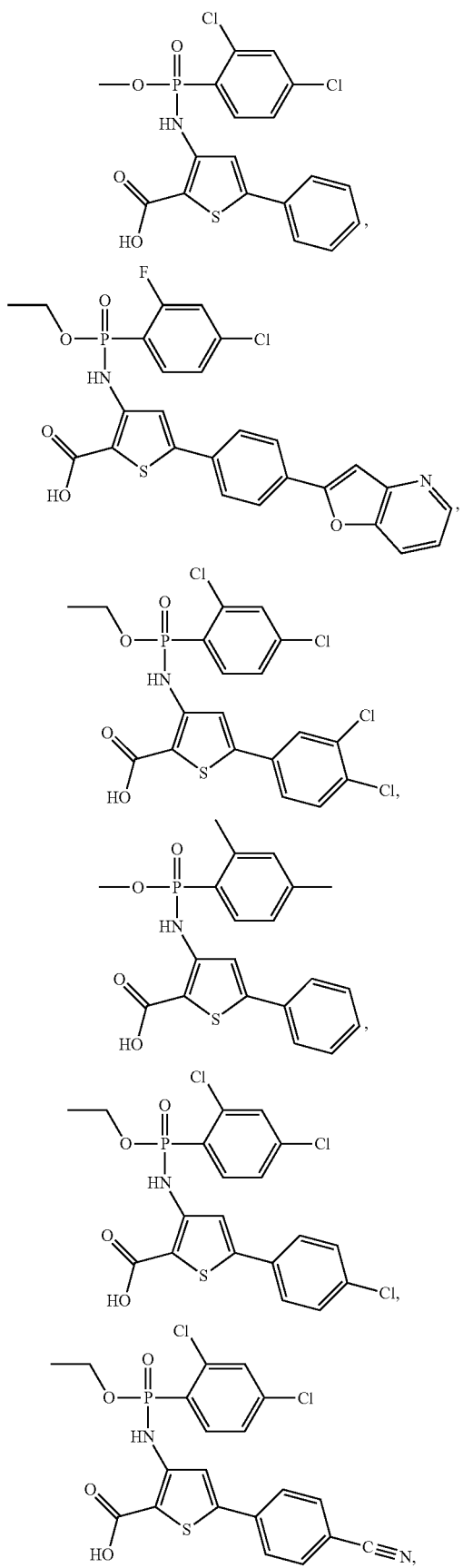
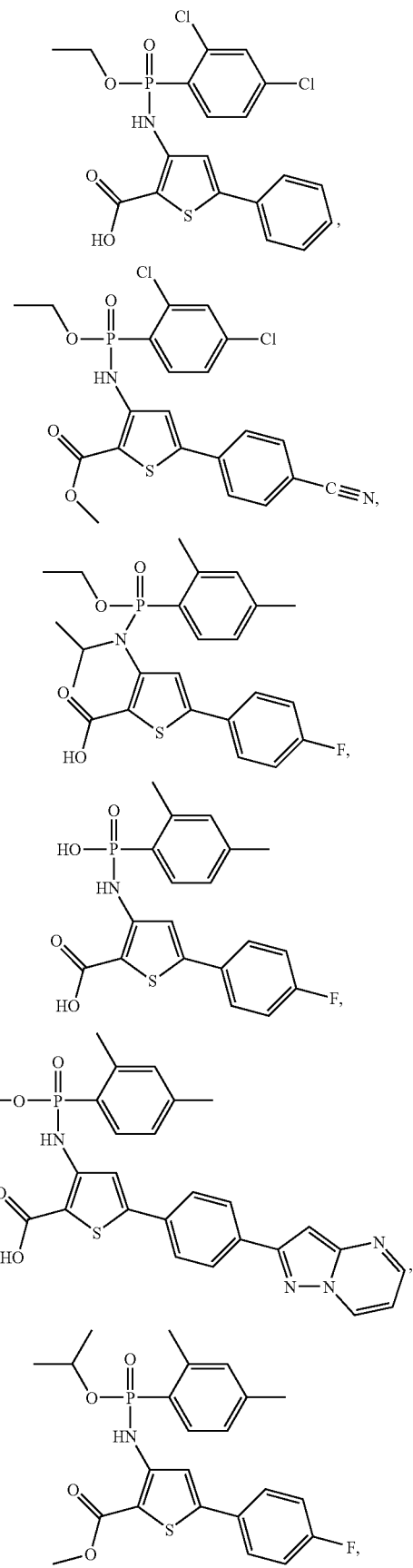

197
-continued
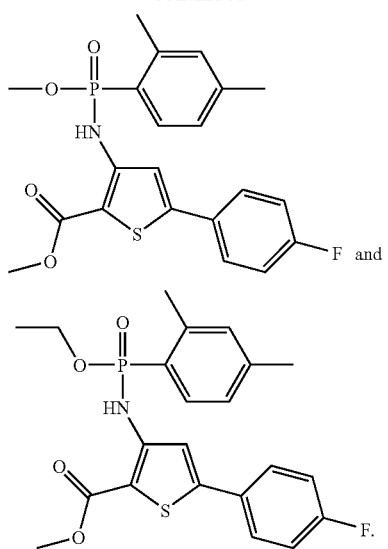
In certain embodiments, provided herein are the following compounds according to formula IVA:
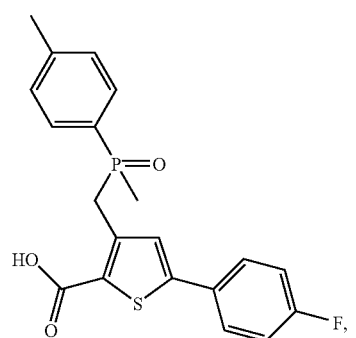
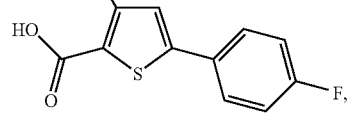
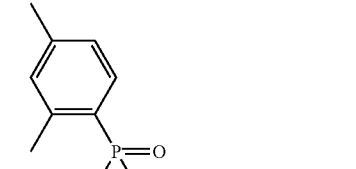
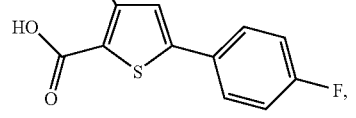
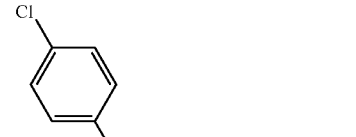
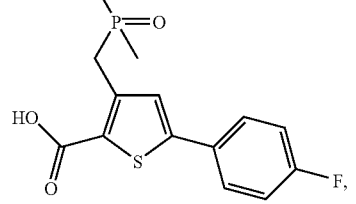
198
-continued
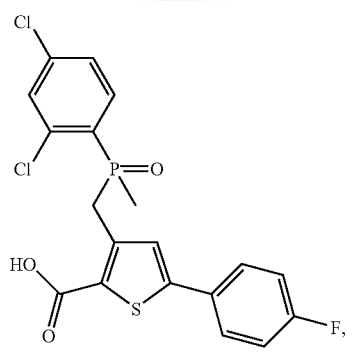
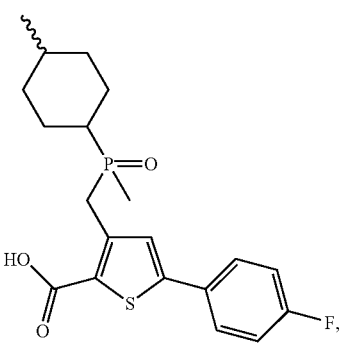
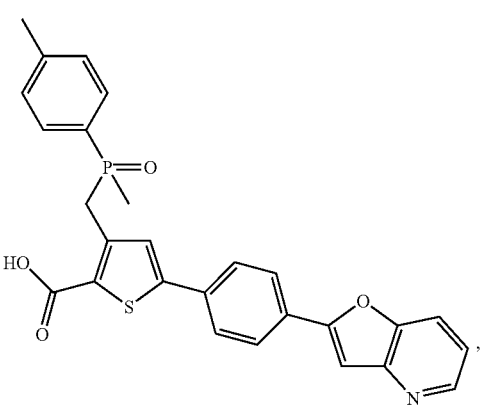

199
-continued
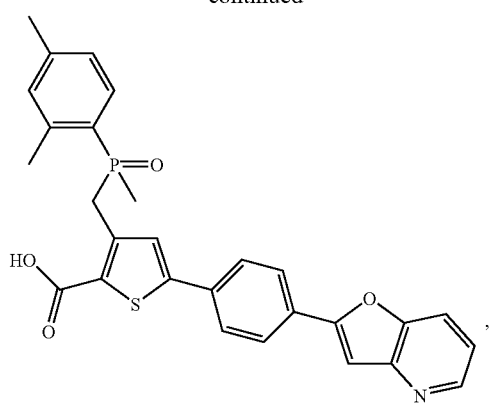
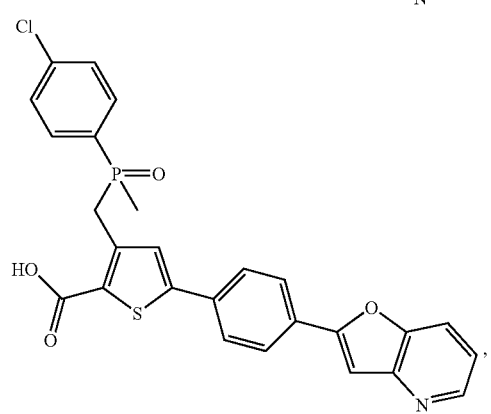
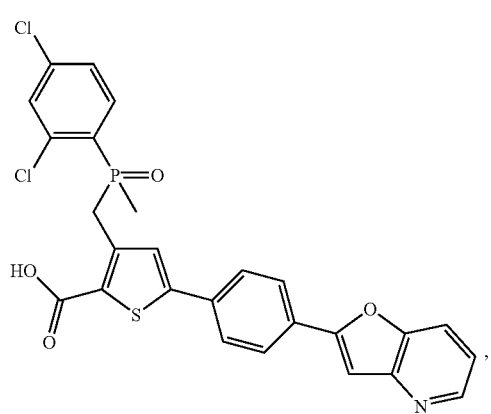
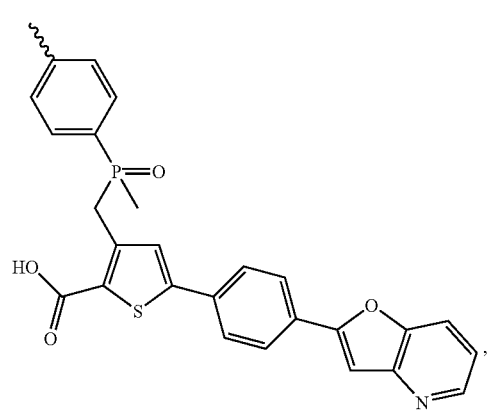
200
-continued
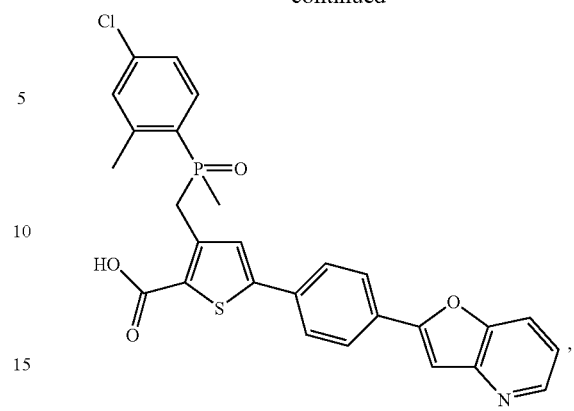
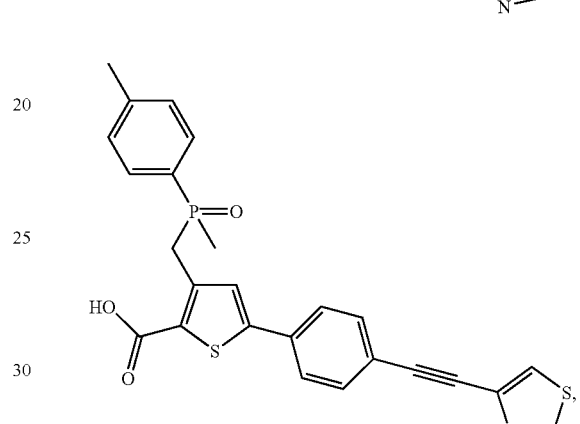
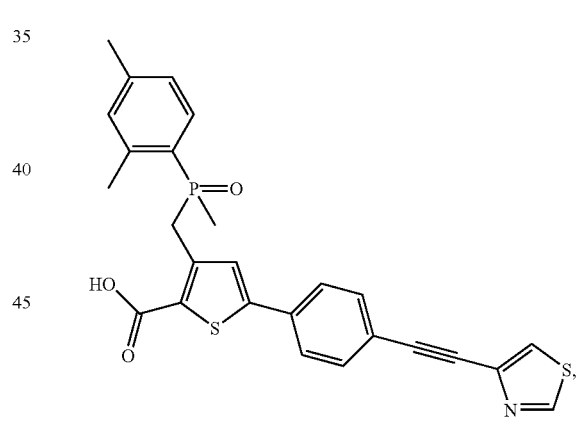
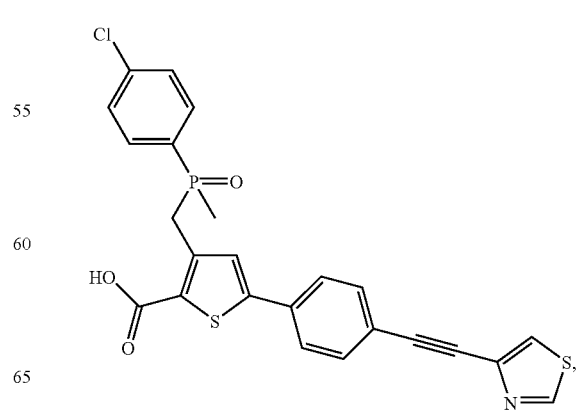

201
-continued
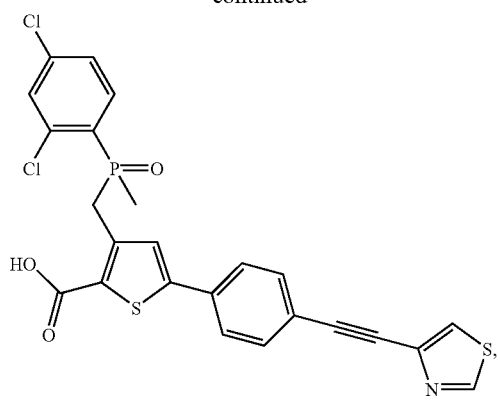
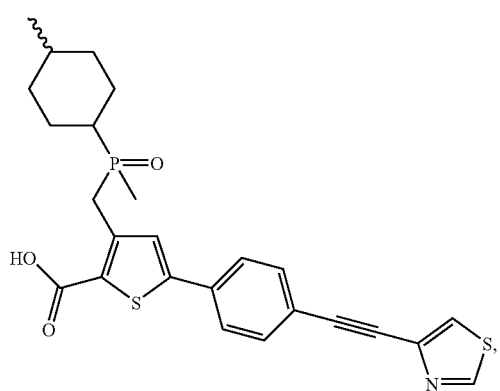
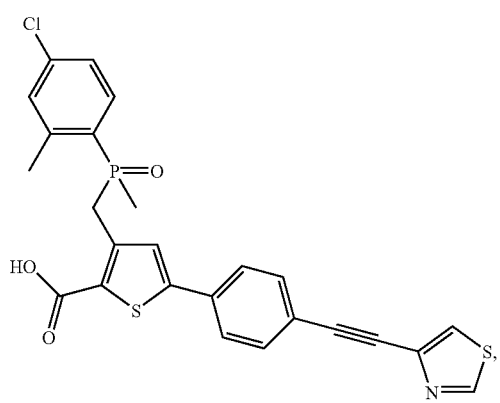
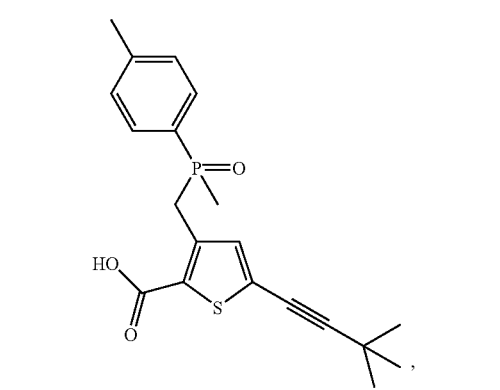
202
-continued
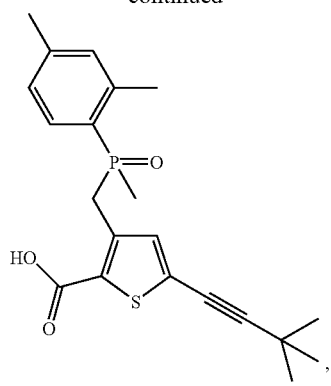
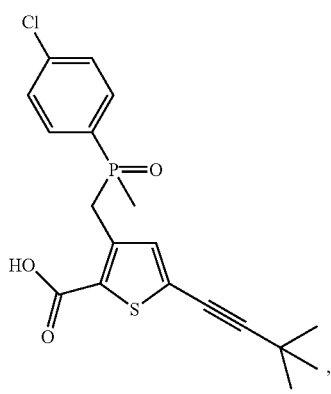
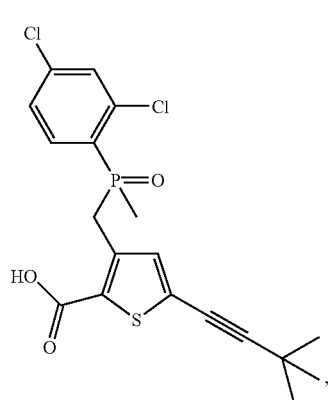
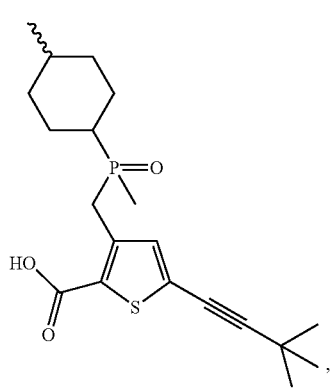

203
-continued
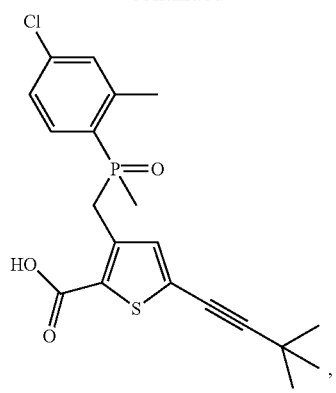
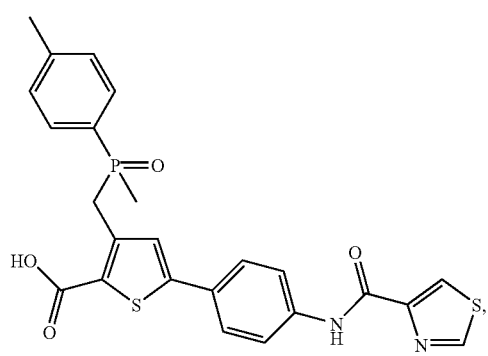
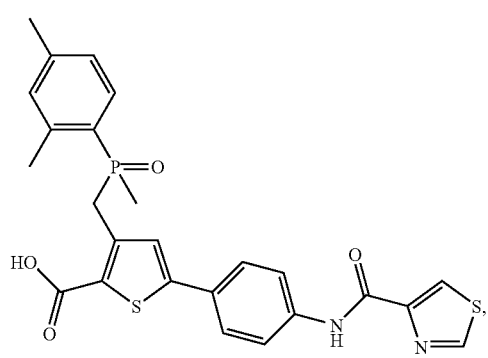
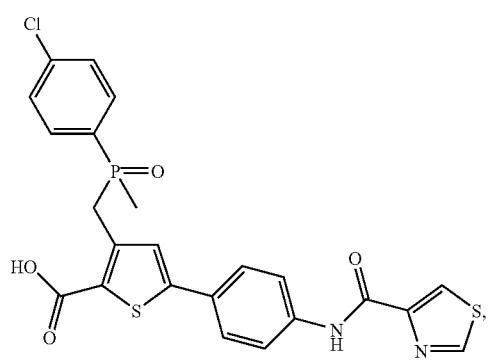
204
-continued
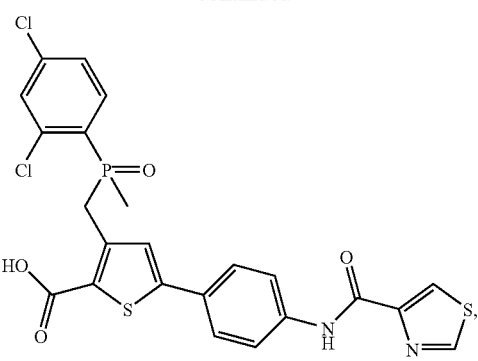
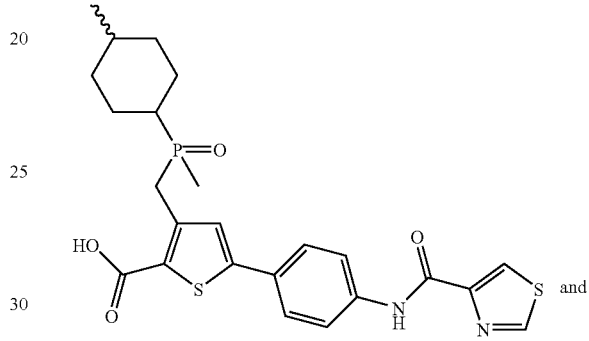
and
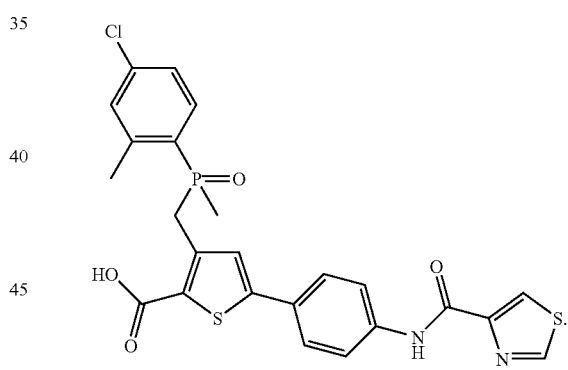
In certain embodiments, provided herein are the following compounds according to formula VIIA:
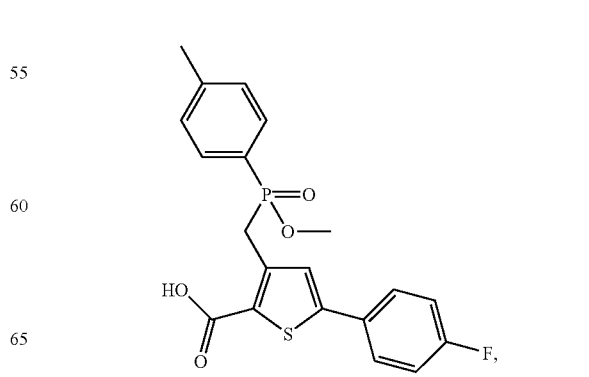

205
-continued
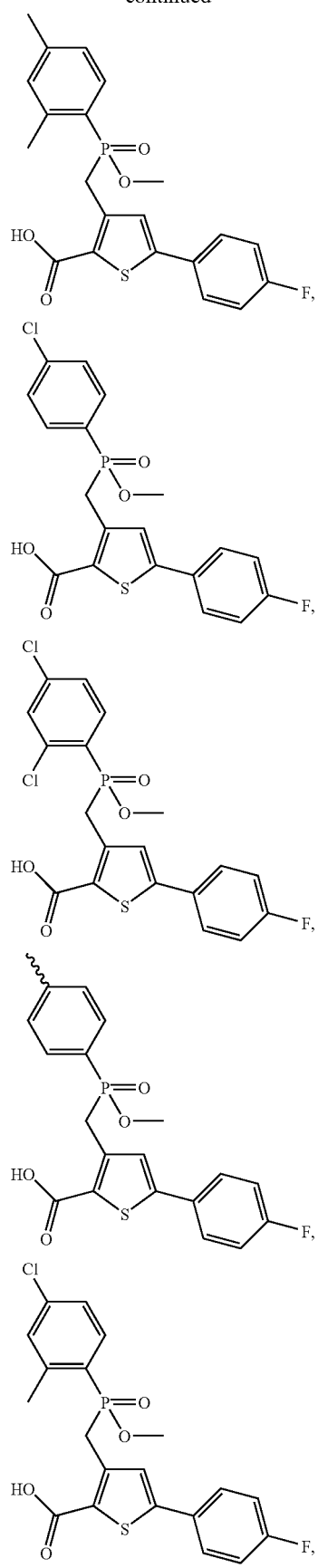
206
-continued
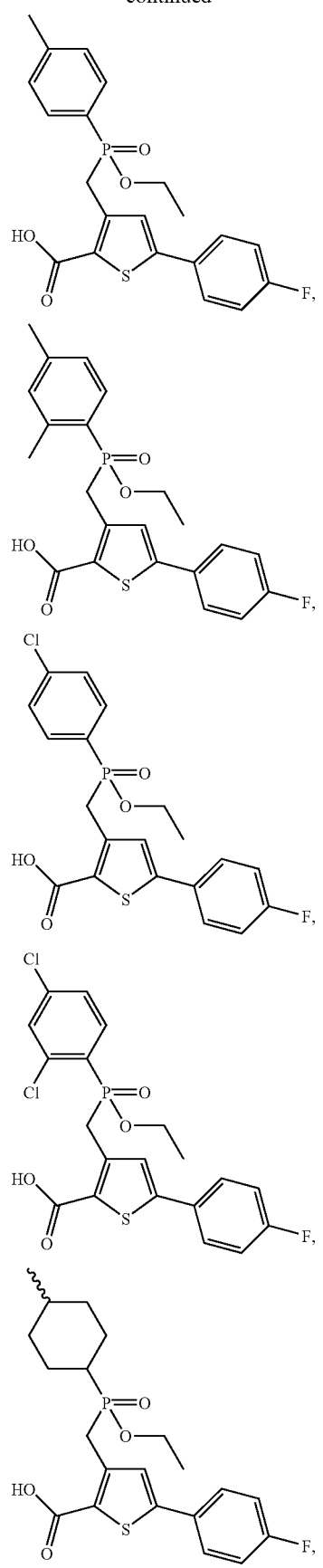

207
-continued
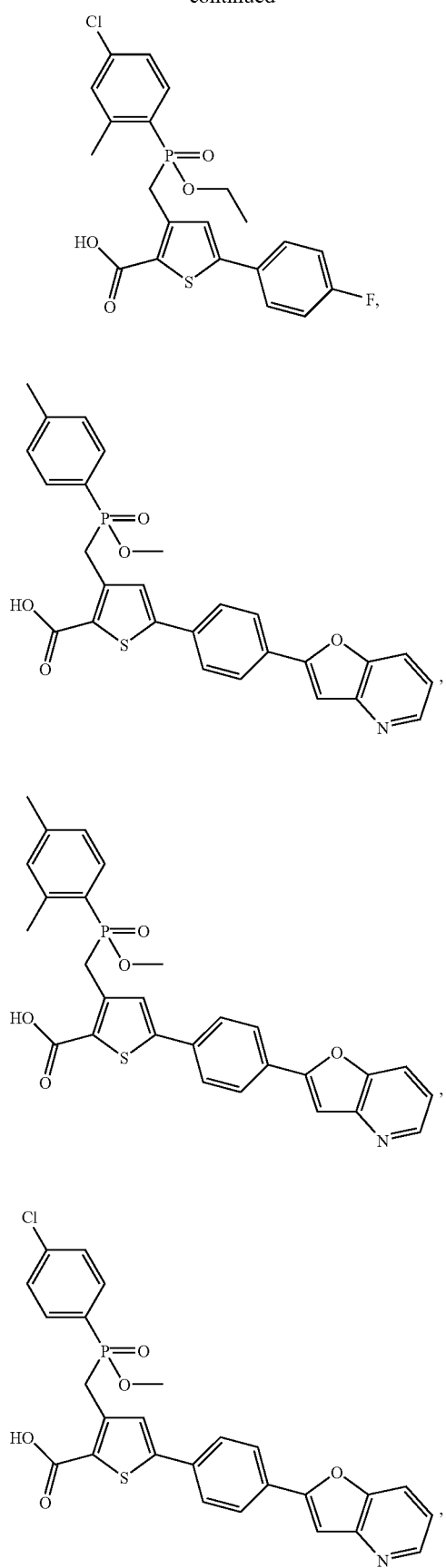
208
-continued
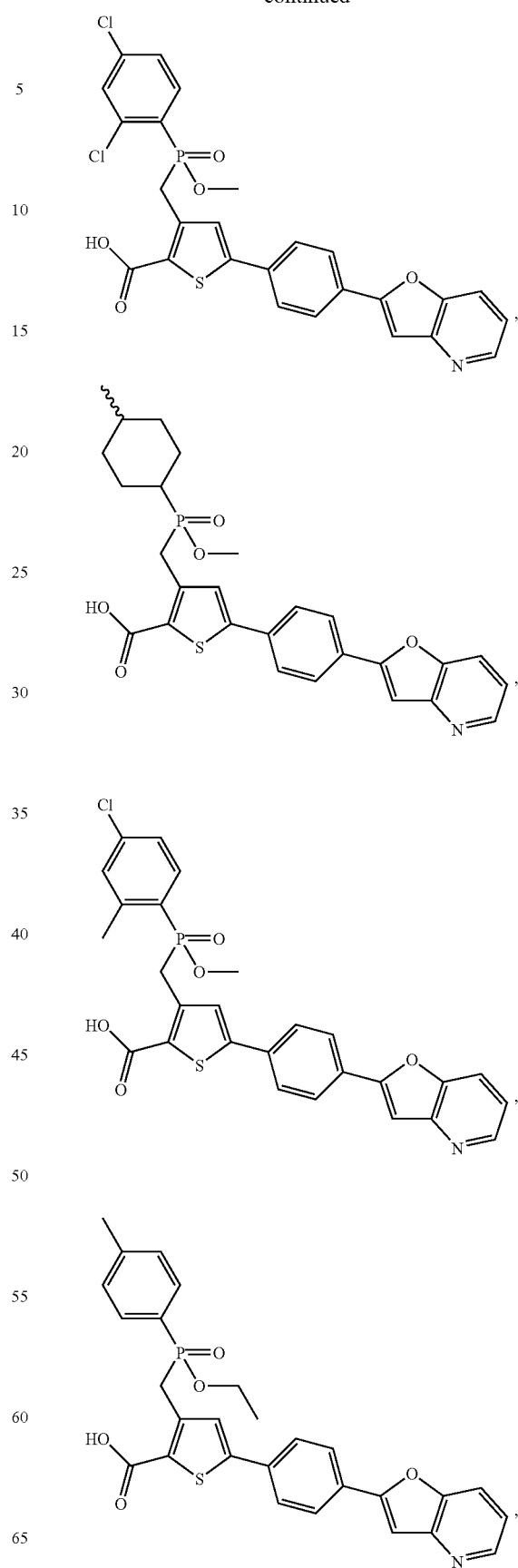

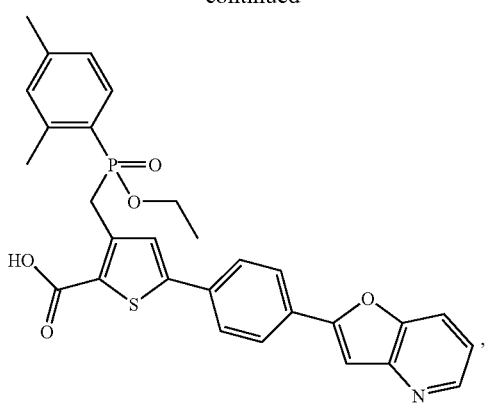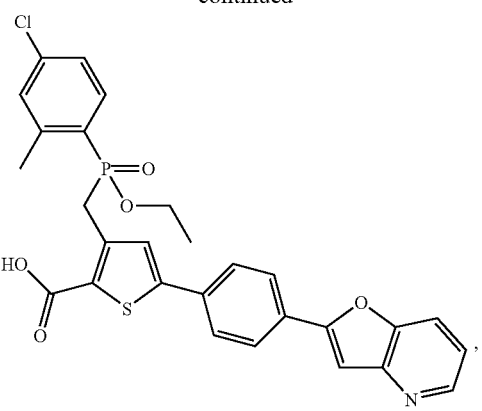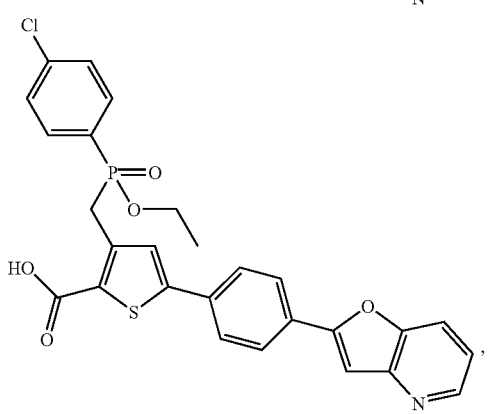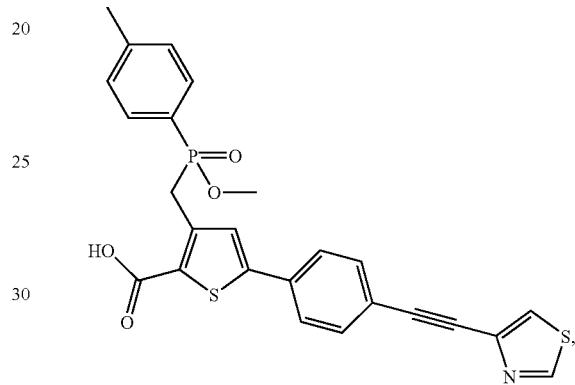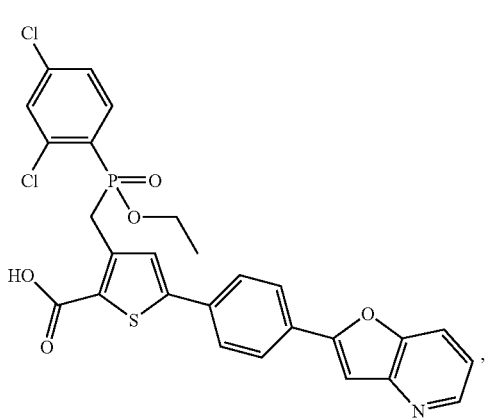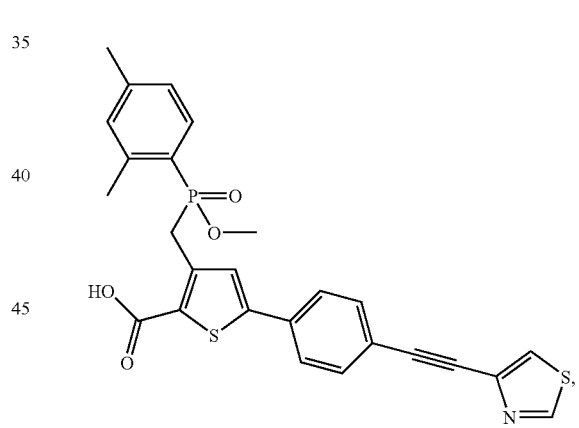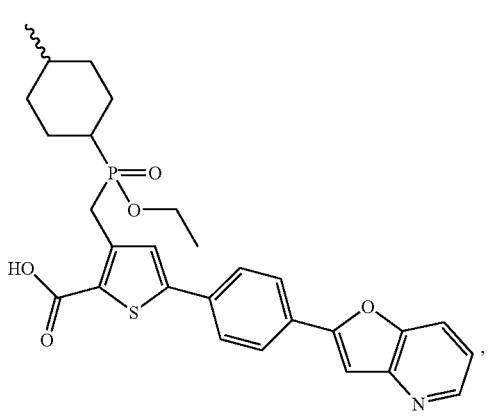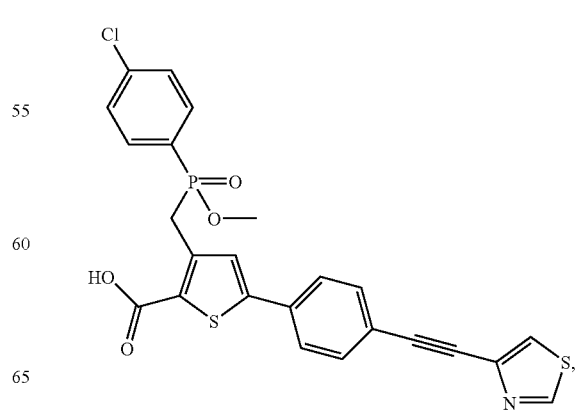

211
-continued
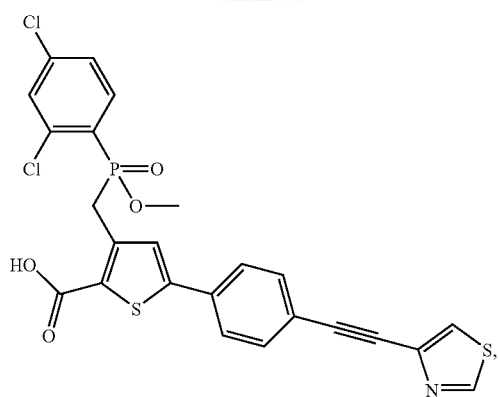
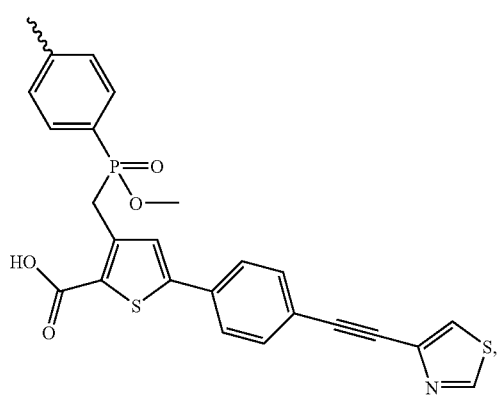
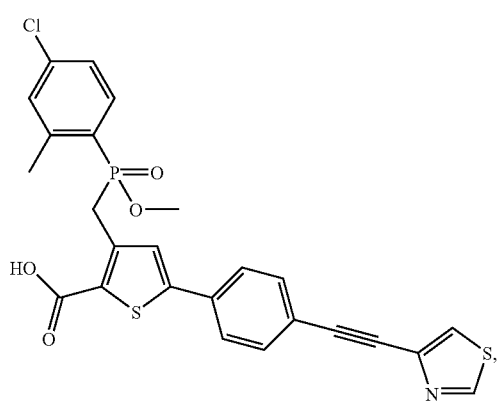
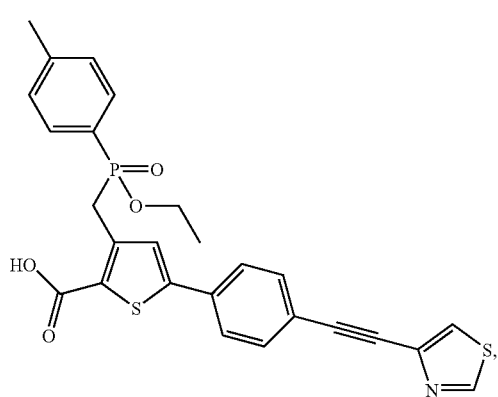
212
-continued
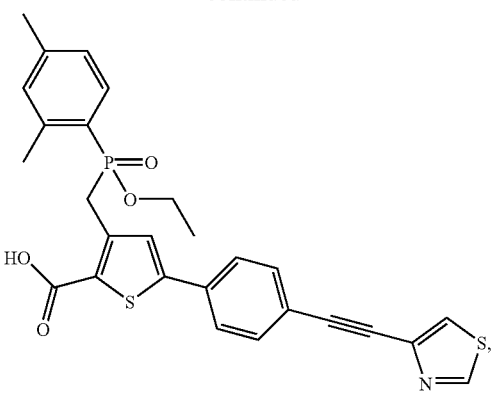
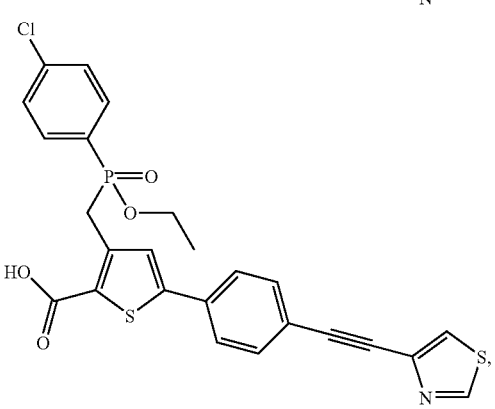
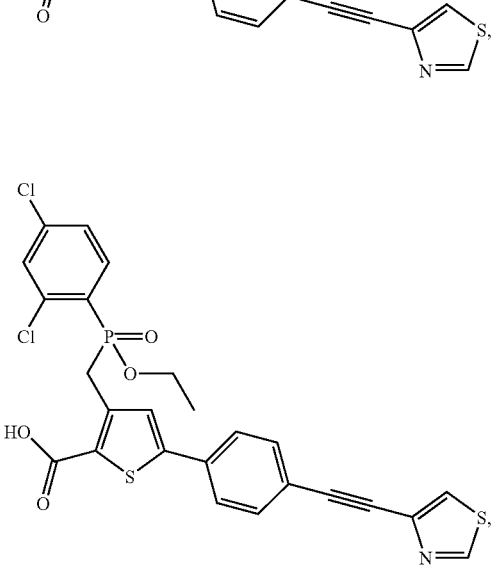
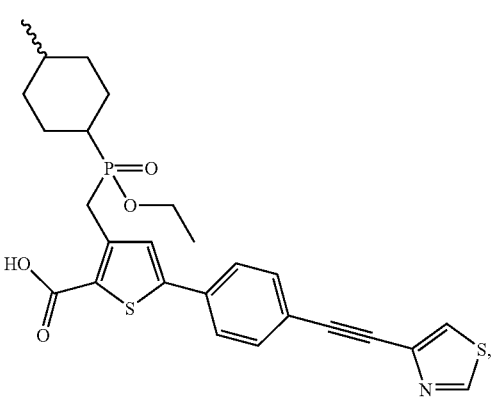

213
-continued
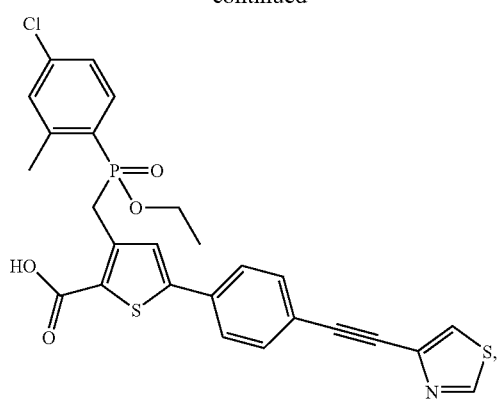
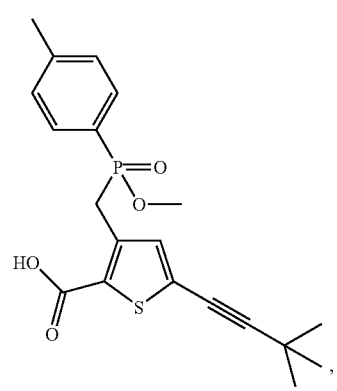
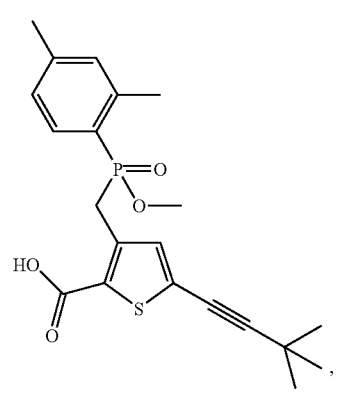
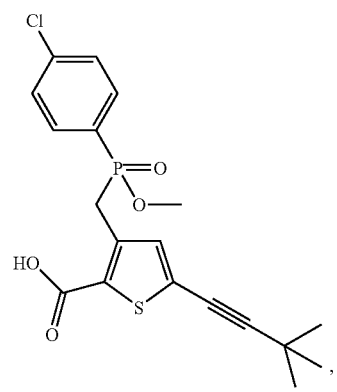
214
-continued
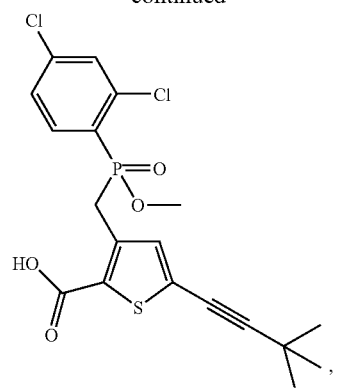
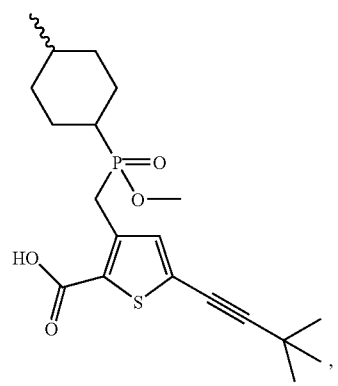
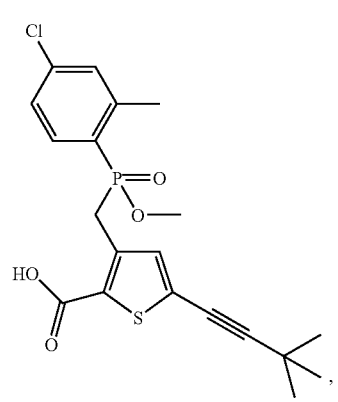
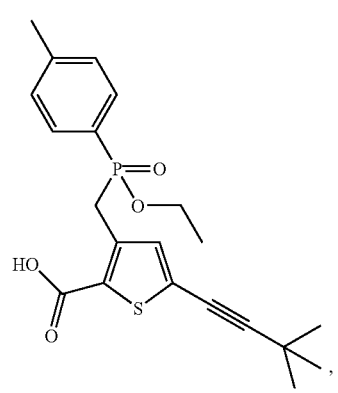

215 -continued
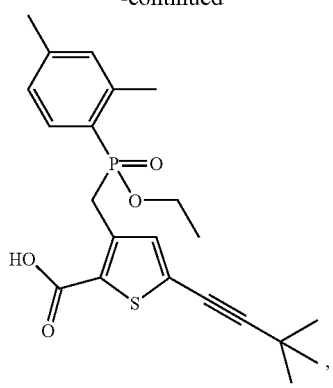
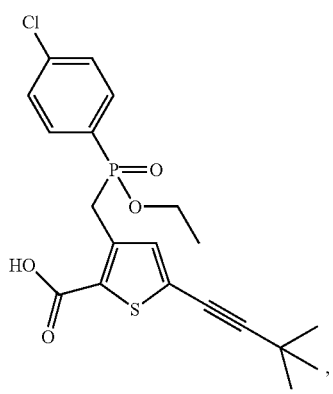
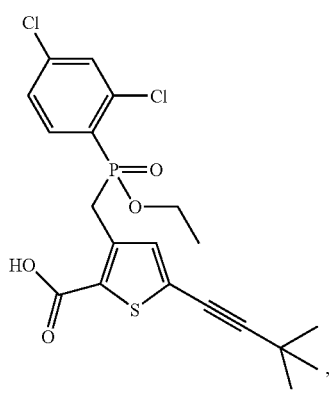
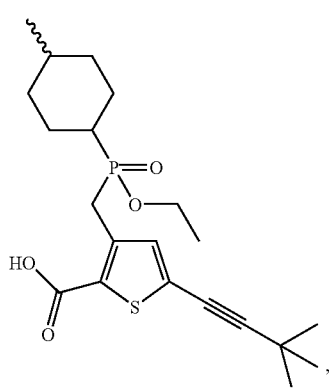
216 -continued
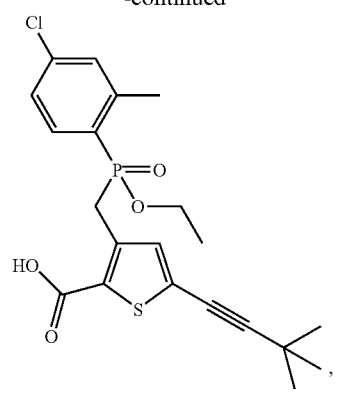
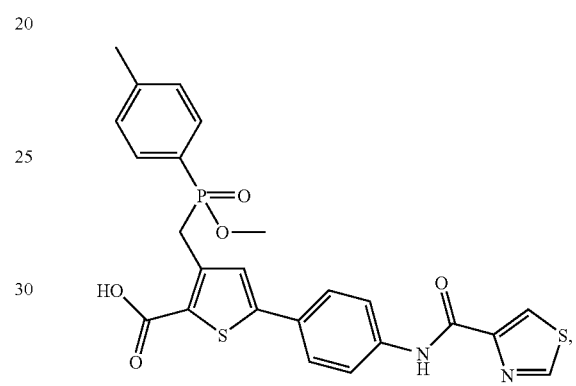
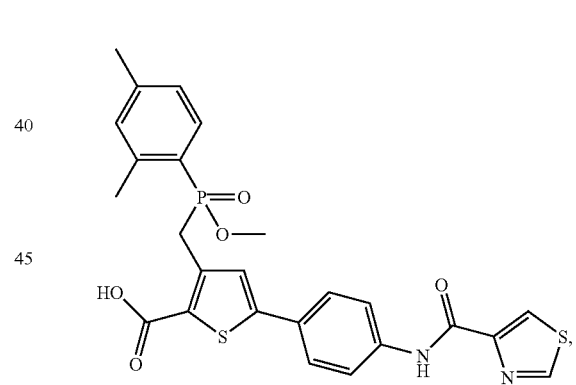
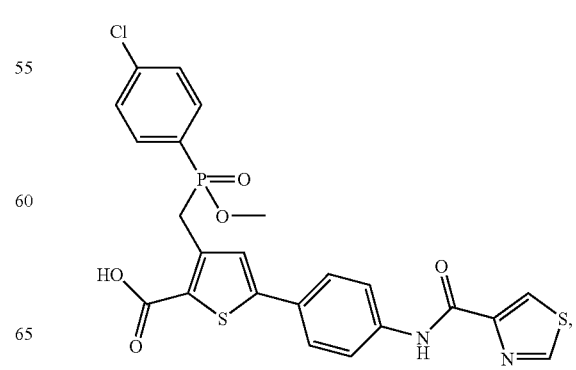

217
-continued
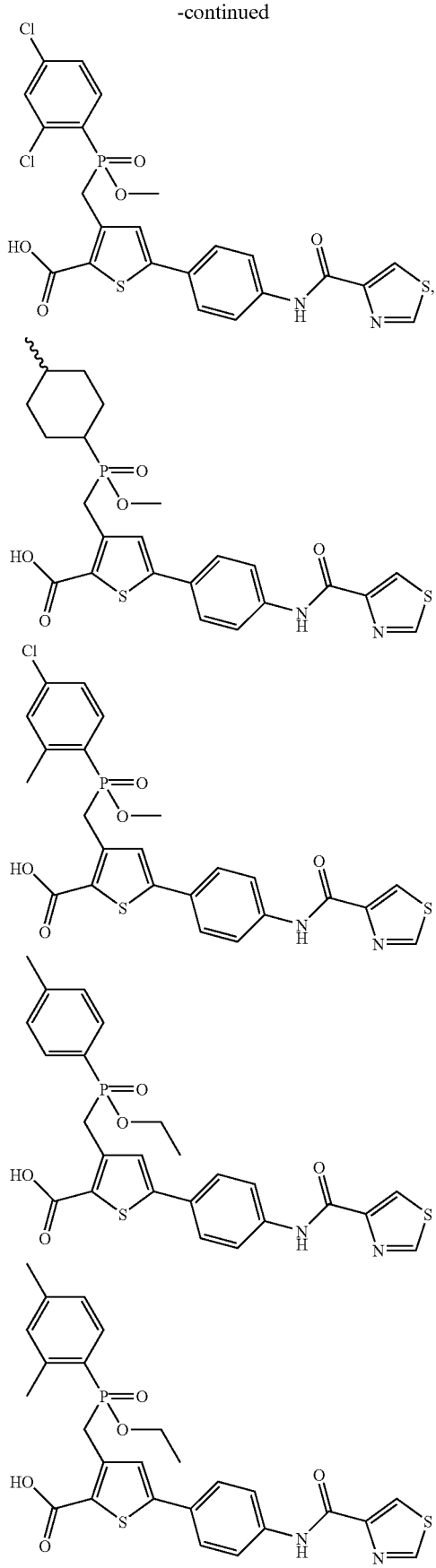
218
-continued
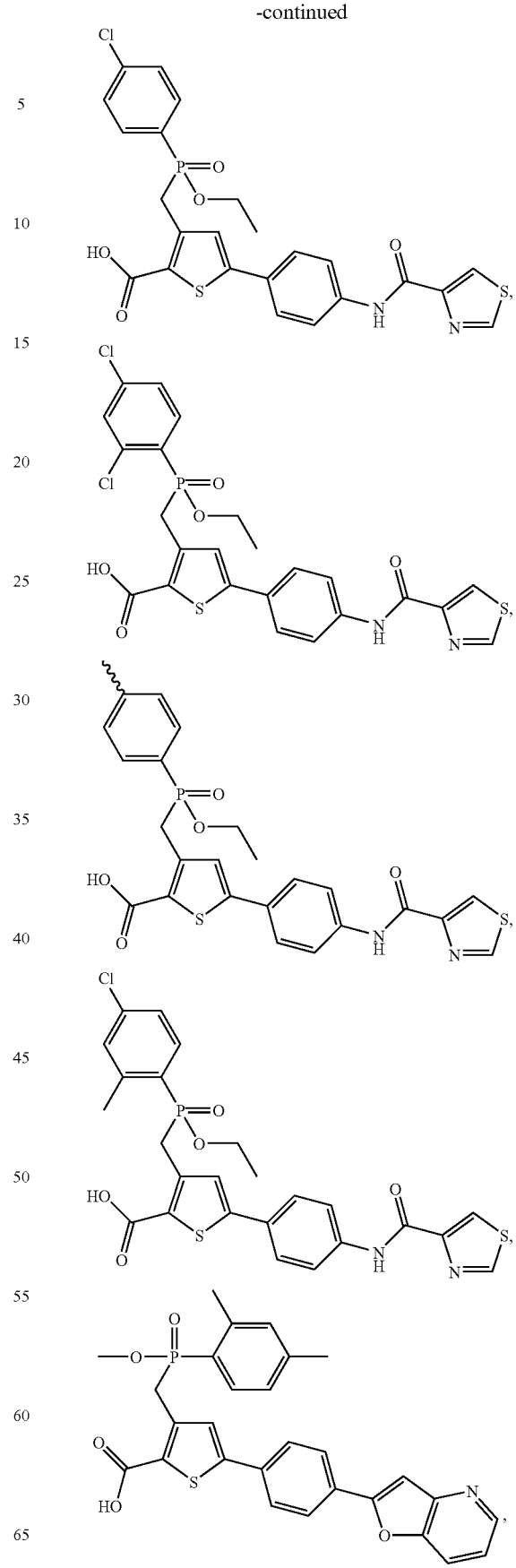

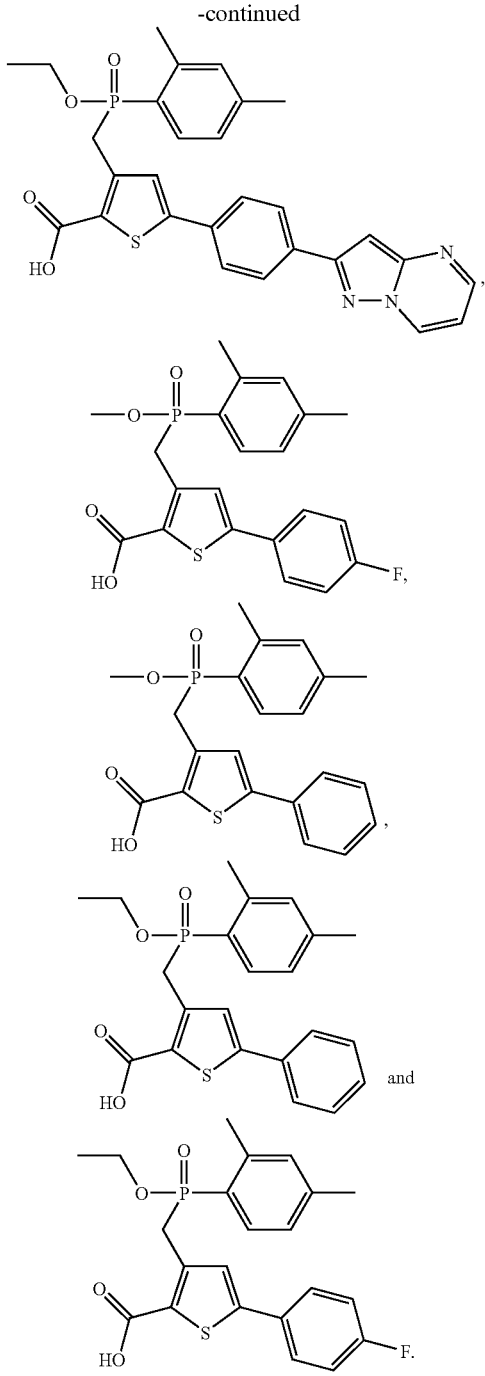

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible via a low energy barrier, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of an enantiomeric pair, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, IA, IIA, IIIA, IVA, VA, VIA, VIIA, IB, IIB, IIIB, IVB, VB, VIB, VIIB or XX and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In certain embodiments, provided herein is an isotopically enriched compound selected from the group consisting of isotopically enriched compound of Formula I, isotopically enriched compound of Formula IA, isotopically enriched compound of Formula IIA, isotopically enriched compound of Formula IIIA, isotopically enriched compound of Formula IVA, isotopically enriched compound of Formula VA, isotopically enriched compound of Formula VIA, and isotopically enriched compound of Formula VIIA, isotopically enriched compound of Formula IB, isotopically enriched compound of Formula IIB, isotopically enriched compound of Formula IIIB, isotopically enriched compound of Formula IVB, isotopically enriched compound of Formula VB, isotopically enriched compound of Formula VIB, isotopically enriched compound of Formula VIIB, isotopically enriched compound of Formula XX and combinations thereof.

In certain embodiments, provided herein is an isotopically enriched compound selected from the group consisting of isotopically enriched compound 1, isotopically enriched compound 2, isotopically enriched compound 3, isotopically enriched compound 4, isotopically enriched compound 5, isotopically enriched compound 6, isotopically enriched compound 7, isotopically enriched compound 8, isotopically enriched compound 9, isotopically enriched compound 10, isotopically enriched compound 11, isotopically enriched compound 12, isotopically enriched compound 13, isotopically enriched compound 14, isotopically enriched compound 15, isotopically enriched compound 16, isotopically enriched compound 17, isotopically enriched compound 18, isotopically enriched compound 19, isotopically enriched compound 20, isotopically enriched compound 21, isotopically enriched compound 22, isotopically enriched compound 23, isotopically enriched compound 24, isotopically enriched compound 25, isotopically enriched compound 26, isotopically enriched compound 27, isotopically enriched compound 28, isotopically enriched compound 29, isotopically enriched compound 30, isotopically enriched compound 31, isotopically enriched compound 32, isotopically enriched compound 33, isotopically enriched compound 34, isotopically enriched compound 35, isotopically enriched compound 36, isotopically enriched compound 37, isotopically enriched compound 38, isotopically enriched compound 39, isotopically enriched compound 40, isotopically enriched compound 41, isotopically enriched compound 42, isotopically enriched compound 43, isotopically enriched compound 44, isotopically enriched compound 45, isotopically enriched compound 46, isotopically enriched compound 47, isotopically enriched compound 48, isotopically enriched compound 49, isotopically enriched compound 50, isotopically enriched compound 51, isotopically enriched compound 52, isotopically enriched compound 53, isotopically enriched compound 54, isotopically enriched compound 55, isotopically enriched compound 56, isotopically enriched compound 57, isotopically enriched compound 58, isotopically enriched compound 59, isotopically enriched compound 60, isotopically enriched compound 61, isotopically enriched compound 62, isotopically enriched compound 63, isotopically enriched compound 64, isotopically enriched compound 65, isotopically enriched compound 66, isotopically enriched compound 67, isotopically enriched compound 68, isotopically enriched compound 69, isotopically enriched compound 70, isotopically enriched compound 71, isotopically enriched compound 72, isotopically enriched compound 73, isotopically enriched compound 74, isotopically enriched compound 75, isotopically enriched compound 76, isotopically enriched compound 77, isotopically enriched compound 78, isotopically enriched compound 79, isotopically enriched compound 80, isotopically enriched compound 81, isotopically enriched compound 82, isotopically enriched compound 83, isotopically enriched compound 84, isotopically enriched compound 85, isotopically enriched compound 86, isotopically enriched compound 87, isotopically enriched compound 88, isotopically enriched compound 89, isotopically enriched compound 90, isotopically enriched compound 91, isotopically enriched compound 92, isotopically enriched compound 93, isotopically enriched compound 94, isotopically enriched compound 95, isotopically enriched compound 96, isotopically enriched compound 97, isotopically enriched compound 98, isotopically enriched compound 99, isotopically enriched compound 100, isotopically enriched compound 101, isotopically enriched compound 102, isotopically enriched compound 103, isotopically enriched compound 104, isotopically enriched compound 105, isotopically enriched compound 106, isotopically enriched compound 107, isotopically enriched compound 108, isotopically enriched compound 109, isotopically enriched compound 110, isotopically enriched compound 111, isotopically enriched compound 112, isotopically enriched compound 113, isotopically enriched compound 114, isotopically enriched compound 115, isotopically enriched compound 116, isotopically enriched compound 117, isotopically enriched compound 118, isotopically enriched compound 119, isotopically enriched compound 120, isotopically enriched compound 121, isotopically enriched compound 122, isotopically enriched compound 123, isotopically enriched compound 124, isotopically enriched compound 125, isotopically enriched compound 126, isotopically enriched compound 127, isotopically enriched compound 128, isotopically enriched compound 129, isotopically enriched compound 130, isotopically enriched compound 131, isotopically enriched compound 132, isotopically enriched compound 133, isotopically enriched compound 134, isotopically enriched compound 135, isotopically enriched compound 136, isotopically enriched compound 137, isotopically enriched compound 138, isotopically enriched compound 139, isotopically enriched compound 140, isotopically enriched compound 141, isotopically enriched compound 142, isotopically enriched compound 143, isotopically enriched compound 144, isotopically enriched compound 145, isotopically enriched compound 146, isotopically enriched compound 147, isotopically enriched compound 148, isotopically enriched compound 149, isotopically enriched compound 150, isotopically enriched compound 151, isotopically enriched compound 152, isotopically enriched compound 153, isotopically enriched compound 154, isotopically enriched compound 155, isotopically enriched compound 156, isotopically enriched compound 157, isotopically enriched compound 158, isotopically enriched compound 159, isotopically enriched compound 160, isotopically enriched compound 161, isotopically enriched compound 162, isotopically enriched compound 163, isotopically enriched compound 164, isotopically enriched compound 165, isotopically enriched compound 166, isotopically enriched compound 167, isotopically enriched compound 168, isotopically enriched compound 169, isotopically enriched compound 170, isotopically enriched compound 171, isotopically enriched compound 172, isotopically enriched compound 173, isotopically enriched compound 174, isotopically enriched compound 175, isotopically enriched compound 176, isotopically enriched compound 177, isotopically enriched compound 178, isotopically enriched compound 179, isotopically enriched compound 180, isotopically enriched compound 181, isotopically enriched compound 182, isotopically enriched compound 183, isotopically enriched compound 184, isotopically enriched compound 185, isotopically enriched compound 186, isotopically enriched compound 187, isotopically enriched compound 188, isotopically enriched compound 189, isotopically enriched compound 190, isotopically enriched compound 191, isotopically enriched compound 190, isotopically enriched compound 191, isotopically enriched compound 192, isotopically enriched compound 193, isotopically enriched compound 194, isotopically enriched compound 195, isotopically enriched compound 196, isotopically enriched compound 197, isotopically enriched compound 198, isotopically enriched compound 199, isotopically enriched compound 200, isotopically enriched compound 201 and combinations thereof.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e,g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Methods of Synthesis

The compound provided herein can be prepared, isolated, or obtained by any method apparent to one of skill in the art. For example, the compound of Formula IA can be prepared as shown in Scheme 1. In certain embodiments, $R^1$, $R^2$, $R^3$, $R^4$, $R^5$, and L are as defined herein.

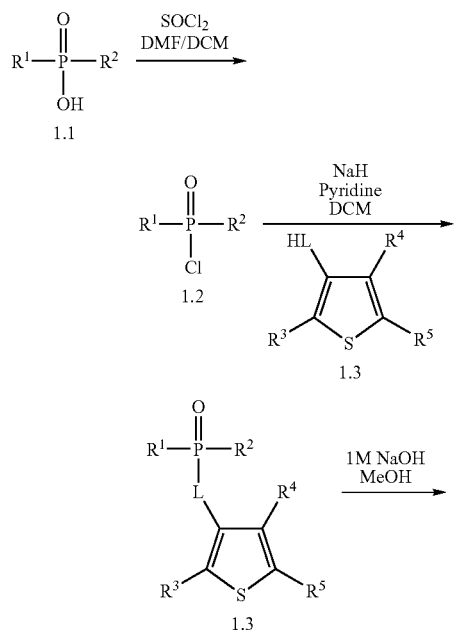

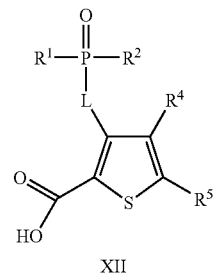

In certain embodiments, a phosphorus compound of Formula 1.1, or a derivative thereof, can react with a chlorinating agent such as thionyl chloride in a solvent such as a mixture of dimethylformamide (DMF) and dichloromethane (DCM) to form a compound of Formula 1.2. The compound of Formula 1.2 can react with a thiophene of Formula 1.3 in the presence of a base, such as sodium hydride and pyridine, in a solvent, such as DCM to form the compound of Formula of IA. Hydrolysis of the compound of Formula of IA by a base such as 1 M sodium hydroxide in a solvent, such as methanol, can yield a compound of Formula of XII. Protecting groups can be used where suitable according to the judgment of one of skill in the art. In some embodiments, $R^1$ of Formulae 1.1 and 1.2 are $OR^6$; and $R^2$ of Formulae 1.1 and 1.2 are aryl. In further embodiments, $R^1$ of Formulae 1.1 and 1.2 are —OMe or —OEt; and $R^2$ of Formulae 1.1 and 1.2 are

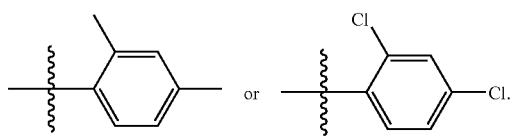

In some embodiments, $R^1$ in Scheme 1 is $OR^6$. In certain embodiments, the compound of Formula IIA can be prepared as shown in Scheme 2, where $R^2$, $R^3$, $R^4$, $R^5$, $R^6$, and L are as defined herein.

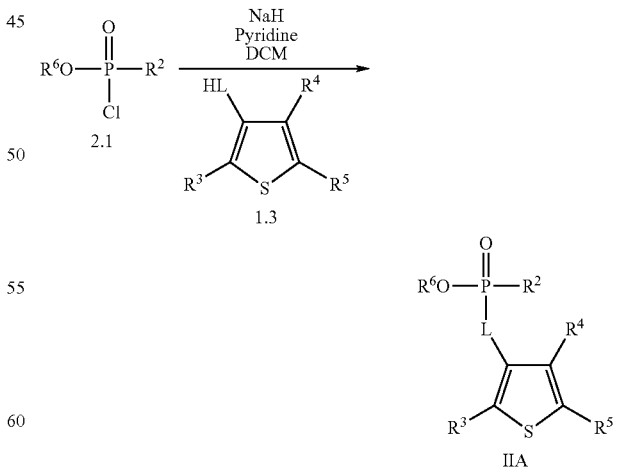

In some embodiments, L in Scheme 1 is $NR^{16}$. In certain embodiments, the compound of Formula IIIA can be prepared as shown in Scheme 3, where $R^2$, $R^3$, $R^4$, $R^5$ and $R^{16}$ are as defined herein.

Scheme 3

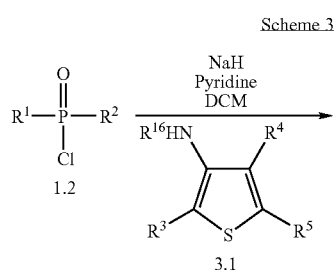

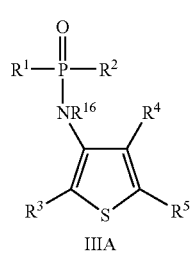

In some embodiments, $R^3$ in Scheme 1 is —C(O)OR$^8$. In certain embodiments, the compound of Formula VA can be prepared as shown in Scheme 4, where $R^1$, $R^2$, $R^4$, $R^5$, $R^6$, $R^8$, and L are as defined herein.

Scheme 4

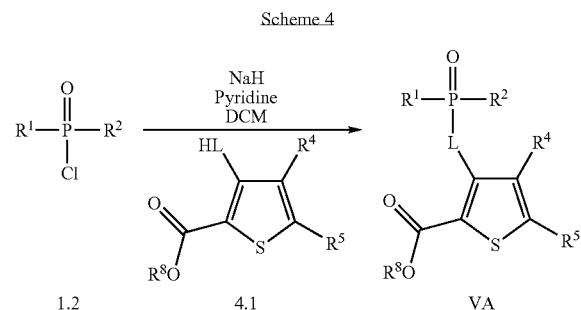

In some embodiments, $R^1$ in Scheme 1 is OR$^6$. In further embodiments, L of Formulae 1.3 and IA of Scheme 1 is NR$^{16}$. In yet further embodiments, $R^3$ of Formulae 1.3 and IA of Scheme 1 is —C(O)OR$^8$. In some embodiments, the compound of Formula VIA can be prepared as shown in Scheme 5, where $R^2$, $R^4$, $R^5$, $R^6$, $R^8$ and $R^{16}$ are as defined herein.

Scheme 5

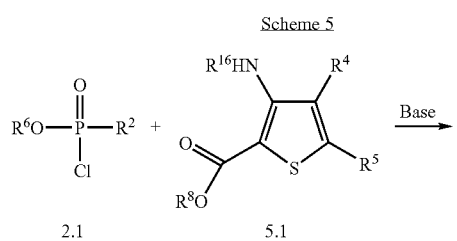

-continued

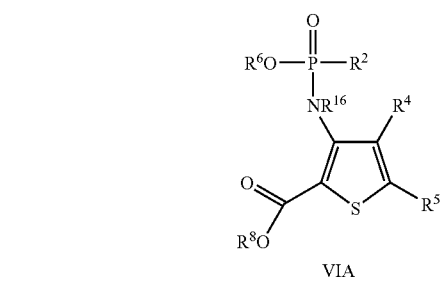

In certain embodiments, each of $R^4$ and $R^8$ in the compound of Formula VIA is independently H. In further embodiments, the compound of Formula VIA where each of $R^4$ and $R^8$ is independently H can be prepared as shown in Scheme 6.

Scheme 6

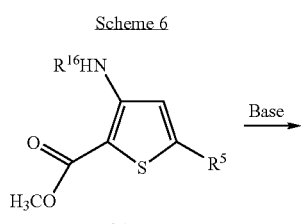

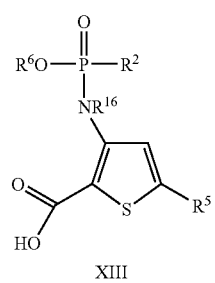

In certain embodiments, each of $R^4$, $R^8$, and $R^{16}$ in the compound of Formula VIA is independently H. In further embodiments, the compound of Formula VIA where each of $R^4$, $R^8$, and $R^{16}$ is independently H can be prepared as shown in Scheme 7.

Scheme 7

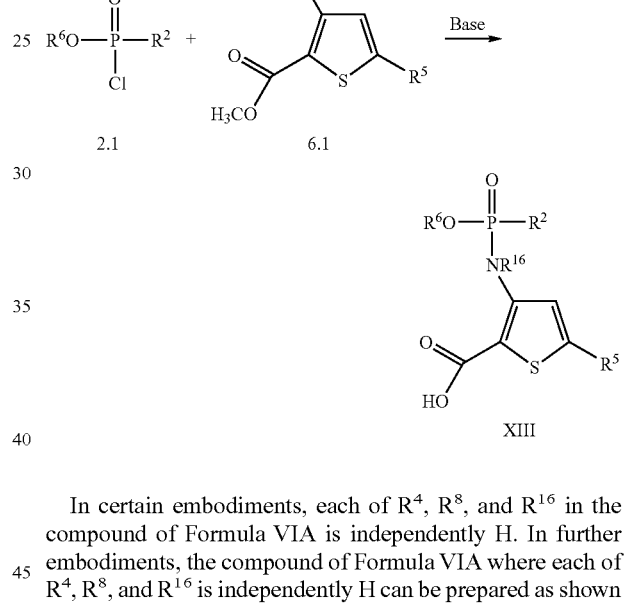

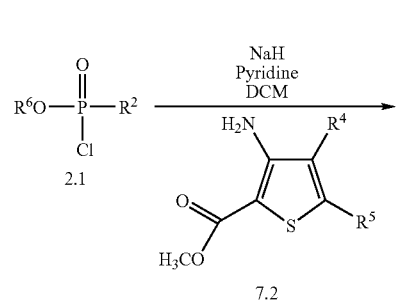

-continued

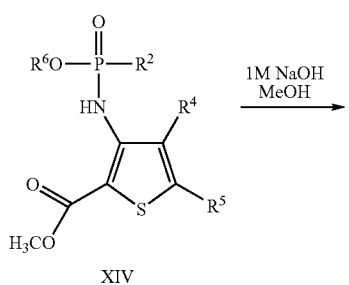
XIV

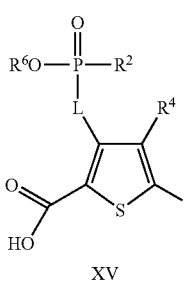
XV

In certain embodiments, L in Scheme 1 is O. In further embodiments, the compound of Formula IA where L is O can be prepared as shown in Scheme 8.

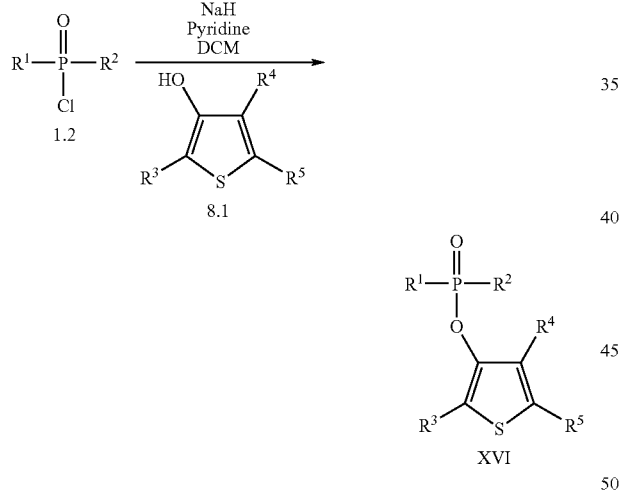

In certain embodiments, L in Scheme 1 is S. In further embodiments, the compound of Formula IA where L is S can be prepared as shown in Scheme 9.

Scheme 9

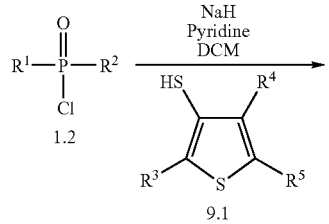

-continued

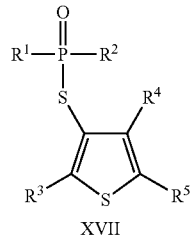
XVII

The compound provided herein can be prepared, isolated, or obtained by any method apparent to one of skill in the art. For example, the compound of Formula IB can be prepared as shown in Scheme 1B. In certain embodiments, $R^1$, $R^2$, $R^3$, $R^5$, and L are as defined herein.

Scheme 1B

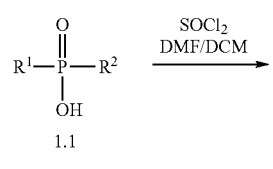

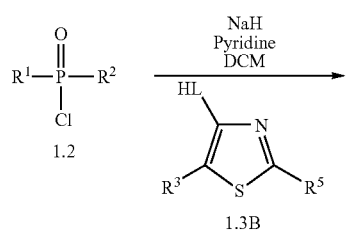

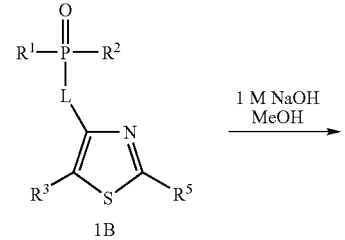
1B

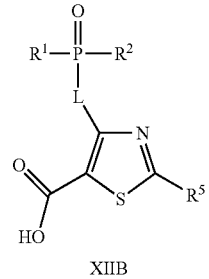
XIIB

In certain embodiments, a phosphorus compound of Formula 1.1, or a derivative thereof, can react with a chlorinating agent such as thionyl chloride in a solvent such as a mixture of dimethylformamide (DMF) and dichloromethane (DCM) to form a compound of Formula 1.2. The compound of Formula 1.2 can react with a thiazole of Formula 1.3B in the presence of a base, such as sodium hydride and pyridine, in a solvent, such as DCM to form the compound of Formula of IB. Hydrolysis of the compound of Formula of IB by a base such as 1 M sodium hydroxide in a solvent, such as methanol, can yield a compound of Formula of XIIB. Protecting groups can be used where suitable according to the judgment of one of skill in the art. In some embodiments, $R^1$ of Formulae 1.1 and 1.2 are $OR^6$; and $R^2$ of Formulae 1.1 and 1.2 are aryl. In further embodiments, $R^1$ of Formulae 1.1 and 1.2 are —OMe or —OEt; and $R^2$ of Formulae 1.1 and 1.2 are

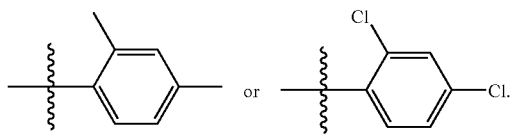

In some embodiments, $R^1$ in Scheme 1B is $OR^6$. In certain embodiments, the compound of Formula IIB can be prepared as shown in Scheme 2B, where $R^2$, $R^3$, $R^5$, $R^6$, and L are as defined herein.

Scheme 2B

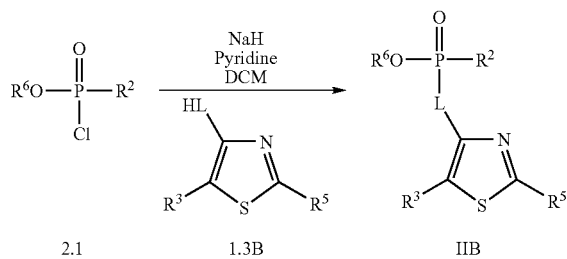

In some embodiments, L in Scheme 1B is $NR^{16}$. In certain embodiments, the compound of Formula IIIB can be prepared as shown in Scheme 3B, where $R^2$, $R^3$, $R^5$ and $R^{16}$ are as defined herein.

Scheme 3B

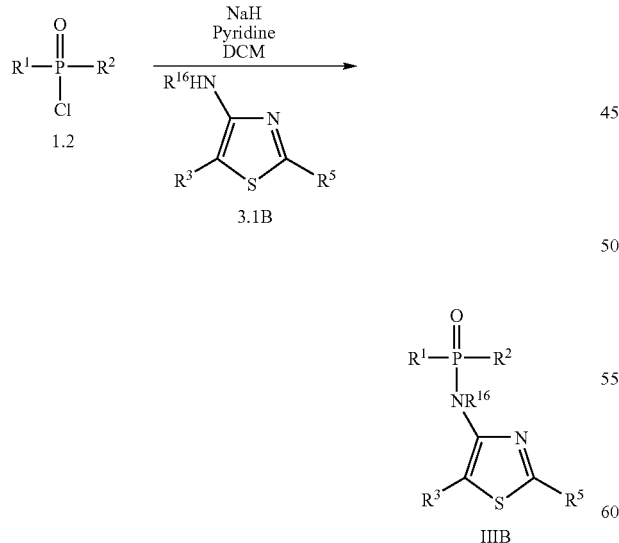

In some embodiments, $R^3$ in Scheme 1B is —C(O)OR$^8$. In certain embodiments, the compound of Formula VB can be prepared as shown in Scheme 4B, where $R^1$, $R^2$, $R^5$, $R^6$, $R^8$, and L are as defined herein.

Scheme 4B

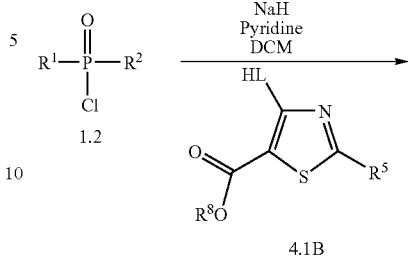

In some embodiments, $R^1$ in Scheme 1B is $OR^6$. In further embodiments, L of Formulae 1.3B and IB of Scheme 1B is $NR^{16}$. In yet further embodiments, $R^3$ of Formulae 1.3B and IB of Scheme 1 is —C(O)OR$^8$. In some embodiments, the compound of Formula VIB can be prepared as shown in Scheme 5B, where $R^2$, $R^5$, $R^6$, $R^8$ and $R^{16}$ are as defined herein.

Scheme 5B

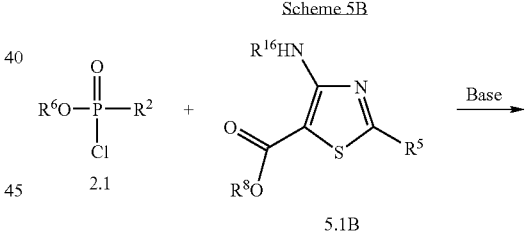

In certain embodiments, $R^8$ in the compound of Formula VIB is independently H. In further embodiments, the compound of Formula VIB where $R^8$ is independently H can be prepared as shown in Scheme 6B.

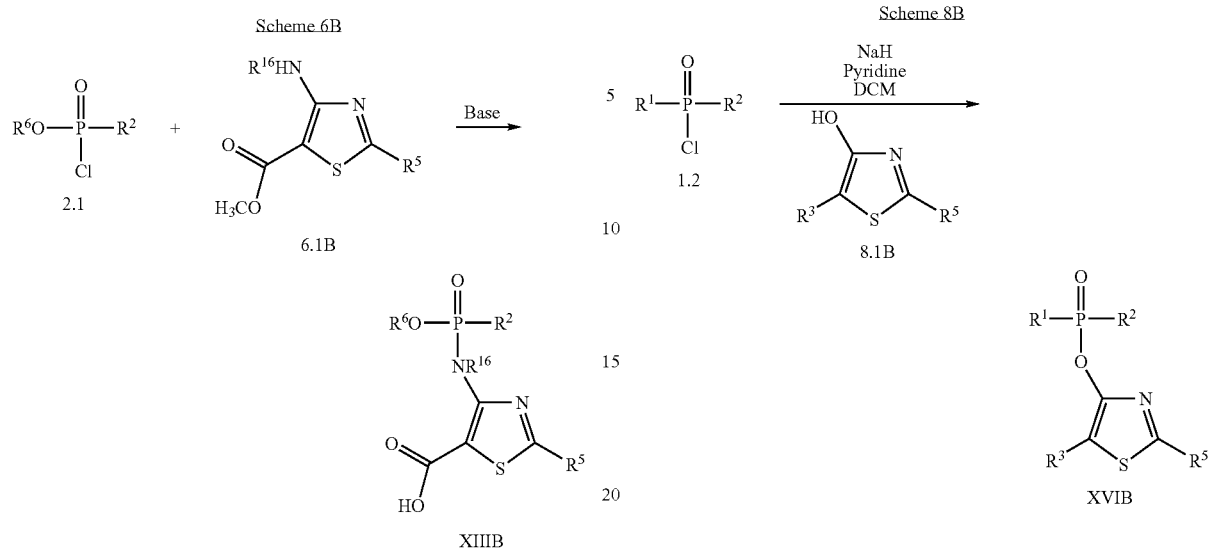

In certain embodiments, each of $R^8$, and $R^{16}$ in the compound of Formula VIB is independently H. In further embodiments, the compound of Formula VIB where each of $R^8$, and $R^{16}$ is independently H can be prepared as shown in Scheme 7B.

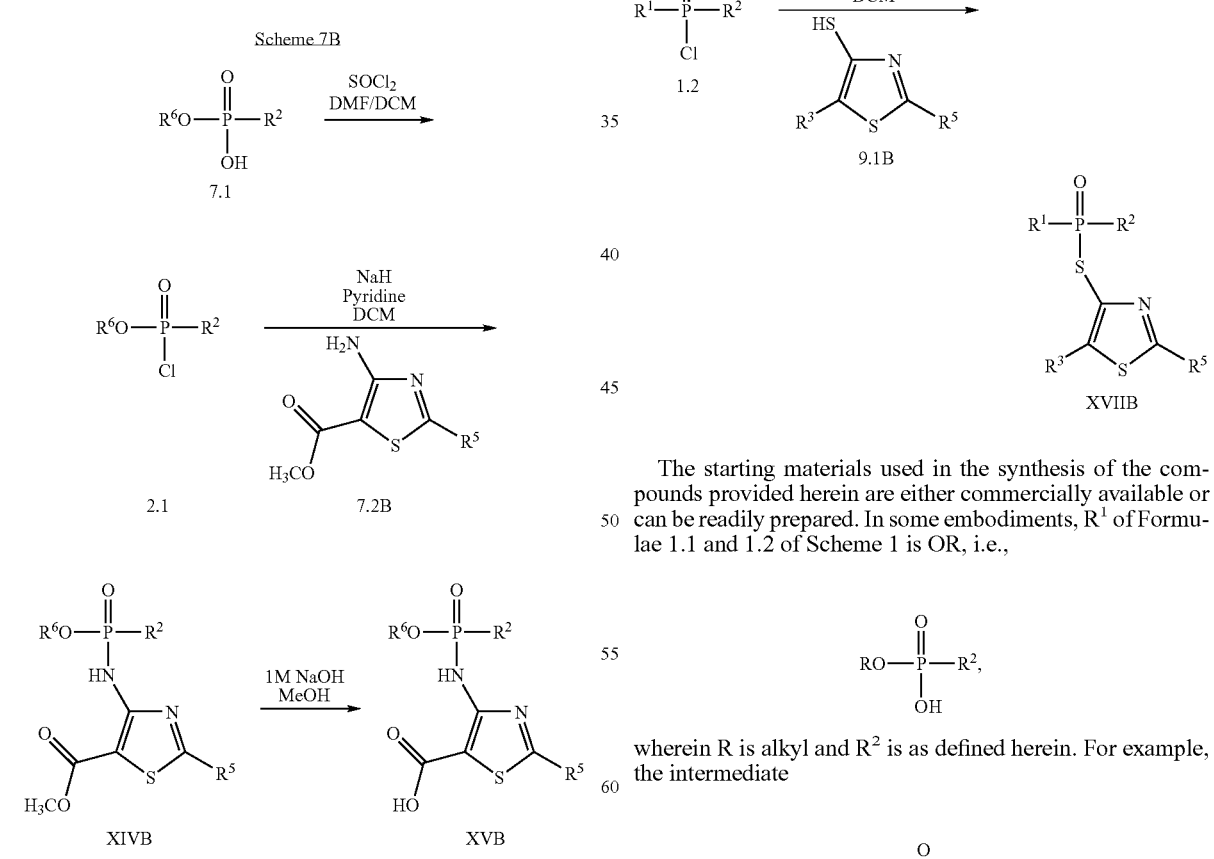

In certain embodiments, L in Scheme 1B is O. In further embodiments, the compound of Formula IB where L is O can be prepared as shown in Scheme 8B.

In certain embodiments, L in Scheme 1B is S. In further embodiments, the compound of Formula IB where L is S can be prepared as shown in Scheme 9B.

The starting materials used in the synthesis of the compounds provided herein are either commercially available or can be readily prepared. In some embodiments, $R^1$ of Formulae 1.1 and 1.2 of Scheme 1 is OR, i.e., wherein R is alkyl and $R^2$ is as defined herein. For example, the intermediate can be prepared according to Scheme 10 below. In certain embodiments, R of P(OR)₃ used in Scheme 10 below is methyl or ethyl.

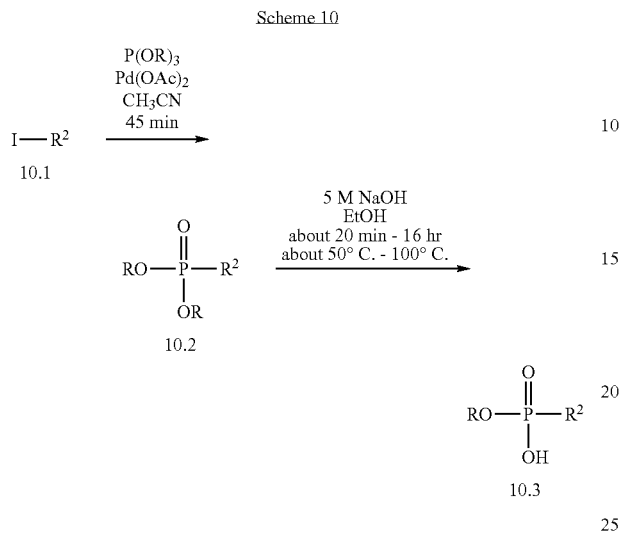

In certain embodiments, a compound of Formula 10.1, or a derivative thereof, can react with a phoshite P(OR)₃ and a palladium catalyst, Pd(OAc)₂, in the presence of a solvent, such as acetonitrile, for 45 minutes to form a compound of Formula 10.2. The compound of Formula 10.2 can react with a base, such as 5 M sodium hydroxide, in the presence of a solvent, such as ethanol, at about 50° C. to about 100° C. for about 20 minutes to about 16 hours, to form a compound of Formula 10.3. Protecting groups can be used where suitable according to the judgment of one of skill in the art.

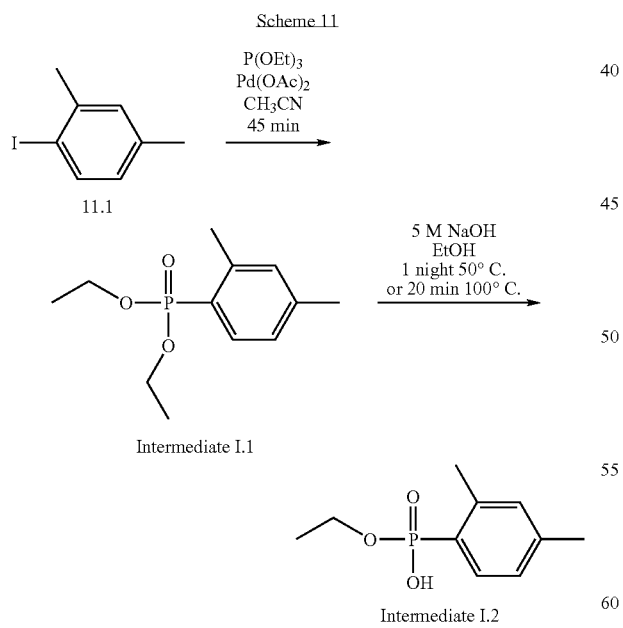

In certain embodiments, compound 11.1, or a derivative thereof, can react with a phoshite P(OEt)₃ and a palladium catalyst, Pd(OAc)₂, in the presence of a solvent, such as acetonitrile, for 45 minutes to form Intermediate I.1. Intermediate I.1 can react with a base, such as 5 M sodium hydroxide, in the presence of a solvent, such as ethanol, at about 50° C. to about 100° C. for about 20 minutes to about 16 hours, to form Intermediate I.2. Protecting groups can be used where suitable according to the judgment of one of skill in the art.

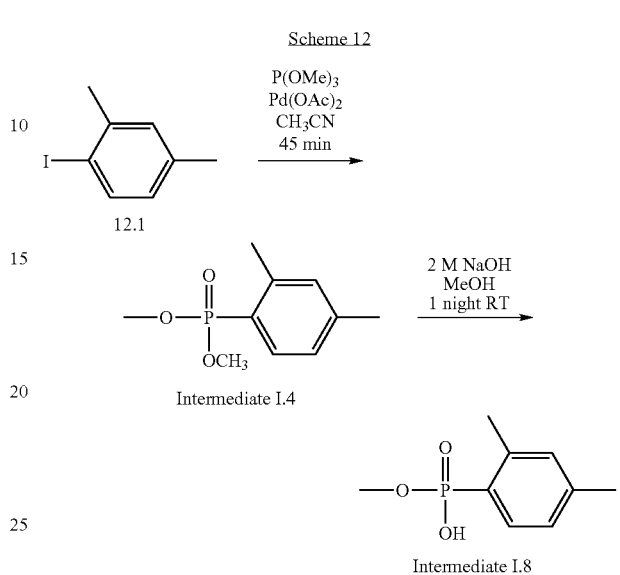

In certain embodiments, compound 12.1, or a derivative thereof, can react with a phoshite P(OMe)₃ and a palladium catalyst, Pd(OAc)₂, in the presence of a solvent, such as acetonitrile, for 45 minutes to form Intermediate I.4. Intermediate I.4 can react with a base, such as 2 M sodium hydroxide, in the presence of a solvent, such as methanol, at room temperature for about 16 hours, to form Intermediate I.8. Protecting groups can be used where suitable according to the judgment of one of skill in the art.

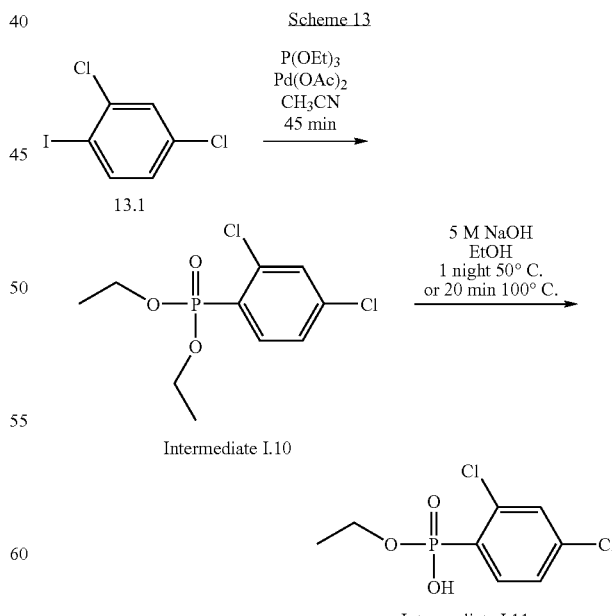

In certain embodiments, compound 13.1, or a derivative thereof, can react with a phoshiteP(OEt)₃ and a palladium catalyst, Pd(OAc)₂, in the presence of a solvent, such as acetonitrile, for 45 minutes to form Intermediate I.10. Intermediate I.10 can react with a base, such as 5 M sodium hydroxide, in the presence of a solvent, such as ethanol, at about 50° C. to about 100° C. for about 20 minutes to about 16 hours, to form Intermediate I.11. Protecting groups can be used where suitable according to the judgment of one of skill in the art.

An alternative strategy is shown in Scheme 14. In certain embodiments, a compound of Formula 14.2, or a derivative thereof, can react with $R^{16}X$ in the presence of a base and a solvent to form a compound of Formula VIA, where $R^2$, $R^4$, $R^5$, $R^6$, and $R^8$ are as defined herein. In further embodiments, $R^{16}$ of Formula 14.1 is alkyl. Protecting groups can be used where suitable according to the judgment of one of skill in the art.

Scheme 14

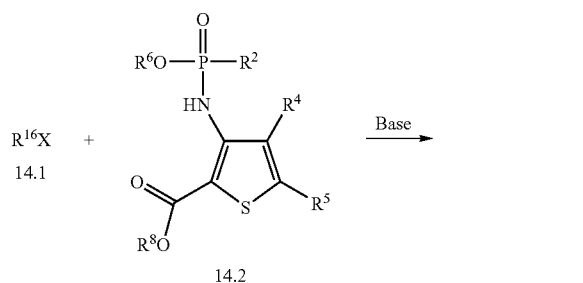

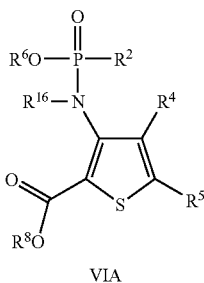

VIA

In some embodiments, $R^8$ of Formulae 14.2 and VIA of Scheme 14 is H, where $R^2$, $R^4$, $R^5$, $R^6$, and $R^{16}$ are as defined herein. In certain embodiments, a compound of Formula VIA, wherein $R^8$ is H, can be prepared as shown in Scheme 15.

Scheme 15

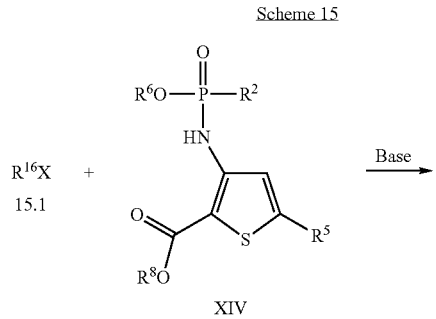

XIV

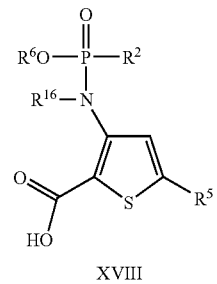

XVIII

In certain embodiments, a compound of Formula 14.2B, or a derivative thereof, can react with $R^{16}X$ in the presence of a base and a solvent to form a compound of Formula VIB, where $R^2$, $R^5$, $R^6$, and $R^8$ are as defined herein. In further embodiments, $R^{16}$ of Formula 14.1 is alkyl. Protecting groups can be used where suitable according to the judgment of one of skill in the art.

Scheme 14B

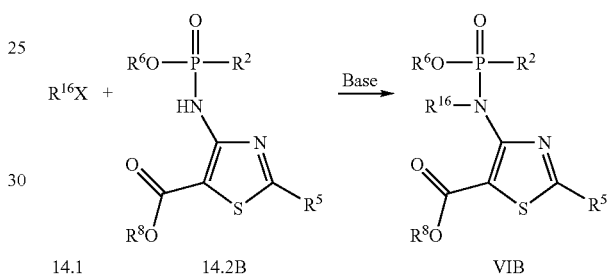

In some embodiments, $R^8$ of Formulae 14.2B and VIB of Scheme 14B is H, where $R^2$, $R^5$, $R^6$, and $R^{16}$ are as defined herein. In certain embodiments, a compound of Formula VIB, wherein $R^8$ is H, can be prepared as shown in Scheme 15B.

Scheme 15B

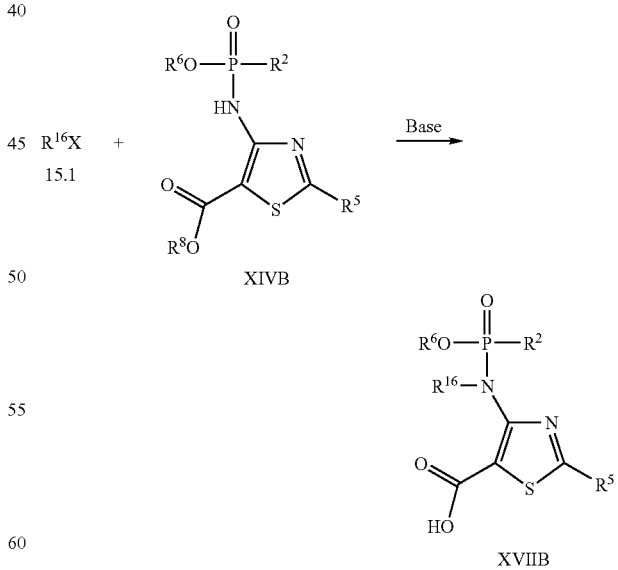

In some embodiments, each of compounds of Formulae 16.1, 17.1, XIX and XXVIX in Schemes 16 and 17 below can be alkylated by a nucleophilic alkylating agent. In general, nucleophilic alkylating agents deliver the equivalent of an alkyl anion, i.e., a carbanion to an electron-deficient carbon atom, e.g., a carbonyl group. Any nucleophilic alkylating agents suitable for alkylating a compound of Formula I can be used herein. Non-limiting examples of suitable nucleophilic alkylating agents include organolithium reagents, organocopper reagents, organosodium reagents and organometallic compounds, e.g., Grignard reagents. Generally, nucleophilic alkylating agents can also displace halide substituents on a carbon atom. In the presence of catalysts, nucleophilic alkylating agents can alkylate alkyl and aryl halides, e.g., Suzuki coupling. Generally, Suzuki coupling is an organic reaction of a nucleophilic alkylating agent with a halide-substituted compound catalyzed by a palladium (0) complex. Suzuki coupling can generally be used to synthesize poly-olefins, styrenes, and substituted biphenyls. In further embodiments, each of compounds of Formulae 17.1, XIX and XXVIX can be alkylated by a nucleophilic alkylating agent. In still further embodiments, each of compounds of Formulae 17.1, XIX and XXVIX can be alkylated by Suzuki coupling. In certain embodiments, the nucleophilic alkylating agent used in Suzuki coupling is a boronic acid, or a derivative thereof. In some embodiments, the nucleophilic alkylating agent by Suzuki coupling is an ester derivative of a boronic acid. In further embodiments, each of compounds of Formulae 17.1, XIX and XXVIX can be alkylated by an ester derivative of a boronic acid.

An alternative strategy is shown in Scheme 16. In certain embodiments, a compound of Formula 16.1, or a derivative thereof, can first react with lithium diisopropylamide (LDA) in the presence of a solvent, such as THF, and then react with iodine to form a compound of Formula XIX, where $R^2$, $R^6$ and $R^8$ are as defined herein. The compound of Formula XIX can react with a nucleophilic alkylating agent, such as a compound of Formula 16.2 in the presence of a palladium catalyst, such as Pd(DtBPF)Cl$_2$, a base, such as sodium hyrogencarbonate (NaHCO$_3$) and a solvent, such as a mixture of dioxane and water, to form a compound of Formula XXVI. In further embodiments, $R^8$ of Formulae 16.1, XXVI and XIX is alkyl. In still further embodiments, $R^5$ of Formulae 16.2 and XXVI is as defined herein. Protecting groups can be used where suitable according to the judgment of one of skill in the art.

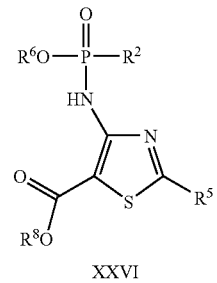

XXVI

An alternative strategy is shown in Scheme 17. In certain embodiments, a compound of Formula XXVI, or a derivative thereof, can be prepared as shown in Scheme 17, where $R^2$, $R^5$, $R^6$ and $R^8$ are as defined herein. The compound of Formula 17.1, or a derivative thereof, can react with a nucleophilic alkylating agent, such as a compound of Formula 16.2, in the presence of a palladium catalyst, such as Pd(PPh$_3$)$_4$, a base, such as K$_3$PO$_4$ and a solvent, such as DMF to form a compound of Formula XXVII. The compound of Formula XXVII can react with a compound of Formula 17.2 in the presence of a palladium catalyst, such as Pd$_2$dba$_3$, a base, such as K$_3$PO$_4$ and a solvent, such as toluene, to form a compound of Formula XXVI. In some embodiments, $R^8$ of Formulae 17.1, XXVI and XXVII is alkyl. Protecting groups can be used where suitable according to the judgment of one of skill in the art.

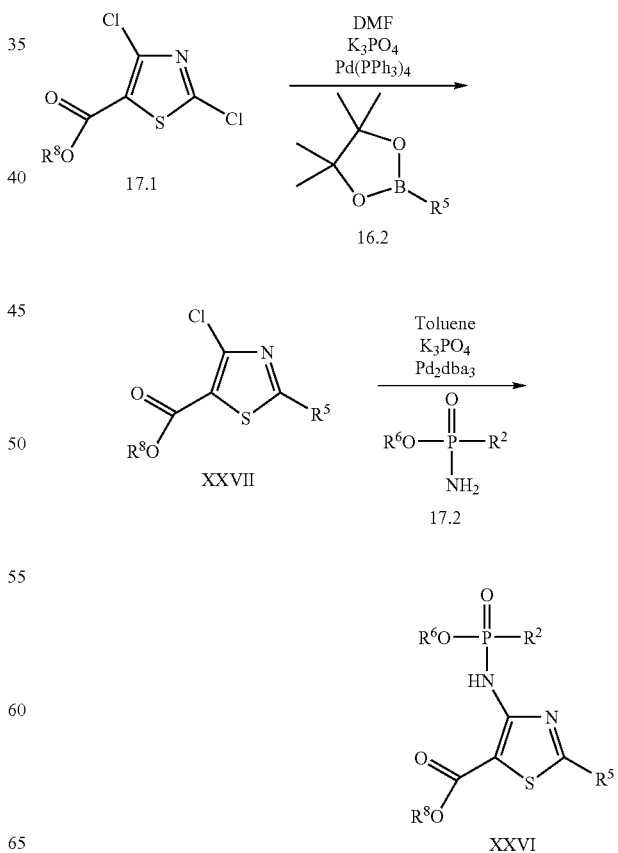

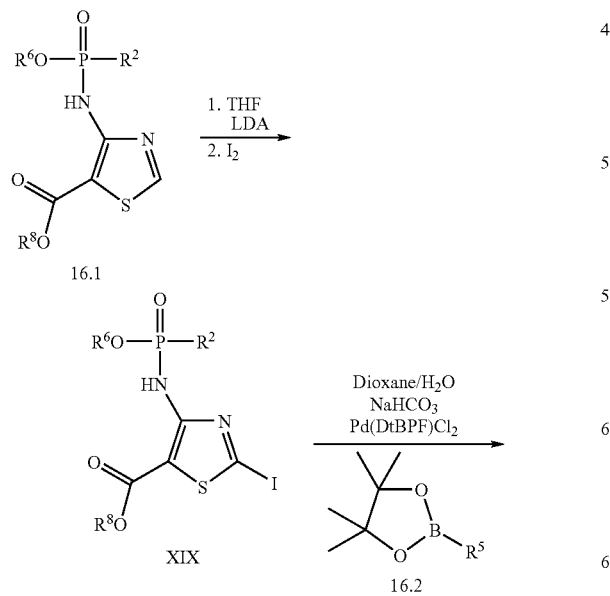

In further embodiments, the boron agent in Scheme 17 is a boronic acid having Formula 18.1:

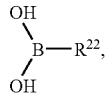
(18.1)

wherein $R^{22}$ alkyl, alkenyl, alkynyl, aryl, aralkyl, alkaryl, cycloalkyl, heterocyclyl or heteroaryl. In some embodiments, the boronic acid disclosed herein is 4-chlorophenylboronic acid.

In further embodiments, a compound of Formula XXVIII can be prepared according to Scheme 18. In some embodiments, The compound of Formula 17.1, or a derivative thereof, can react with a nucleophilic alkylating agent, such as 4-chlorophenyl-boronic acid, in the presence of a palladium catalyst, such as Pd(PPh$_3$)$_4$, a base, such as K$_3$PO$_4$ and a solvent, such as DMF to form a compound of Formula)(XVIII. The compound of Formula XXVIII can react with a compound of Formula 17.2 in the presence of a palladium catalyst, such as Pd$_2$ dba$_3$, a base, such as K$_3$PO$_4$ and a solvent, such as toluene, to form a compound of Formula XXIX. The compound of Formula XXIX can react with a boron agent, such as a compound of Formula 18.1, in the presence of a palladium catalyst, such as Pd(PPh$_3$)$_4$, a base, such as K$_3$PO$_4$ and a solvent, such as DMF to form a compound of Formula XXX.

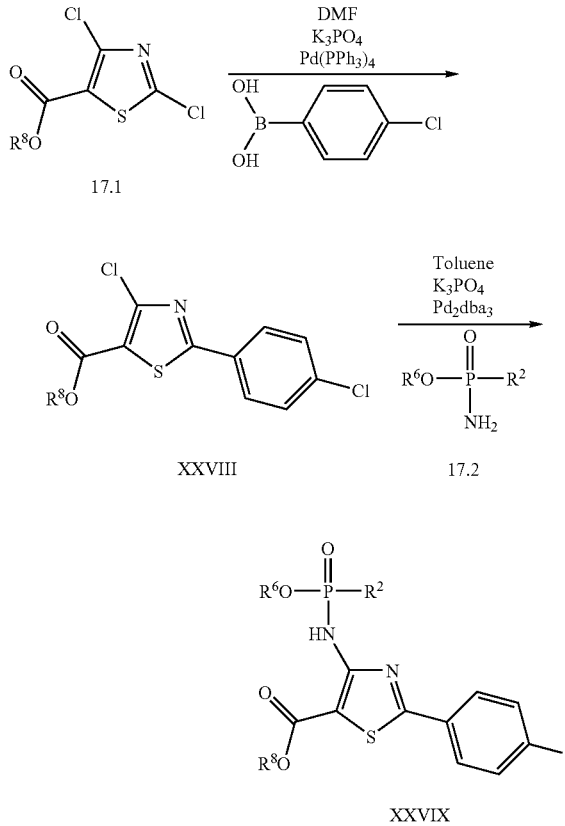

Scheme 18

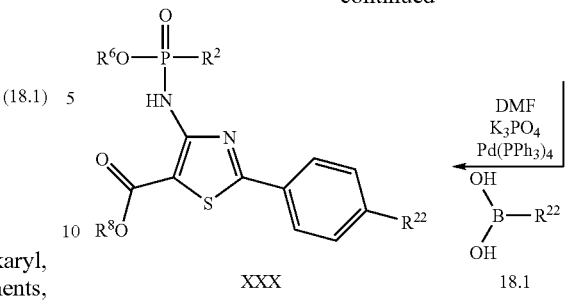

XXX          18.1

In some embodiments, R$^1$ of Formula 1.1, 1.2, IA, IIIA, VA, IB, IIIB, VB, XII, XVI, XVII, XIIB, XVIB, or XVIIB is —OR$^6$. In some embodiments, R$^6$ of Formula 1.1, 1.2, IA, IIIA, VA, XII, XVI, XVII, XIIB, XVIB, or XVIIB is H, methyl, or ethyl. In further embodiments, R$^6$ of Formula 2.1, 5.1, 6.1, 7.1, 14.1, 14.2, 5.1B, 6.1B, 7.1B, 14.2B, IIA, VIA, XIII, XIV, XV, XIIIB, XIVB, or XVB is H, methyl or ethyl.

In certain embodiments, R$^2$ of Formula 1.1, 1.2, 2.1, 7.1, 7.1B, 10.1, 10.2, 10.3, 14.2, 14.2B, IA, IIA, IIIA, VA, VIA, XII, XIII, XIV, XV, XVI, XVII, IB, IIB, IIIB, VB, VIB, XIIB, XIIIB, XIVB, XVB, XVIB, or XVIIB is aryl. In further embodiments, R$^2$ of Formula 1.1, 1.2, 2.1, 7.1, 7.1B, 10.1, 10.2, 10.3, 14.2, 14.2B, IA, IIA, IIIA, VA, VIA, XII, XIII, XIV, XV, XVI, XVII, IB, IIB, IIIB, VB, VIB, XIIB, XIIIB, XIVB, XVB, XVIB or XVIIB is

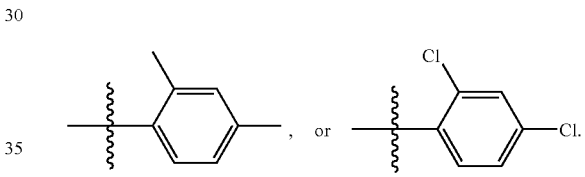

In some embodiments, R$^3$ of Formula 1.3, 3.1, 8.1, 9.1, 3.1B, 8.1B, 9.1B, IA, IIA, IIIA, XVI, XVII, IB, IIB, IIIB, XVIB, or XVIIB is —C(O)OR$^8$. In further embodiments, R$^8$ of Formula 4.1, 5.1, 6.1, 7.2, 14.2, 4.1B, 5.1B, 6.1B, 7.2B, 14.2B, VA, VIA, XII, XIII, XIV, XV, VB, VIB, XIIB, XIIIB, XIVB or XVB is H or methyl.

In some embodiments, R$^4$ of Formula 1.3, 3.1, 4.1, 5.1, 7.2, 8.1, 9.1, 14.2, 3.1B, 4.1B, 5.1B, 7.2B, 8.1B, 9.1B, 14.2B, IA, IIA, IIIA, VA, VIA, XII, XVI, XVII, IB, IIB, IIIB, VB, VIB, XIIB, XVIB or XVIIB is H or halogen.

In certain embodiments, R$^5$ of Formula 1.3, 3.1, 4.1, 5.1, 6.1, 7.2, 8.1, 9.1, 14.2, 3.1B, 4.1B, 5.1B, 6.1B, 7.2B, 8.1B, 9.1B, 14.2B, IA, IIA, IIIA, VA, VIA, XII, XIII, XIV, XV, XVI, XVII, IB, IIB, IIIB, VB, VIB, XIIB, XIIIB, XIVB, XVB, XVIB or XVIIB is alkyl or aryl. In further embodiments, R$^5$ of Formula 1.3, 3.1, 4.1, 5.1, 6.1, 7.2, 8.1, 9.1, 14.2, 3.1B, 4.1B, 5.1B, 6.1B, 7.2B, 8.1B, 9.1B, 14.2B, IA, IIA, IIIA, VA, VIA, XII, XIII, XIV, XV, XVI, XVII, IB, IIB, IIIB, VB, VIB, XIIB, XIIIB, XIVB, XVB, XVIB or XVIIB is

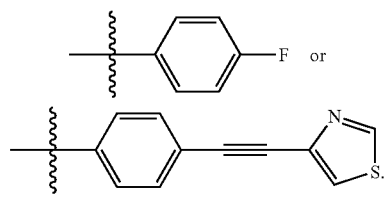

In some embodiments, L of Formula 1.3, 4.1, 4.1B, IA, IIA, VA, XII, IB, IIB, VB, or XIIB is $NR^{16}$. In further embodiments, $R^{16}$ of Formula 1.3, 4.1, 4.1B, IA, IIA, VA, XII, IB, IIB, VB, or XIIB is H.

In certain embodiments, $R^{16}$ of Formula 3.1, 5.1, 6.1, 3.1B, 5.1B, 6.1B, 14.1, IIIA, VIA, XIII, IIIB, VIB or XIIIB is H.

Pharmaceutical Compositions

Provided herein are pharmaceutical compositions comprising a compound provided herein as an active ingredient, including a single enantiomer, a mixture of an enantiomeric pair, an individual diastereomer, or a mixture of diastereomers thereof; or a pharmaceutically acceptable salt, solvate, or prodrug thereof, in a pharmaceutically acceptable vehicle, carrier, diluent, or excipient, or a mixture thereof; in combination with one or more pharmaceutically acceptable diluents, excipients or carriers. In certain embodiments, the pharmaceutical composition comprises at least one release controlling excipient or carrier. In certain embodiments, the pharmaceutical composition comprises at least one nonrelease controlling excipient or carrier. In certain embodiments, the pharmaceutical composition comprises at least one release controlling and at least one nonrelease controlling diluents, excipients or carriers.

The compound provided herein may be administered alone, or in combination with one or more other compounds provided herein, one or more other active ingredients. The pharmaceutical compositions that comprise a compound provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In some embodiments, the pharmaceutical compositions are provided in a dosage form for oral administration, which comprise a compound provided herein, including a single enantiomer, a mixture of an enantiomeric pair, an individual diastereomer, or a mixture of diastereomers thereof; or a pharmaceutically acceptable salt, solvate, or prodrug thereof; and one or more pharmaceutically acceptable diluents, excipients or carriers.

In another embodiment, the pharmaceutical compositions are provided in a dosage form for parenteral administration, which comprise a compound provided herein, including a single enantiomer, a mixture of an enantiomeric pair, an individual diastereomer, or a mixture of diastereomers thereof; or a pharmaceutically acceptable salt, solvate, or prodrug thereof; and one or more pharmaceutically acceptable diluents, excipients or carriers.

In yet another embodiment, the pharmaceutical compositions are provided in a dosage form for topical administration, which comprise a compound provided herein, including a single enantiomer, a mixture of an enantiomeric pair, an individual diastereomer, or a mixture of diastereomers thereof; or a pharmaceutically acceptable salt, solvate, or prodrug thereof; and one or more pharmaceutically acceptable diluents, excipients or carriers.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W. R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as drotrecogin-α, and hydrocortisone.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In some embodiments, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In some embodiments, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as /–leucine, mannitol, or magnesium stearate. The lactose may be anhydrous or in the form of the monohydrate. Other suitable diluents, excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In some embodiments, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other diluents, excipients or carriers in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional diluents, excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable diluents, excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable diluents, excipients or carriers.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other diluents, excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

Provided herein are methods for treating or preventing a hepatitis C viral infection in a subject, which comprises administering to a subject infected with HCV a therapeutically effective amount of a compound provided herein, including a single enantiomer, a mixture of an enantiomeric pair, an individual diastereomer, or a mixture of diastereomers thereof or a pharmaceutically acceptable salt, solvate, or prodrug thereof. In some embodiments, the subject is a mammal. In another embodiment, the subject is a human.

In certain embodiments, administration of a therapeutically effective amount of a compound provided herein, including a single enantiomer, a mixture of an enantiomeric pair, an individual diastereomer, or a mixture of diastereomers thereof or a pharmaceutically acceptable salt, solvate, or prodrug thereof, results in a 1, 2, 3, 4, 5, 10, 15, 20, 25, 50, 75, 100-fold or more reduction in the replication of the virus relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein, including a single enantiomer, a mixture of an enantiomeric pair, an individual diastereomer, or a mixture of diastereomers thereof or a pharmaceutically acceptable salt, solvate, or prodrug thereof, results in a 10%, 20%, 30%, 40%, 50%, 60%, 70%, 80%, 90%, 95%, 99% or more reduction in the viral titer relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein, including a single enantiomer, a mixture of an enantiomeric pair, an individual diastereomer, or a mixture of diastereomers thereof or a pharmaceutically acceptable salt, solvate, or prodrug thereof, results in a 1, 2, 3, 4, 5, 10, 15, 20, 25, 50, 75, 100 or more fold reduction in the viral titer relative to a subject without administration of the compound, as determined at 1 day, 2 days, 3 days, 4 days, 5 days, 10 days, 15 days, or 30 days after the administration by a method known in the art.

Further provided herein is a method for inhibiting the replication of an HCV virus, which comprises contacting the virus with a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof.

Additionally, provided herein is a method for inhibiting replication of a virus in a host, which comprises contacting the host with a therapeutically effective amount of the compound of Formula I, II, III, IV, V, VI, VII or XX, including a single enantiomer, a mixture of an enantiomeric pair, an individual diastereomer, or a mixture of diastereomers thereof; or a pharmaceutically acceptable salt, solvate, or prodrug thereof. In some embodiments, the host is a cell. In another embodiment, the host is a human cell. In yet another embodiment, the host is a mammal. In still another embodiment, the host is human.

Additionally, provided herein is a method for inhibiting replication of a virus in a cell, which comprises contacting the cell with a therapeutically effective amount of the compound of Formula I, II, III, IV, V, VI, VII or XX, including a single enantiomer, a mixture of an enantiomeric pair, an individual diastereomer, or a mixture of diastereomers thereof; or a pharmaceutically acceptable salt, solvate, or prodrug thereof. In some embodiments, the cell is a human cell.

In certain embodiments, administration of a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the replication of the virus relative to a subject without administration of the compound, as determined at 1 day, 2 days, 3 days, 4 days, 5 days, 10 days, 15 days, or 30 days after the administration by a method known in the art, e.g., determination of viral titer.

In certain embodiments, the contacting of the cell with a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the virus titer relative to the virus without such contact, as determined at 1 day, 2 days, 3 days, 4 days, 5 days, 10 days, 15 days, or 30 days after the initial contact, by a method known in the art.

In certain embodiments, the contacting of the cell with a therapeutically effective amount of a compound provided herein, including a single enantiomer, a mixture of an enantiomeric pair, an individual diastereomer, or a mixture of diastereomers thereof or a pharmaceutically acceptable salt, solvate, or prodrug thereof, results in a 1, 2, 3, 4, 5, 10, 15, 20, 25, 50, 75, 100-fold or more reduction in the virus titer relative to the virus without such contact, as determined at 1 day, 2 days, 3 days, 4 days, 5 days, 10 days, 15 days, or 30 days after the initial contact, by a method known in the art.

In certain embodiments, the contacting of the cell with a therapeutically effective amount of a compound provided herein, including a single enantiomer, a mixture of an enantiomeric pair, an individual diastereomer, or a mixture of diastereomers thereof or a pharmaceutically acceptable salt, solvate, or prodrug thereof, results in a 10%, 20%, 30%, 40%, 50%, 60%, 70%, 80%, 90%, 95%, 99% or more reduction in the viral titer relative to the virus without such contact, as determined at 1 day, 2 days, 3 days, 4 days, 5 days, 10 days, 15 days, or 30 days after the initial contact by a method known in the art.

In certain embodiments, the contacting of the cell with a therapeutically effective amount of a compound provided herein, including a single enantiomer, a mixture of an enantiomeric pair, an individual diastereomer, or a mixture of diastereomers thereof or a pharmaceutically acceptable salt, solvate, or prodrug thereof, results in a 1, 2, 3, 4, 5, 10, 15, 20, 25, 50, 75, 100 or more fold reduction in the viral titer relative to the virus without such contact, as determined at 1 day, 2 days, 3 days, 4 days, 5 days, 10 days, 15 days, or 30 days after the initial contact, by a method known in the art.

Also provided herein is a method for treating, preventing, or ameliorating one or more symptoms of a liver disease or disorder associated with an HCV infection, comprising administering to a subject having the disease or disorder a therapeutically effective amount of the compound provided herein, including a single enantiomer, a mixture of an enantiomeric pair, an individual diastereomer, or a mixture of diastereomers thereof or a pharmaceutically acceptable salt, solvate, or prodrug thereof. Non-limiting examples of diseases associated with HCV infection include chronic hepatitis, cirrhosis, hepatocarcinoma, or extra hepatic manifestation.

Provided herein is a method for inhibiting the activity of an HCV polymerase, which comprises contacting the polymerase with an effective amount of a compound provided herein, including a single enantiomer, a mixture of an enantiomeric pair, an individual diastereomer, or a mixture of diastereomers thereof; or a pharmaceutically acceptable salt, solvate, or prodrug thereof. In some embodiments, the polymerase is hepatitis C NS5B polymerase.

Depending on the condition, disorder, or disease, to be treated and the subject's condition, a compound provided herein may be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1000 milligram, from about 0.1 to about 500 milligrams, or from 0.5 about to about 100 milligram active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

Combination Therapy

The compounds provided herein may also be combined or used in combination with other therapeutic agents useful in the treatment and/or prevention of an HCV infection.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of a compound provided herein and another therapy (e.g., a prophylactic or therapeutic agent) which has been or is currently being used to treat, prevent, or manage a disease or disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The compound provided herein can be administered in combination or alternation with another therapeutic agent, such as an anti-HCV agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

It has been recognized that drug-resistant variants of HCV can emerge after prolonged treatment with an antiviral agent. Drug resistance most typically occurs due to the mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameters of the drug can be altered by such combination or alternation therapy. In general, combination therapy is typically preferred over alternation therapy because it induces multiple simultaneous stresses on the virus.

In certain embodiments, the compound provided herein is combined with one or more agents selected from the group consisting of an interferon, ribavirin, amantadine, an interleukin, a NS3 protease inhibitor, a cysteine protease inhibitor, a phenanthrenequinone, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, and a ribozyme.

In certain embodiments, the compound provided herein is combined with a HCV protease inhibitor, including, but not limited to, Medivir HCV protease inhibitor (Medivir/Tobotec); ITMN-191 (InterMune), SCH 503034 (Schering), VX950 (Vertex); substrate-based NS3 protease inhibitors as disclosed in WO 98/22496; Attwood et al., *Antiviral Chemistry and Chemotherapy* 1999, 10, 259-273; DE 19914474; WO 98/17679; WO 99/07734; non-substrate-based NS3 protease inhibitors, such as 2,4,6-trihydroxy-3-nitro-benzamide derivatives (Sudo et al., *Biochem. Biophys. Res. Commun.* 1997, 238, 643-647), RD3-4082, RD3-4078, SCH 68631, and a phenanthrenequinone (Chu et al., *Tetrahedron Letters* 1996, 37, 7229-7232); SCH 351633 (Chu et al., *Bioorganic and Medicinal Chemistry Letters* 1999, 9, 1949-1952); Eglin c, a potent polymerase inhibitor (Qasim et al., *Biochemistry* 1997, 36, 1598-1607).

Other suitable protease inhibitors for the treatment of HCV include those disclosed in, for example, U.S. Pat. No. 6,004, 933, which discloses a class of cysteine protease inhibitors of HCV endopeptidase 2.

Additional hepatitis C virus NS3 protease inhibitors include those disclosed in, for example, Llinds-Brunet et al., *Bioorg. Med. Chem. Lett.* 1998, 8, 1713-1718; Steinkühler et al., *Biochemistry* 1998, 37, 8899-8905; U.S. Pat. Nos. 5,538, 865; 5,990,276; 6,143,715; 6,265,380; 6,323,180; 6,329,379; 6,410,531; 6,420,380; 6,534,523; 6,642,204; 6,653,295; 6,727,366; 6,838,475; 6,846,802; 6,867,185; 6,869,964; 6,872,805; 6,878,722; 6,908,901; 6,911,428; 6,995,174; 7,012,066; 7,041,698; 7,091,184; 7,169,760; 7,176,208; 7,208,600; U.S. Pat. App. Pub. Nos.: 2002/0016294, 2002/0016442; 2002/0037998; 2002/0032175; 2004/0229777; 2005/0090450; 2005/0153877; 2005/176648; 2006/0046956; 2007/0021330; 2007/0021351; 2007/0049536; 2007/0054842; 2007/0060510; 2007/0060565; 2007/0072809; 2007/0078081; 2007/0078122; 2007/0093414; 2007/0093430; 2007/0099825; 2007/0099929; 2007/0105781; WO 98/17679; WO 98/22496; WO 99/07734; WO 00/059929; WO 00/09543; WO 02/060926; WO 02/08187; WO 02/008251; WO 02/008256; WO 02/08198; WO 02/48116; WO 02/48157; WO 02/48172; WO 03/053349; WO 03/064416; WO 03/064456; WO 03/099274; WO 03/099316; WO 2004/032827; WO 2004/043339; WO 2005/037214; WO 2005/037860; WO 2006/000085; WO 2006/119061; WO 2006/122188; WO 2007/001406; WO 2007/014925; WO 2007/014926; and WO 2007/056120.

Other protease inhibitors include thiazolidine derivatives, such as R$^D$-1-6250, RD4 6205, and RD4 6193, which show relevant inhibition in a reverse-phase HPLC assay with an NS3/4A fusion protein and NS5A/5B substrate (Sudo et al., *Antiviral Research* 1996, 32, 9-18); thiazolidines and benzanilides identified in Kakiuchi et al., *FEBS Lett.* 1998, 421, 217-220; Takeshita et al., *Analytical Biochemistry* 1997, 247, 242-246.

Suitable helicase inhibitors include, but are not limited to, those disclosed in U.S. Pat. No. 5,633,358; and WO 97/36554.

Suitable nucleotide polymerase inhibitors include, but are not limited to, gliotoxin (Ferrari et al., *Journal of Virology* 1999, 73, 1649-1654), and the natural product cerulenin (Lohmann et al., *Virology* 1998, 249, 108-118).

Suitable interfering RNA (iRNA) based antivirals include, but are not limited to, short interfering RNA (siRNA) based antivirals, such as Sirna-034 and those described in WO/03/070750, WO 2005/012525, and U.S. Pat. Pub. No. 2004/0209831.

Suitable antisense phosphorothioate oligodeoxynucleotides (S-ODN) complementary to sequence stretches in the 5' non-coding region (NCR) of HCV virus include, but are not limited to those described in Alt et al., *Hepatology* 1995, 22, 707-717, and nucleotides 326-348 comprising the 3' end of the NCR and nucleotides 371-388 located in the core coding region of HCV RNA (Alt et al., *Archives of Virology* 1997, 142, 589-599; Galderisi et al., *Journal of Cellular Physiology* 1999, 181, 251-257);

Suitable inhibitors of IRES-dependent translation include, but are not limited to, those described in Japanese Pat. Pub. Nos.: JP 08268890 and JP 10101591.

Suitable ribozymes include those disclosed in, for example, U.S. Pat. Nos. 6,043,077; 5,869,253 and 5,610,054.

Suitable nucleoside analogs include, but are not limited to, the compounds described in U.S. Pat. Nos. 6,660,721; 6,777,395; 6,784,166; 6,846,810; 6,927,291; 7,094,770; 7,105,499; 7,125,855; and 7,202,224; U.S. Pat. Pub. Nos. 2004/0121980; 2005/0009737; 2005/0038240; and 2006/0040890; WO 99/43691; WO 01/32153; WO 01/60315; WO 01/79246; WO 01/90121, WO 01/92282, WO 02/18404; WO 02/32920, WO 02/48165, WO 02/057425; WO 02/057287; WO 2004/002422, WO 2004/002999, and WO 2004/003000.

Other miscellaneous compounds that can be used as second agents include, for example, 1-amino-alkylcyclohexanes (U.S. Pat. No. 6,034,134), alkyl lipids (U.S. Pat. No. 5,922,757), vitamin E and other antioxidants (U.S. Pat. No. 5,922,757), squalene, amantadine, bile acids (U.S. Pat. No. 5,846,964), N-(phosphonacetyl)-L-aspartic acid (U.S. Pat. No. 5,830,905), benzenedicarboxamides (U.S. Pat. No. 5,633,388), polyadenylic acid derivatives (U.S. Pat. No. 5,496,546), 2',3'-dideoxyinosine (U.S. Pat. No. 5,026,687), benzimidazoles (U.S. Pat. No. 5,891,874), plant extracts (U.S. Pat. Nos. 5,725,859; 5,837,257; and 6,056,961), and piperidines (U.S. Pat. No. 5,830,905).

In certain embodiments, one or more compounds provided herein are administered in combination or alternation with an anti-hepatitis C virus interferon, including, but not limited to, INTRON® A (interferon alfa-2b) and PEGASYS® (Peginterferon alfa-2a); ROFERON® A (recombinant interferon alfa-2a), INFERGEN® (interferon alfacon-1), and PEG-INTRON® (pegylated interferon alfa-2b). In some embodiments, the anti-hepatitis C virus interferon is INFERGEN®, IL-29 (PEG-Interferon lambda), R7025 (Maxy-alpha), BELEROFON®, oral interferon alpha, BLX-883 (LOCTERON®), omega interferon, MULTIFERON®, medusa interferon, ALBUFERON®, or REBIF®.

In certain embodiments, one or more compounds provided herein are administered in combination or alternation with an anti-hepatitis C virus polymerase inhibitor, such as ribavirin, viramidine, NM 283 (valopicitabine), PSI-6130, R1626, HCV-796, or R7128.

In certain embodiments, the one or more compounds provided herein are administered in combination with ribavirin and an anti-hepatitis C virus interferon, such as INTRON® A (interferon alfa-2b), PEGASYS® (Peginterferon alfa-2a), ROFERON® A (recombinant interferon alfa-2a), INFERGEN® (interferon alfacon-1), and PEG-INTRON® (pegylated interferon alfa-2b), In certain embodiments, one or more compounds provided herein are administered in combination or alternation with an anti-hepatitis C virus protease inhibitor, such as ITMN-191, SCH 503034, VX950 (telaprevir), or Medivir HCV protease inhibitor.

In certain embodiments, one or more compounds provided herein are administered in combination or alternation with an anti-hepatitis C virus vaccine, including, but not limited to, TG4040, PEVIPRO™, CGI-5005, HCV/MF59, GV1001, IC41, and INNO0101 (E1).

In certain embodiments, one or more compounds provided herein are administered in combination or alternation with an anti-hepatitis C virus monoclonal antibody, such as AB68 or XTL-6865 (formerly HepX-C); or an anti-hepatitis C virus polyclonal antibody, such as cicavir.

In certain embodiments, one or more compounds provided herein are administered in combination or alternation with an anti-hepatitis C virus immunomodulator, such as ZADAXIN® (thymalfasin), NOV-205, or oglufanide.

In certain embodiments, one or more compounds provided herein are administered in combination or alternation with NEXAVAR®, doxorubicin, PI-88, amantadine, JBK-122, VGX-410C, MX-3253 (celgosivir), SUVUS® (BIVN-401 or virostat), PF-03491390 (formerly IDN-6556), G126270, UT-231B, DEBIO-025, EMZ702, ACH-0137171, MitoQ, ANA975, AVI-4065, bavituximab (tarvacin), ALINIA® (nitrazoxanide) or PYN 17.

In certain embodiments, the compounds provided herein can be combined with one or more steroidal drugs known in the art, including, but not limited to the group including, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, the compounds provided herein can be combined with one or more antibacterial agents known in the art, including, but not limited to the group including amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to the group including amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, the compounds provided herein can be combined with one or more anticoagulants known in the art, including, but not limited to the group including acenocoumarol, argatroban, bivalirudin, lepirudin, fondaparinux, heparin, phenindione, warfarin, and ximelagatran.

In certain embodiments, the compounds provided herein can be combined with one or more thrombolytics known in the art, including, but not limited to the group including anistreplase, reteplase, t-PA (alteplase activase), streptokinase, tenecteplase, and urokinase.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, the compounds provided herein can be combined with one or more antiplatelet agents known in the art, including, but not limited to, abciximab, cilostazol, clopidogrel, dipyridamole, ticlopidine, and tirofibin.

The compounds provided herein can also be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y (AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as paclitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporine; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

In certain embodiments, the pharmaceutical compositions provided herein further comprise a second antiviral agent as described herein. In some embodiments, the second antiviral is selected from the group consisting of an interferon, ribavirin, an interleukin, an NS3 protease inhibitor, a cysteine protease inhibitor, a phenanthrenequinone, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, and a ribozyme. In another embodiment, the second antiviral agent is an interferon. In yet another embodiment, the t interferon is selected from the group consisting of pegylated interferon alpha 2a, interferon βlphcon-1, natural interferon, ALBUFERON®, interferon beta-1a, omega interferon, interferon alpha, interferon gamma, interferon tau, interferon delta, and interferon gamma-1b.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer, a mixture of an enantiomeric pair, an individual diastereomer, or a mixture of diastereomers thereof; or a pharmaceutically acceptable salt, solvate, or prodrug thereof.

In certain embodiments, the kit includes a container comprising a dosage form of the compound provided herein, including a single enantiomer, a mixture of an enantiomeric pair, an individual diastereomer, or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr (hours); min (minutes); TLC (thin layer chromatography); HPLC (high performance liquid chromatography); SCX (strong cation exchange); MS (mass spectrometry); ESI (electrospray ionization); $R_t$ (retention time); $SiO_2$ (silica); THF (tetrahydrofuran); $CD_3OD$ (deuterated methanol); $CDCl_3$ (deuterated chloroform); DCE (dichloroethane); DCM (dichloromethane); DMF (dimethylformamide); DMSO (dimethylsulfoxide); EtOAc (ethyl acetate); $CHCl_3$ (chloroform); DMF (N,N-dimethylformamide); DMA (N,N-dimethyacetamide); MeOH (methanol); EtOH (ethanol); HCl (hydrochloric acid); LiOH (lithium hydroxide); NaOH (sodium hydroxide); KOH (potassium hydroxide); $Cs_2CO_3$ (cesium carbonate); DIPEA (N,N-diisopropylethylamine); TEA (triethylamine); DBU (1,8-diazabicyclo[5.4.0]undec-7-ene; CDI (carbonyldiimidazole); TBTU (O-(benzotriazol-1-yl)-N,N,N',N'-tetramethyluronium tetrafluoroborate); Ac (acetyl); Me (methyl); Et (ethyl); tBu (tent-butyl); Boc (tert-butoxylcarbony); Bn (benzyl); and Ts (tosylate).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated in Schemes 19 to 24 are intended to exemplify the applicable chemistry through the use of specific examples and are not indicative of the scope of the disclosure.

Scheme 19

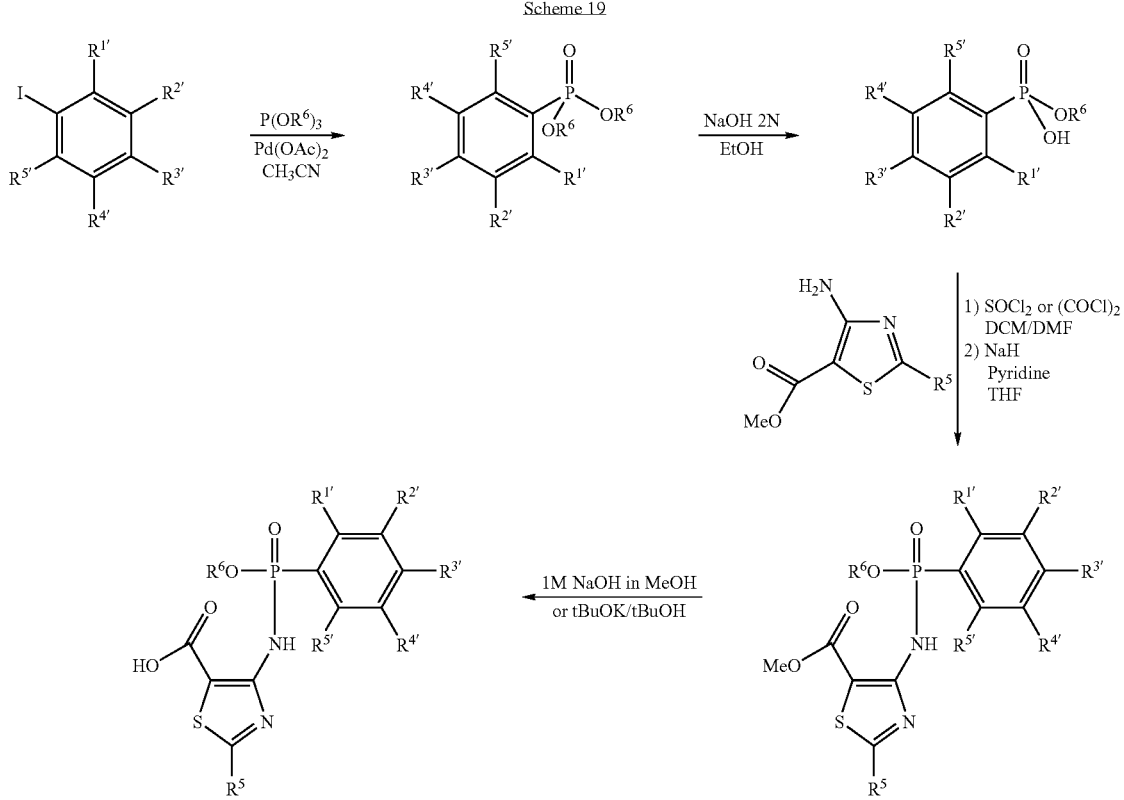

Scheme 20
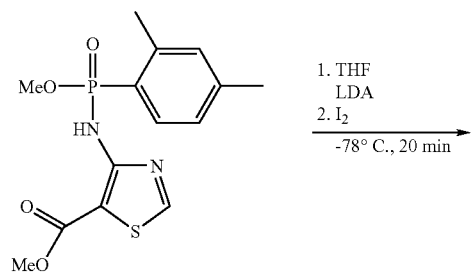
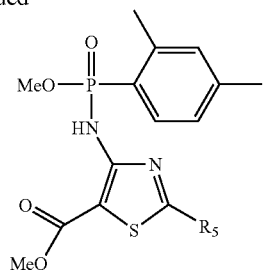
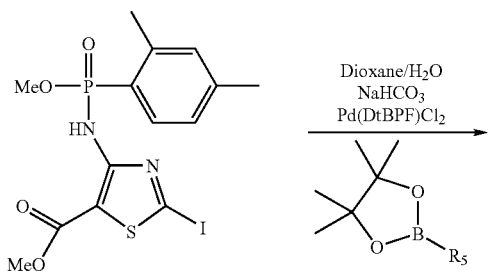
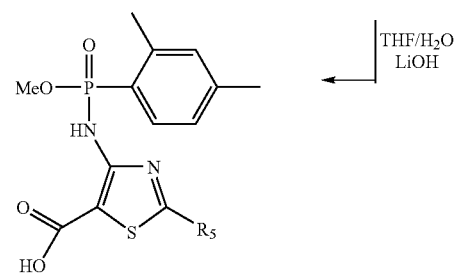
Scheme 21
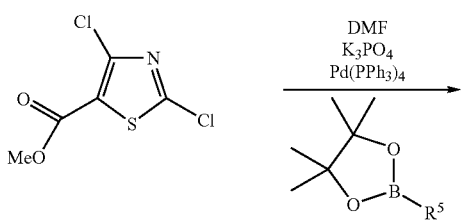
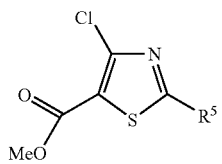
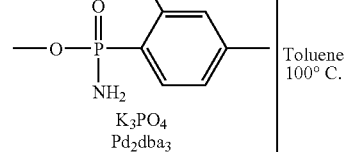
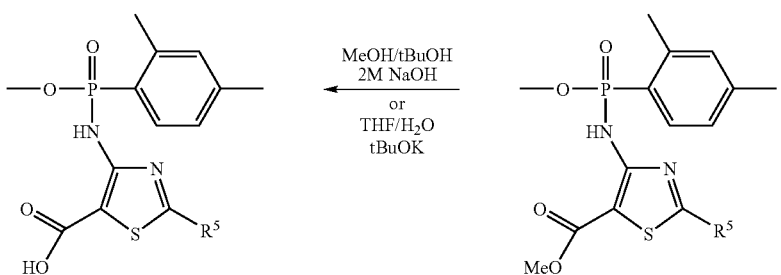
Scheme 22
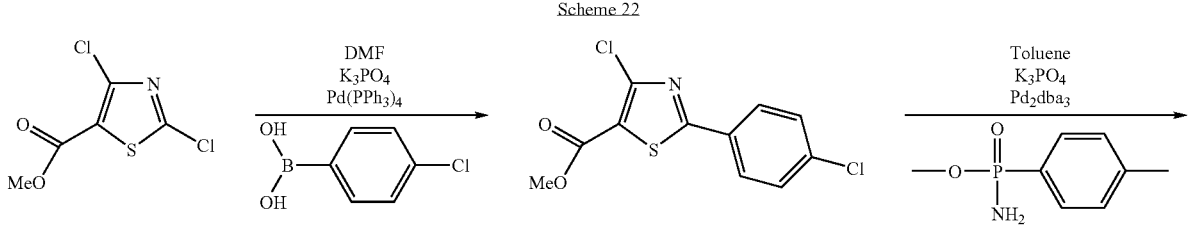

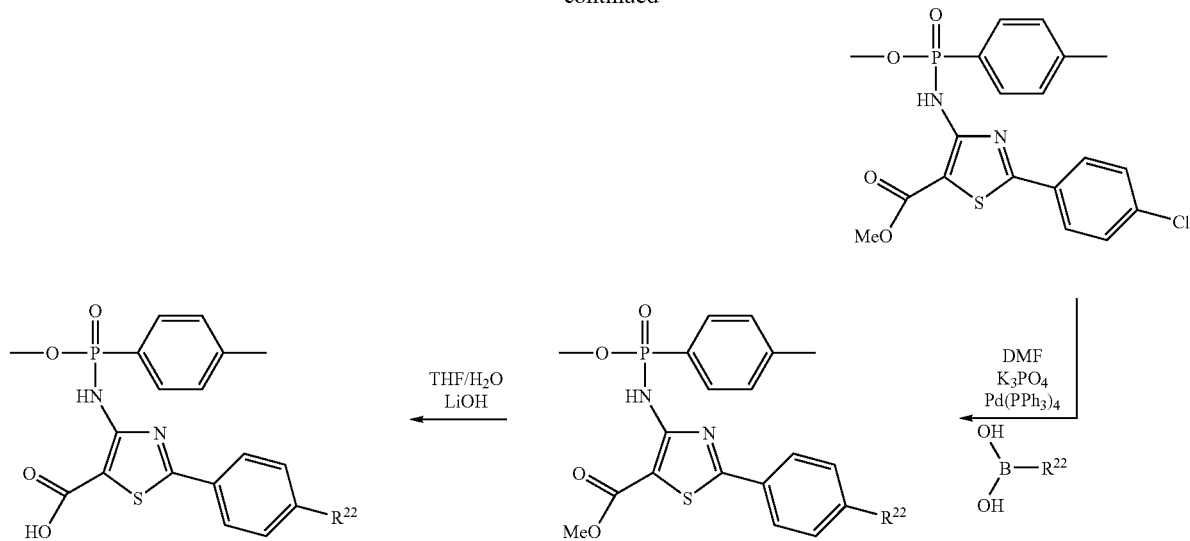
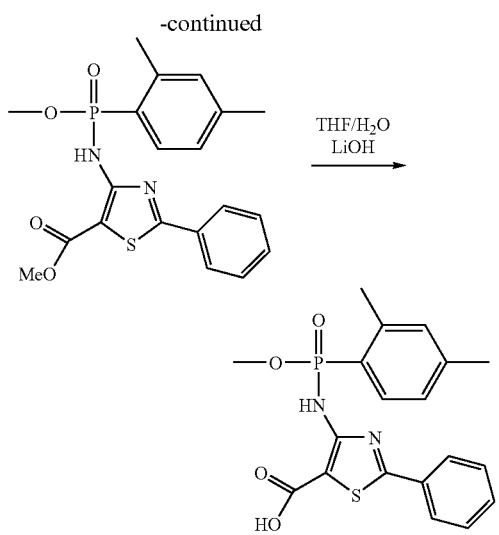
Scheme 23
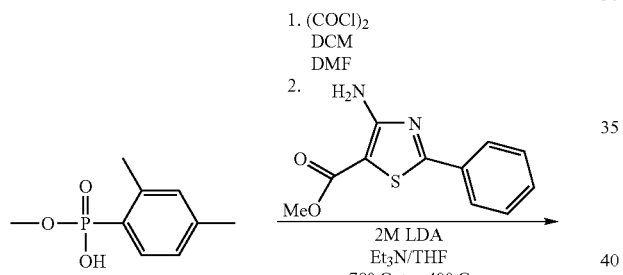
Scheme 24
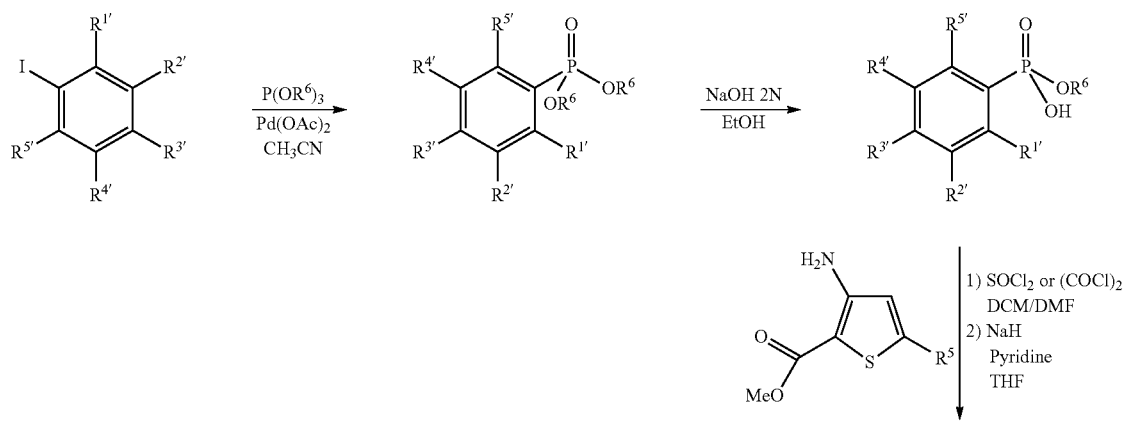

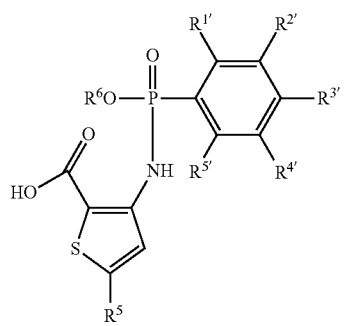

⇌ 1M NaOH in MeOH or tBuOK/tBuOH

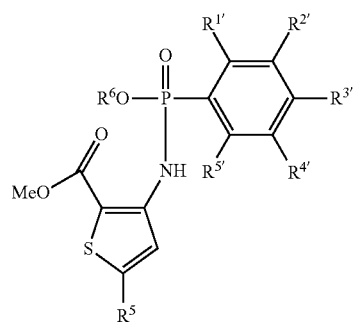

Intermediate I.1

(2,4-Dimethyl-phenyl)-phosphonic acid diethyl ester

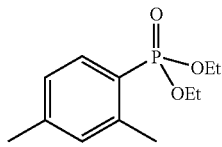

4-Iodo-m-xylene (4.31 mmol), triethyl phosphite (6.03 mmol) and palladium acetate (0.43 mmol) were mixed together in acetonitrile (10 ml), in a microwave tube. The vessel was sealed and placed in a microwave to react at 160° C., for 45 minutes. After cooling to room temperature, acetonitrile was removed. The crude material was purified by silica gel chromatography (eluent: stepwise gradient of ethyl acetate (0-30%) in petroleum ether) to yield Intermediate I.1 as an oil (84%). Intermediate I.1 was characterized by the following spectroscopic data: $^1$H NMR (CDCl$_3$, 400 MHz) δ (ppm) 1.32 (t, J=8.0 Hz, 6H), 2.35 (s, 3H), 2.53 (s, 3H), 4.07-4.14 (m, 4H), 7.07-7.08 (m, 2H), 7.77-7.83 (m, 1H); $^{31}$P NMR (CDCl$_3$, 162 MHz) δ (ppm) 20.15 (s, 1P); and MS (ESI, EI$^+$) m/z=243 (MH$^+$).

Intermediate I.2

(2,4-Dimethyl-phenyl)-phosphonic acid ethyl ester

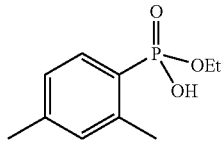

Intermediate I.1 (3.59 mmol) was dissolved in a mixture of ethanol (7.2 ml) and 2 M sodium hydroxide aqueous solution (7.2 ml). The solution was stirred at room temperature for 3 days. Reaction mixture was diluted with methyl tert-butyl ether and washed with water. Aqueous phase was acidified to pH 1 with a 2 N HCl aqueous solution. After extraction with ethyl acetate, the organic phase was dried over sodium sulfate and concentrated in vacuo to give a colorless oil, pure enough to be used for the next step without further purification (33%). Intermediate I.2 was characterized by the following spectroscopic data: $^1$H NMR (CDCl$_3$, 400 MHz) δ (ppm) 1.30 (t, J=8.0 Hz, 3H), 2.34 (s, 3H), 2.54 (s, 3H), 4.02-4.10 (m, 2H), 7.02-7.06 (m, 2H), 7.74-7.80 (m, 1H), 10.92 (s, 1H); $^{31}$P NMR (CDCl$_3$, 162 MHz) δ (ppm) 22.64 (s, 1P); and MS (ESI, EI$^+$) m/z=215 (MH$^+$).

Intermediate I.3

2-Thiophenecarboxylic methylester, 3-N-[2,4-dimethyl-phenyl)-phosphonamidate ethyl ester]-5-(4-fluorophenyl)

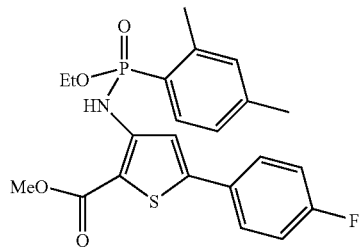

To a stirred solution of Intermediate I.2 (0.467 mmol) in anhydrous dichloromethane (2 ml) and a few drops of dry dimethylformamide, was added thionyl chloride (1.634 mmol), dropwise, at 0° C. and under nitrogen. The resulting solution was stirred under nitrogen at room temperature for 2.5 hours. Then, anhydrous toluene was added and solvents removed. The crude mixture was taken in anhydrous pyridine (1 ml) and added dropwise to a suspension of methyl 3-amino-5-(4-fluorophenyl)thiophene-2-carboxylate (0.389 mmol) and sodium hydride 60% (dispersion in mineral oil, 1.556 mmol) in anhydrous tetrahydrofuran (1 ml). This mixture was stirred at room temperature for 24 hours. The reaction was quenched with water and the solution neutralized with a 2 N HCl aqueous solution until pH 7. After extraction with ethyl acetate, the organic phase was dried over sodium sulfate and evaporated to dryness. The residue was purified by chromatography (eluent: stepwise gradient of ethyl acetate (0-20%) in petroleum ether) to give Intermediate I.3 (25%) which was characterized by the following spectroscopic data: $^1$H NMR (CDCl$_3$, 400 MHz) δ (ppm) 1.40 (t, J=8.0 Hz, 3H), 2.33 (s, 3H), 2.61 (s, 3H), 3.87 (s, 3H), 4.23-4.27 (m, 2H), 7.06-7.08 (m, 2H), 7.42 (s, 1H), 7.51-7.54 (m, 2H), 7.79-7.84 (m, 1H), 8.40 (d, J=12.0 Hz 1H); $^{31}$P NMR (CDCl$_3$, 162

MHz) δ (ppm) 17.10 (s, 1P); $^{19}$F NMR (CDCl$_3$, 376 MHz) δ (ppm) −111.76 (s, 1F); and MS (ESI, EI$^+$) m/z=448 (MH$^+$).

Example I.1

2-Thiophenecarboxylic acid, 3-N-[(2,4-dimethyl-phenyl)-phosphonamidate ethyl ester]-5-(4-fluorophenyl) (Compound 22)

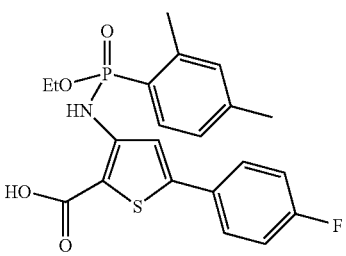

Intermediate I.3 (0.037 mmol) was dissolved in a mixture of methanol (0.57 ml) and 1 M aqueous sodium hydroxide solution (0.57 ml). The solution was stirred at room temperature for 5 days. Then water was added and the solution was acidified to pH 3 by addition of a 2 N HCl aqueous solution. After extraction with ethyl acetate, the organic phase was dried over sodium sulfate and concentrated. The residue was purified by chromatography on silica gel (eluent: stepwise gradient of methanol (0-2%) in methylene chloride) to furnish Example I.1 as a colorless oil (79%) characterized by the following spectroscopic data: $^1$H NMR (CDCl$_3$, 400 MHz) δ (ppm) 1.26 (t, J=8.0 Hz, 3H), 2.34 (s, 3H), 2.61 (s, 3H), 4.24-4.32 (m, 2H), 7.04-7.09 (m, 4H), 7.32 (s, 1H), 7.50-7.53 (m, 2H), 7.79-7.84 (m, 1H), 8.40 (d, J=12.0 Hz 1H); $^{31}$P NMR (CDCl$_3$, 162 MHz) δ (ppm) 17.28 (s, 1P); $^{19}$F NMR (CDCl$_3$, 376 MHz) δ (ppm)-111.40 (s, 1F); and MS (ESI, EI$^+$) m/z=456 (MNa$^+$).

Intermediate I.4

(2,4-Dimethyl-phenyl)-phosphonic acid dimethyl ester

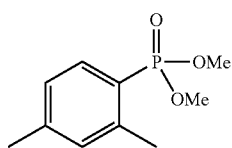

4-Iodo-m-xylene (8.62 mmol), trimethyl phosphite (12.07 mmol) and palladium acetate (0.86 mmol) were mixed together in acetonitrile (12 ml), in a microwave tube. The vessel was sealed and placed in a microwave to react at 160° C., for 45 minutes. After cooling to room temperature, acetonitrile was removed. The crude material was purified by silica gel chromatography to yield Intermediate I.4 as an oil (95%). Intermediate I.4 was characterized by the following spectroscopic data: $^1$H NMR (CDCl$_3$, 400 MHz) δ (ppm) 2.35 (s, 3H), 2.51 (s, 3H), 3.74 (d, J=12.0 Hz, 6H), 7.08-7.09 (m, 2H), 7.75-7.81 (m, 1H); $^{31}$P NMR (CDCl$_3$, 162 MHz) δ (ppm) 23.18 (s, 1P); and MS (ESI, EI$^+$) m/z=215 (MH$^+$)

Intermediate I.5

(2,4-Dimethyl-phenyl)-phosphonic acid methyl ester

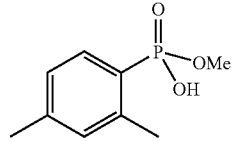

Intermediate I.4 (9.34 mmol) was dissolved in a mixture of methanol (19 ml) and aqueous 2 M sodium hydroxide solution (19 ml). The solution was stirred at room temperature for 2 days. Reaction mixture was diluted with methyl tert-butyl ether and washed with water. Aqueous phase was acidified to pH 1 with a 2 N HCl aqueous solution. After extraction with ethyl acetate, the organic phase was dried over sodium sulfate and concentrated in vacuo to give Intermediate I.5 as yellow oil, pure enough to be used for the next step without further purification (98%). Intermediate I.5 was characterized by the following spectroscopic data: $^1$H NMR (CDCl$_3$, 400 MHz) δ (ppm) 2.27 (s, 3H), 2.46 (s, 3H), 3.62 (d, J=8.0 Hz, 3H), 6.95-7.00 (m, 2H), 7.67-7.73 (m, 1H), 11.30 (s, 1H); $^{31}$P NMR (CDCl$_3$, 162 MHz) δ (ppm) 23.97 (s, 1P); and MS (ESI, EI$^+$) m/z=201 (MH$^+$).

Intermediate I.6

2-Thiophenecarboxylic methylester, 3-N-[(2,4-dimethyl-phenyl)-phosphonamidate methyl ester]-5-(4-fluorophenyl)

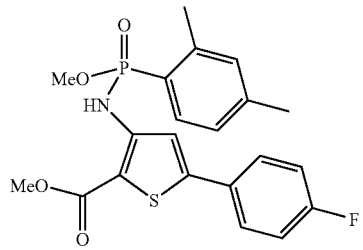

To a stirred solution of Intermediate I.5 (4.0 mmol) in anhydrous dichloromethane (5 ml) and a few drops of dimethylformamide, was added dropwise thionyl chloride (11.12 mmol). The resulting solution was stirred under nitrogen at room temperature for 2.5 hours. Then, toluene was added and the solvents removed. The crude mixture was taken in anhydrous pyridine (5 ml) and added dropwise to a suspension of methyl 3-amino-5-(4-fluorophenyl)thiophene-2-carboxylate (2.66 mmol) and sodium hydride 60% (dispersion in mineral oil, 10.64 mmol) in anhydrous tetrahydrofuran (5 ml). This mixture was stirred at room temperature for 2 days. The reaction was quenched with water and the solution neutralized with 2 N HCl aqueous solution until pH 7. After extraction with ethyl acetate, the organic phase was dried over sodium sulfate and evaporated to dryness. The residue was purified by chromatography (eluent: stepwise gradient of ethyl acetate (0-30%) in petroleum ether) to give Intermediate I.6 (31%) which was characterized by the following spectroscopic data: $^1$H NMR (CDCl$_3$, 400 MHz) δ (ppm) 2.34 (s, 3H), 2.60 (s, 3H), 3.85 (d, J=12.0 Hz, 6H), 7.06-7.08 (m, 2H), 7.40 (s, 1H), 7.51-7.55 (m, 2H), 7.78-7.84 (m, 1H), 8.40 (d, J=12.0 Hz 1H); $^{31}$P NMR (CDCl$_3$, 162 MHz) δ (ppm) 18.76 (s, 1P); $^{19}$F NMR (CDCl$_3$, 376 MHz) δ (ppm) −111.70 (s, 1F); and MS (ESI, EI$^+$) m/z=434 (MH$^+$).

Example I.2

2-Thiophenecarboxylic acid, 3-N-[(2,4-dimethyl-phenyl)-phosphonamidate methyl ester]-5-(4-fluorophenyl) (Compound 21)

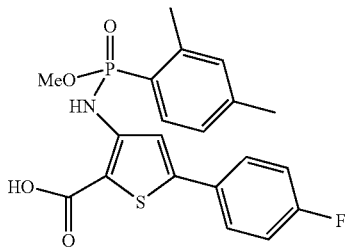

Example I.2 was synthesized from Intermediate I.6 as described for Example I.1. Example I.2 was obtained as an oil (77%) and characterized by the following spectroscopic data: $^1$H NMR (CDCl$_3$, 400 MHz) δ (ppm) 2.34 (s, 3H), 2.60 (s, 3H), 3.88 (d, J=12.0 Hz, 3H), 7.03-7.09 (m, 4H), 7.26 (s, 1H), 7.49-7.52 (m, 2H), 7.78-7.84 (m, 1H), 8.49 (d, J=12.0 Hz 1H), $^{31}$P NMR (CDCl$_3$, 162 MHz) δ (ppm) 18.92 (s, 1P); $^{19}$F NMR (CDCl$_3$, 376 MHz) δ (ppm) −111.40 (s, 1F); and MS (ESI, EI$^+$) m/z=420 (MH$^+$).

Intermediate I.7

Phenyl-phosphonic acid dimethyl ester

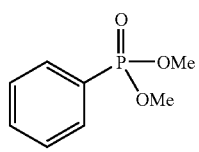

Intermediate I.7 was synthesized from 4-iodobenzyl as described for Intermediate I.4. Intermediate I.7 was obtained as a colorless oil and characterized by the following spectroscopic data: $^1$H NMR (CDCl$_3$, 400 MHz) δ (ppm) 3.76 (d, J=10.8 Hz, 6H), 7.46-7.51 (m, 2H), 7.56-7.59 (m, 1H), 7.78-7.84 (m, 2H); and $^{31}$P NMR (CDCl$_3$, 162 MHz) δ (ppm) 21.59 (s, 1P).

Intermediate I.8

Phenyl phosphonic acid methyl ester

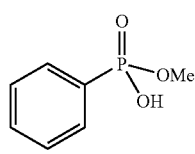

Intermediate I.8 was synthesized from Intermediate I.7 as described for Intermediate I.2. Intermediate I.8 was obtained as a colorless oil (50%) and characterized by the following spectroscopic data. $^1$H NMR (CDCl$_3$, 400 MHz) δ (ppm) 3.72 (d, J=12.0 Hz, 3H), 7.44-7.46 (m, 2H), 7.54-7.56 (m, 1H), 7.80-7.83 (m, 2H), 10.58 (bs, 1H); and $^{31}$P NMR (CDCl$_3$, 162 MHz) δ (ppm) 22.10 (s, 1P).

Intermediate I.9

2-Thiophenecarboxylic methylester, 3-N-(phenyl-phosphonamidate methyl ester)-5-phenyl

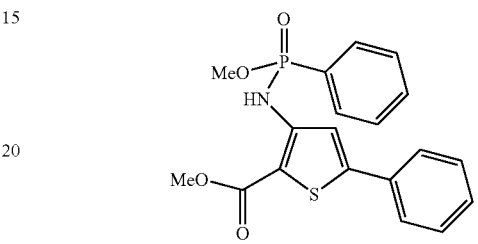

Intermediate I.9 was synthesized from Intermediate I.8 as described for Intermediate I.3. Intermediate I.9 was obtained as an oil (20%) and characterized by the following spectroscopic data: $^1$H NMR (CDCl$_3$, 400 MHz) δ (ppm) 3.80 (m, 6H), 7.29-7.32 (m, 3H), 7.38-7.42 (m, 3H), 7.46-7.50 (m, 3H), 7.77-7.82 (m, 2H), 8.37 (d, J=12.0 Hz 1H); $^{31}$P NMR (CDCl$_3$, 162 MHz) δ (ppm) 17.96 (s, 1P); and MS (ESI, EI$^+$) m/z=388 (MH$^+$).

Example I.3

2-Thiophenecarboxylic acid, 3-N-(phenyl-phosphonamidate methyl ester)-5-phenyl (Compound 25)

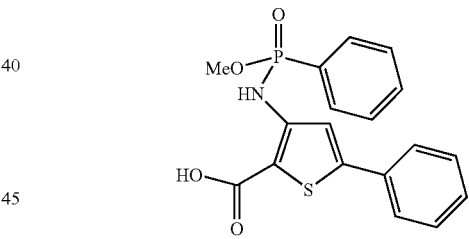

Example I.3 was synthesized from Intermediate I.9 as described for Example I.2. The desired compound was obtained after lyophilization as a pale green solid (23%) and characterized by the following spectroscopic data: $^1$H NMR (CDCl$_3$, 400 MHz) δ (ppm) 3.73 (d, J=12.0 Hz, 3H), 7.29-7.80 (m, 12H); $^{31}$P NMR (CDCl$_3$, 162 MHz) δ (ppm) 17.05 (s, 1P); and MS (ESI, EI$^+$) m/z=374 (MH$^+$).

Intermediate I.10

(2,4-Dichloro-phenyl)-phosphonic acid diethyl ester

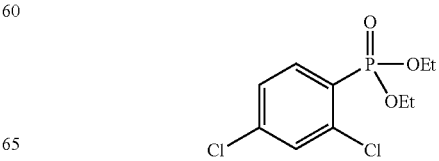

Intermediate I.10 was prepared starting from 1,3-dichloro-4-iodobenzene as described for Intermediate I.1. Intermediate I.10 (77%) was characterized by the following spectroscopic data: $^1$H NMR (CDCl$_3$, 400 MHz) δ (ppm) 1.35 (t, J=8.0 Hz, 3H), 4.12-4.21 (m, 2H), 7.33-7.36 (m, 1H), 7.47-7.49 (m, 1H), 7.92-7.98 (m, 1H), 10.33 (s, 1H); $^{31}$P NMR (CDCl$_3$, 162 MHz) δ (ppm) 13.47 (s, 1P); and MS (ESI, EI$^+$) m/z=283 (MH$^+$).

Intermediate I.11

(2,4-Dimethyl-phenyl)-phosphonic acid ethyl ester

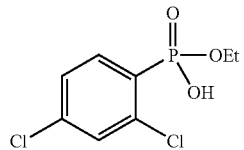

Intermediate I.11 was prepared starting from Intermediate I.10 as described for Intermediate I.2. Intermediate I.11 (63%) was characterized by the following spectroscopic data: $^1$H NMR (CDCl$_3$, 400 MHz) δ (ppm) 1.35 (t, J=8.0 Hz, 3H), 4.12-4.16 (m, 2H), 7.29-7.31 (m, 1H), 7.45-7.47 (m, 1H), 7.82-7.88 (m, 1H), 10.33 (s, 1H); $^{31}$P NMR (CDCl$_3$, 162 MHz) δ (ppm) 15.54 (s, 1P); and MS (ESI, EI$^+$) m/z=255 (MH$^+$).

Intermediate I.12

2-Thiophenecarboxylic methylester, 3-N-[2,4-dichloro-phenyl)-phosphonamidate methyl ester]-5-(4-fluorophenyl)

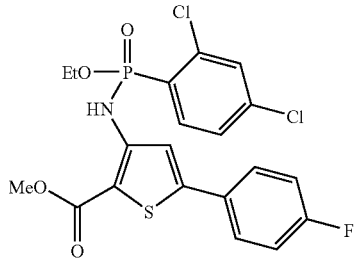

Intermediate I.12 was prepared starting from Intermediate I.11 as described for Intermediate I.3. Intermediate I.12 (23%) was characterized by the following spectroscopic data: $^1$H NMR (CDCl$_3$, 400 MHz) δ (ppm) 1.42 (t, J=8.0 Hz, 3H), 4.25-4.28 (m, 2H), 7.05-7.98 (m, 2H), 7.35-7.37 (m, 1H), 7.46-7.48 (m, 1H), 7.531-7.57 (m, 3H), 8.04-8.09 (m, 1H), 8.77 (d, J=8.0 Hz, 1H); $^{31}$P NMR (CDCl$_3$, 162 MHz) δ (ppm) 11.02 (s, 1P); and MS (ESI, EI$^+$) m/z=488 (MH$^+$).

Example I.4

2-Thiophenecarboxylic acid, 3-N-[(2,4-dichloro-phenyl)-phosphonamidate methyl ester]-5-(4-fluorophenyl) (Compound 23)

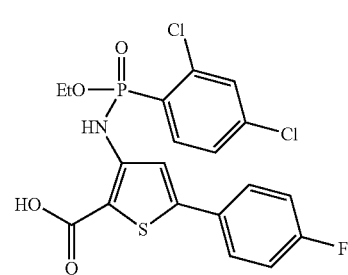

Example I.4 was synthesized from Intermediate I.12 as described for Example I.1. Example I.4 was obtained as an oil (77%) and characterized by the following spectroscopic data: $^1$H NMR (CDCl$_3$, 400 MHz) δ (ppm) 1.43 (m, 3H), 4.28-4.29 (m, 2H), 7.07 (m, 2H), 7.36-7.56 (m, 5H), 8.05-8.09 (m, 1H), 8.76 (d, J=8.0 Hz 1H); $^{31}$P NMR (CDCl$_3$, 162 MHz) δ (ppm) 11.13 (s, 1P); and MS (ESI, EI$^+$) m/z=497 (MNO.

Intermediate I.13

Methyl 3-N-[(2,4-dichloro-phenyl)-phosphonamidate ethyl ester]-5-(4-pyrazolo[1,5-a]pyrimidin-2-ylphenyl)-2-thiophenecarboxylate

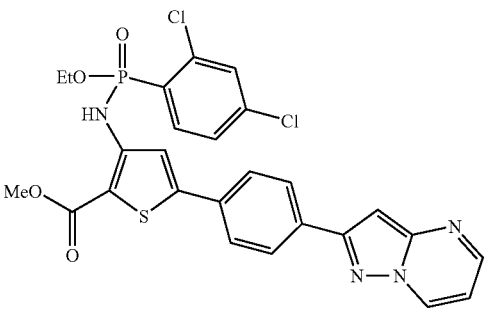

Intermediate I.13 was prepared starting from Intermediate I.11 and Intermediate VII.2 as described for Intermediate I.3. Intermediate I.13 (34%) was characterized by the following spectroscopic data: $^1$H NMR (DMSOd$_6$, 400 MHz) δ (ppm) 1.34 (t, J=7 Hz, 3H), 3.84 (s, 3H), 4.20 (q, J=7 Hz, 2H), 7.06 (dd, J=4 and 7 Hz, 1H), 7.31 (s, 1H), 7.58 (s, 1H), 7.61-7.66 (m, 2H), 7.71-7.76 (m, 2H), 7.80-7.84 (m, 1H), 8.05-8.15 (m, 3H), 8.55 (d, J=4 Hz, 1H), 8.67 (d, J=9 Hz, 1H), 9.14 (d, J=7 Hz, 1H); and MS (ESI, EI$^+$) m/z=586.8 (MH$^+$).

Example I.5

3-N-[(2,4-dichloro-phenyl)-phosphonamidate ethyl ester]-5-(4-pyrazolo[1,5-a]pyrimidin-2-ylphenyl)-2-thiophenecarboxylic acid (Compound 11)

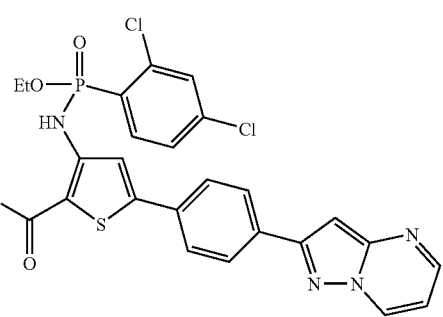

Intermediate I.13 (0.036 mmol) was dissolved in tert-butanol (2 ml), potassium tert-butoxide (0.18 mmol) was added and the reaction mixture was stirred at 37° C. for 18 hours. The reaction mixture was diluted with ethyl acetate and washed with 2 N HCl. The aqueous phase was extracted with ethyl acetate, dried over sodium sulfate and evaporated to dryness. The residue was purified by semi-preparative HPLC (eluent: stepwise gradient of 30-70% acetonitrile in water). The expected compound was obtained after lyophilization as a yellow solid (25%) and characterized by the following spectroscopic data: $^1$H NMR (CDCl$_3$, 400 MHz) δ (ppm) 1.45 (t, J=7.1 Hz, 3H), 4.31 (q, J=7.1 Hz, 2H), 6.85 (dd, J=4.2 and 7.1 Hz, 1H), 7.01 (s, 1H), 7.38 (dt, J=2.2 and 8.3 Hz, 1H), 7.48 (dd, J=1.9 and 4.7 Hz, 1H), 7.59 (s, 1H), 7.66-7.72 (m, 2H), 7.98-8.03 (m, 2H), 8.09 (dd, J=8.1 and 14.0 Hz, 1H), 8.48 (dd, J=1.3 and 4.1 Hz, 1H), 8.70 (d, J=6.8 Hz, 1H), 8.84 (d, J=9.9 Hz, 1H); $^{31}$P NMR (CDCl$_3$, 162 MHz) δ (ppm) 11.02 (s, 1P); and MS (ESI, EI$^+$) m/z=528.85 (MH$^+$)

Intermediate I.14

Methyl 3-N-[(2,4-dimethyl-phenyl)-phosphonamidate ethyl ester]-5-(4-pyrazolo[1,5-a]pyrimidin-2-ylphenyl)-2-thiophenecarboxylate

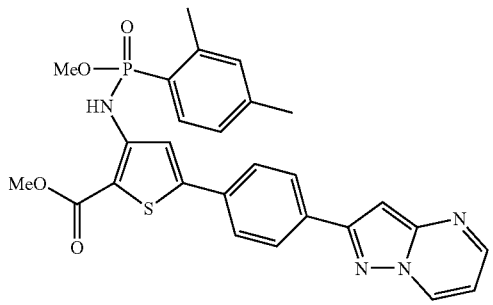

Intermediate I.14 was prepared starting from Intermediate I.5 and Intermediate VII.2 as described for Intermediate I.6. Intermediate I.14 was obtained as a yellow solid (3%) and characterized by MS (ESI, EI$^+$) m/z=533 (MH$^+$).

Example I.6

3-N-[(2,4-dimethyl-phenyl)-phosphonamidate ethyl ester]-5-(4-pyrazolo[1,5-a]pyrimidin-2-ylphenyl)-2-thiophenecarboxylic acid (Compound 26)

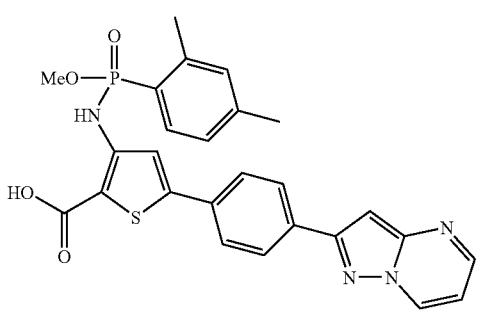

Example I.6 was prepared starting from Intermediate I.14 as described for Example I.5. Example I.6 was obtained as a yellow solid (7% yield), which was characterized by the following spectroscopic data: $^1$H NMR (CDCl$_3$, 400 MHz) δ (ppm) 2.34 (s, 3H), 2.63 (s, 3H), 3.89 (d, J=13 Hz, 3H), 6.83 (dd, J=4.3 and 7.4 Hz, 1H), 7.01 (s, 1H), 7.05-7.13 (m, 2H), 7.41 (m, 1H), 7.62-7.69 (m, 2H), 7.83 (dd, J=8 and 14 Hz, 1H), 7.96-8.03 (m, 2H), 8.45-8.56 (m, 2H), 8.70 (d, J=8 Hz, 1H) and; $^{31}$P NMR (CDCl$_3$, 162 MHz) δ (ppm) 18.81 (s, 1P); and MS (ESI, EI$^+$) m/z=475 (MH$^+$).

Intermediate I.15

Methyl 3-N-[(2,4-dichloro-phenyl)-phosphonamidate ethyl ester]-5-(4-phenyl-ethynyl-1,3-thiazole)-2-thiophenecarboxylate

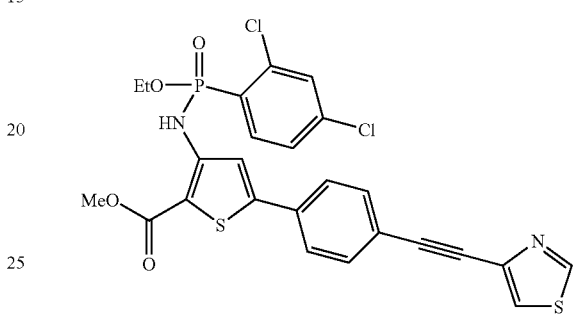

Intermediate I.15 was prepared starting from Intermediate VII.4 as described for Intermediate I.13. Intermediate I.15 was obtained in a 26% yield and characterized by MS (ESI, EI$^+$) m/z=575/577 (MH$^+$).

Example I.7

3-N-[(2,4-dichloro-phenyl)-phosphonamidate ethyl ester]-5-(4-phenyl-ethynyl-1,3-thiazole)-2-thiophenecarboxylic acid (Compound 24)

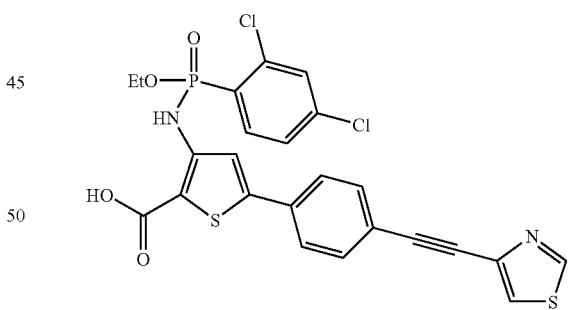

Intermediate I.15 (0.078 mmol) was dissolved in diethyl ether (1.5 ml), potassium tert-butoxide (0.39 mmol) was added and the reaction mixture was stirred at room temperature for 1.5 hours. The reaction mixture was diluted with ethyl acetate and washed with 2 N HCl. The aqueous phase was extracted with ethyl acetate, dried over sodium sulfate and evaporated to dryness. The residue was purified by semi-preparative HPLC (eluent: stepwise gradient of 30-95% acetonitrile in water). Example I.7 was obtained after lyophilization as a yellow solid (43%) and characterized by the following spectroscopic data: $^1$H NMR (CDCl$_3$, 400 MHz) δ (ppm) 1.41 (t, J=7 Hz, 3H), 4.26 (q, J=7 Hz, 2H), 7.32-7.39 (m, 1H), 7.41-7.46 (m, 1H), 7.52-7.62 (m, 6H), 7.98-8.11 (m, 1H), 8.71-8.81 (m, 1H), 8.81-8.86 (m, 1H); $^{31}$P NMR (CDCl$_3$, 162 MHz) δ (ppm) 11.1 (s, 1P); and MS (ESI, EI$^+$) m/z=561/563 (MH$^+$).

Intermediate I.16

2-Thiophenecarboxylic methylester, 3-N-[(2,4-dimethyl-phenyl)-phosphonamidate methyl ester]-5-phenyl

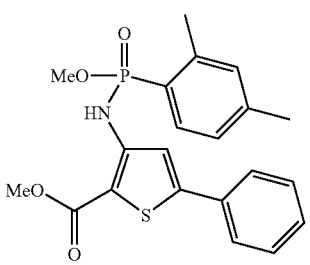

Intermediate I.16 was synthesized from Intermediate I.5 as described for Intermediate I.3. Intermediate I.16 was obtained as a yellow oil (10%) and characterized by: MS (ESI, EI$^+$) m/z=415.96 (MH$^+$).

Example I.8

2-Thiophenecarboxylic acid, 3-N-[(2,4-dimethyl-phenyl)-phosphonamidate methyl ester]-5-phenyl (Compound 27)

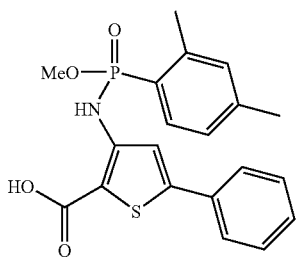

To Intermediate I.16 (0.14 mmol) in dry THF was added sodium trimethylsilanolate (TMSONa) under nitrogen atmosphere. The solution was stirred at 50° C. for 26 hours, then cooled to room temperature and quenched with a 1 M citric acid solution. The organic layer was extracted with ethyl acetate, washed with brine, dried over sodium sulfate and concentrated under vacuum. The residue was purified by semi-preparative HPLC (eluent: stepwise gradient of 30-95% acetonitrile in water) to give 4 mg of Example I.8 as a pale yellow gum (7%) and characterized by the following spectroscopic data: $^1$H NMR (DMSO, 400 MHz) δ (ppm) 2.27 (s, 3H), 2.53 (s, 3H), 3.74 (d, J=11.4 Hz, 3H), 7.14 (brd, 2H), 7.26 (s, 1H), 7.34-7.44 (m, 3H), 7.53 (brd, 2H), 7.73 (dd, J=13.9 Hz, J=8.2 Hz, 1H), 9.1 (brs, 1H); $^{31}$P NMR (DMSO, 162 MHz) δ (ppm) 17.08 (s, 1P); and MS (ESI, EI$^+$) m/z=401.96 (MH$^+$).

Intermediate I.17

2-Thiophenecarboxylic methylester, 5-iodo-3-N-[(2,4-dichlorophenyl)-phosphonamidate ethyl ester]

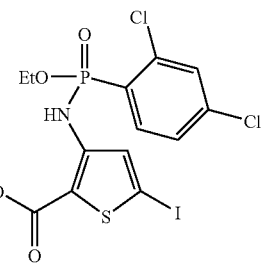

Intermediate I.17 was synthesized from Intermediate I.11 and methyl 3-amino-5-iodo-2-thiophenecarboxylate (according to the general procedure in WO 2008/043791 A2) as described for Intermediate I.3. Intermediate I.17 was obtained as a pale yellow solid (30%) and characterized by the following spectroscopic data: $^1$H NMR (CDCl$_3$, 400 MHz) δ (ppm) 1.34 (t, J=7.1 Hz, 3H), 4.10-4.22 (m, 2H), 3.78 (s, 3H), 7.30 (td, J=8.3 Hz, J=2.2 Hz, 1H), 7.39 (dd, J=4.6 Hz, J=1.9 Hz, 1H), 7.53 (s, 1H), 7.97 (dd, J=14.0 Hz, J=8.3 Hz, 1H), 8.66 (d, J=10.1 Hz, 1H), $^{31}$P NMR (CDCl$_3$, 162 MHz) δ (ppm) 10.92 (s, 1P); and MS (ESI, EI$^+$) m/z=519.67 (MH$^+$).

Intermediate I.18

2-Thiophenecarboxylic methylester, 3-N-[2,4-dichlorophenyl)-phosphonamidate ethyl ester]-5-phenyl

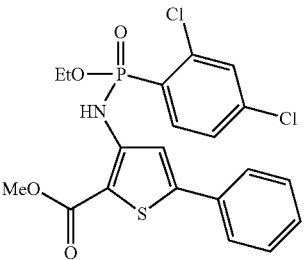

To Intermediate I.17 (0.23 mmol) in a DMF/H$_2$O mixture (2 ml/0.35 ml) were added successively benzene boronic acid (0.26 mmol), sodium carbonate (0.68 mmol), and tetrakis (triphenylphosphine)palladium(0) (0.011 mmol). The resulting mixture was stirred at 80° C. in a sealed tube for 5 hours, down to room temperature, diluted with ethyl acetate and transferred in a reparatory funnel. 1 M aqueous HCl was added and the organic layer was extracted twice. The combined organic layers were washed with brine, dried over sodium sulfate and concentrated under vacuum. The residue was purified by flash chromatography (eluent: stepwise gradient of ethyl acetate (0-30%) in petroleum ether) to give Intermediate I.18 (70%). Intermediate I.18 was characterized by the following spectroscopic data: $^1$H NMR (CDCl$_3$, 400 MHz) δ (ppm) 1.44 (t, J=7.1 Hz, 3H), 3.90 (s, 3H), 4.20-4.36

(m, 2H), 7.33-7.42 (m, 4H), 7.47 (dd, J=4.6 Hz, J=1.9 Hz, 1H), 7.57-7.61 (m, 3H), 8.08 (dd, J=14.0 Hz, J=8.3 Hz, 1H), 8.78 (d, J=10.2 Hz, 1H); $^{31}$P NMR (CDCl$_3$, 162 MHz) δ (ppm) 10.98 (s, 1P); and MS (ESI, EI$^+$) m/z=491.77 (MH$^+$).

Example I.9

2-Thiophenecarboxylic acid, 3-N-[(2,4-dichlorophenyl)-phosphonamidate ethyl ester]-5-phenyl (Compound 28)

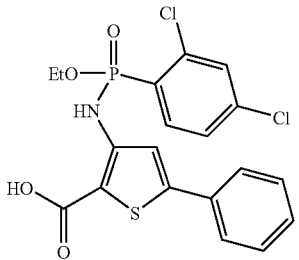

Example I.9 was synthesized from Intermediate I.18 as described for Example I.1. Example I.9 was obtained as a beige powder (51%) and characterized by the following spectroscopic data: $^1$H NMR (DMSO, 400 MHz) δ (ppm) 1.31 (t, J=7.0 Hz, 3H), 4.07-4.23 (m, 2H), 7.32-7.46 (m, 4H), 7.48-7.64 (m, 3H), 7.57-7.61 (m, 3H), 7.77 (brd, J=2.8 Hz, 1H), 8.04 (dd, J=13.6 Hz, J=8.4 Hz, 1H); $^{31}$P NMR (DMSO, 162 MHz) δ (ppm) 9.94 (s, 1P); and MS (ESI, EI$^+$) m/z=411.83 (M-[CO$_2$H]2H$^+$).

Intermediate I.19

2-Thiophenecarboxylic methylester, 3-N-[(2,4-dichlorophenyl)-phosphonamidate methyl ester]-5-(4-cyanophenyl)

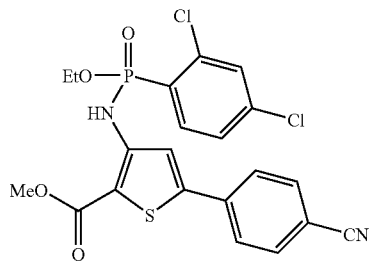

Intermediate I.19 was synthesized from Intermediate I.17 using 4-cyanophenyl boronic acid as described for Intermediate I.18. Intermediate I.19 was obtained as a white powder (42%) and characterized by the following spectroscopic data: $^1$H NMR (CDCl$_3$, 400 MHz) δ (ppm) 1.36 (t, J=7.1 Hz, 3H), 3.83 (s, 3H), 4.10-4.27 (m, 2H), 7.30 (td, J=8.3 Hz, J=2.2 Hz, 1H), 7.41 (dd, J=4.6 Hz, J=1.9 Hz, 1H), 7.57-7.64 (m, 4H), 7.69 (s, 1H), 8.00 (dd, J=14.1 Hz, J=8.3 Hz, 1H), 8.70 (d, J=10.4 Hz, 1H); $^{31}$P NMR (CDCl$_3$, 162 MHz) δ (ppm) 11.12 (s, 1P); and MS (ESI, EI$^+$) m/z=494.84 (MH$^+$).

Example I.10

2-Thiophenecarboxylic acid, 3-N-[(2,4-dichlorophenyl)-phosphonamidate ethyl ester]-5-(4-cyanophenyl) (Compound 29)

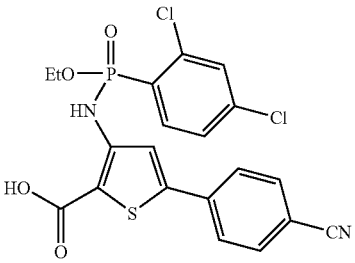

To Intermediate I.19 (0.10 mmol) in tert-butanol (2 ml) was added tert-butoxide (0.5 mmol). The solution was stirred at 45° C. for 5 hours, then cooled to room temperature, diluted with ethyl acetate and transferred in a reparatory funnel. 1 M aqueous HCl was added and the organic layer was extracted twice. The combined organic layers were washed with brine, dried over sodium sulfate and concentrated under vacuum. The residue was purified by flash chromatography (eluent: stepwise gradient of methanol (0-20%) in methylene chloride) to give a beige residue which was precipitated from ethanol to give pure Example I.10 (31%) as an off-white powder. Example I.10 was characterized by the following spectroscopic data: $^1$H NMR (DMSO, 400 MHz) δ (ppm) 1.30 (t, J=7.1 Hz, 3H), 4.05-4.17 (m, 2H), 7.43 (s, 1H), 7.56 (brd, J=7.30 Hz, 1H), 7.64-7.84 (m, 4H), 7.99 (dd, J=13.7 Hz, J=8.2 Hz, 1H), 10.72 (brd, J=8.0 Hz, 1H); $^{31}$P NMR (DMSO, 162 MHz) δ (ppm) 10.21 (s, 1P); and MS (ESI, EI$^+$) m/z=436.80 (M-[CO$_2$H]2H$^+$).

Example I.11

2-Thiophenecarboxylic acid, 3-N-[(2,4-dichlorophenyl)-phosphonamidate ethyl ester]-5-(4-chlorophenyl) (Compound 30)

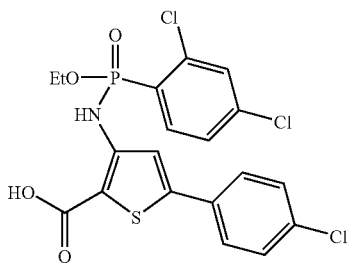

Intermediate I.17 was condensed with 4-chlorophenyl boronic acid as described for the preparation of Intermediate I.18. After the usual work-up and purification on silica gel by flash chromatography, the expected 5-(4-chlorophenyl) thiophene derivative was pure enough to be treated with tert-butoxide in tert-butanol under the same conditions as described for Example I.10. Example I.11 was obtained as a white powder (32% from Intermediate I.17) and characterized by the following spectroscopic data: $^1$H NMR (DMSO, 400 MHz) δ (ppm) 1.32 (t, J=7.1 Hz, 3H), 4.10-4.25 (m, 2H), 7.44 (s, 1H), 7.47-7.74 (m, 4H), 7.80 (dd, J=4.3 Hz, J=1.8 Hz, 1H), 8.05 (dd, J=13.7 Hz, J=8.3 Hz, 1H), 8.82 (brd, J=8.3 Hz, 1H); $^{31}$P NMR (DMSO, 162 MHz) δ (ppm) 9.90 (s, 1P); and MS (ESI, EI$^+$) m/z=491.7 (MH$^+$).

Example I.12

2-Thiophenecarboxylic acid, 3-N-[(2,4-dichlorophenyl)-phosphonamidate ethyl ester]-5-(3,4-dichlorophenyl) (Compound 31)

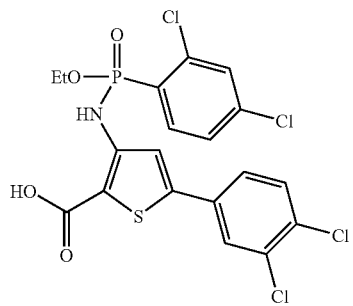

Intermediate I.17 was condensed with 3,4-dichlorophenyl boronic acid as described for the preparation of Intermediate I.18. After the usual work-up and purification on silica gel by flash chromatography, the expected 5-(3,4-dichlorophenyl) thiophene derivative was pure enough to be treated with tert-butoxide in tert-butanol under the same conditions as described for Example I.10. Example I.12 was obtained as a white powder (30% from Intermediate I.17) and characterized by the following spectroscopic data: $^1$H NMR (DMSO, 400 MHz) δ (ppm) 1.31 (t, J=7.1 Hz, 3H), 4.07-4.23 (m, 2H), 7.45 (s, 1H), 7.51-7.83 (m, 5H), 8.04 (dd, J=13.8 Hz, J=8.3 Hz, 1H), 9.54 (brs, 1H); $^{31}$P NMR (DMSO, 162 MHz) δ (ppm) 10.08 (s, 1P); and MS (ESI, EI$^+$) m/z=525.68 (MH$^+$).

Example I.13

2-Thiophenecarboxylic acid, 3-N-[(2,4-dichlorophenyl)-phosphonamidate ethyl ester]-5-(4-benzyloxyphenyl)

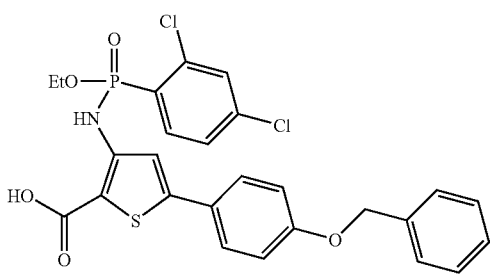

Intermediate I.17 was condensed with 4-benzyloxybenzene boronic acid as described for the preparation of Intermediate I.18. After the usual work-up and purification on silica gel by flash chromatography, the expected 5-(4-benzyloxyphenyl)thiophene derivative was pure enough to be treated with tert-butoxide in tert-butanol under the same conditions as described for Example I.10. Example I.13 was obtained as a white powder (32% from Intermediate I.17) and characterized by the following spectroscopic data: $^1$H NMR (DMSO, 400 MHz) δ (ppm) 1.32 (t, J=7.1 Hz, 3H), 4.08-4.25 (m, 2H), 7.45 (s, 1H), 7.51-7.83 (m, 5H), 5.14 (s, 2H), 7.07 (brd, J=8.8 Hz, 1H), 7.26-7.56 (m, 8H), 7.61 (brd, J=8.3 Hz, 1H), 7.79 (dd, J=4.4 Hz, J=1.8 Hz, 1H), 8.06 (dd, J=8.4 Hz, J=13.7 Hz, 1H), 8.92 (brd, J=8.5 Hz, 1H); and MS (ESI, EI$^+$) m/z=517.8 (M-[CO$_2$H]H$^+$).

Example I.14

2-Thiophenecarboxylic acid, 3-N-[(2,4-dichlorophenyl)-phosphonamidate ethyl ester]-5-[4-benzo[b]thiophen-2-yl]-phenyl)

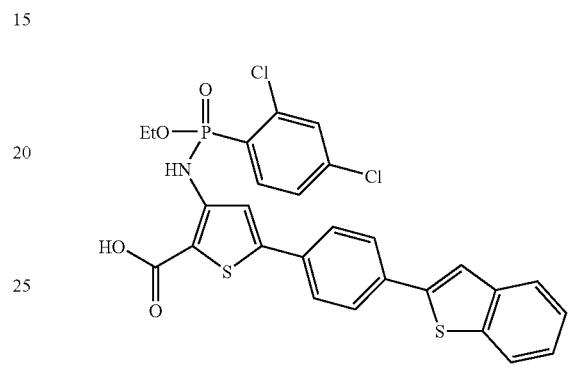

Intermediate I.17 was condensed with benzo[b]thiophene-2-boronic acid as described for the preparation of Intermediate I.18. After the usual work-up and purification on silica gel by flash chromatography, the expected 5-([4-benzo[b]thiophen-2-yl]-phenyl)thiophene derivative was pure enough to be treated with tert-butoxide in tert-butanol under the same conditions as described for Example I.10. Example I.14 was obtained as pale yellow powder (47% from Intermediate I.17) and characterized by the following spectroscopic data: $^1$H NMR (DMSO, 400 MHz) δ (ppm) 1.33 (t, J=7.1 Hz, 3H), 4.09-4.25 (m, 2H), 7.40 (m, 3H), 7.64 (brd, J=8.4 Hz, 1H), 7.75-7.91 (m, 3H), 7.97 (m, 1H), 8.05 (dd, J=13.7 Hz, J=8.4 Hz, 1H), 8.95 (brs, 1H); and MS (ESI, EI$^+$) m/z=511.7 (MH$^+$).

Intermediate I.20

(2-Fluoro-4-chloro-phenyl)-phosphonic acid diethyl ester

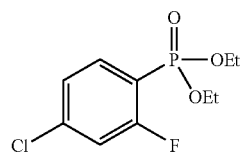

Intermediate I.20 was prepared starting from 4-chloro-2-fluoro-iodobenzene as described for Intermediate I.1. Intermediate I.20 was characterized by the following spectroscopic data: $^1$H NMR (CDCl$_3$, 400 MHz) δ (ppm) 1.36 (t, J=4.0 Hz, 6H), 4.13-4.22 (m, 4H), 7.16-7.27 (m, 2H), 7.78-7.83 (m, 1H); $^{31}$P NMR (CDCl$_3$, 162 MHz) δ (ppm) 18.02 (s, 1P); and MS (ESI, EI$^+$) m/z=243 (MH$^+$).

Intermediate I.21

(2-Fluoro-4-chloro-phenyl)-phosphonic acid ethyl ester

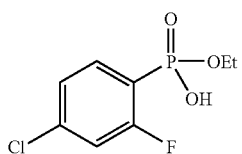

Intermediate I.21 was prepared starting from Intermediate I.20 as described for Intermediate I.2.

Intermediate I.22

2-Thiophenecarboxylic methylester, 3-N-[2-fluoro-4-chlorophenyl)-phosphonamidate ethyl ester]-5-[4-(furo[3,2-b]pyridine-2-ylphenyl)]

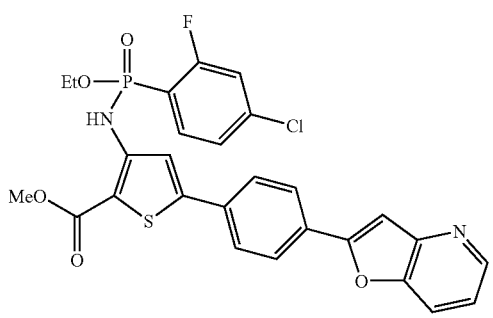

Intermediate I.22 was prepared starting from Intermediate I.21 and Intermediate VII.6 as described for Intermediate I.3. Intermediate I.22 was characterized by the following spectroscopic data: $^1$H NMR (DMSO, 400 MHz) δ (ppm) 1.33 (m, 3H), 3.85 (m, 3H), 4.20-4.21 (m, 2H), 7.34-8.53 (7 m, 12H); and $^{31}$P NMR (CDCl$_3$, 162 MHz) δ (ppm) 8.73 (s, 1P).

Example I.15

2-Thiophenecarboxylic acid, 3-N-[(2-fluoro-4-chlorophenyl)-phosphonamidate ethyl ester]-5-[4-(furo[3,2-b]pyridine-2-ylphenyl)]

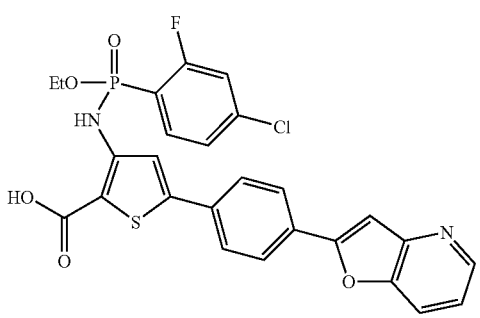

Example I.15 was prepared starting from Intermediate I.22 following the conditions described for Example I.10. Example I.15 was characterized by the following spectroscopic data: $^1$H NMR (DMSO, 400 MHz) δ (ppm) 1.31 (t, J=8.0 Hz, 3H), 4.13-4.17 (m, 2H), 7.32 (m, 1H), 7.45 (m, 2H), 7.60 (m, 3H), 7.70 (m, 3H), 7.82-7.88 (m, 3H), 8.5 (m, 1H); $^{31}$P NMR (CDCl$_3$, 162 MHz) δ (ppm) 8.92 (s, 1P); $^{19}$F NMR (CDCl$_3$, 376 MHz) δ (ppm) -102.28 (s, 1F); and MS (ESI, EI$^+$) m/z=556.77 (MH$^+$).

Scheme 25

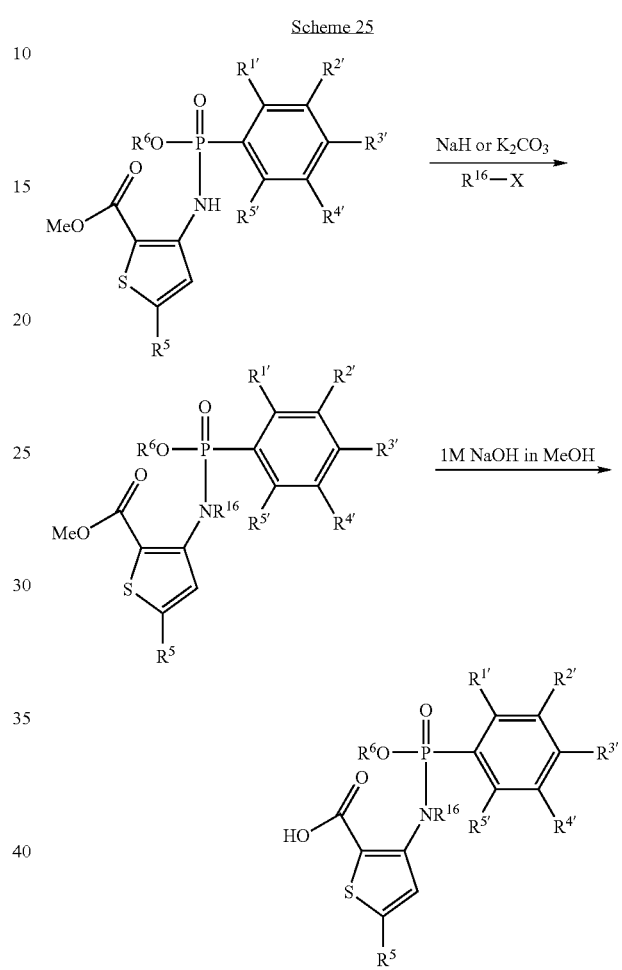

Intermediate II.1

2-Thiophenecarboxylic methylester, 3-N-methyl-N-[2,4-dimethyl-phenyl)-phosphonamidate methyl ester]-5-(4-fluorophenyl)

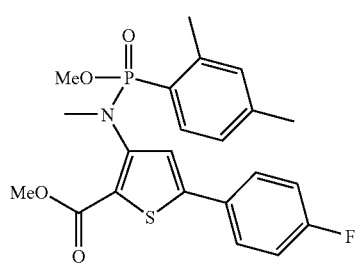

To a solution of Intermediate I.6 (0.115 mmol) in anhydrous dimethylformamide (1.5 ml) was added, under nitrogen, sodium hydride (60% dispersion in oil, 0.173 mmol). The reaction mixture was stirred at room temperature for 5 minutes and 2-bromopropane was added. The solution was heated at 60° C. overnight. The reaction mixture was cooled down to room temperature and diluted with ethyl acetate. After extraction with water, the organic phase was dried over sodium sulfate and evaporated to dryness. The crude mixture was filtered through silica gel (eluent: stepwise gradient of ethyl acetate (0-70%) in petroleum ether) to give Intermediate II.1, which was engaged for the next step without further purification.

Example II.1

2-Thiophenecarboxylic acid, 3-N-methyl-N-[(2,4-dimethyl-phenyl)-phosphonamidate methyl ester]-5-(4-fluorophenyl) (Compound 32)

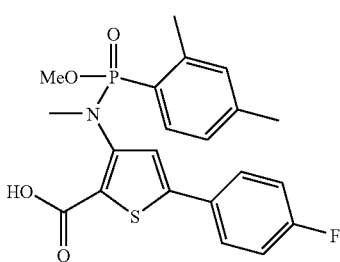

Example II.1 was synthesized from Intermediate II.1 as described for Example I.2. Example II.1 was obtained after lyophilization as a pale green solid (5% for the 2 steps) and characterized by the following spectroscopic data: $^1$H NMR (CDCl$_3$, 400 MHz) δ (ppm) 2.37 (s, 3H), 2.51 (s, 3H), 3.05 (d, J=8.0 Hz, 3H), 3.88 (d, J=12.0 Hz, 3H), 6.97 (s, 1H), 7.06-7.12 (m, 4H), 7.47-7.51 (m, 2H), 7.67-7.69 (m, 1H); $^{31}$P NMR (CDCl$_3$, 162 MHz) δ (ppm) 26.68 (s, 1P); $^{19}$F NMR (CDCl$_3$, 376 MHz) δ (ppm)-111.79 (s, 1F); and MS (ESI, EI$^+$) m/z=456 (MNa$^+$).

Intermediate II.2

2-Thiophenecarboxylic methylester, 3-N-isopropyl-N-[(2,4-dimethyl-phenyl)-phosphonamidate ethyl ester]-5-(4-fluorophenyl)

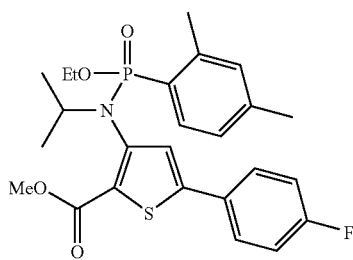

To a solution of Intermediate I.3 (0.223 mmol) in anhydrous dimethylformamide (2.2 ml) was added, under nitrogen, potassium carbonate (1.15 mmol), followed by 2-iodopropane (0.892 mmol). The reaction mixture was stirred for one day at 60° C. and 3 more days at 80° C. The reaction was stopped by addition of ethyl acetate and neutralized with a 1 M NaOH aqueous solution. After extraction, the organic phase was dried over sodium sulfate and evaporated to dryness. The crude mixture was purified on silica gel (eluent: stepwise gradient of ethyl acetate (0-30%) in petroleum ether) to give Intermediate II.2 (34%), which was characterized by the following spectroscopic data: $^1$H NMR (CDCl$_3$, 400 MHz) δ (ppm) 1.14-1.16 (m, 3H), 1.21-1.23 (m, 3H), 1.26-1.30 (m, 3H), 2.30 (s, 3H), 2.57 (s, 3H), 3.71 (s, 3H), 4.02-4.06 (m, 1H), 4.17-4.19 (m, 2H), 6.91-7.13 (m, 5H), 7.46-7.52 (m, 3H); $^{31}$P NMR (CDCl$_3$, 162 MHz) δ (ppm) 20.77 (s, 1P); $^{19}$F NMR (CDCl$_3$, 376 MHz) δ (ppm)-112.22 (s, 1F); and MS (ESI, EI$^+$) m/z=490 (MH$^+$).

Example II.2

2-Thiophenecarboxylic acid, 3-N-isopropyl-N-[(2,4-dimethyl-phenyl)-phosphonamidate ethyl ester]-5-(4-fluorophenyl) (Compound 33)

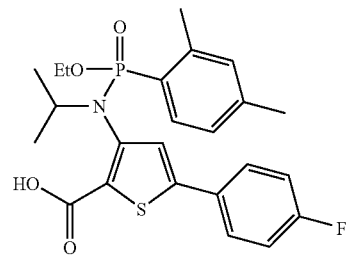

Example II.2 was synthesized from Intermediate II.2 as described for Example I.1. The desired compound was obtained after lyophilization as a white solid (44%) and characterized by the following spectroscopic data: $^1$H NMR (CDCl$_3$, 400 MHz) δ (ppm) 1.08-1.12 (m, 6H), 1.22-1.26 (m, 3H), 2.20 (s, 3H), 2.44 (s, 3H), 4.0-4.10 (m, 3H), 6.89-7.10 (m, 5H), 7.42-7.54 (m, 3H); $^{31}$P NMR (CDCl$_3$, 162 MHz) δ (ppm) 21.45 (s, 1P); $^{19}$F NMR (CDCl$_3$, 376 MHz) δ (ppm)-114.62 (s, 1F); and MS (ESI, EI$^+$) m/z=476 (MH$^+$).

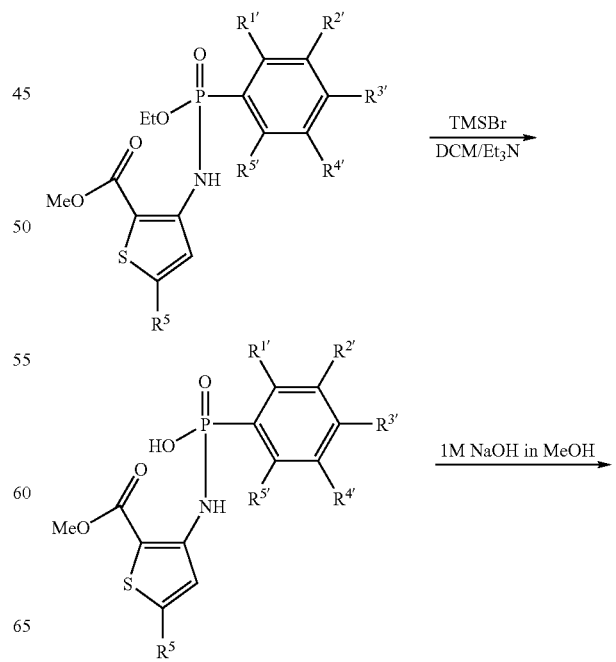

Scheme 26

Intermediate III.1

2-Thiophenecarboxylic methylester, 3-N-[(2,4-dimethyl-phenyl)-phosphonamidate]-5-(4-fluorophenyl)

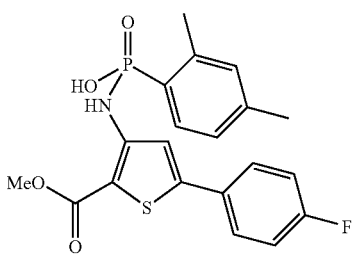

To a solution of Intermediate I.3 (0.112 mmol) in anhydrous 1,2-dichloroethane (5.0 ml) was added, under nitrogen, triethylamine (0.672 mmol), followed by trimethylsilylbromide (0.559 mmol). The reaction mixture was stirred overnight at room temperature. Then, methanol was added and solvents evaporated to dryness. The crude mixture was purified on C18 reverse phase chromatography (eluent: stepwise gradient of acetonitrile (0-50%) in water) to give Intermediate III.1 (85%) as a triethylammonium salt, which was characterized by the following spectroscopic data: $^1$H NMR (CDCl$_3$, 400 MHz) δ (ppm) 2.16 (s, 3H), 2.49 (s, 3H), 3.70 (s, 3H), 6.83-6.88 (m, 4H), 7.36 (m, 3H), 7.84-7.99 (m, 2H); $^{31}$P NMR (CDCl$_3$, 162 MHz) δ (ppm) 7.40 (s, 1P); $^{19}$F NMR (CDCl$_3$, 376 MHz) δ (ppm)-112.22 (s, 1F); and MS (ESI, EI$^+$) m/z=490 (MH$^+$).

Example III.1

2-Thiophenecarboxylic acid, 3-N-[(2,4-dimethyl-phenyl)-phosphonamidate]-5-(4-fluorophenyl)

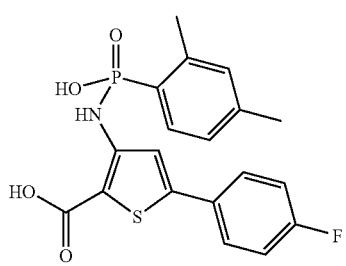

Intermediate III.1 (0.088 mmol) was dissolved in a mixture of methanol (1.3 ml) and aqueous 1 M sodium hydroxide solution (1.3 ml). The solution was stirred at room temperature for 4 days. The reaction mixture was lyophilized and purified on C18 reverse phase chromatography. Example III.1 was eluted with water as its sodium salt and lyophilized to give a yellow solid (48%) which was lyophilized and characterized by the following spectroscopic data: $^1$H NMR (CDCl$_3$, 400 MHz) δ (ppm) 2.13 (s, 3H), 2.51 (s, 3H), 6.83 (m, 2H), 6.90-6.95 (m, 2H), 7.21 (s, 1H), 7.39-7.42 (m, 2H), 7.66-7.72 (m, 1H); $^{31}$P NMR (CDCl$_3$, 162 MHz) δ (ppm) 8.74 (s, 1P); $^{19}$F NMR (CDCl$_3$, 376 MHz) δ (ppm)-116.82 (s, 1F); and MS (ESI, EI$^+$) m/z=404 (MH$^+$).

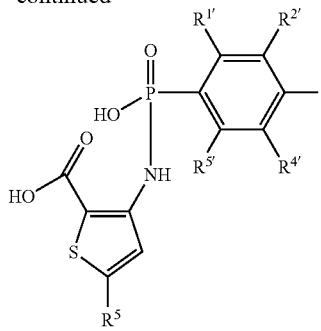

Scheme 27

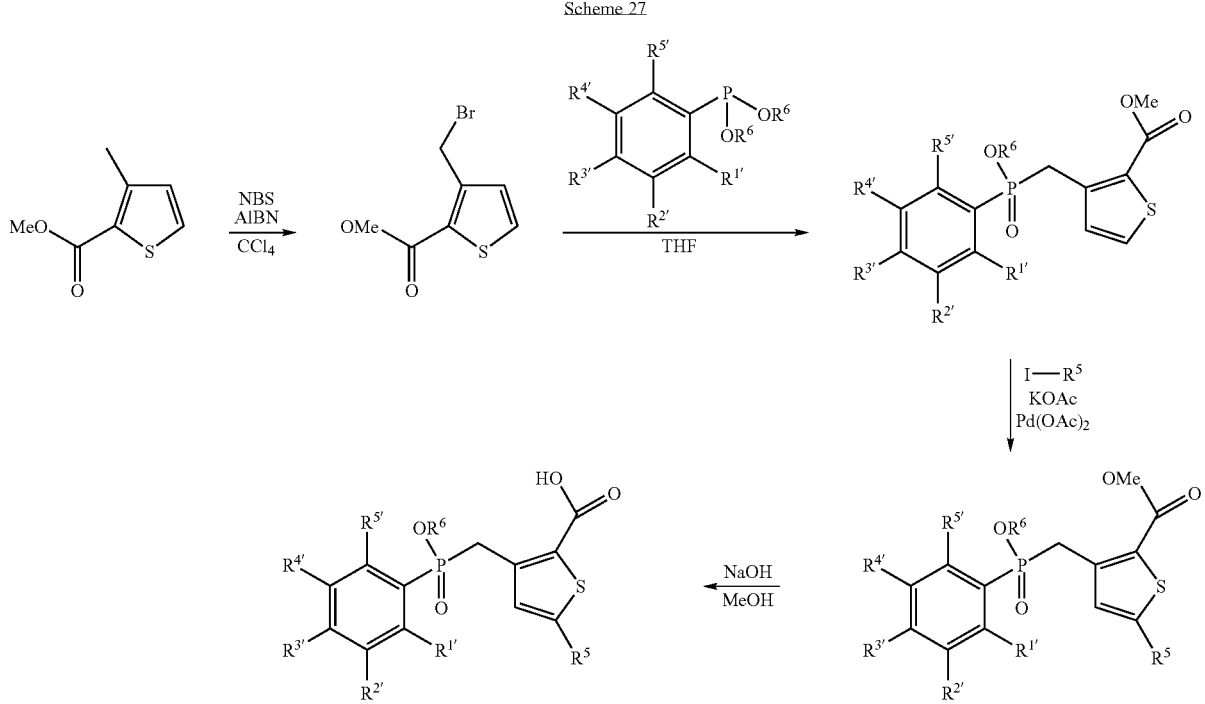

Intermediate IV.1

Methyl 3-(bromomethyl)thiophene-2-carboxylate

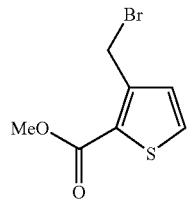

A mixture of methyl 3-methylthiophene-2-carboxylate (13.2 mmol), N-Bromosuccinimide (13.2 mmol) and a catalytic amount of azobis-isobutyronitrile in carbon tetrachloride were heated at reflux under nitrogen. The reaction mixture was irradiated with a 500 W UV lamp for 1.5 hours, cooled down to room temperature and then filtered under autocup 0.45 μm, followed by the evaporation of the filtrate. The residue was purified by chromatography on silica gel (eluent: stepwise gradient of 3-5% diethyl ether in petroleum ether) to give 2.13 g of Intermediate IV.1 (69%), which was characterized by $^1$H NMR (CDCl$_3$, 400 MHz) δ (ppm) 3.90 (s, 3H), 4.92 (s, 2H), 7.18 (d, J=5.3 Hz, 1H), 7.47 (d, J=5.3 Hz, 1H).

Intermediate IV.2

Methyl 3-methylene[(2,4-dimethyl-phenyl)-phosphinate ethyl ester]thiophene-2-carboxylate

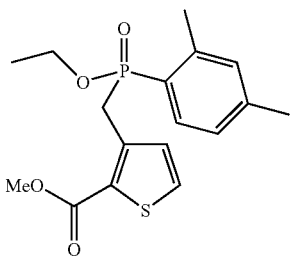

At room temperature, under nitrogen, a 0.5 M solution of 2,4-dimethylphenyl magnesium bromide (11.5 mmol) in THF was added to a solution of diethylchlorophosphite (13.8 mmol) in THF (30 ml). The reaction mixture was then heated at reflux for 1 hour and 45 minutes, then Intermediate IV.1 (13.8 mmol) was added portion wise and the reaction mixture was refluxed for 1.5 hours. Afterwards, the reaction mixture was cooled down to room temperature and quenched with water (pH 5), decanted, extracted with ethyl acetate. The organic phase were combined, dried over sodium sulfate and evaporated to dryness. The residue was purified by chromatography on silica gel (eluent: stepwise gradient of 0-5% methanol in dichloromethane) to give 3.15 g of Intermediate IV.2 (73%), which was characterized by the following spectroscopic data: $^1$H NMR (CDCl$_3$, 400 MHz) δ (ppm) 1.29 (t, J=7.0 Hz, 3H), 2.33 (s, 3H), 2.49 (s, 3H), 3.71 (s, 3H), 3.85-3.99 (m, 3H), 4.06-4.11 (m, 1H), 7.00-7.02 (m, 2H), 7.13 (dd, J=5.2 and 1.6 Hz, 1H), 7.39 (d, J=5.2 Hz, 1H), 7.54 (dd, J=7.6 and 12.4 Hz, 1H); $^{31}$P NMR (CDCl$_3$, 162 MHz) δ (ppm) 39.9 (s, 1P); and MS (ESI, EI$^+$) m/z=353 (MH$^+$).

Intermediate IV.3

Methyl 3-methylene[(2,4-dimethyl-phenyl)-phosphinate ethyl ester]-5-(4-fluorophenyl) thiophene-2-carboxylate

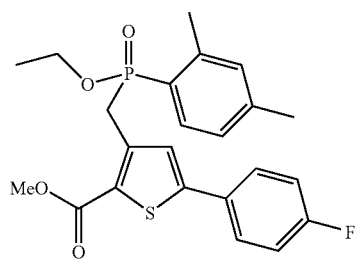

At room temperature, Intermediate IV.2 (0.87 mmol) was added to a solution of 4-fluoroiodobenzene (0.44 mmol) in dimethylacetamide. Potassium acetate (0.87 mmol) and palladium acetate (0.1 mmol) were added, the reaction vessel was sealed and heated at 140° C. for 6 hours. Then, the reaction mixture was cooled down to room temperature and poured into water, extracted with dichloromethane, dried over sodium sulfate and evaporated to dryness. The residue was purified by HPLC preparative (eluent: stepwise gradient of acetonitrile (30-95%) in water) to give 16 mg of Intermediate IV.3 (8%), which was characterized by the following spectroscopic data: $^1$H NMR (CDCl$_3$, 400 MHz) δ (ppm) 1.22 (t, J=7.0 Hz, 3H), 2.26 (s, 3H), 2.45 (s, 3H), 3.65 (s, 3H), 3.80-3.90 (m, 3H), 4.01-4.07 (m, 1H), 6.94-7.03 (m, 4H), 7.16 (s, 1H), 7.40-7.60 (m, 3H); $^{31}$P NMR (CDCl$_3$, 162 MHz) δ (ppm) 39.9 (s, 1P); $^{19}$F NMR (CDCl$_3$, 376 MHz) δ (ppm)-112.3 (s, 1F); and MS (ESI, EI$^+$) m/z=447 (MH$^+$).

Example IV.1

3-Methylene[(2,4-dimethyl-phenyl)-phosphinate ethyl ester]-5-(4-fluorophenyl) thiophene-2-carboxylic acid

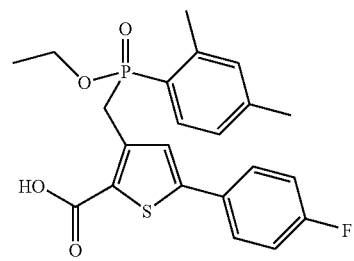

Intermediate IV.3 (0.036 mmol) was dissolved in a mixture of methanol (0.50 ml) and aqueous 2 M sodium hydroxide solution (0.50 ml). The solution was stirred at room temperature for 4 hours. Then, water was added and the solution was acidified to pH 1 by addition of a 2 N HCl aqueous solution. After extraction with dichloromethane, the organic phase were combined and dried over sodium sulfate and concentrated. The residue was purified by chromatography on silica gel (eluent: stepwise gradient of methanol (0-10%) in methylene chloride), and then triturated in diethyl ether to yield 5 mg of Example IV.1 as a beige powder (32%), which was characterized by the following spectroscopic data: $^1$H NMR (DMSOd$_6$, 400 MHz) δ (ppm) 1.19 (t, J=6.8 Hz, 3H), 2.28 (s, 3H), 3.81-3.89 (m, 1H), 3.92-4.02 (m, 2H), 4.10-4.25 (m, 1H), 6.99 (s, 1H), 7.05-7.10 (m, 2H), 7.20-7.24 (m, 2H), 7.42-7.53 (m, 2H), 7.58-7.63 (m, 1H); $^{31}$P NMR (DMSOd$_6$, 162 MHz) δ (ppm) 41.5 (s, 1P); $^{19}$F NMR (DMSOd$_6$, 376 MHz) δ (ppm)-114.4 (s, 1F); and MS (ESI, EI$^+$) m/z=433 (MH$^+$).

Scheme 28

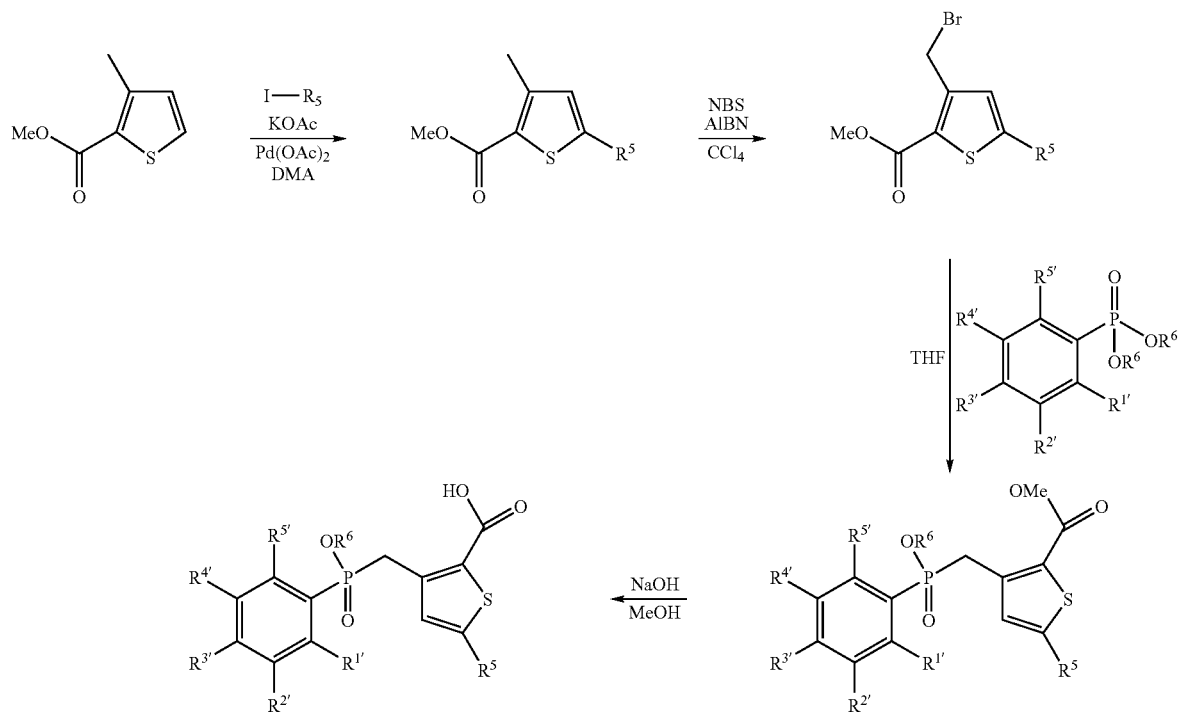

Intermediate V.1
Methyl 3-methyl-5-phenyl-thiophene-2-carboxylate

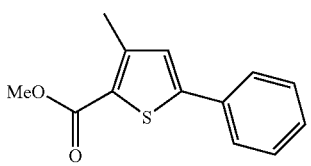

At room temperature, a solution of 4-iodobenzene (9.6 mmol) and methyl 3-methylthiophene-2-carboxylate (19.2 mmol) in dimethylacetamide (20 ml) were degassed with nitrogen for 15 minutes. Potassium acetate (0.87 mmol) and palladium acetate (0.02 mmol) were added, the reaction vessel was sealed and heated at 150° C. for 1 hour. Then, the reaction mixture was cooled down to room temperature and poured into water, extracted with dichloromethane, washed with brine, dried over sodium sulfate and evaporated to dryness. The residue was purified by chromatography on silica gel (eluent: gradient of 3% diethyl ether in petroleum ether) to give 100 mg of Intermediate V.1 (22%) as a yellow solid, which was characterized by the following spectroscopic data: $^1$H NMR (CDCl$_3$, 400 MHz) δ (ppm) 2.57 (s, 3H), 3.88 (s, 3H), 7.13 (s, 1H), 7.32-7.34 (m, 3H), 7.59-7.64 (m, 2H); and MS (ESI, EI$^+$) m/z=233 (MH$^+$).

Intermediate V.2
Methyl 3-(bromomethyl)-5-phenyl-thiophene-2-carboxylate

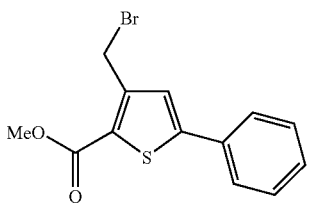

A mixture of Intermediate V.1 (2.07 mmol), N-Bromosuccinimide (2.07 mmol) and a catalytic amount of azobisisbutyronitrile in carbon tetrachloride were heated at reflux under nitrogen. The reaction mixture was irradiated with a 500 W UV lamp for 1 hour, cooled down to room temperature and then filtered under autocup 0.45 μm, followed by the evaporation of the filtrate. The residue was purified by chromatography on silica gel (eluent: stepwise gradient of 0-5% diethyl ether in petroleum ether) to give 616 mg of Intermediate V.2 (80%) as a yellow solid, which was characterized by $^1$H NMR (CDCl$_3$, 400 MHz) δ (ppm) 3.92 (s, 3H), 4.92 (s, 2H), 7.38 (m, 4H), 7.61-7.64 (m, 2H).

Intermediate V.3

Methyl 3-methylene[(2,4-dimethyl-phenyl)-phosphinate ethyl ester]-5-phenyl-thiophene-2-carboxylate

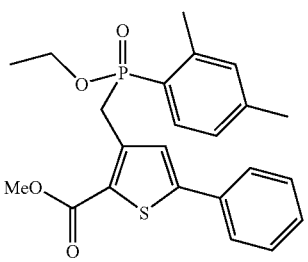

At room temperature, under nitrogen, a 0.5 M solution of 2,4-dimethylphenyl magnesium bromide (0.71 mmol) in THF was added to a solution of diethylchlorophosphite (0.85 mmol) in THF (3 ml). The reaction mixture was then heated at reflux for 2 hours, then Intermediate V.2 (0.85 mmol) was added portion wise and the reaction mixture was refluxed for 2 hours. Afterwards, the reaction mixture was cooled down to room temperature and quenched with water (pH 1), basified with a saturated solution of sodium bicarbonate (pH 7-8), extracted with ethyl acetate, dried over sodium sulfate and evaporated to dryness, yielding a crude containing some H-phosphinate. The residue was dissolved in acetonitrile and N,O-(bistrimethylsilyl)acetamide(0.36 mmol) was added. The reaction mixture was refluxed for 2 hours. Then, the reaction mixture was cooled down to room temperature and quenched with water, acetonitrile was evaporated and the aqueous phase was extracted with dichloromethane, dried over sodium sulfate and evaporated to dryness. The residue was purified by chromatography on silica gel (eluent: step-wise gradient of 0-5% methanol in dichloromethane) and semi-preparative HPLC (eluent: stepwise gradient of 30-95% acetonitrile in water) to give 70 mg of Intermediate V.3 (23%) as a yellow syrup, which was characterized by the following spectroscopic data: $^1$H NMR (CDCl$_3$, 400 MHz) δ (ppm) 1.23 (t, J=6.8 Hz, 3H), 2.25 (s, 3H), 2.45 (s, 3H), 3.65 (s, 3H), 3.81-3.92 (m, 3H), 4.01-4.09 (m, 1H), 6.90-7.00 (m, 2H), 7.22 (s, 1H), 7.23-7.36 (m, 3H), 7.45-7.57 (3 J=7.6, 3H); $^{31}$P NMR (CDCl$_3$, 162 MHz) δ (ppm) 39.97 (s, 1P); and MS (ESI, EI$^+$) m/z=429 (MH').

Example V.1

3-Methylene[(2,4-dimethyl-phenyl)-phosphinate ethyl ester]-5-phenyl-thiophene-2-carboxylic acid

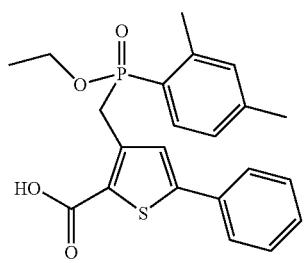

Intermediate V.3 (0.054 mmol) was dissolved in a mixture of methanol (1 ml) and aqueous 2 M sodium hydroxide solution (1 ml). The solution was stirred at room temperature for 4 hours. Then, water was added and the solution was acidified to pH 1 by addition of a 2 N HCl aqueous solution. After extraction with dichloromethane, the organic phase were combined and dried over sodium sulfate and concentrated. The residue was purified by semi-preparative HPLC (eluent: stepwise gradient of 30-95% acetonitrile in water) to give 20 mg of Example V.1 (44%) as a pale yellow solid, which was characterized by the following spectroscopic data: $^1$H NMR (CDCl$_3$, 400 MHz) δ (ppm) 1.33 (t, J=6.8 Hz, 3H), 2.34 (s, 3H), 2.53 (s, 3H), 3.73-3.88 (m, 1H), 3.89-4.08 (m, 2H), 4.11-4.25 (m, 1H), 6.98 (s, 1H), 7.02-7.12 (m, 2H), 7.29-7.45 (m, 3H), 7.46-7.7 (m, 2H), 7.60-7.72 (m, 1H); $^{31}$P NMR (CDCl$_3$, 162 MHz) δ (ppm) 41.9 (s, 1P); and MS (ESI, EI$^+$) m/z=415 (MH$^+$).

Scheme 29

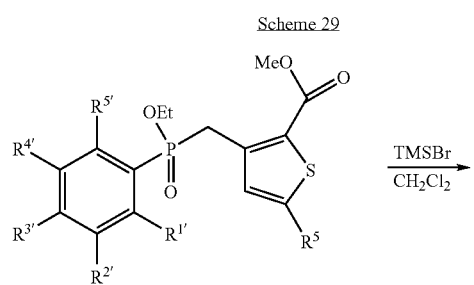

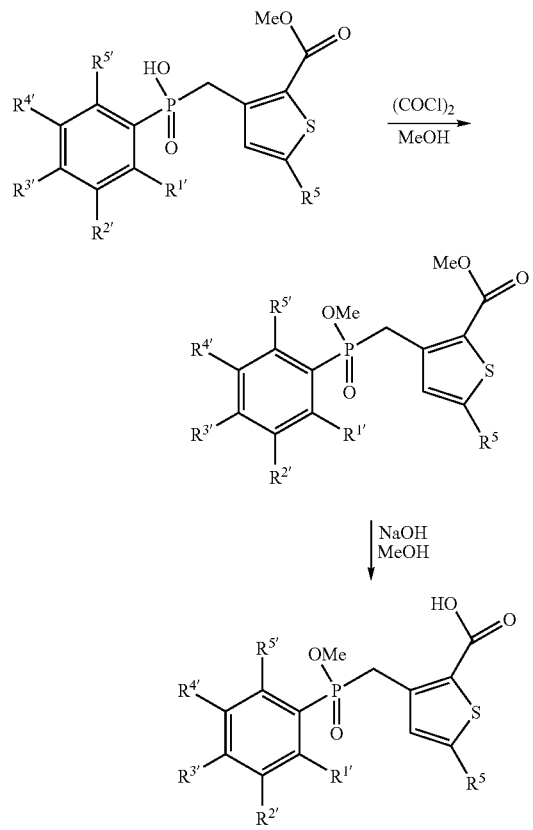

Intermediate VI.1

Methyl 3-methylene[(2,4-dimethyl-phenyl)-phosphinic acid]-5-phenyl-thiophene-2-carboxylate

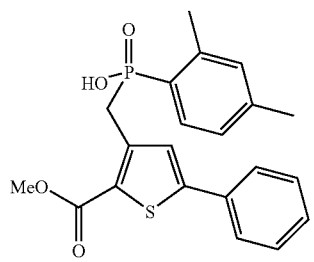

At room temperature, under nitrogen, to a solution of Intermediate V.3 (0.11 mmol) in dichloromethane (2 ml) was added trimethylsilylbromide (0.55 mmol) dropwise. The reaction mixture was stirred at room temperature for 2 hours, quenched with methanol and evaporated. The residue was purified by chromatography on silica gel (eluent: stepwise gradient of 0-5% methanol in dichloromethane containing few drops of acetic acid) to yield 59 mg of Intermediate VI.1, which was characterized by the following spectroscopic data: $^1$H NMR (CDCl$_3$, 400 MHz) δ (ppm) 2.13 (s, 3H), 2.36 (s, 3H), 3.40-3.90 (m, 5H), 6.61-6.73 (m, 1H), 6.74-6.84 (m, 1H), 6.89-7.04 (m, 1H), 7.11-7.24 (m, 3H), 7.25-7.37 (m, 2H), 7.38-7.50 (m, 1H); $^{31}$P NMR (CDCl$_3$, 162 MHz) δ (ppm) 39.22 (s, 1P); and MS (ESI, EI$^+$) m/z=401 (MH$^+$).

Intermediate VI.2

3-Methylene[(2,4-dimethyl-phenyl)-phosphinate methyl ester]-5-phenyl-thiophene-2-carboxylic acid

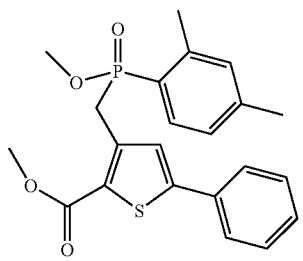

At room temperature, under nitrogen, to a solution of Intermediate VI.1 (0.11 mmol) in dichloromethane (2 ml) was added a catalytic amount of dimethylformamide and oxalyl chloride (0.33 mmol). The reaction mixture was stirred at room temperature for 2 hours, then methanol (0.5 ml) was added and stirring continued for 1 hour. The resulting mixture was evaporated to dryness to give 56 mg of crude Intermediate VI.2, which was characterized by MS (ESI, EI$^+$) m/z=415 (MH$^+$).

Example VI.1

3-Methylene[(2,4-dimethyl-phenyl)-phosphinate methyl ester]-5-phenyl-thiophene-2-carboxylic acid

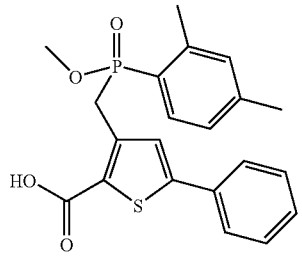

Intermediate VI.2 (0.11 mmol) was dissolved in a mixture of methanol (0.5 ml) and aqueous 2 M sodium hydroxide solution (0.5 ml). The solution was stirred at room temperature for 4 hours. Then water was added and the solution was acidified to pH 3 by addition of a 2 N HCl aqueous solution. After extraction with ethyl acetate, the organic phase were combined and dried over sodium sulfate and concentrated. The residue was purified by semi-preparative HPLC (eluent: stepwise gradient of 30-95% acetonitrile in water) to give 21 mg of Example VI.1 (48% over 3 steps) as a white solid, which was characterized by the following spectroscopic data: $^1$H NMR (CDCl$_3$, 400 MHz) δ (ppm) 2.25 (s, 3H), 2.44 (s, 3H), 3.65 (d, J=11.2 Hz, 3H), 3.71-3.85 (m, 1H), 3.88-4.04 (m, 1H), 6.89-7.05 (m, 3H), 7.21-7.36 (m, 3H), 7.39-7.49 (m, 2H), 7.50-7.622 (m, 1H); $^{31}$P NMR (CDCl$_3$, 162 MHz) δ (ppm) 43.46 (s, 1P); and MS (ESI, EI$^+$) m/z=401 (MH$^+$).

Scheme 30

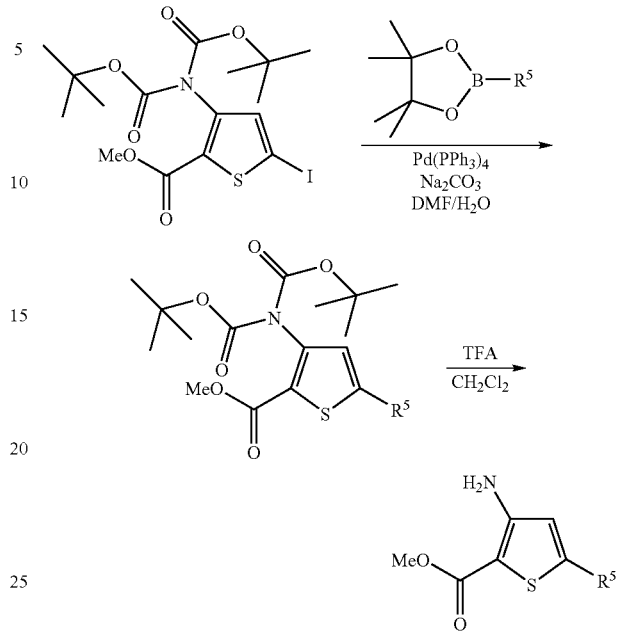

Intermediate VII.1

Methyl 3-(bis[terbutoxycarbonyl]amino)-5-(4-pyrazolo[1,5-a]pyrimidin-2-yl-phenyl)-2-thiophenecarboxylate

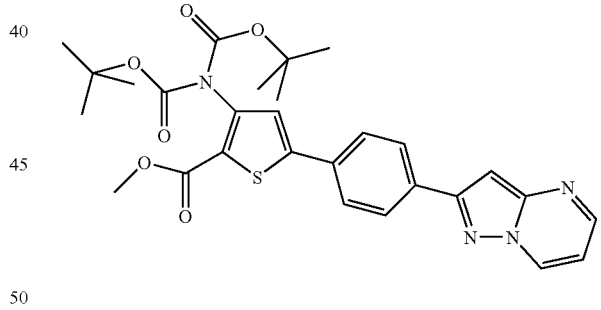

Methyl 3-(bis[terbutoxycarbonyl]amino)-5-iodo-2-thiophenecarboxylate (1 mmol) and 2-[4-(4-4,4,5,5,-tetramethyl-1,3,2-dioxaborolan-2-yl)phenyl]pyrazolo[1,5a]pyrimidine (1.4 mmol) were dissolved in dimethylformamide (32 ml). Sodium carbonate (4 mmol) in water (2.5 ml) and tetrakis (triphenylphosphine) palladium (0.1 mmol) were added. The reaction mixture was heated at 100° C. for 3 hours. Then, the reaction mixture was cooled down to room temperature and evaporated. The residue was partitioned between water and dichloromethane. The aqueous phase was extracted with dichloromethane, dried over sodium sulfate and evaporated to dryness. The residue was purified by chromatography on silica gel (eluent: stepwise gradient of 5-50% ethyl acetate in petroleum ether) to give 100 mg (18%) of Intermediate VII.1 as a pale yellow solid, which was characterized by the following spectroscopic data: $^1$H NMR (CDCl$_3$, 400 MHz) δ (ppm) 1.48 (s, 18H), 3.87 (s, 3H), 6.84 (dd, J=7 and 4 Hz, 1H), 7.04 (s, 1H), 7.19 (s, 1H), 7.71-7.75 (m, 2H), 8.03-8.07 (m, 2H), 8.49 (d, J=4 Hz, 1H), 8.70 (d, J=7 Hz, 1H); and MS (ESI, EI⁺) m/z=574 (MNa⁺).

Intermediate VII.2

Methyl 3-amino-5-(4-pyrazolo[1,5-a]pyrimidin-2-yl-phenyl)-2-thiophenecarboxylate

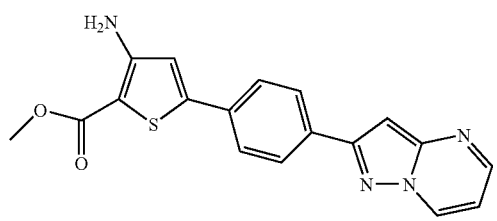

Intermediate VII.1 (0.18 mmol) was dissolved in dichloromethane (1 ml) and trifluoroacetic acid (0.2 ml) was added. The reaction mixture was stirred at room temperature for 3 hours and then evaporated to dryness. The residue was partitioned between water and dichloromethane. The aqueous phase was extracted with dichloromethane, dried over sodium sulfate and evaporated to dryness to give 60 mg of Intermediate VII.2 as yellow solid, which was characterized by the following spectroscopic data: ¹H NMR (DMSOd₆, 400 MHz) δ (ppm) 3.74 (s, 3H), 6.61 (s, 2H), 7.03-7.08 (m, 2H), 7.30 (s, 1H), 7.72-7.77 (m, 2H), 8.08-8.13 (m, 2H), 8.55 (dd, J=1.8 and 4 Hz, 1H), 9.14 (ddd, J=1, 1.7 and 7 Hz, 1H); and MS (ESI, EI⁺) m/z=350.9 (MH⁺).

Intermediate VII.3

Methyl 3-(bis[terbutoxycarbonyl]amino)-5-(4-phenyl-ethynyl-1,3-thiazole)-2-thiophenecarboxylate

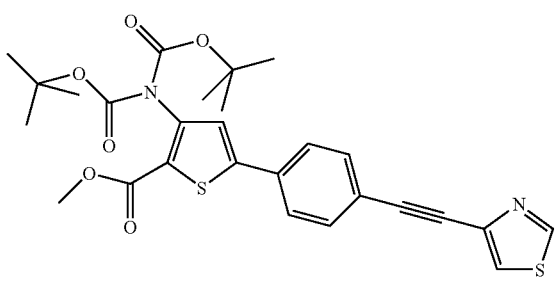

Methyl 3-(bis[terbutoxycarbonyl]amino)-5-iodo-2-thiophenecarboxylate (1.19 mmol) and 2-[4-(4-4,4,5,5-tetramethyl-1,3,2-dioxaborolan-2-yl)phenyl]ethynyl)1,3-thiazole (0.91 mmol) were dissolved in dimethylformamide (24 ml). Sodium carbonate (4 mmol) and tetrakis(triphenylphosphine) palladium (0.1 mmol) were added. The reaction mixture was heated in a MPS sealed tube at 100° C. for 3.5 hours. Then, the reaction mixture was cooled down to room temperature and filtered. The filtrate was partitioned between water and dichloromethane. The aqueous phase was extracted with dichloromethane, dried over sodium sulfate and evaporated to dryness. The residue was purified by chromatography on silica gel (eluent: stepwise gradient of 5-50% ethyl acetate in petroleum ether) to give 369 mg (7.5%) of Intermediate VII.3 as a brown solid, which was characterized by ¹H NMR (CDCl₃, 400 MHz) δ (ppm) 1.45 (s, 18H), 3.87 (s, 3H), 7.15 (s, 1H), 7.61 (s, 5H), 8.83 (d, J=2 Hz, 1H).

Intermediate VII.4

Methyl 3-amino-5-(4-phenyl-ethynyl-1,3-thiazole)-2-thiophenecarboxylate

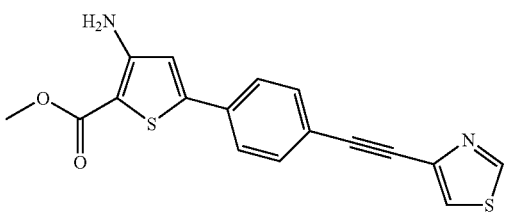

Intermediate VII.4 was prepared starting from Intermediate VII.3 as described for Intermediate VII.2. Intermediate VII.4 was obtained as a brown solid, which was characterized by MS (ESI, EI⁺) m/z=341 (MH⁺).

Intermediate VII.5

Methyl 3-(bis[terbutoxycarbonyl]amino)-5-(4-furo[3,2-b]pyridine-2-ylphenyl)-2-thiophenecarboxylate

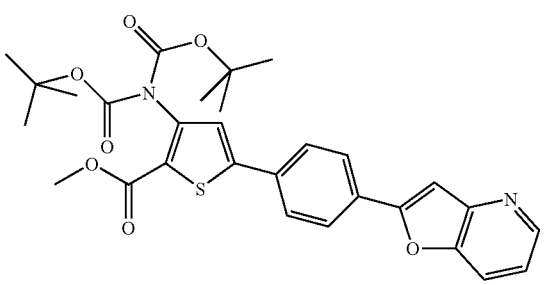

Intermediate VII.5 was prepared starting from methyl 3-(bis[ter-butoxycarbonyl]amino)-5-iodo-2-thiophenecarboxylate and 2-[4(4,4,5,5-tetramethyl-1,3,2-dioxaborolan-2-yl)phenyl]furo[3,2-b]pyridine (according to the general procedure in WO 2008/017688) as described for Intermediate VII.1. Intermediate VII.5 was used for the next step without purification.

Intermediate VII.6

Methyl 3-amino-5-(4-furo[3,2-b]pyridine-2-ylphenyl)-2-thiophenecarboxylate

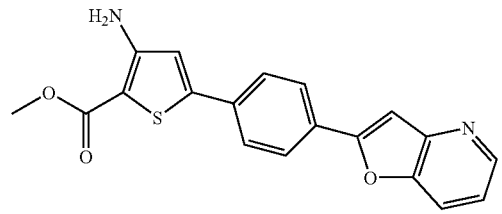

Intermediate VII.6 was prepared starting from Intermediate VII.5 as described for Intermediate VII.2. Intermediate VII.6 was obtained as a brown solid, which was characterized by MS (ESI, EI$^+$) m/z=351 (MH$^+$).

Intermediate I.25

5-Thiazolecarboxylic methyl ester, 4-chloro-2-[phenyl-pyrazolo[1,5-a]pyrimidine]

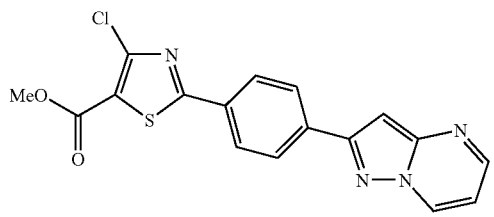

In a 100 ml round bottom flask, were added methyl-2,4-dichlorothiazolo-5-carboxylate (2.82 mmol), 2-[4-(4,4,5,5-tetramethyl-1,3,2-dioxaborolan-2-yl)phenyl]pyrazolo[1,5-a]pyrimidine (3.39 mmol) (according to the general procedure in WO 2007071434A1) and potassium phosphate tribasic (11.3 mmol) in dimethylformamide (30 ml). Pd(PPh$_3$)$_4$ (0.282 mmol) was then added to the 100 ml round bottom flask. Afterwards, the reaction mixture was stirred under nitrogen for about 5 hours at about 80° C. The reaction mixture was taken in ethyl acetate and then washed with water and brine. The aqueous layer was extracted with ethyl acetate and the organic layer concentrated under diminished pressure. The crude product was purified by silica gel chromatography to give Intermediate I.25, which was characterized by the following spectroscopic data: MS (ESI, EI$^+$) m/z=371.08 (MH$^+$).

Intermediate I.26

(2,4-dimethyl-phenyl)-O-methoxy-phosphonamidate

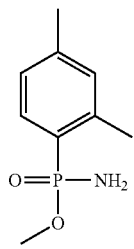

Under nitrogen atmosphere at room temperature, a first solution was prepared by adding Intermediate I.4 (38 mmol) into dichloromethane (130 ml) and several drops of dimethylformamide. Oxalyl chloride (114 mmol) was added quickly into the reaction mixture. Afterwards, the reaction mixture was stirred at room temperature for about 2 hours. The reaction mixture was evaporated in vacuum, followed by addition of 20 ml of tetrahydrofurane under nitrogen atmosphere. In a second reaction flask, a second solution was prepared by bubbling NH$_3$ gas was into 80 ml of tetrahydrofurane for about 10 minutes at about 0° C. The second solution was added dropwise to the first solution at about 0° C. The mixture of the two solutions was stirred at about 0° C. for about 1 hour. Then, the mixture of the two solutions was allowed to warm to room temperature, followed by stirring overnight. The solvents were removed under pressure to form Intermediate I.12 in 47% yield, which was characterized by the following spectroscopic data: $^1$H NMR (CDCl$_3$, 400 MHz) δ (ppm) 2.34 (s, 3H), 2.2.57 (s, 3H), 3.71 (d, J=11.43 Hz, 3H), 7.04-7.07 (m, 2H), 7.78 (dd, J=7.72 Hz and 14.16 Hz, 1H); $^{31}$P NMR (CDCl$_3$, 162 MHz) δ (ppm) 25.08 (s, 1P); and MS (ESI, EI$^+$) m/z=200.08 (MH$^+$).

Intermediate I.27

5-Thiazolecarboxylic methyl ester, 4-chloro-2-[4-methoxy-phenyl]

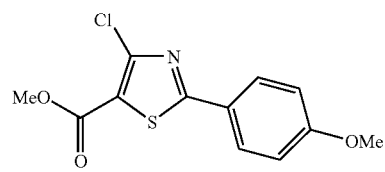

Intermediate I.13 was synthesized from methyl 2,4-dichlorothiazole-5-carboxylate (1.88 mmol) and 4-methoxyphenylboronic acid (2.26 mmol) following the procedure as described for Intermediate I.27 to give Intermediate I.13 as a beige solid in 51% yield, which was characterized by the following spectroscopic data: $^1$H NMR (CDCl$_3$, 400 MHz) δ (ppm) 3.88 (s, 3H), 3.92 (s, 3H), 6.97 (d, J=8.87 Hz, 2H), 7.91 (d, J=8.91 Hz, 2H); and MS (ESI, EI$^+$) m/z=284.05 (MH$^+$).

Intermediate I.28

5-Thiazolecarboxylic methyl ester, 4-chloro-2-[4-chloro-phenyl]

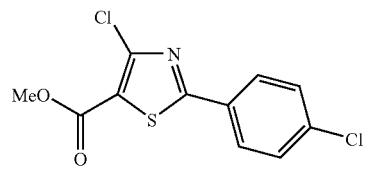

Methyl-2,4-dichlorothiazolo-5-carboxylate (8.14 mmol), 4-chlorophenylboronic acid (8.95 mmol) and potassium phosphate tribasic (24.42 mmol) were added to dimethylformamide (240 ml). Pd(PPh$_3$)$_4$ (0.814 mmol) was then added into the reaction mixture. The reaction mixture was then stirred under nitrogen atmosphere for about 4 hours at about 95° C. After cooling at room temperature, K$_3$PO$_4$ was filtered and the reaction mixture was diluted in dichloromethane and washed with water. The organic layer was concentrated under diminished pressure and the residue was purified by silica gel chromatography to give Intermediate I.28 as a yellow solid in 39%, which was characterized by the following spectroscopic data: $^1$H NMR (CDCl$_3$, 400 MHz) δ (ppm) 3.93 (s, 3H), 7.45 (d, J=8.51 Hz, 2H), 7.90 (d, J=8.51 Hz, 2H); and MS (ESI, EI$^+$) m/z=288.16 (MH$^+$).

Example VIII.1

5-Thiazolecarboxylic methyl ester, 4-N-[(2,4-dimethyl-phenyl)-phosphonamidate methyl ester] (Compound 191)

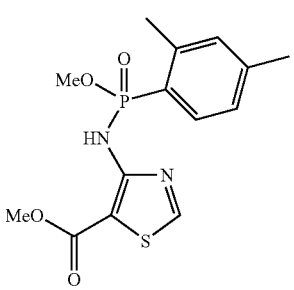

To a stirred solution of intermediate 1.5 (0.409 mmol) in anhydrous dichloromethane (1 ml) and dimethylformamide (40 µl), was added dropwise oxalyl chloride (1.00 mmol), to form a first solution. The first solution was stirred under nitrogen at room temperature for about 1 hour. Afterwards, the solvents were removed and the crude product of the first solution was then diluted with tetrahydrofurane (2 ml). A second solution was prepared after 4-aminothiazole-5-carboxylic acid methyl ester (0.316 mmol) has been solubilized in anhydrous tetrahydrofurane (2 ml), which was then added with 60% NaH (0.948 mmol). The first solution was added dropwise into the second solution at about 0° C. and the reaction mixture was stirred for about 2 hours at room temperature. The reaction mixture was quenched with 0.5 M NH$_4$Cl solution and diluted with ethyl acetate. The organic layer was washed with water and concentrated under reduced pressure. The residue was purified by silica gel chromatography (eluent: stepwise gradient of methanol (0-2%) in dichloromethane) to give Example VIII.1 in 67% yield, which was characterized by the following spectroscopic data: $^1$H NMR (CDCl$_3$, 400 MHz) δ (ppm) 2.32 (s, 3H), 2.59 (s, 3H), 3.85 (d, J=11.53 Hz, 3H), 3.87 (s, 3H), 7.03-7.09 (m, 2H), 7.84 (dd, J=7.70 Hz and 14.52 Hz, 1H) 8.20 (d, J=8.79 Hz, 1H), 8.58 (s, 1H); $^{31}$P NMR (CDCl$_3$, 162 MHz) δ (ppm) 17.66; and MS (ESI, EI$^+$) m/z=341.15 (MH$^+$).

Example VIII.2

5-Thiazolecarboxylic methyl ester, 2-iodo-4-N-[(2,4-dimethyl-phenyl)-phosphonamidate methyl ester] (Compound 192)

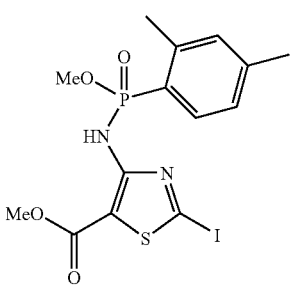

Example VIII.1 (0.088 mmol) was diluted in tetrahydrofurane (1 ml) and the mixture was cooled down to about −78° C. A solution of 2M lithium diisopropylamide in tetrahydrofurane (0.26 mmol) and iodide (0.176 mmol) diluted in tetrahydrofurane (1 ml) were added into the mixture. After being stirred for about 10 minutes, the mixture was then treated with an ammonium chloride solution. Afterwards, ethyl acetate was added and the mixture washed with sodium thiosulfate. The organic layer was concentrated under diminished pressure and the residue was purified by silica gel chromatography to give the Example VIII.2 as a yellow oil in 30% yield, which was characterized by the following spectroscopic data: $^1$H NMR (CDCl$_3$, 400 MHz) δ (ppm) 2.35 (s, 3H), 2.60 (s, 3H), 3.83 (s, 3H), 3.86 (d, J=11.58 Hz, 3H), 7.05 (d, J=5.30 Hz, 1H), 7.06-7.09 (m, 1H), 7.85 (dd, J=7.81 Hz and 14.38 Hz, 1H), 8.10 (d, J=9 Hz, 1H); $^{31}$P NMR (CDCl$_3$, 162 MHz) δ (ppm) 17.13 (s, 1P); and MS (ESI, EI$^+$) m/z=467.13 (MH$^+$).

Example VIII.3

5-Thiazolecarboxylic methyl ester, 4-N-[2,4-dimethyl-phenyl)-phosphonamidate methyl ester]-2-[phenyl-8aH-imidazo[1,2-a]pyridine] (Compound 193)

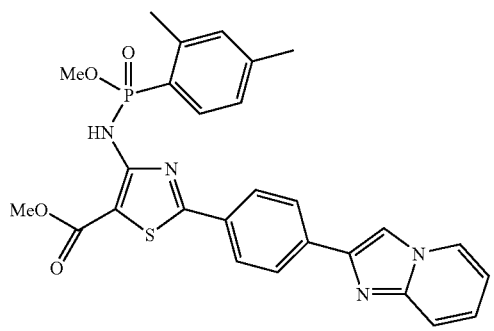

Example VIII.2 (0.429 mmol), 2-[4-(4,4,5,5-tetramethyl-1,3,2-dioxaborolan-2-yl)phenyl]imidazo[1,2-a]pyridine (according to the general procedure in WO 2007/071434A1) (0.515 mmol), sodium bicarbonate (1.29 mmol) and Pd(DtBPF)Cl$_2$ (0.0429 mmol) were added to a mixture of dioxane (3.9 ml) and water (0.9 ml). The reaction flask was purged with nitrogen and the mixture was stirred at about 80° C. for about 1.5 hours under microwave irradiation. The mixture was then partitioned between ethyl acetate and water. The aqueous layer was extracted with ethyl acetate and the organic layers were evaporated. The crude product was purified by silica gel chromatography to give Example VIII.3 as a brown foam in 72% yield, which was characterized by the following spectroscopic data: $^1$H NMR (DMSO, 400 MHz) δ (ppm) 2.29 (s, 3H), 3.77 (d, J=11.48 Hz, 3H), 3.85 (s, 3H), 6.90-6.94 (m, 1H), 7.10-7.12 (m, 1H), 7.21-7.24 (m, 1H), 7.25-7.29 (m, 1H), 7.59 (d, J=9.05 Hz, 1H), 7.82 (d, J=8.46 Hz, 2H), 7.93 (dd, J=7.83 Hz and 13.91 Hz, 1H), 8.07 (d, J=8.46 Hz, 2H), 8.15 (d, J=7.66 Hz, 1H), 8.53 (s, 1H), 8.54 (d, J=7.08 Hz, 1H); $^{31}$P NMR (DMSO, 162 MHz) δ (ppm) 15.63 (s, 1P); and MS (ESI, EI$^+$) m/z=533.32 (MH$^+$).

Example VIII.4

5-Thiazolecarboxylic acid, 4-N-[(2,4-dimethyl-phenyl)-phosphonamidate methyl ester]-2-[phenyl-8aH-imidazo[1,2-a]pyridine] (Compound 183)

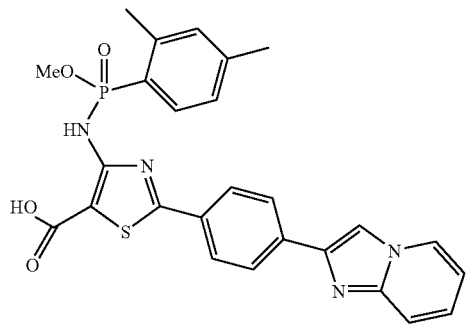

A solution of lithium hydroxide (1.41 mmol) in water was added to Example VIII.3 (0.282 mmol) in a mixture of tetrahydrofurane (2.8 ml) and water (2.8 ml). The reaction mixture was stirred at about 45° C. for about 24 hours. The reaction mixture was then diluted with ethyl acetate and extracted with HC12N. The organic layer was concentrated under reduced pressure and the residue was triturated to give Example VIII.4 as a yellow solid in 50% yield, which was characterized by the following spectroscopic data: $^1$H NMR (DMSO, 400 MHz) δ (ppm) 2.29 (s, 3H), 3.77 (d, J=11.50 Hz, 3H), 7.11 (d, J=4.96 Hz, 1H), 7.18-7.21 (m, 1H), 7.40-7.44 (m, 1H), 7.84-7.95 (m, 4H), 8.13 (d, J=8.37 Hz, 2H), 8.28 (d, J=7.80 Hz, 1H), 8.85 (d, J=6.74 Hz, 1H), 8.88 (s, 1H); $^{31}$P NMR (DMSO, 162 MHz) 6 (ppm) 15.56 (s, 1P); and MS (ESI, EI$^+$) m/z=519.40 (MH$^+$).

Example VIII.5

5-Thiazolecarboxylic methyl ester, 4-N-[(2,4-dimethyl-phenyl)-phosphonamidate methyl ester]-2-[phenyl-5-methyl-pyrazolo[1,5-a]pyrimidin-7-ylamine] (Compound 194)

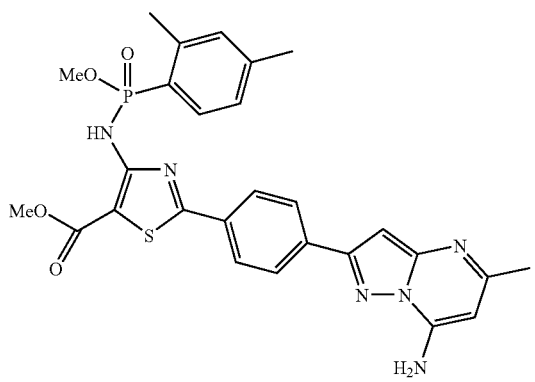

Pd(DtBPF)Cl$_2$ (0.15 mmol) was added to a yellow mixture of Example VIII.2 (1.5 mmol), 5-methyl-2-[4-(4,4,5,5-tetramethyl-1,3,2-dioxaborolan-2-yl)phenyl]pyrazolo[1,5-a]pyrimidin-7-amine (1.95 mmol) (according to the general procedure in WO 2007071434A1), sodium bicarbonate (4.52 mmol) in a mixture of dioxane (20 ml) and water (5 ml) at room temperature under vacuum and then nitrogen atmosphere. The reaction mixture was heated at about 90° C. for about 3 hours under microwave irradiation. Afterwards, the reaction mixture was dissolved in a mixture of ethyl acetate and water. The aqueous layer was extracted with ethyl acetate. The organic layer was washed with water and concentrated under reduced pressure. The residue was purified by silica gel chromatography to give Example VIII.5 as a beige solid in 30%, which was characterized by the following spectroscopic data: $^1$H NMR (CDCl$_3$, 400 MHz) δ (ppm) 2.37 (s, 3H), 2.41 (s, 3H), 2.62 (s, 3H), 3.90 (s, 3H), 3.91 (d, J=11.65 Hz, 3H), 5.82 (s, 1H), 6.06 (brs, 2H), 6.62 (s, 1H), 7.08 (d, J=5.21 Hz, 1H), 7.18-7.21 (m, 1H), 7.64 (brs, 2H), 7.83 (brs, 2H), 8.07 (dd, J=7.83 Hz and 14.37 Hz, 1H), 8.25 (d, J=9.00 Hz, 1H); MS (ESI, EI$^+$) m/z=563.17 (MH$^+$).

Example VIII.6

5-Thiazolecarboxylic acid, 4-N-[(2,4-dimethyl-phenyl)-phosphonamidate methyl ester]-2-[phenyl-5-methyl-pyrazolo[1,5-a]pyrimidin-7-ylamine] (Compound 181)

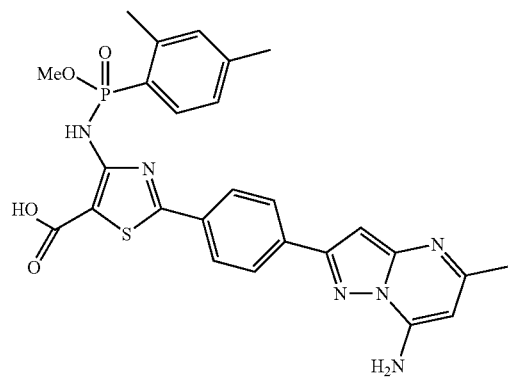

A solution of lithium hydroxide (0.93 mmol) in water (5 ml) was added to a mixture of Example VIII.5 (0.186 mmol) in tetrahydrofurane (5 ml). The mixture was stirred at room temperature for about 2 days. Then, the reaction mixture was treated with diethyl ether. The aqueous layer was washed with diethyl ether, heated with HCl 1N and concentrated to form a yellow powder. Afterwards, the yellow powder was filtered and washed with water to give Example VIII.6 in 65% yield. Example 6 was characterized by the following spectroscopic data: $^1$H NMR (DMSO-d$_6$, 400 MHz) δ (ppm) 2.33 (s, 3H), 3.30 (s, 3H), 3.70 (d, J=11.46 Hz, 3H), 5.96 (s, 1H), 6.75 (s, 1H), 7.06-7.07 (m, 1H), 7.12-7.14 (m, 1H), 7.58 (brs, 2H), 7.76 (d, J=8.26 Hz, 2H), 7.85 (dd, J=7.93 Hz and 13.65 Hz, 1H), 8.06 (d, J=8.26 Hz, 2H), 10.03 (brs, 1H); $^{31}$P NMR (DMSO-d$_6$, 162 MHz) δ (ppm) 15.82 (s, 1P); and MS (ESI, EI$^+$) m/z=549.25 (MH$^+$).

Example VIII.7

5-Thiazolecarboxylic methyl ester, 4-N-[(2,4-dimethyl-phenyl)-phosphonamidate methyl ester]-2-[phenyl-pyrazolo[1,5-a]pyrimidin-yl-amine] (Compound 195)

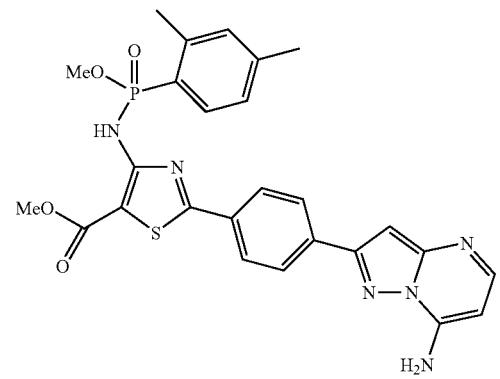

Example VIII.7 was synthesized from Example VIII.2 (0.214 mmol) and 2-[4-(4,4,5,5-tetramethyl-1,3,2-dioxaborolan-2-yl)phenyl]pyrazolo[1,5-a]pyrimidin-7-amine (0.257 mmol) (according to the general procedure in WO 2007071434A1) following the procedure as described for the Example VIII.3 to give Example VIII.7 as a yellow powder in 23%, which was characterized by the following spectroscopic data: $^1$H NMR (CDCl$_3$, 400 MHz) δ (ppm) 2.37 (s, 3H), 2.62 (s, 3H), 3.91 (s, 3H), 3.92 (d, J=11.28 Hz, 3H), 5.97 (d, J=5.25 Hz, 1H), 6.34 (brs, 1H), 6.75 (s, 1H), 7.08 (d, J=5.07 Hz, 1H), 7.18-7.20 (m, 1H), 7.26 (s, 1H), 7.66 (d, J=7.96 Hz, 2H), 7.86 (d, J=7.96 Hz, 2H), 8.03-8.09 (m, 2H), 8.24 (d, J=9.09 Hz, 1H); and $^{31}$P NMR (CDCl$_3$, 162 MHz) δ (ppm) 18.03 (s, 1P); and MS (ESI, EI$^+$) m/z=549.12 (MH$^+$).

Example VIII.8

5-Thiazolecarboxylic acid, 4-N-[(2,4-dimethyl-phenyl)-phosphonamidate methyl ester]-2-[phenyl-pyrazolo[1,5-a]pyrimidin-yl-amine] (Compound 180)

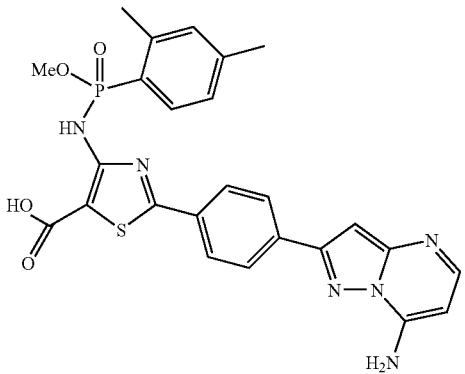

Example VIII.8 was synthesized from Example VIII.7 (0.145 mmol) following the procedure as described for Example VIII.4. The aqueous layer was filtered and the precipitate was purified by silica gel chromatography to give Example VIII.8 as a beige solid in 24% yield. Example VIII.8 was characterized by the following spectroscopic data: $^1$H NMR (DMSO, 400 MHz) δ (ppm) 2.29 (s, 3H), 3.76 (d, J=11.46 Hz, 3H), 6.24 (d, J=5.83 Hz, 1H), 7.05 (s, 1H), 7.11 (d, J=4.82 Hz, 1H), 7.18-7.21 (m, 1H), 7.88 (d, J=8.39 Hz, 2H), 7.92 (dd, J=7.90 Hz and 13.84 Hz, 1H), 8.17-8.20 (m, 3H), 8.29 (d, J=7.77 Hz, 1H), 8.66 (brs, 1H); $^{31}$P NMR (DMSO, 162 MHz) δ (ppm) 15.56 (s, 1P); and MS (ESI, EI$^+$) m/z=535.33 (MH$^+$).

Example VIII.9

5-Thiazolecarboxylic methyl ester, 4-N-[2,4-dimethyl-phenyl)-phosphonamidate methyl ester]-2-[phenyl-5-methyl-pyrazolo[1,5-a]pyrimidine] (Compound 196)

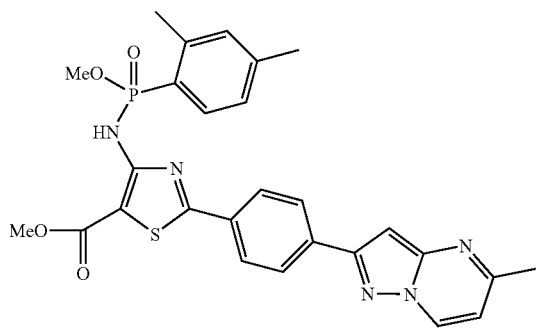

Example VIII.9 was synthesized from Example VIII.2 (0.32 mmol) and 5-methyl-2-[4-(4,4,5,5-tetramethyl-1,3,2-dioxaborolan-2-yl)phenyl]pyrazolo[1,5-a]pyrimidine (0.384 mmol) (according to the general procedure in WO 2007071434A1) following the procedure as described for Example VIII.3 to give Example VIII.9 in 57%, which was characterized by the following spectroscopic data: $^1$H NMR (CDCl$_3$, 400 MHz) δ (ppm) 2.33 (s, 3H), 2.61 (s, 3H), 2.63 (s, 3H), 3.89 (s, 3H), 3.90 (d, J=11.45 Hz, 3H), 6.71 (d, J=7.10 Hz, 1H), 6.88 (s, 1H), 7.04 (d, J=5.40 Hz, 1H), 7.12-7.15 (m, 1H), 7.85 (d, J=8.32 Hz, 2H), 7.99 (d, J=8.32 Hz, 2H), 8.05 (dd, J=7.85 Hz and 14.18 Hz, 1H), 8.18 (d, J=8.43 Hz, 1H), 8.54 (d, J=7.16 Hz, 1H); and $^{31}$P NMR (CDCl$_3$, 162 MHz) δ (ppm) 17.08 (s, 1P); and MS (ESI, EI$^+$) m/z=548.31 (MH$^+$).

Example VIII.10

5-Thiazolecarboxylic acid, 4-N-[(2,4-dimethyl-phenyl)-phosphonamidate methyl ester]-2-[phenyl-5-methyl-pyrazolo[1,5-a]pyrimidine](Compound 182)

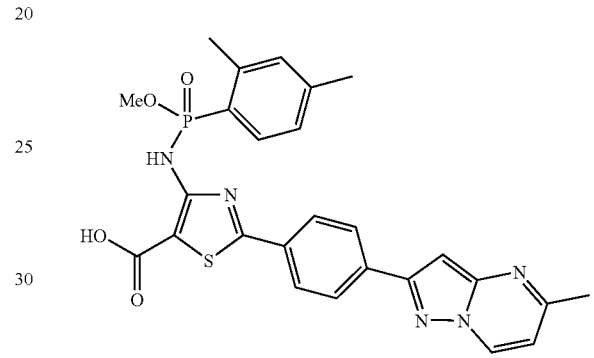

Example VIII.10 was synthesized from Example VIII.9 (0.174 mmol) following the procedure as described for Example VIII.4. The crude product was purified by silica gel chromatography to give Example VIII.10 as a yellow solid in 25% yield, which was characterized by the following spectroscopic data: $^1$H NMR (DMSO-d$_6$, 400 MHz) δ (ppm) 2.28 (s, 3H), 2.53 (s, 3H), 3.76 (d, J=11.31 Hz, 3H), 6.95 (d, J=6.50 Hz, 1H), 7.10 (brs, 1H), 7.14 (s, 1H), 7.20-7.22 (m, 1H), 7.84 (d, J=7.47 Hz, 2H), 7.91 (dd, J=7.62 Hz and 13.33 Hz, 1H), 8.10 (d, J=7.48 Hz, 2H), 8.39 (brs, 1H), 8.98 (d, J=6.49 Hz, 1H); $^{31}$P NMR (DMSO-d$_6$, 162 MHz) δ (ppm) 15.55 (s, 1P); and MS (ESI, EI$^+$) m/z=534.45 (MH$^+$).

Example VIII.11

5-Thiazolecarboxylic methyl ester, 4-N-[(2,4-dimethyl-phenyl)-phosphonamidate methyl ester]-2-[phenyl-pyrazolo[1,5-a]pyrimidine] (Compound 197)

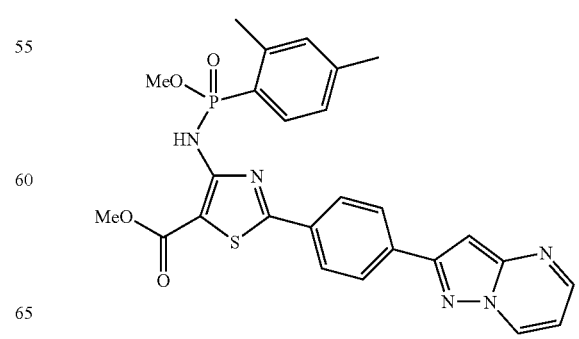

In a tube, Intermediate I.25 (0.485 mmol) and Intermediate I.26 (0.728 mmol), K$_3$PO$_4$ (0.728 mmol) and X-Phos (i.e. 2-dicyclohexylphosphino-2',4',6'-triisopropylbiphenyl) (0.121 mmol) were added to toluene (4 ml) under nitrogen atmosphere. Pd$_2$ dba$_3$ (0.0485 mmol) was then added into tube and the reaction mixture was stirred at about 100° C. for about 2 hours. The reaction mixture was diluted in ethyl acetate and washed with water and brine. The organic layers were concentrated under diminished pressure and the residue was purified by silica gel chromatography to give Example VIII.11 as a yellow solid in 8% yield, which was characterized by the following spectroscopic data: MS (ESI, EI$^+$) m/z=534.01 (MH$^+$)

Example VIII.12

5-Thiazolecarboxylic acid, 4-N-[(2,4-dimethyl-phenyl)-phosphonamidate methyl ester]-2-[phenyl-pyrazolo[1,5-a]pyrimidine] (Compound 186)

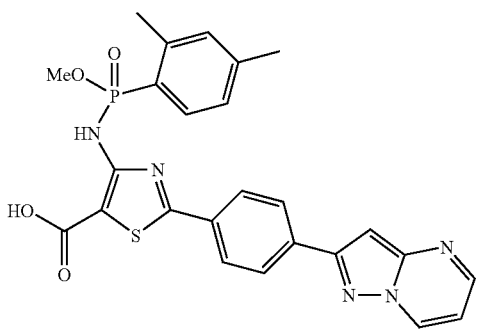

Example VIII.11 (0.037 mmol) was added to tent-butanol (0.4 ml), methanol (1.2 ml) and 2 M sodium hydroxide (1.2 ml). The reaction mixture was stirred at about 40° C. for about 5 hours. The reaction mixture was diluted with ethyl acetate and washed with HCl 2N. The aqueous layer was extracted with ethyl acetate and the organic layer was concentrated under reduced pressure. The residue was purified by semi-preparative HPLC to give Example VIII.12 as a yellow solid in 31%, which was characterized by the following spectroscopic data: $^1$H NMR (CDCl$_3$, 400 MHz) δ (ppm) 2.35 (s, 3H), 2.66 (s, 3H), 3.94 (d, J=11.60 Hz, 3H), 6.85-6.87 (m, 1H), 7.05-7.06 (m, 2H), 7.14-7.17 (m, 1H), 7.84 (d, J=8.39 Hz, 2H), 8.01 (d, J=8.20 Hz, 2H), 8.06 (dd, J=7.52 Hz and 13.98 Hz, 1H), 8.50-8.51 (m, 1H), 8.70-8.72 (m, 1H), 8.88-8.90 (m, 1H); $^{31}$P NMR (CDCl$_3$, 162 MHz) δ (ppm) 18.24 (s, 1P); and MS (ESI, EI$^+$) m/z=520.18 (MH$^+$).

Example VIII.13

5-Thiazolecarboxylic methyl ester, 4-N-[(2,4-dimethyl-phenyl)-phosphonamidate methyl ester]-2-[4-methoxy-phenyl] (Compound 198)

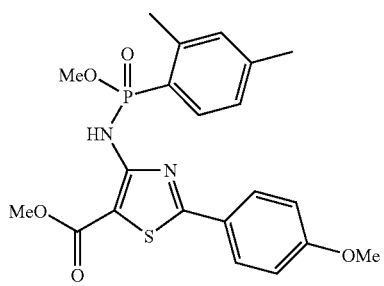

Example VIII.13 was synthesized from Intermediate I.27 (0.176 mmol) and Intermediate I.26 (0.264 mmol) following the procedure as described for Example VIII.11 to give Example VIII.13 as a yellow oil in 70% yield, which was characterized by the following spectroscopic data: $^1$H NMR (CDCl$_3$, 400 MHz) δ (ppm) 2.32 (s, 3H), 2.60 (s, 3H), 3.85 (s, 3H), 3.87 (s, 3H), 3.88 (d, J=11.40 Hz, 3H), 6.88 (d, J=8.85 Hz, 2H), 7.03 (d, J=5.41 Hz, 1H), 7.08-7.11 (m, 1H), 7.71 (d, J=8.85 Hz, 2H), 8.00 (dd, J=7.81 Hz and 14.16 Hz, 1H), 8.16 (d, J=8.48 Hz, 1H); $^{31}$P NMR (CDCl$_3$, 162 MHz) δ (ppm) 17.10 (s, 1P); and MS (ESI, EI$^+$) m/z=447.06 (MH$^+$).

Example VIII.14

5-Thiazolecarboxylic acid, 4-N-[(2,4-dimethyl-phenyl)-phosphonamidate methyl ester]-2-[4-methoxy-phenyl] (Compound 187)

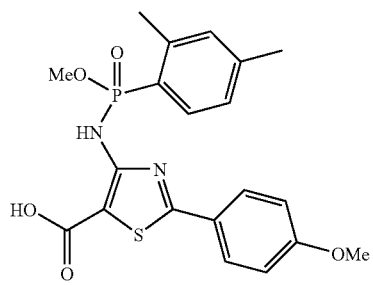

Example VIII.14 was synthesized from Example VIII.13 (0.176 mmol) following the procedure as described for Example VIII.12 to give Example VIII.14 as a beige solid in 3% yield, which was characterized by the following spectroscopic data: $^1$H NMR (CDCl$_3$, 400 MHz) δ (ppm) 2.30 (s, 3H), 2.61 (s, 3H), 3.83 (s, 3H), 3.89 (d, J=11.50 Hz, 3H), 6.85 (d, J=8.28 Hz, 2H), 6.99-7.00 (m, 1H), 7.06-7.09 (m, 1H), 7.66 (d, J=8.31 Hz, 2H), 7.99 (dd, J=8.28 Hz and 13.86 Hz, 1H), 8.82 (brs, 1H); $^{31}$P NMR (CDCl$_3$, 162 MHz) δ (ppm) 18.27 (s, 1P); and MS (ESI, EI$^+$) m/z=432.96 (MH$^+$).

Example VIII.15

5-Thiazolecarboxylic methyl ester, 4-N-[(2,4-dimethyl-phenyl)-phosphonamidate methyl ester]-2-[4-chloro-phenyl] (Compound 188)

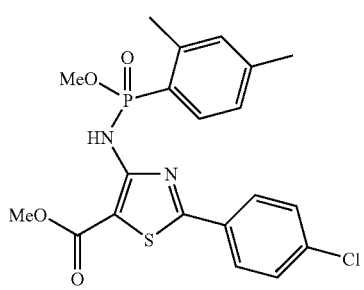

Example VIII.15 was synthesized from Intermediate I.28 (2.78 mmol) and Intermediate I.26 (4.17 mmol) following the procedure as described for Example VIII.11 to give Example VIII.15 as a brown foam in 60% yield, which was characterized by the following spectroscopic data: $^1$H NMR (CDCl$_3$, 400 MHz) δ (ppm) 2.33 (s, 3H), 2.59 (s, 3H), 3.87 (d, J=11.47 Hz, 3H), 3.88 (s, 3H), 6.98-7.08 (m, 2H), 7.35 (d, J=8.54 Hz, 2H), 7.68 (d, J=8.54 Hz, 2H), 8.00 (dd, J=7.88 Hz and 14.17 Hz, 1H), 8.16 (d, J=8.29 Hz, 1H); $^{31}$P NMR (CDCl$_3$, 162 MHz) δ (ppm) 17.06 (s, 1P); and MS (ESI, EI$^+$) m/z=451.19 (MH$^+$).

Example VIII.16

5-Thiazolecarboxylic methyl ester, 4-N-[(2,4-dimethyl-phenyl)-phosphonamidate methyl ester]-2-[2-phenyl-benzo[b]thiophene] (Compound 199)

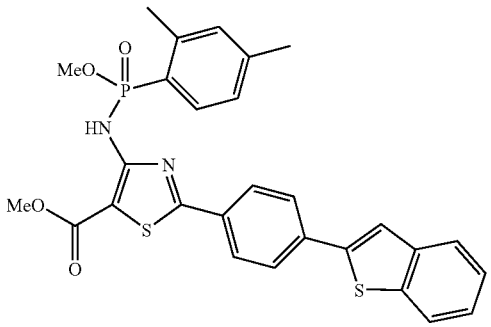

Example VIII.15 (0.72 mmol), benzo[b]thiophene-2-boronic acid (0.864 mmol) and potassium phosphate tribasic (2.88 mmol) were added to dimethylformamide (11 ml). Pd(DtBPF)Cl$_2$ (0.072 mmol) was then added into the reaction mixture and the reaction mixture was stirred under nitrogen atmosphere for about 50 minutes at about 80° C. under microwave irradiation. The reaction mixture was diluted in dichloromethane and washed with water. The organic layer was concentrated under diminished pressure and the residue was purified by silica gel chromatography to give Example VIII.16 as a brown solid in 88%, which was characterized by the following spectroscopic data: $^{31}$P NMR (CDCl$_3$, 162 MHz) δ (ppm) 17.06 (s, 1P); and MS (ESI, EI$^+$) m/z=549.25 (MH$^+$).

Example VIII.17

5-Thiazolecarboxylic acid, 4-N-[(2,4-dimethyl-phenyl)-phosphonamidate methyl ester]-2-[2-phenyl-benzo[b]thiophene] (Compound 184)

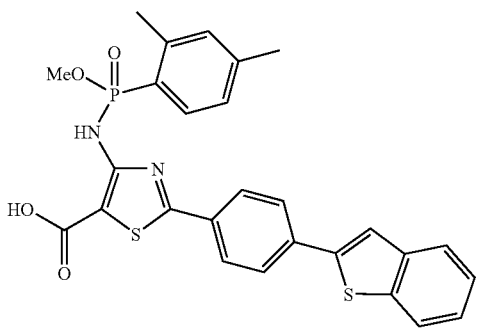

Example VIII.17 was synthesized from Example VIII.16 (0.365 mmol) following the procedure as described for Example VIII.4 to give Example VIII.17 as a yellow solid in 35% yield, which was characterized by the following spectroscopic data: $^1$H NMR (DMSO-d$_6$, 400 MHz) δ (ppm) 2.28 (s, 3H), 3.76 (d, J=11.26 Hz, 3H), 7.10 (brs, 1H), 7.20-7.22 (m, 1H), 7.36-7.43 (m, 2H), 7.83-7.92 (m, 6H), 7.99-8.01 (m, 2H), 8.29 (d, J=6.81 Hz, 1H); and $^{31}$P NMR (DMSO-d$_6$, 162 MHz) δ (ppm) 15.51 (s, 1P); and MS (ESI, EI$^+$) m/z=535.14 (MH$^+$).

Example VIII.18

5-Thiazolecarboxylic methyl ester, 4-N-[(2,4-dimethyl-phenyl)-phosphonamidate methyl ester]-2-[2-phenyl-benzofuran] (Compound 200)

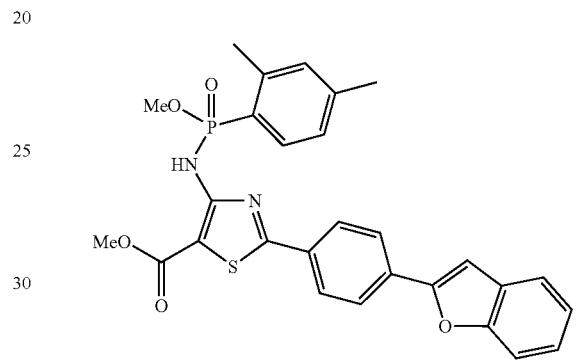

Example VIII.18 was synthesized from Example VIII.15 (0.72 mmol) and benzo[b]furan-2-boronic acid (0.864 mmol) following the procedure as described for Example VIII.16 to give Example VIII.18 as a brown solid in 88% yield, which was characterized by the following spectroscopic data: $^{31}$P NMR (CDCl$_3$, 162 MHz) δ (ppm) 17.08 (s, 1P); and MS (ESI, EI$^+$) m/z=533.25 (MH$^+$).

Example VIII.19

5-Thiazolecarboxylic acid, 4-N-[(2,4-dimethyl-phenyl)-phosphonamidate methyl ester]-2-[2-phenyl-benzofuran] (Compound 185)

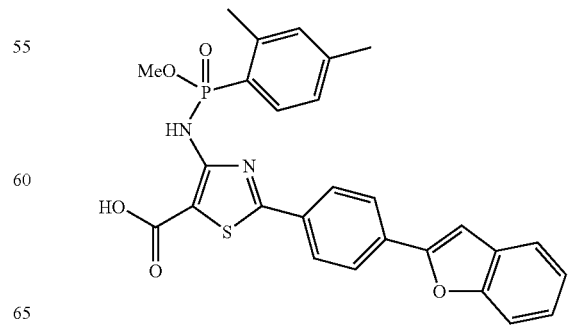

Example VIII.19 was synthesized from Example VIII.18 (0.376 mmol) following the procedure as described for Example VIII.4 to give Example VIII.19 as a yellow solid in 35% yield, which was characterized by the following spectroscopic data: $^1$H NMR (DMSO-$d_6$, 400 MHz) δ (ppm) 2.28 (s, 3H), 3.76 (d, J=11.48 Hz, 3H), 7.11 (d, J=4.80 Hz, 1H), 7.20-7.23 (m, 1H), 7.27-7.30 (m, 1H), 7.34-7.38 (m, 1H), 7.61 (s, 1H), 7.67 (dd, J=7.74 Hz and 16.21 Hz, 2H), 7.87 (d, J=8.31 Hz, 2H), 7.92 (dd, J=7.76 Hz and 13.90 Hz, 1H), 8.01 (d, J=8.32 Hz, 2H), 8.32 (d, J=7.19 Hz, 1H); and $^{31}$P NMR (DMSO-$d_6$, 162 MHz) δ (ppm) 15.53 (s, 1P); and MS (ESI, EI$^+$) m/z=519.21 (MH$^+$).

Example VIII.20

5-Thiazolecarboxylic methyl ester, 4-N-[2,4-dimethyl-phenyl)-phosphonamidate methyl ester]-2-phenyl (Compound 201)

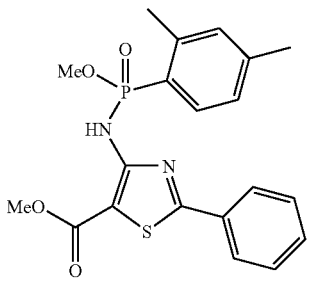

A first solution was prepared by adding dropwise oxalyl chloride (7.98 mmol) into a stirred solution of Intermediate I.5 (2.66 mmol) in anhydrous dichloromethane (8 ml) and few drops of dimethylformamide. The first solution was stirred under nitrogen atmosphere at room temperature overnight. The solvents were removed and to the resultant oil were added at about 0° C. under nitrogen atmosphere triethylamine (8.25 mmol) and tetrahydrofurane (5 ml). 4-amino-2-phenyl-thiazole-5-carboxylic acid methyl ester (2.13 mmol) was solubilized in anhydrous tetrahydrofurane (10 ml) and the reaction mixture was cooled down to about −78° C. A solution of 2 M LDA in tetrahydrofurane (2.55 mmol) was added dropwise to the reaction mixture. A second solution was prepared after stirring at about −78° C. for about 5 minutes. The first solution was added dropwise into the second solution and the mixture was stirred for about 1 hour before the temperature increased to about −40° C. The reaction mixture was quenched with NH$_4$Cl solution and diluted with ethyl acetate. The aqueous layer was extracted with ethyl acetate and the organic layer dried over sodium sulphate, followed by the evaporation to dryness. The residue was purified by silica gel chromatography to give Example VIII.20 as an orange solid in 18% yield, which was characterized by the following spectroscopic data: $^1$H NMR (CDCl$_3$, 400 MHz) δ (ppm) 2.32 (s, 3H), 2.61 (s, 3H), 3.88 (s, 3H), 3.89 (d, J=11.52 Hz, 3H), 7.03 (d, J=5.26 Hz, 1H), 7.09-7.12 (m, 1H), 7.36-7.46 (m, 3H), 7.75-7.77 (m, 2H), 8.01 (dd, J=7.81 Hz and 14.14 Hz, 1H), 8.16 (d, J=8.56 Hz, 1H); $^{31}$P NMR (CDCl$_3$, 162 MHz) δ (ppm) 17.04 (s, 1P); and MS (ESI, EI$^+$) m/z=417.03 (MH$^+$).

Example VIII.21

5-Thiazolecarboxylic acid, 4-N-[(2,4-dimethyl-phenyl)-phosphonamidate methyl ester]-2-phenyl (Compound 190)

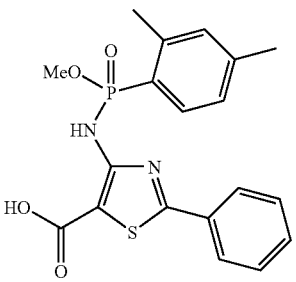

Example VIII.20 (0.12 mmol) and potassium tertbutoxyde (0.96 mmol) were added to tetrahydrofurane (1 ml) and few drops of water. The reaction mixture was stirred at room temperature for about 2 hours. The reaction mixture was diluted with ethyl acetate and washed with HCl 1N. The organic layer was concentrated under reduced pressure. The residue was purified by semi preparative HPLC to give Example VIII.21 as a beige powder in 36% yield, which was characterized by the following spectroscopic data: $^1$H NMR (CDCl$_3$, 400 MHz) δ (ppm) 2.33 (s, 3H), 2.64 (s, 3H), 3.92 (d, J=11.54 Hz, 3H), 7.02-7.04 (m, 1H), 7.09-7.13 (m, 1H), 7.37-7.46 (m, 3H), 7.74 (d, J=7.49 Hz, 2H), 8.02 (dd, J=7.87 Hz and 14.27 Hz, 1H), 8.81-8.84 (m, 1H); $^{31}$P NMR (CDCl$_3$, 162 MHz) δ (ppm) 18.33 (s, 1P); and MS (ESI, EI$^+$) m/z=402.82 (MH$^+$).

Scheme 31

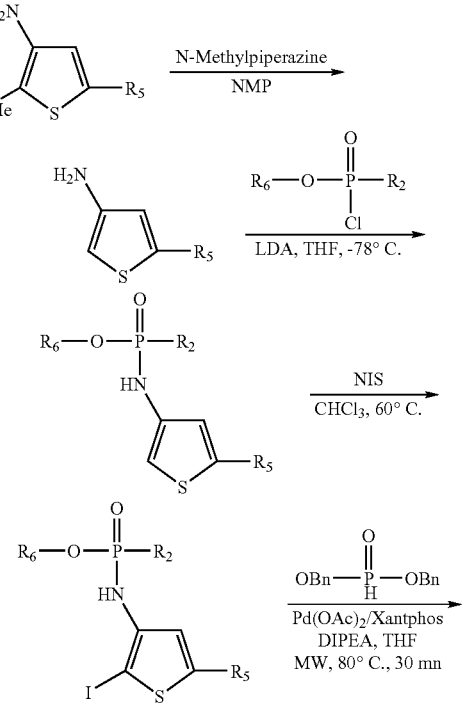

-continued

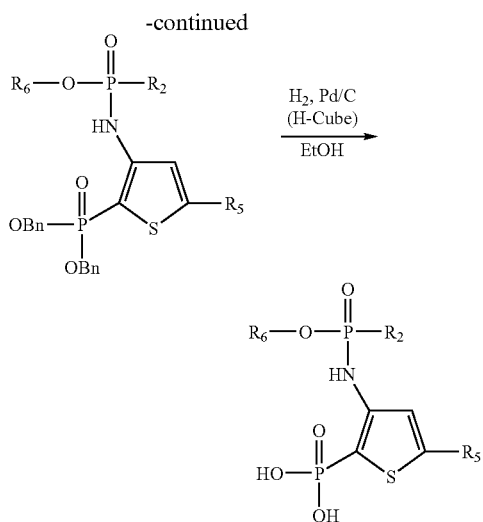

H₂, Pd/C
(H-Cube)
EtOH

Intermediate IX.1

5-(4-bromo-phenyl)-thiophen-3-ylamine

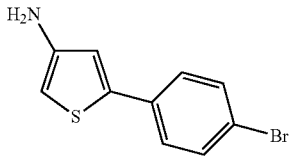

3-amino-5-(4-bromophenyl)thiophene-2-carboxylic acid (11.21 mmol), N-methyl piperazine (11.21 mmol) and N-methylpyrrolidinone (13.5 mL) were mixed together The reaction mixture was stirred at 160° C. for 5 hours and cooled down to room temperature. EtOAc and water were added, organics were separated, dried over Na₂SO₄, concentrated under reduced pressure and filtrated over silica (DCM/MeOH). Diisopropyl ether was added to the crude material and the residue obtained was filtered to give Intermediate IX.1 as a beige solid in 44% yield, which was characterized by the following spectroscopic data: MS (ESI, EI⁺) m/z=255 (MH⁺).

Intermediate IX.2

4-N-[(2,4-dimethylphenyl)-phosphonamidate methyl ester]-2-(4-bromo-phenyl)-thiophene

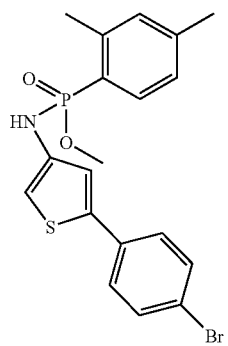

To a stirred solution of Intermediate I.5 (2.56 mmol) in DCM (4 ml) and anhydrous DMF (20 µl) was added dropwise and under nitrogen oxalyl chloride (6.30 mmol). The mixture was stirred at room temperature for 2 hours. Solvents were concentrated. The residue was dissolved in anh THF (4 ml) and was added to a solution of Intermediate IX.1 (1.97 mmol) and LDA (5.91 mmol) in anh THF (4 ml) at −78° C. The reaction mixture was stirred for 2 hrs at room temperature. EtOAc and saturated NH₄Cl solution were then added. Organics were separated, dried over sodium sulfate, concentrated in vacuo and purified by silica gel chromatography (PE/EtOAc) to give Intermediate IX.2 as a beige foam in 69% yield, which was characterized by the following spectroscopic data: ¹H NMR (CDCl₃, 400 MHz) δ (ppm) 2.27 (s, 3H), 2.46 (s, 3H), 3.62 (d, J=8.0 Hz, 3H), 5.92 (d, J=6.78 Hz, 1H), 6.29 (s, 1H), 6.88 (s, 1H), 6.96-7.00 (m, 2H), 7.27 (d, J=7.96 Hz, 1H), 7.38 (d, J=7.96 Hz, 2H), 7.68 (dd, J=7.54 Hz and J=14.25 Hz, 2H); ³¹P NMR (CDCl₃, 162 MHz) δ (ppm) 19.37 (s, 1P); and MS (ESI, EI⁺) m/z=437 (MH⁺).

Intermediate IX.3

4-N-[(2,4-dimethylphenyl)-phosphonamidate methyl ester]-2-[(benzofuran-2-yl)-phenyl]-thiophene

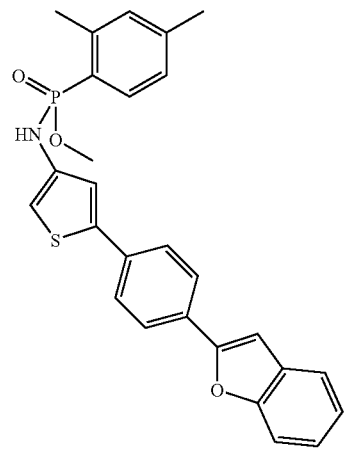

Intermediate IX.2 (8.02 mmol), benzo(b)-furan-2-boronic acid (12.03 mmol), tetrakis triphenylphosphine palladium (0.40 mmol), sodium carbonate (24.06 mmol) and H₂O (0.8 ml) were mixed together in anhydrous DMF (8 ml) under nitrogen. After nitrogen purge the reaction mixture was stirred at 80° C. for 3 hours. EtOAC and water were added. Organics were separated, dried over sodium sulfate, concentrated in vacuo and purified by silica gel chromatography (DCM/MeOH) to give Intermediate IX.3 as a beige solid in 84% yield, which was characterized by the following spectroscopic data: ¹H NMR (CDCl₃, 400 MHz) δ (ppm) 2.35 (s, 3H), 2.65 (s, 3H), 3.87 (d, J=11.4 Hz, 3H), 6.02 (d, J=6.20 Hz, 1H), 6.40 (s, 1H), 7.04-7.09 (m, 4H), 7.22 (t, J=7.50 Hz, 1H), 7.30 (t, J=7.50, 1H), 7.53 (d, J=8.03 Hz, 1H), 7.57-7.60 (m, 3H), 7.77 (dd, J=7.80 Hz and J=14.15 Hz, 1H), 7.84 (d, J=8.45 Hz, 2H), ³¹P NMR (CDCl₃, 162 MHz) δ (ppm) 19.41 (s, 1P); and MS (ESI, EI⁺) m/z=474 (MH⁺)

Intermediate IX.4

3-N-[(2,4-dimethylphenyl)-phosphonamidate methyl ester]-5-[(benzofuran-2-yl)-phenyl]-2-iodo-thiophene

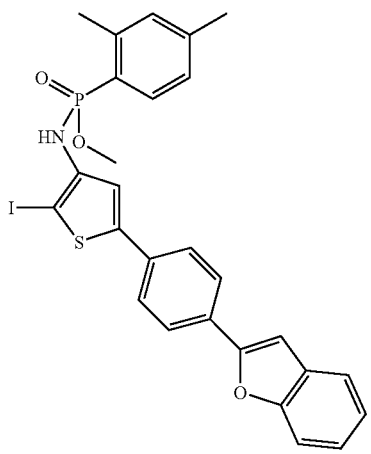

To a stirred solution of Intermediate IX.3 (0.16 mmol) in chloroform (3 ml) was added N-Iodosuccinimide (0.17 mmol). The reaction mixture was stirred at room temperature for 16 hours. DCM and water were added. Organics were separated, dried over sodium sulfate, concentrated in vacuo and purified by silica gel chromatography (PE/EtOAc) to give Intermediate IX.4 as a beige solid in 60% yield, which was characterized by the following spectroscopic data: $^1$H NMR (DMSO-d$_6$, 400 MHz) δ (ppm) 2.29 (s, 3H), 2.55 (s, 3H), 3.73 (d, J=11.01 Hz, 3H), 7.09-7.17 (m, 2H), 7.19 (s, 1H), 7.25 (t, J=7.25 Hz, 1H), 7.32 (t, J=7.25 Hz, 1H), 7.41 (d, J=8.70 Hz, 1H), 7.46 (s, 1H), 7.56 (d, J=8.70 Hz, 2H), 7.65 (dd, J=7.73 Hz and J=13.05 Hz, 2H), 7.70 (dd, J=7.73 Hz and J=13.50 Hz, 1H), 7.91 (d, J=8.21 Hz, 2H); $^{31}$P NMR (DMSO-d$_6$, 162 MHz) δ (ppm) 18.91 (s, 1P); and MS (ESI, EI$^+$) m/z=600 (MH$^+$).

Intermediate IX.5

3-N-[(2,4-dimethylphenyl)-phosphonamidate methyl ester]-5-[(benzofuran-2-yl)-phenyl]-2-thiophene-2-O-benzylphosphonic acid

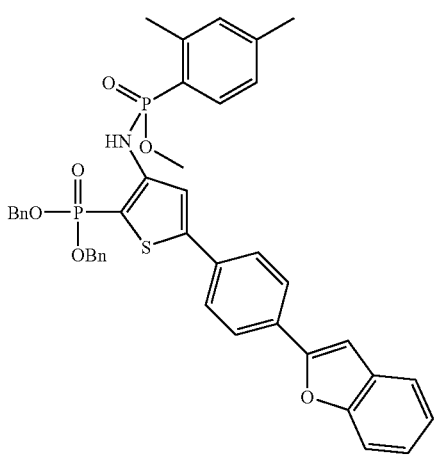

Intermediate IX.4 (0.75 mmol), dibenzyl-H-phosphite (0.9 mmol), Pd(OAc)$_2$ (0.075 mmol), Xantphos (0.15 mmol), diisopropylethylamine (0.9 mmol) and H$_2$O (0.0375 mmol) in THF (7.5 ml) were mixed together under nitrogen and stirred under microwave irradiations at 60° C. for 30 minutes. H$_2$O and EtOAc were added to the reaction mixture. Organics were separated, dried over sodium sulfate, concentrated in vacuo and purified by silica gel chromatography (DCM/MeOH) to give Intermediate IX.5 as a white solid in 60% yield, which was characterized by the following spectroscopic data: $^{31}$P NMR (CDCl$_3$, 162 MHz) δ (ppm) 14.90 (s, 1P), 18.93 (s, 1P); and MS (ESI, EI$^+$) m/z=734 (MH$^+$).

Example IX.1

3-N-[(2,4-dimethylphenyl)-phosphonamidate methyl ester]-5-[(benzofuran-2-yl)-phenyl]-2-thiophene-2-phosphonic acid

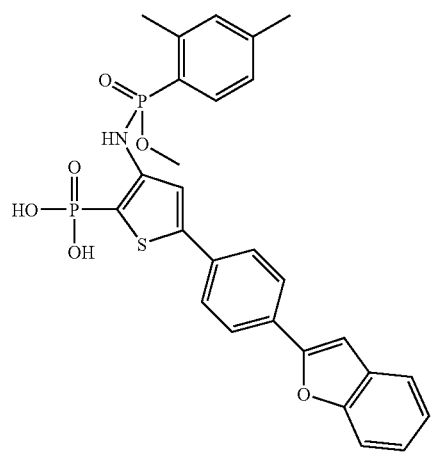

Intermediate IX.5 (8.86 mmol) was dissolved in EtOH (1.8 ml) and was hydrogenated with H$_{cube}$ device (Thalesnano) with Pd/C (10%), at 20° C. and 10 bars. Solvent was evaporated and a mixture of MeOH/Et$_2$O (1/9) was added. The precipitate formed was filtered and dried over sodium sulfate to give Example IX.1 as a beige solid in 36% yield, which was characterized by the following spectroscopic data: $^1$H NMR (DMSO-d$_6$, 400 MHz) δ (ppm) 2.24 (s, 3H), 2.48 (s, 3H), 3.70 (d, J=10.78 Hz, 3H), 7.08 (m, 2H), 7.25 (t, J=7.25 Hz, 1H), 7.32 (t, J=7.25 Hz, 1H), 7.35 (m, 1H), 7.43 (s, 1H), 7.58-7.63 (m, 4H), 7.76 (dd, J=7.53 Hz and J=14.15 Hz, 1H), 7.90 (d, J=8.13 Hz, 2H), 8.64 (d, J=9.60 Hz, 1H), 11.8 (brs, 2H); $^{31}$P NMR (DMSO-d$_6$, 162 MHz) δ (ppm) 8.80 (s, 1P), 17.30 (s, 1P); and MS (ESI, EI$^+$) m/z=554 (MH$^+$).

Scheme 32

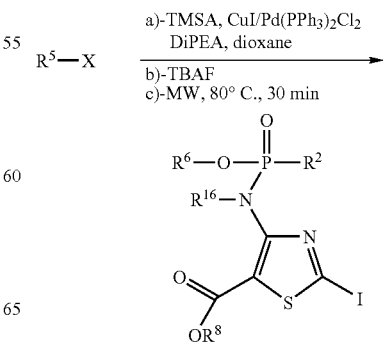

a)-TMSA, CuI/Pd(PPh$_3$)$_2$Cl$_2$ DiPEA, dioxane
b)-TBAF
c)-MW, 80° C., 30 min

-continued

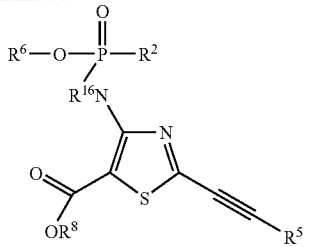

Intermediate X.1

5-Thiazolecarboxylic methyl ester,
4-N-[(2,4-dimethyl-phenyl)-phosphonamidate methyl ester]

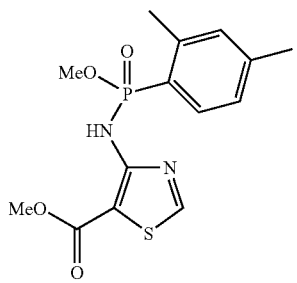

To a stirred solution of the Intermediate I.5 (0.409 mmol) in anhydrous dichloromethane (1 ml) and dimethylformamide (40 μl), was added dropwise oxalyl chloride (1.00 mmol). The resulting solution was stirred under nitrogen at room temperature for 1 hour. The solvents were removed and the crude mixture diluted with tetrahydrofurane (2 ml). The 4-aminothiazole-5-carboxylic acid methyl ester (0.316 mmol) was solubilized in anhydrous tetrahydrofurane (2 ml) and 60% NaH was added (0.948 mmol). The P—Cl mixture was added dropwise at 0° C. and the mixture stirred for 2 hours at room temperature. The reaction was quenched with 0.5M NH$_4$Cl solution and diluted with ethyl acetate. The organic layer was washed with water and concentrated under reduced pressure. The residue was purified by silica gel chromatography (eluent: stepwise gradient of methanol (0-2%) in dichloromethane) to give Intermediate X.1 in 67% yield, which was characterized by the following spectroscopic data: $^1$H NMR (CDCl$_3$, 400 MHz) δ (ppm) 2.32 (s, 3H), 2.59 (s, 3H), 3.85 (d, J=11.53 Hz, 3H), 3.87 (s, 3H), 7.03-7.09 (m, 2H), 7.84 (dd, J=7.70 Hz and 14.52 Hz, 1H) 8.20 (d, J=8.79 Hz, 1H), 8.58 (s, 1H); $^{31}$P NMR (CDCl$_3$, 162 MHz) δ (ppm) 17.66; and MS (ESI, EI$^+$) m/z=341.15 (MH$^+$).

Intermediate X.2

5-Thiazolecarboxylic methyl ester,
2-iodo-4-N-[(2,4-dimethyl-phenyl)-phosphonamidate methyl ester]

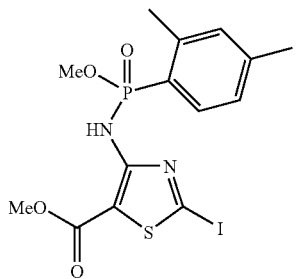

Intermediate X.1 (0.088 mmol) was diluted in tetrahydrofurane (1 ml) and the mixture was cooled down to −78° C. 2M LDA in tetrahydrofurane (0.26 mmol) and iodide (0.176 mmol) diluted in tetrahydrofurane (1 ml) were added. The mixture was stirred for 10 minutes and then, treated with an ammonium chloride solution. Ethyl acetate was added and the mixture washed with sodium thiosulfate. The organic layer was concentrated under diminished pressure and the residue purified by silica gel chromatography to give Intermediate X.2 as a yellow oil in 30% yield, which was characterized by the following spectroscopic data: $^1$H NMR (CDCl$_3$, 400 MHz) δ (ppm) 2.35 (s, 3H), 2.60 (s, 3H), 3.83 (s, 3H), 3.86 (d, J=11.58 Hz, 3H), 7.05 (d, J=5.30 Hz, 1H), 7.06-7.09 (m, 1H), 7.85 (dd, J=7.81 Hz and 14.38 Hz, 1H), 8.10 (d, J=9 Hz, 1H); $^{31}$P NMR (CDCl$_3$, 162 MHz) δ (ppm) 17.13 (s, 1P); and MS (ESI, EI$^+$) m/z=467.13 (MH$^+$).

Intermediate X.3

4-N-[(2,4-dimethylphenyl)-phosphonamidate methyl ester]-2-(5-hydroxy-pyridin-3-ylethynyl)-thiazole-5-carboxylic acid methyl ester

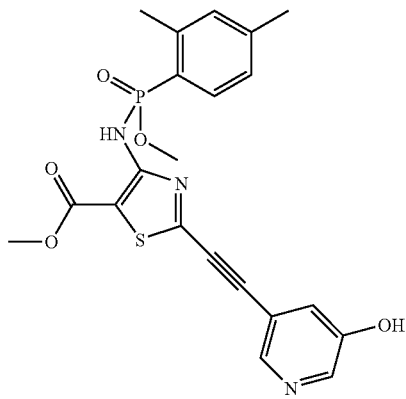

3-bromo-5-hydroxypyridine (0.575 mmol), Pd(Cl)$_2$(PPH$_3$)$_2$ (0.0575 mmol) CuI (0.0575 mmol), diisopropylamine (0.69 mmol) and dioxane (3 ml) were stirred under nitrogen at room temperature for 10 minutes. TMSA (70 μl) was added. The reaction mixture was stirred at 80° C. for 1 hour under microwave irradiations. 1 M TBAF (0.575 mmol) was then added and after a 20 minutes stirring at room temperature, Intermediate X.2 (0.459 mmol) was added. The mixture was stirred at 80° C. under microwave irradiations for 1 hour. EtOAc was then added, the reaction mixture was filtered through celite, washed with water. Organics were separated, dried over sodium sulfate, concentrated in vacuo and purified by silica gel chromatography (DCM/EtOAc) to give Intermediate X.3 as a white solid in 55% yield, which was characterized by the following spectroscopic data: $^{31}$P NMR (DMSO-d$_6$, 162 MHz) δ (ppm) 16.29 (s, 1P); and MS (ESI, EI$^+$) m/z=458 (MH$^+$).

Example X.1

4-N-[(2,4-dimethylphenyl)-phosphonamidate methyl ester]-2-(5-hydroxy-pyridin-3-ylethynyl)-thiazole-5-carboxylic acid

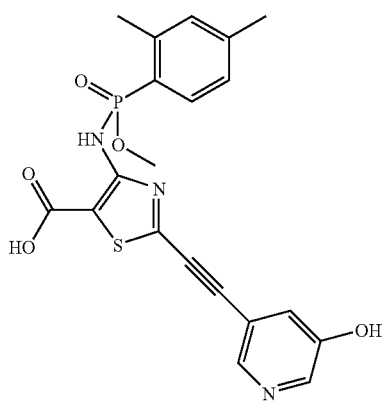

A solution of LiOH (0.545 mmol) in water (2 ml) was added to a solution of Intermediate X.3 (0.109 mmol) in anhydrous THF (2 ml). The reaction mixture was stirred at room temperature for 16 hours. EtOAc was then added, organic layer was washed with saturated NH$_4$Cl solution, dried over sodium sulfate, concentrated in vacuo and purified by semi-preparative chromatography (CH$_3$CN/TFA/H$_2$O; 30%/0.02%/70%) to give Example X.1 as a beige solid in 40% yield, which was characterized by the following spectroscopic data: $^1$H NMR (DMSO-d$_6$, 400 MHz) δ (ppm) 2.29 (s, 3H), 3.70 (d, J=11.54 Hz, 3H), 6.99 (s, 1H), 7.13 (m, 2H), 7.25 (s, 1H), 7.36 (s, 1H), 7.68 (dd, J=8.00 Hz and J=14.50 Hz, 1H), 8.25 (d, J=17.26 Hz, 2H), 8.6 (brs, 1H), 10.44 (s, 1H); $^{31}$P NMR (DMSO-d$_6$, 162 MHz) δ (ppm) 16.16 (s, 1P); and MS (ESI, EI$^+$) m/z=444 (MH$^+$).

Example 1

HCV Replicon ELISA Assay

General procedure: Huh-7 cells containing HCV Con1 subgenomic replicon of genotype 1b (GS4.1 cells) were grown in Dulbecco's Modified Eagle Medium (DMEM) supplemented with 10% fetal bovine serum (FBS), 2 mM GlutaMAX (L-glutamine), 1% MEM nonessential amino acids, 100 IU/mL penicillin, 100 μg/mL streptomycin, and 0.5 mg/mL Geneticin® (G418). For dose-response testing, the cells were seeded in 96-well plates at 7.5×10$^3$ cells/well in a volume of 50 μL, and incubated at 37° C./5% CO$_2$. Three hours after plating, 50 μL of ten 2-fold serial dilutions of compounds (highest concentration, 75 μM) were added, and cell cultures were incubated at 37° C./5% CO$_2$ in the presence of 0.5% DMSO. Alternatively, compounds were tested at a single concentration of 15 μM. In all cases, Huh-7 cells lacking the HCV replicon served as negative control. The cells were incubated in the presence of compounds for 72 hr after which they were monitored for expression of the NS4A protein by enzyme-linked immunosorbent assay (ELISA). For this, the plates were then fixed for 1 min with acetone/methanol (1:1, v/v), washed twice with phosphate-buffered saline (PBS), 0.1% Tween 20, blocked for 1 hr at room temperature with TNE buffer containing 10% FBS and then incubated for 2 hours at 37° C. with the anti-NS4A mouse monoclonal antibody A-236 (ViroGen) diluted in the same buffer. After washing three times with PBS, 0.1% Tween 20, the cells were incubated 1 hr at 37° C. with anti-mouse immunoglobulin G-peroxidase conjugate in TNE, 10% FBS. After washing as described above, the reaction was developed with O-phenylenediamine (Zymed). The reaction was stopped after 30 minutes with 2 NH$_2$SO$_4$, and absorbance was read at 492 nm using a SUNRISE TECAN spectrophotometer. EC$_{50}$ values represent the concentration of a compound where 50% of its maximal effect is observed. IC$_{50}$ values were determined from the % inhibition versus concentration data using a sigmoidal non-linear regression analysis based on four parameters with TECAN MAGELLAN software. When screening at a single concentration, the results were expressed as % inhibition at 15 μM. CC$_{50}$ value refers to concentration of a compound that is required for 50% inhibition of a maximal response in an assay that measures such response.

EC$_{50}$, IC$_{50}$ and CC$_{50}$ results are summarized in Tables 1 and 2, wherein A represents a value smaller than 0.1 μM, B represents a value between 0.1 μM to 8.3 μM, and C represents a value greater than 8.3 μM.

TABLE 1

| Compound | EC$_{50}$ (μM)* | IC$_{50}$ (μM)* | CC$_{50}$ (μM)* |
|---|---|---|---|
| 1 | C | B | C |

TABLE 1-continued
| Compound | EC$_{50}$ (μM)* | IC$_{50}$ (μM)* | CC$_{50}$ (μM)* |
|---|---|---|---|
| 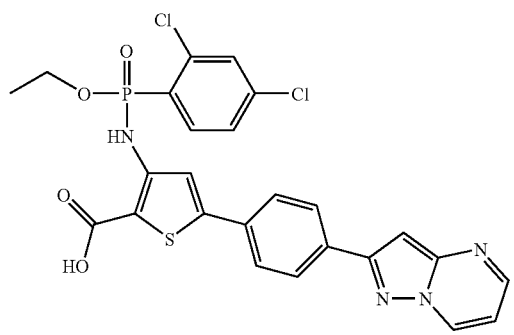 11 | A | A | C |
| 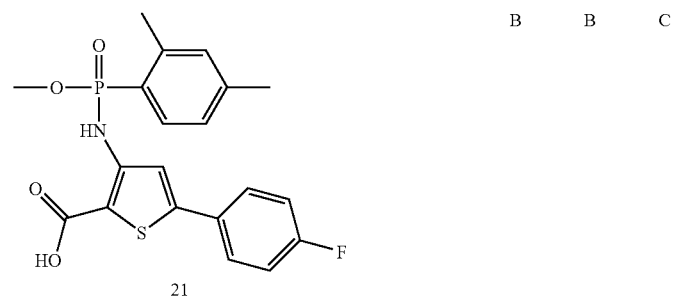 21 | B | B | C |
| 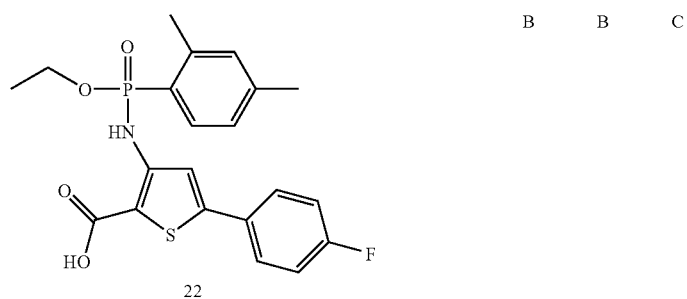 22 | B | B | C |
| 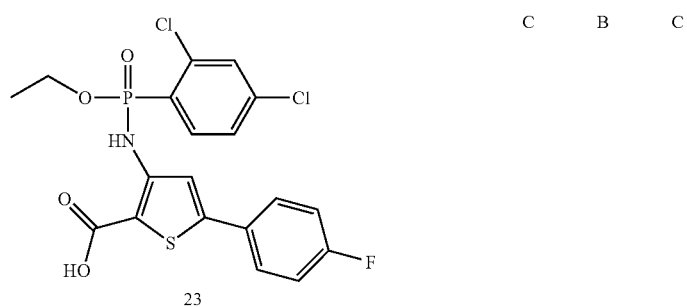 23 | C | B | C |

TABLE 1-continued

| Compound | EC$_{50}$ (μM)* | IC$_{50}$ (μM)* | CC$_{50}$ (μM)* |
|---|---|---|---|
| 24 | B | A | C |
| 25 | C | C | C |
| 26 | A | A | C |
| 27 | B | A | C |
| 28 | C | B | C |

TABLE 1-continued
| Compound | EC$_{50}$ (μM)* | IC$_{50}$ (μM)* | CC$_{50}$ (μM)* |
|---|---|---|---|
| 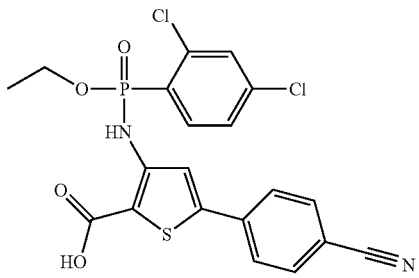 29 | C | N/A | C |
| 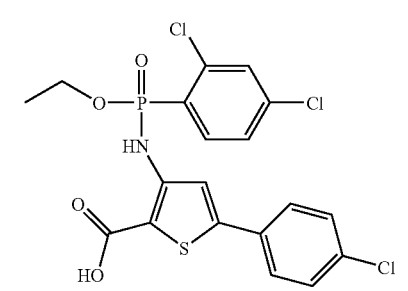 30 | B | B | C |
| 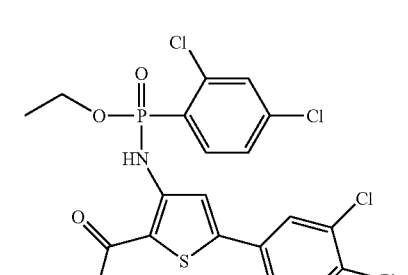 31 | C | B | C |
| 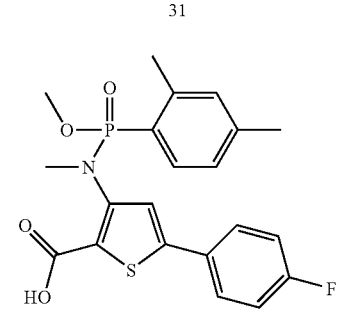 32 | B | B | C |
| 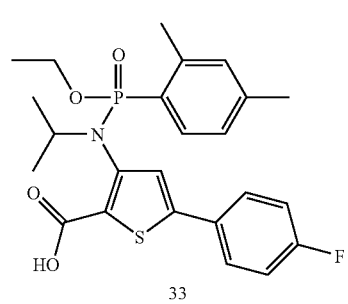 33 | B | B | C |

TABLE 1-continued
| Compound | EC₅₀ (μM)* | IC₅₀ (μM)* | CC₅₀ (μM)* |
|---|---|---|---|
| 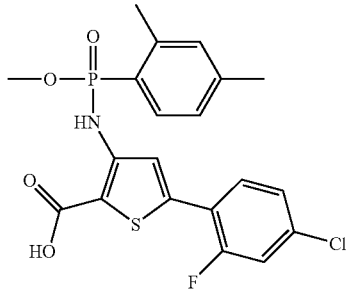 79 | B | A | C |
| 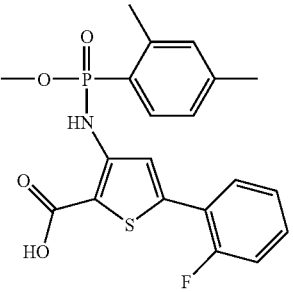 80 | C | B | C |
| 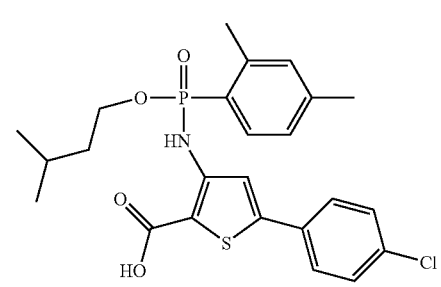 81 | B | B | C |
| 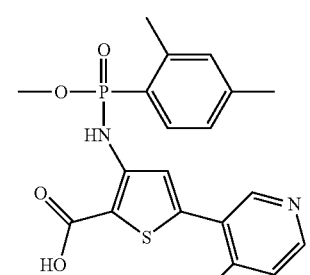 82 | B | B | C |
| 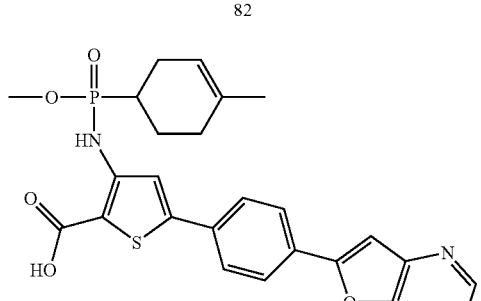 83 | B | A | C |

TABLE 1-continued
| Compound | EC$_{50}$ (μM)* | IC$_{50}$ (μM)* | CC$_{50}$ (μM)* |
|---|---|---|---|
| 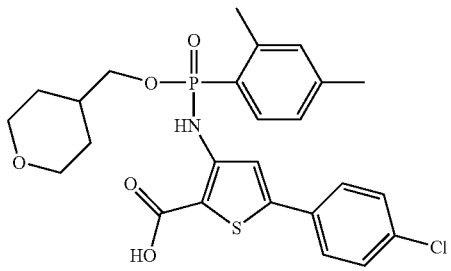 84 | B | B | C |
| 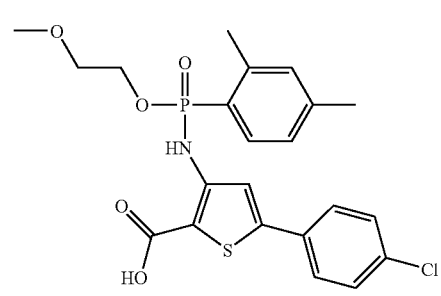 85 | B | B | C |
| 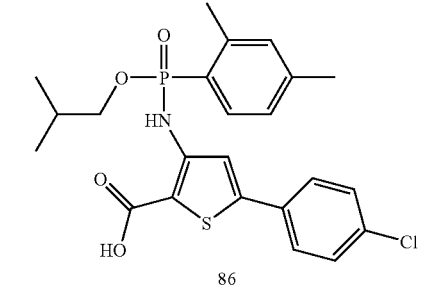 86 | B | B | C |
| 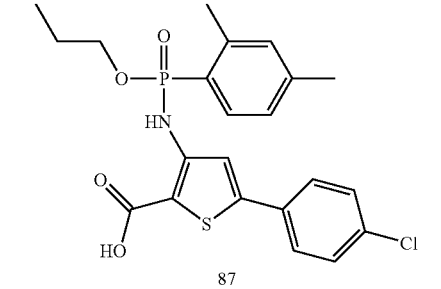 87 | B | B | C |
| 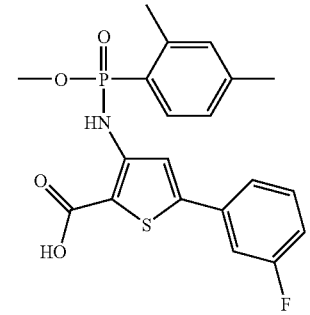 88 | B | B | C |

TABLE 1-continued
| Compound | EC$_{50}$ (μM)* | IC$_{50}$ (μM)* | CC$_{50}$ (μM)* |
|---|---|---|---|
| 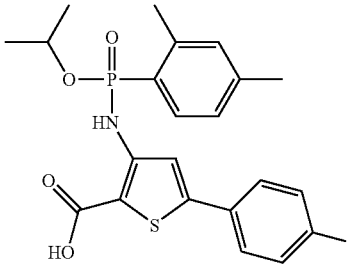 89 | B | B | C |
| 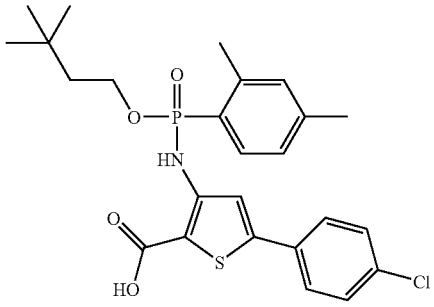 90 | B | B | C |
| 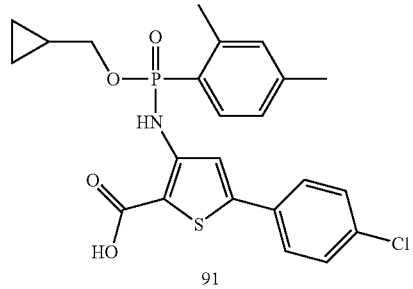 91 | B | B | C |
| 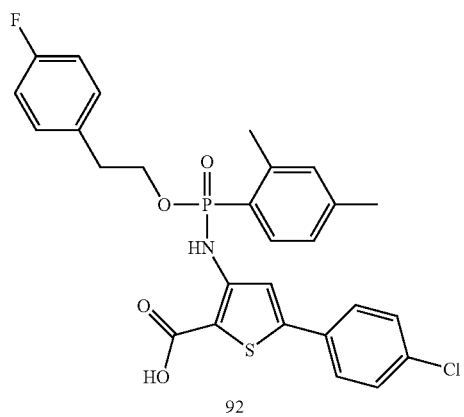 92 | B | B | C |

TABLE 1-continued
| Compound | EC$_{50}$ (μM)* | IC$_{50}$ (μM)* | CC$_{50}$ (μM)* |
|---|---|---|---|
| 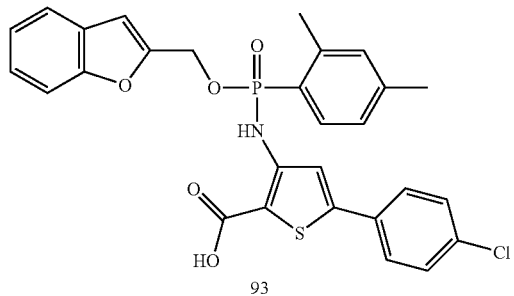 93 | B | B | C |
| 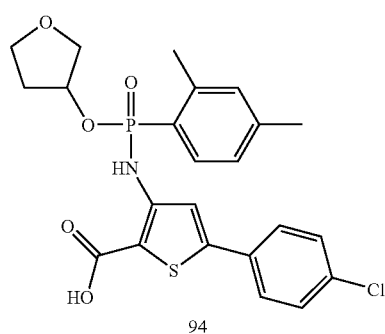 94 | B | B | C |
| 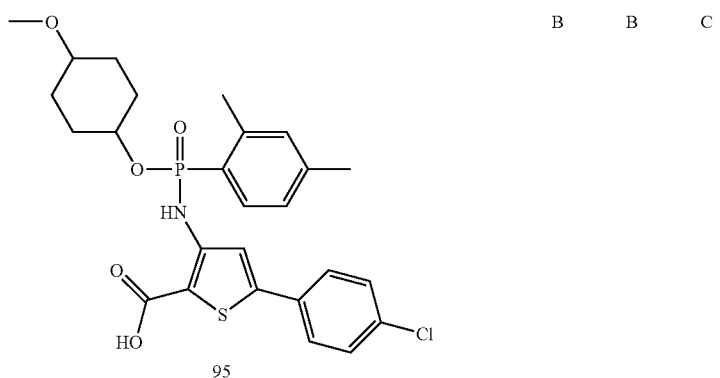 95 | B | B | C |
| 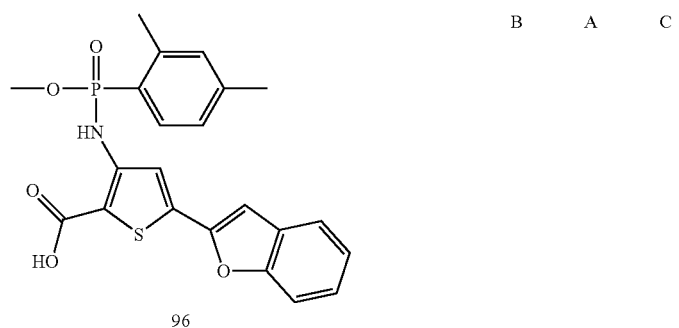 96 | B | A | C |

TABLE 1-continued
| Compound | EC$_{50}$ (μM)* | IC$_{50}$ (μM)* | CC$_{50}$ (μM)* |
|---|---|---|---|
| 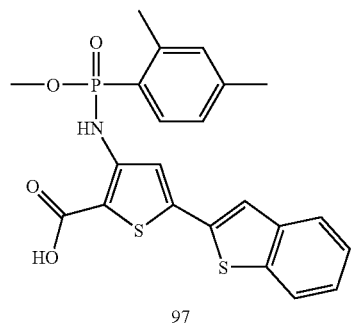 97 | B | A | C |
| 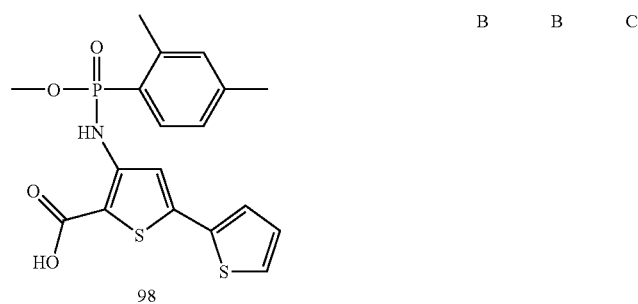 98 | B | B | C |
| 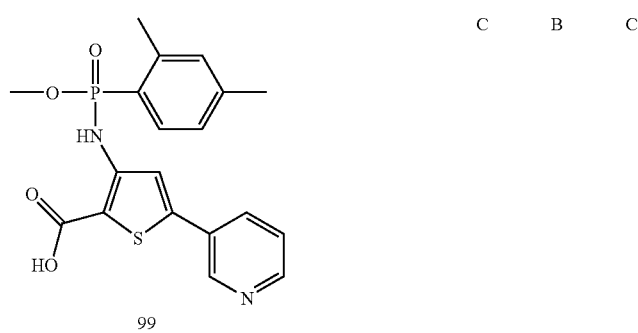 99 | C | B | C |
| 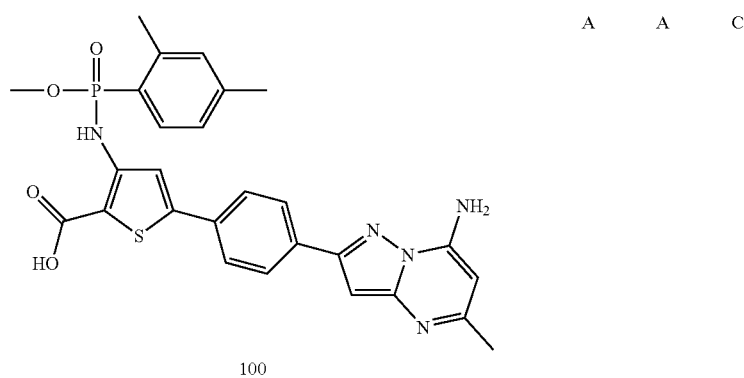 100 | A | A | C |

TABLE 1-continued
| Compound | EC$_{50}$ (μM)* | IC$_{50}$ (μM)* | CC$_{50}$ (μM)* |
|---|---|---|---|
| 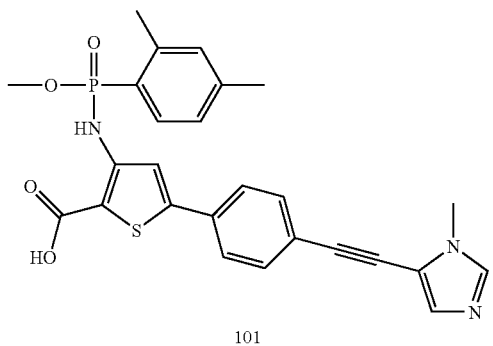 101 | B | A | C |
| 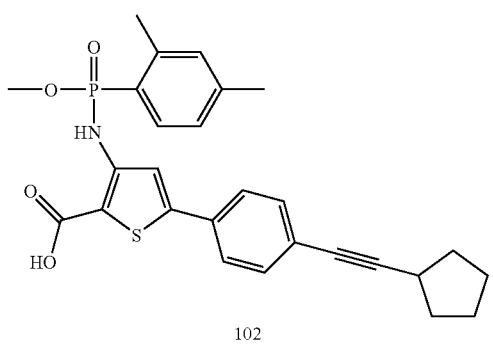 102 | C | B | C |
| 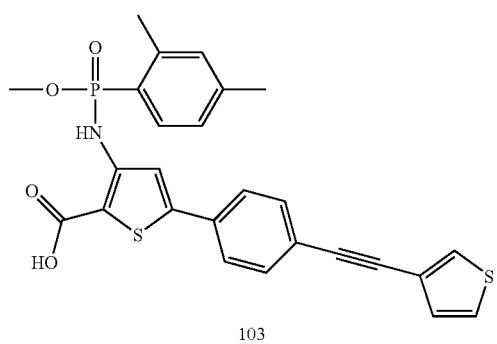 103 | A | A | C |
| 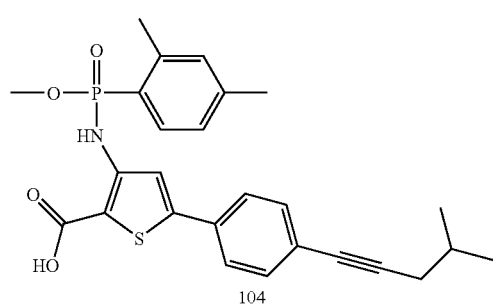 104 | C | B | C |

TABLE 1-continued
| Compound | EC$_{50}$ (μM)* | IC$_{50}$ (μM)* | CC$_{50}$ (μM)* |
|---|---|---|---|
| 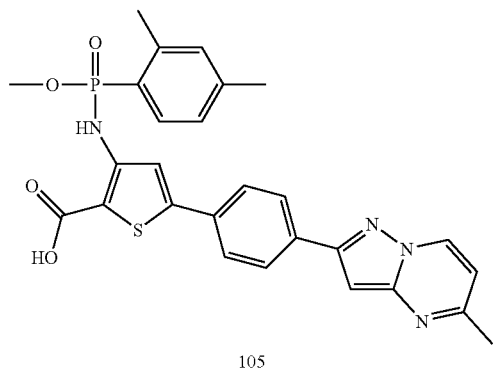 105 | A | A | C |
| 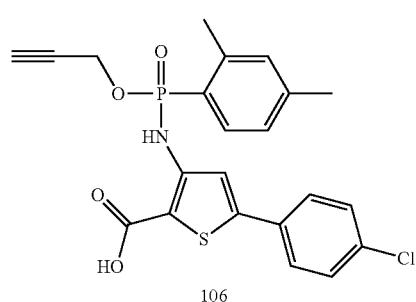 106 | B | B | C |
| 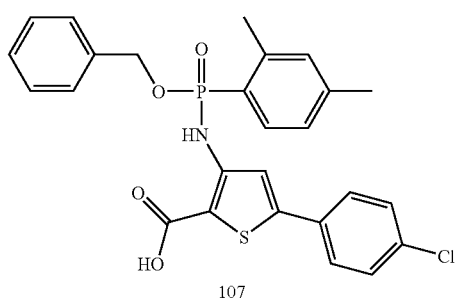 107 | B | N/A | C |
| 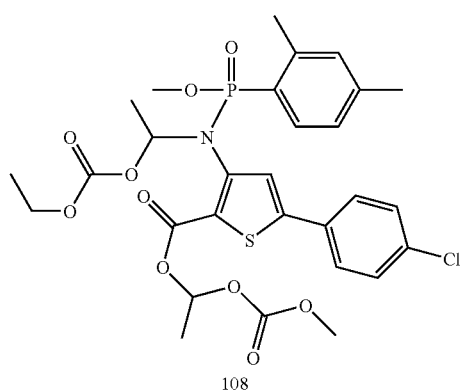 108 | B | C | C |

TABLE 1-continued
| Compound | EC$_{50}$ (μM)* | IC$_{50}$ (μM)* | CC$_{50}$ (μM)* |
|---|---|---|---|
| 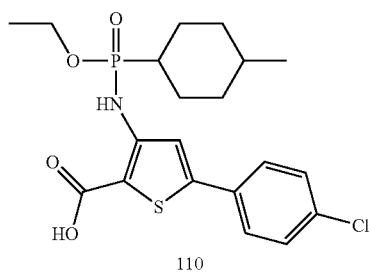 110 | C | B | C |
| 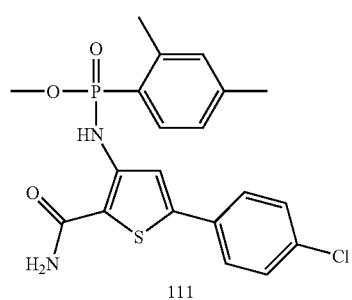 111 | C | C | C |
| 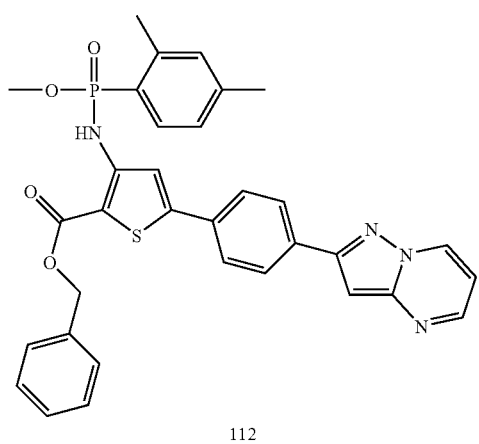 112 | B | B | C |
| 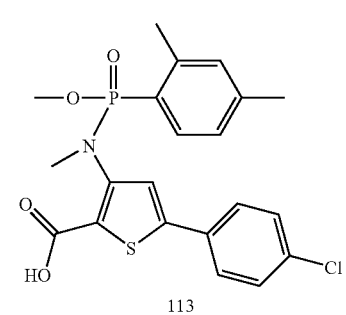 113 | B | A | C |

TABLE 1-continued
| Compound | EC$_{50}$ (μM)* | IC$_{50}$ (μM)* | CC$_{50}$ (μM)* |
|---|---|---|---|
| 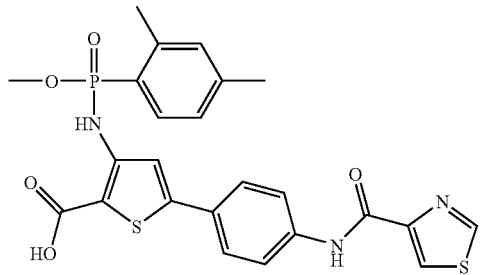 115 | A | A | C |
| 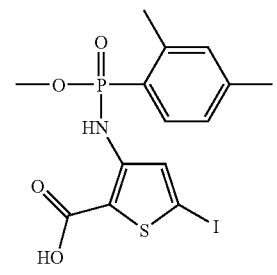 116 | C | B | C |
| 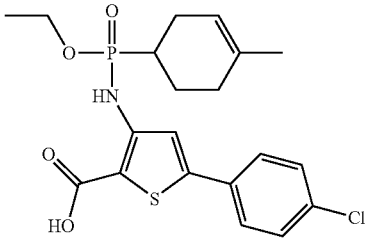 117 | C | B | C |
| 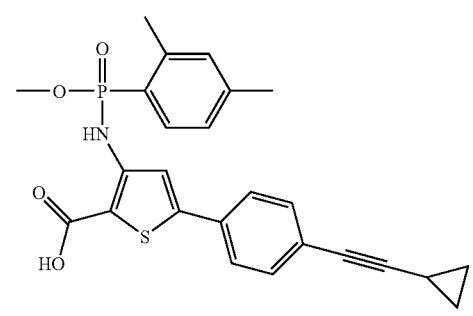 118 | B | A | C |
| 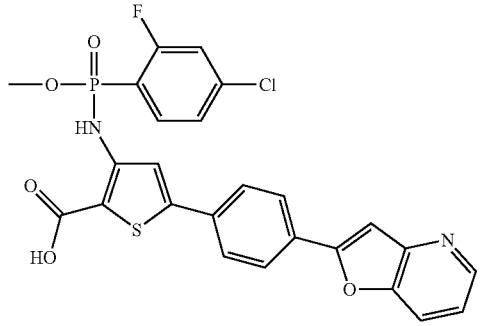 119 | A | A | C |

TABLE 1-continued
| Compound | EC$_{50}$ (μM)* | IC$_{50}$ (μM)* | CC$_{50}$ (μM)* |
|---|---|---|---|
| 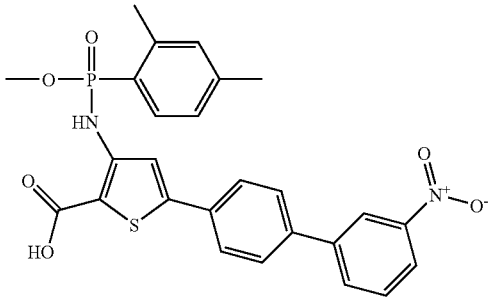 120 | C | B | C |
| 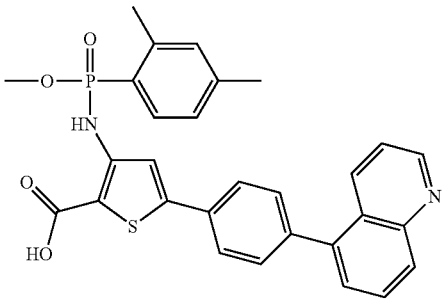 121 | B | A | C |
| 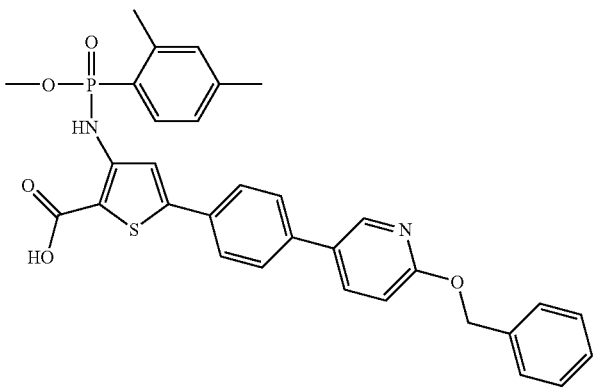 122 | C | B | C |
| 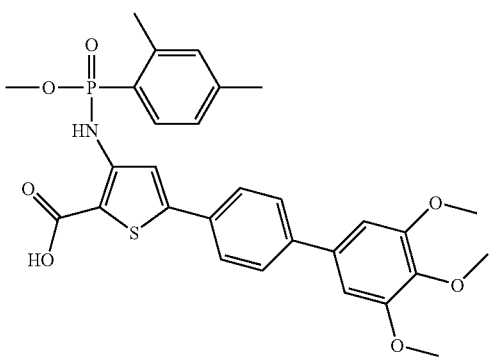 123 | C | B | C |

TABLE 1-continued
| Compound | EC₅₀ (μM)* | IC₅₀ (μM)* | CC₅₀ (μM)* |
|---|---|---|---|
| 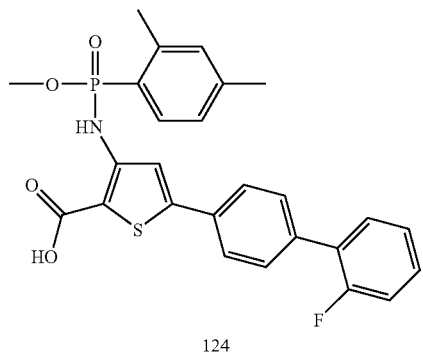 124 | B | B | C |
| 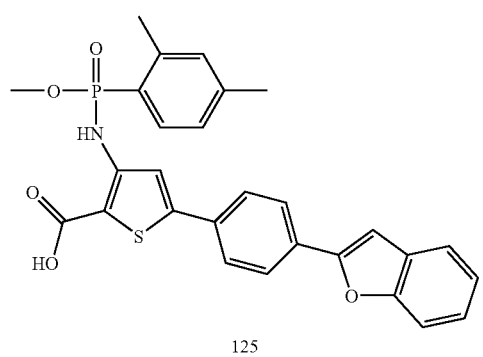 125 | A | A | C |
| 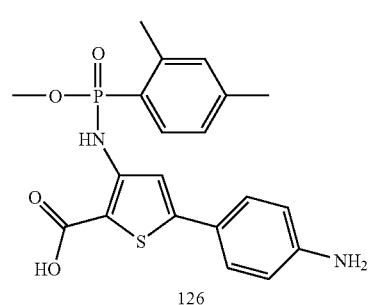 126 | C | B | C |
| 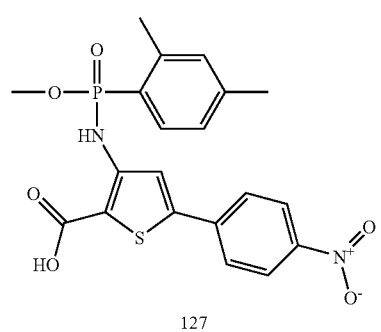 127 | B | A | C |

TABLE 1-continued
| Compound | EC$_{50}$ (μM)* | IC$_{50}$ (μM)* | CC$_{50}$ (μM)* |
|---|---|---|---|
| 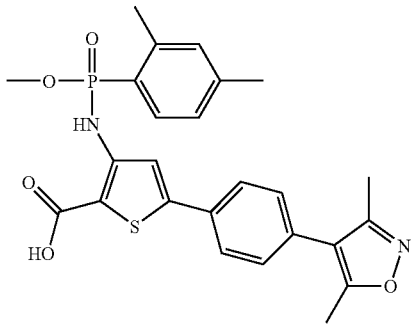 128 | C | B | C |
| 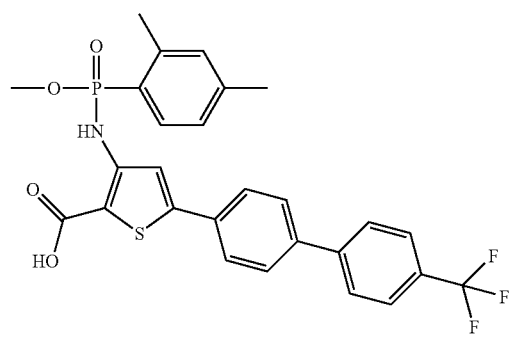 129 | B | A | C |
| 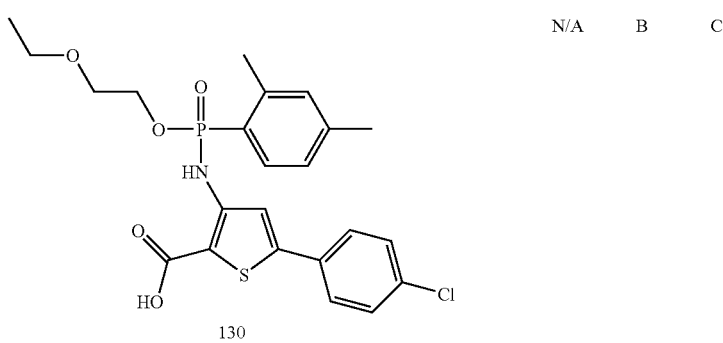 130 | N/A | B | C |
| 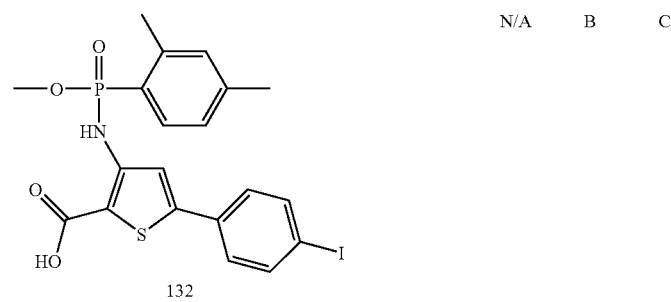 132 | N/A | B | C |

TABLE 1-continued
| Compound | EC$_{50}$ (µM)* | IC$_{50}$ (µM)* | CC$_{50}$ (µM)* |
|---|---|---|---|
| 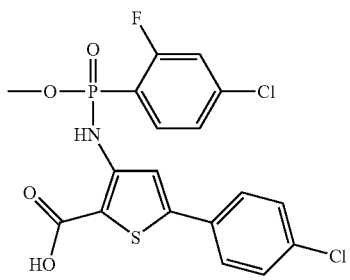 133 | B | B | C |
| 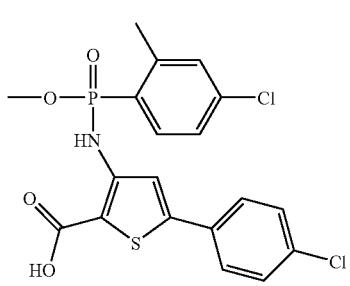 134 | B | A | C |
| 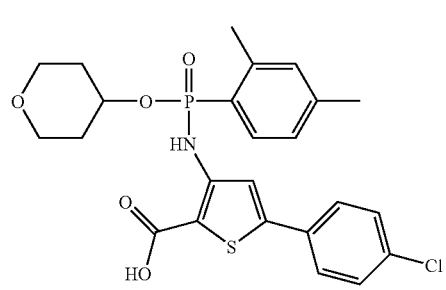 135 | B | A | C |
| 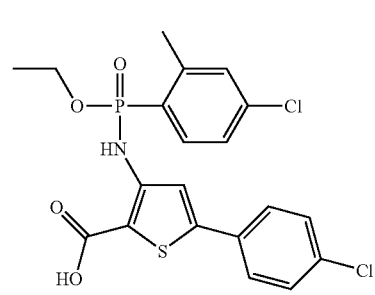 136 | B | A | C |
| 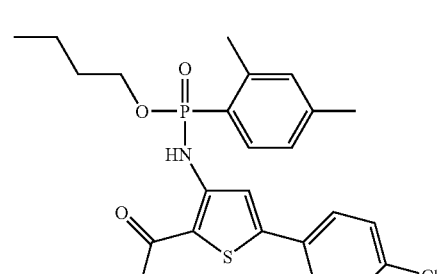 137 | B | B | C |

TABLE 1-continued
| Compound | EC$_{50}$ (μM)* | IC$_{50}$ (μM)* | CC$_{50}$ (μM)* |
|---|---|---|---|
| 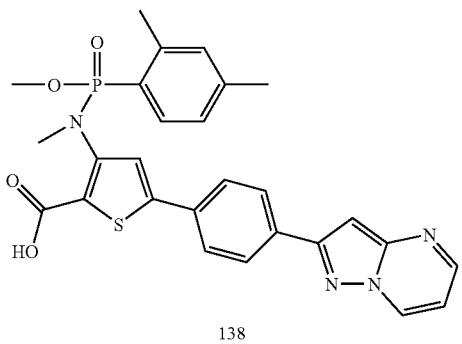 138 | A | A | C |
| 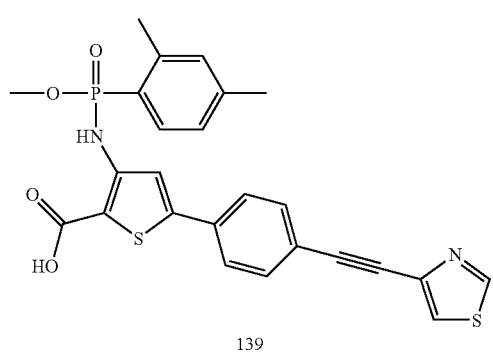 139 | A | A | C |
| 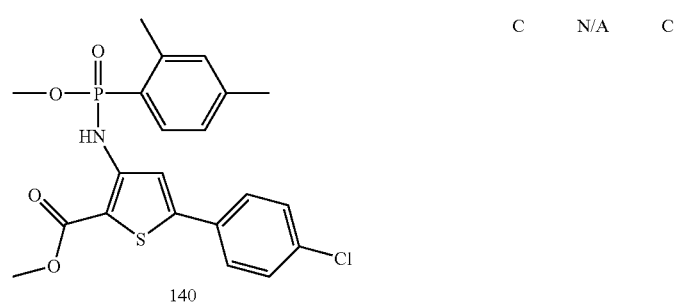 140 | C | N/A | C |
| 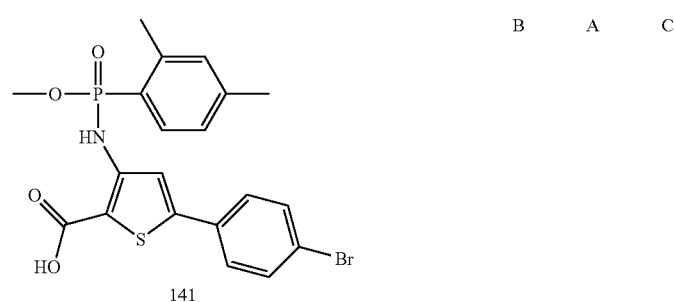 141 | B | A | C |

TABLE 1-continued
| Compound | EC$_{50}$ (µM)* | IC$_{50}$ (µM)* | CC$_{50}$ (µM)* |
|---|---|---|---|
| 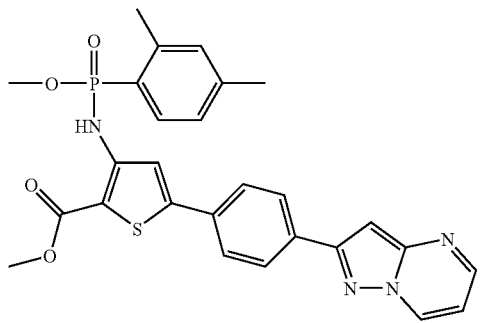 142 | B | N/A | C |
| 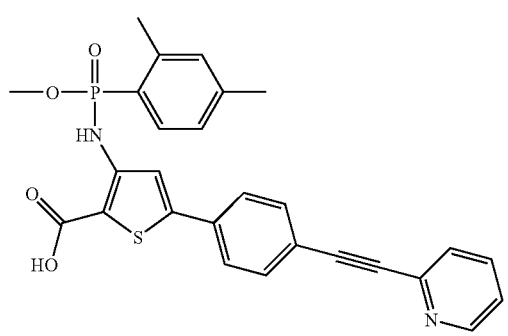 143 | A | A | C |
| 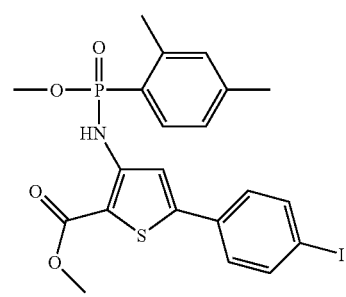 144 | C | N/A | C |
| 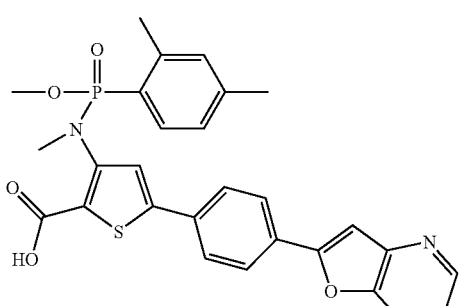 145 | A | A | C |

TABLE 1-continued
| Compound | EC$_{50}$ (μM)* | IC$_{50}$ (μM)* | CC$_{50}$ (μM)* |
|---|---|---|---|
| 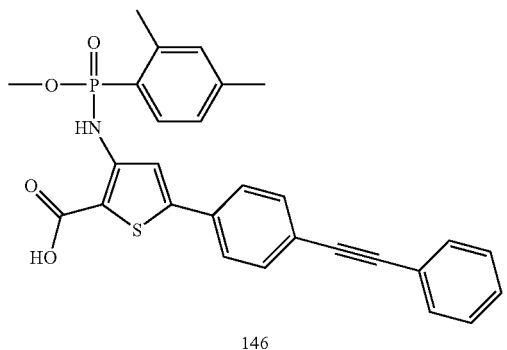 146 | A | A | C |
| 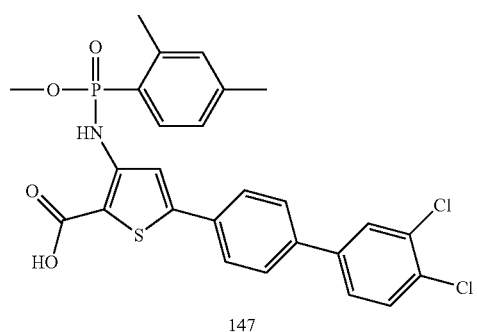 147 | B | B | C |
| 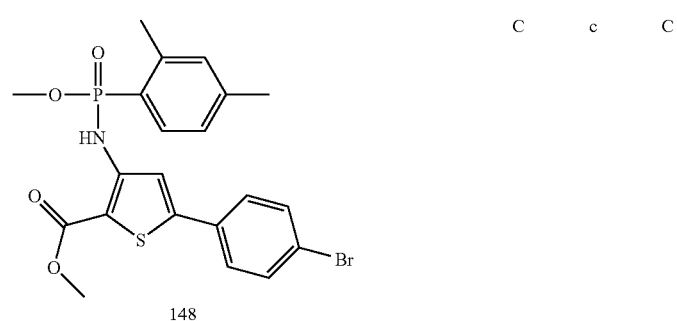 148 | C | c | C |
| 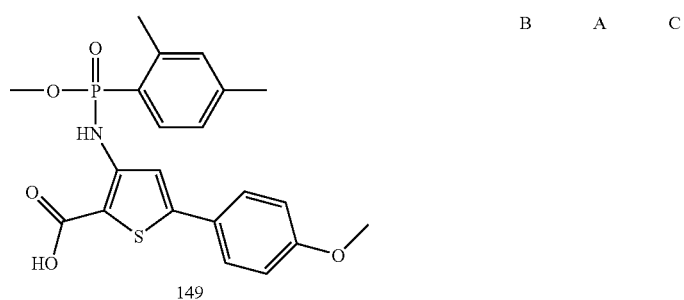 149 | B | A | C |

TABLE 1-continued
| Compound | EC$_{50}$ (µM)* | IC$_{50}$ (µM)* | CC$_{50}$ (µM)* |
|---|---|---|---|
| 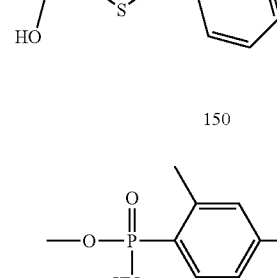<br>150 | A | A | C |
| 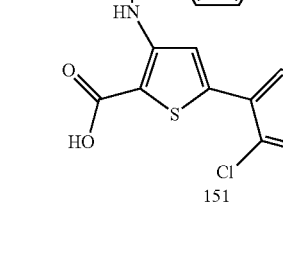<br>151 | C | B | C |
| 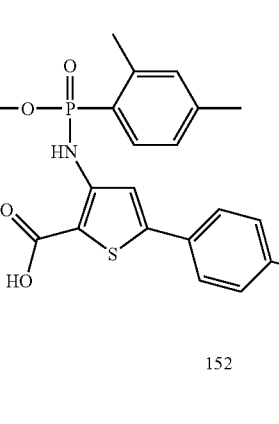<br>152 | A | A | C |
| 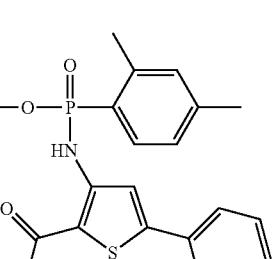<br>153 | A | A | C |

TABLE 1-continued
| Compound | EC$_{50}$ (μM)* | IC$_{50}$ (μM)* | CC$_{50}$ (μM)* |
|---|---|---|---|
| 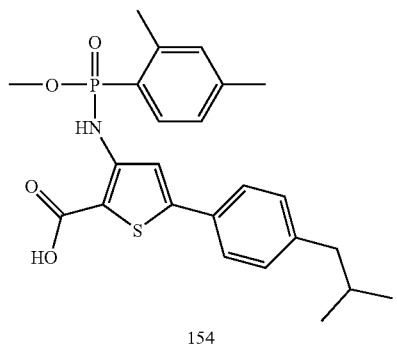 154 | C | B | C |
| 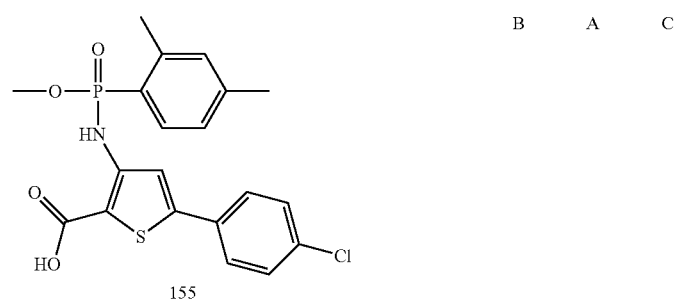 155 | B | A | C |
| 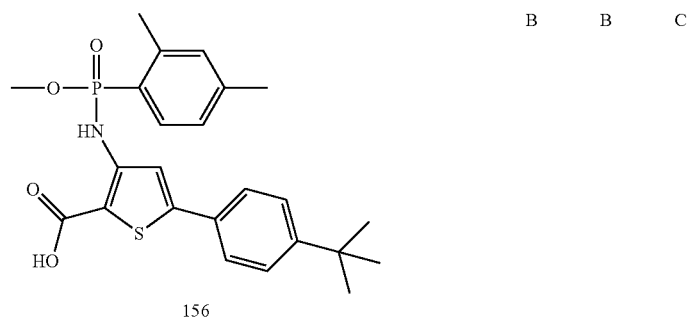 156 | B | B | C |
| 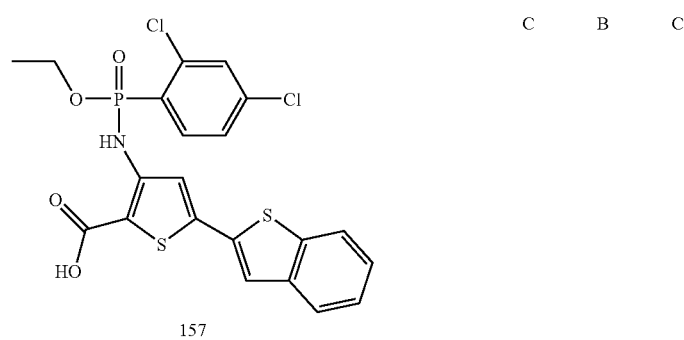 157 | C | B | C |

TABLE 1-continued
| Compound | EC$_{50}$ (µM)* | IC$_{50}$ (µM)* | CC$_{50}$ (µM)* |
|---|---|---|---|
| 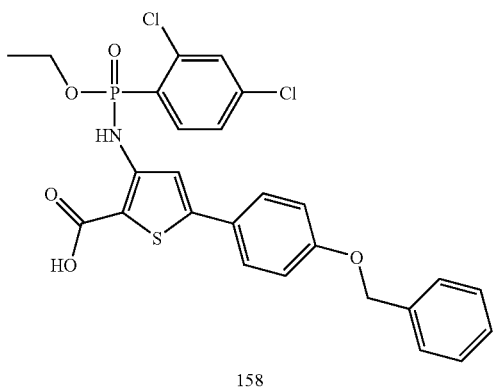 158 | B | B | C |
| 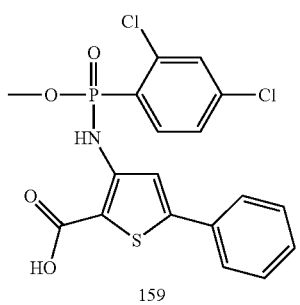 159 | C | B | C |
| 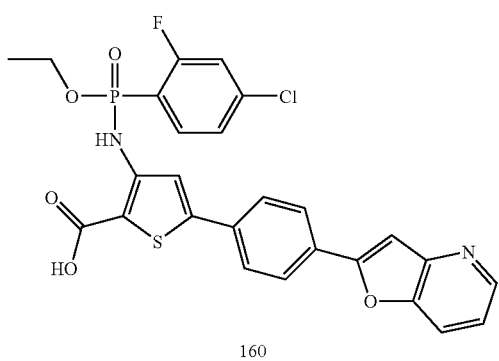 160 | A | A | C |
| 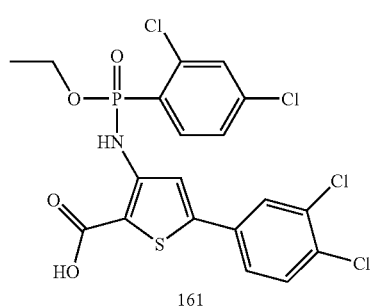 161 | C | B | C |

TABLE 1-continued
| Compound | EC$_{50}$ (μM)* | IC$_{50}$ (μM)* | CC$_{50}$ (μM)* |
|---|---|---|---|
| 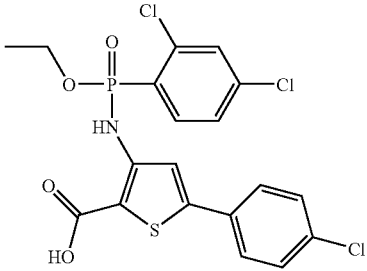 163 | B | B | C |
| 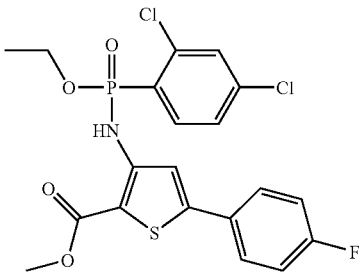 170 | C | N/A | C |
| 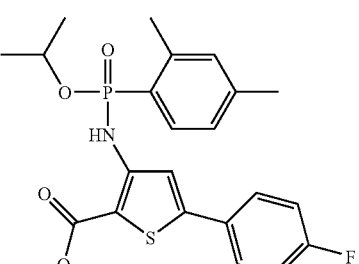 171 | C | C | C |
| 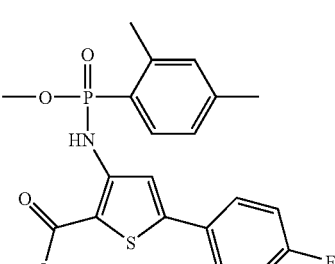 172 | C | C | C |
| 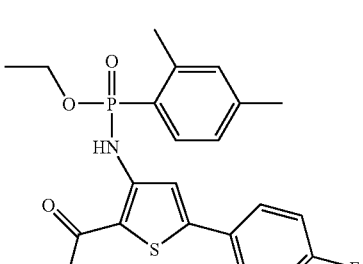 173 | C | C | C |

TABLE 1-continued
| Compound | EC₅₀ (μM)* | IC₅₀ (μM)* | CC₅₀ (μM)* |
|---|---|---|---|
| 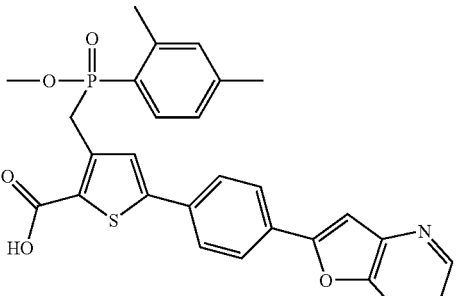 174 | A | A | C |
| 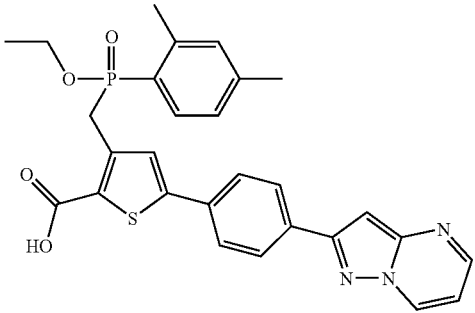 175 | B | A | C |
| 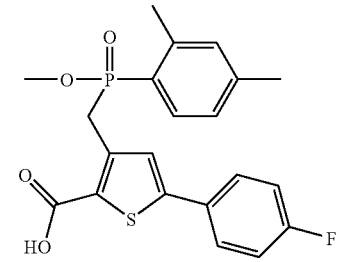 176 | C | B | C |
| 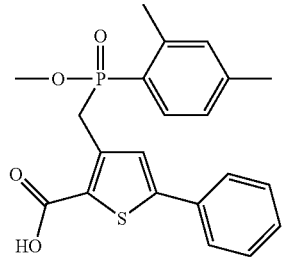 177 | C | B | C |
| 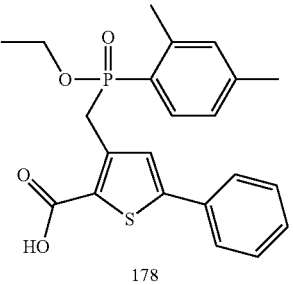 178 | C | B | C |

TABLE 1-continued
| Compound | EC$_{50}$ (µM)* | IC$_{50}$ (µM)* | CC$_{50}$ (µM)* |
|---|---|---|---|
| 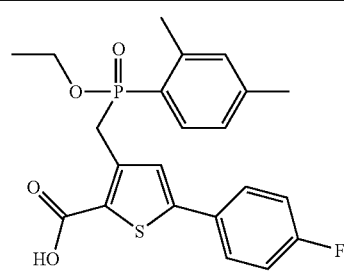<br>179 | C | B | C |
Note:
N/A means not available.
Except Compounds 11 and 26, number of tests performed for determining EC$_{50}$ for all compounds in Table 1 is 2. Number of tests performed for determining EC$_{50}$ for Compounds 11 and 26 is 4 and 5 respectively.
TABLE 2
| Compound | EC$_{50}$ (µM)* | IC$_{50}$ (µM)* | CC$_{50}$ (µM)* |
|---|---|---|---|
| 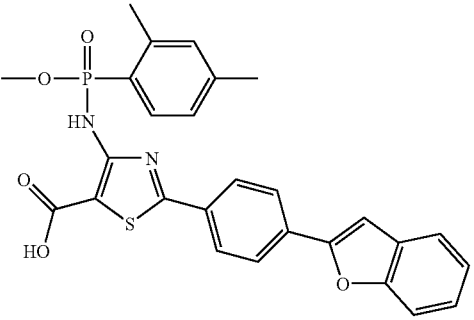<br>185 | A | A | B |
| 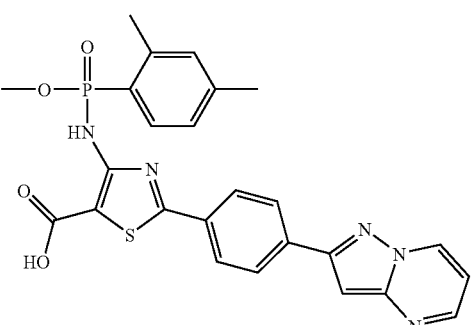<br>186 | A | A | C |
| 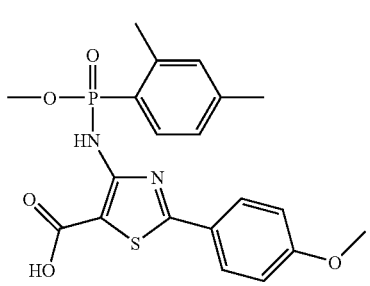<br>187 | C | B | C |

TABLE 2-continued

| Compound | EC$_{50}$ (μM)* | IC$_{50}$ (μM)* | CC$_{50}$ (μM)* |
|---|---|---|---|
| 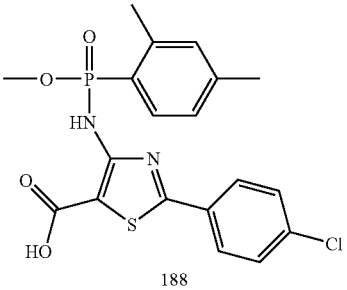 188 | C | B | C |
| 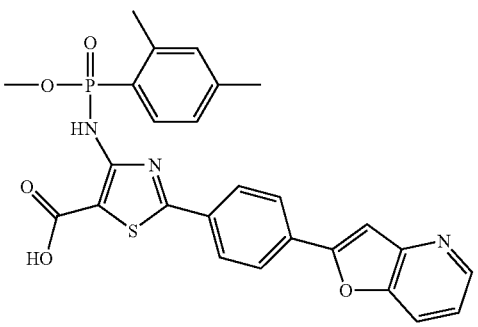 189 | A | A | C |
| 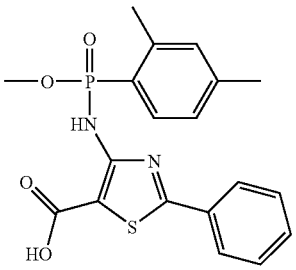 190 | C | B | C |

*Note:
N/A means not available.
The number of tests performed for determining EC$_{50}$, IC$_{50}$ and CC$_{50}$ for all compounds in Table 2 is 2.

Example 2

HCV Replicon Luciferase Reporter Assay

General procedure: Huh-7-derived cell line (Zluc) that harbors an HCV genotype 1b replicon and a luciferase reporter gene was grown in Dulbecco's Modified Eagle Medium (DMEM) supplemented with 10% fetal bovine serum, 2 mM GlutaMAX, 1% MEM nonessential amino acids, 100 IU/mL penicillin, 100 g/mL streptomycin, and 0.5 mg/mL GENETICIN® (G418). For dose response testing the cells were seeded in 96-well plates at 7.5×10$^3$ cells per well in a volume of 50 L, and incubated at 37° C./5% CO$_2$. Drug solutions were made up freshly in Huh-7 media as 2× stocks. Ten additional 5-fold dilutions were prepared from these stocks in DMEM without G418. At least three hours after Zluc cells were seeded, drug treatment was initiated by adding 50 L of drug dilutions to the plates in duplicate. Final concentrations of drug ranged from 100 nM to 0.0000512 nM. Cells were then incubated at 37° C./5% CO$_2$. Alternatively compounds were tested at two concentrations (10 nM and 100 nM). In all cases, Huh-7 (which do not harbors the HCV replicon) served as negative control. After 72 hours of incubation, the inhibition of HCV replication was measured by quantification of photons emitted after mono-oxygenation of 5'-fluoroluciferin to oxyfluoroluciferin by firefly luciferase. For this, media was removed from the plates via gentle tapping. Fifty microliters of ONE-glo luciferase assay reagent was added to each well. The plates were shaken gently for 3 minutes at room temperature and luminescence was measured on a Victor$^3$ V 1420 multilabel counter (Perkin Elmer) with a 1 second read time using a 700 nm cut-off filter. The EC$_{50}$ values were calculated from dose response curves from the resulting best-fit equations determined by MICROSOFT EXCEL and XLfit 4.1 software. When screening at two fixed concentrations, the results were expressed as inhibition at 10 nM and 100 nM.

For cytotoxicity evaluation, Zluc cells were treated with compound as described above, and cell viability was monitored using the CELLTITER 96® Aqueous One Solution cell proliferation assay by adding 20 μL of MTS solution to each well. The plates were then incubated at 37° C./5% CO$_2$ for at least 3 hours. Plates were read at A$_{490}$ nm in a Victor$^3$ V 1420 multilabel counter (PERKIN ELMER) and CC$_{50}$ concentrations were determined using MICROSOFT EXCEL and XLfit 4.1 software.

The EC$_{50}$ results using the HCV replicon luciferase reporter assay are summarized in Table 3, wherein "A" represents a value smaller than 0.1 μM and "B" represents a value between 0.1 μM to 8.3 μM.
TABLE 3
| Compound | EC$_{50}$ (μM)* |
|---|---|
| 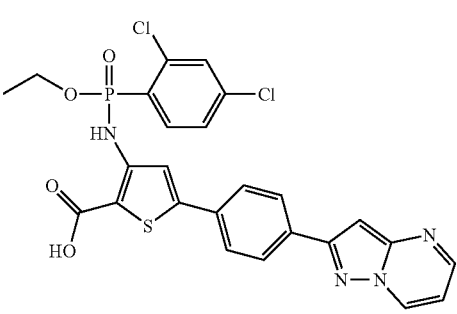 11 | A |
| 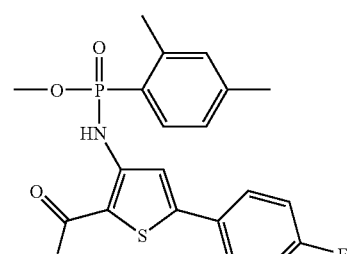 21 | B |
| 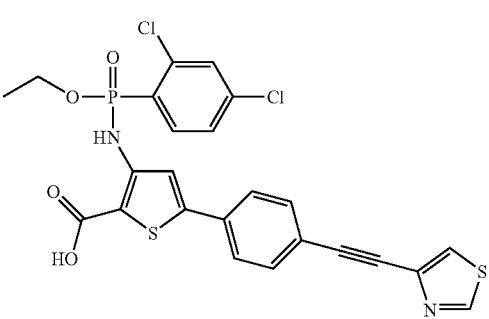 24 | B |
| 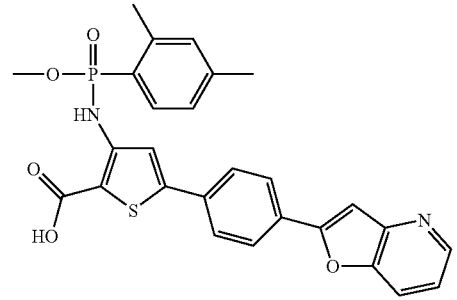 32 | B |
TABLE 3-continued
| Compound | EC$_{50}$ (μM)* |
|---|---|
| 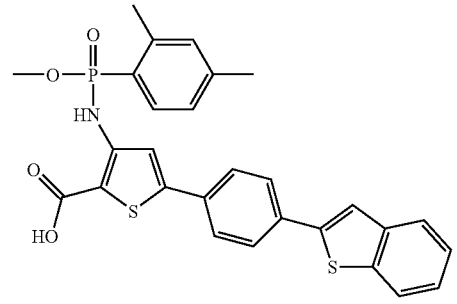 152 | A |
| 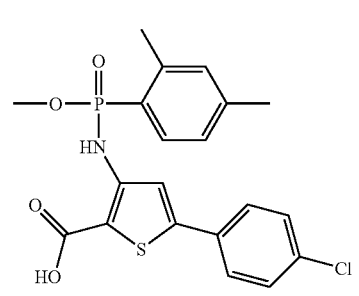 153 | A |
| 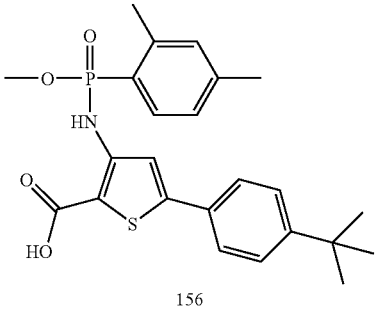 155 | B |
| 156 | B |

TABLE 3-continued

| Compound | EC$_{50}$ (μM)* |
|---|---|
| 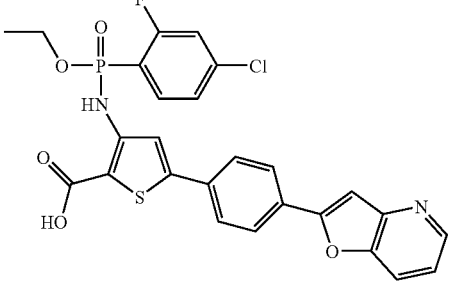 160 | A |
| 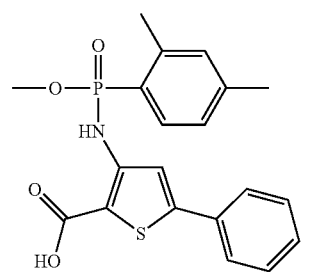 162 | B |
| 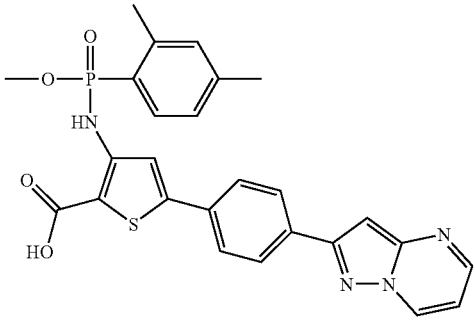 169 | A |

Example 3

HCV Replicon Assay in Human Serum

General procedure: Huh-7-derived cell line (Zluc) that harbors an HCV genotype 1b replicon and a luciferase reporter gene was grown in complete growth medium (Dulbecco's Modified Eagle Medium, 10% fetal bovine serum, 2 mM GlutaMAX, 1% MEM nonessential amino acids, 100 IU/mL penicillin, 100 g/mL streptomycin, and 0.5 mg/mL GENETICIN®). For dose response testing the cells were seeded into columns 2-12 of opaque 96-well tissue culture plates at 7.5× 10³ cells per well in a volume of 50 L assay medium (Dulbecco's Modified Eagle Medium, 2 mM GlutaMAX, 1% MEM nonessential amino acids, 100 IU/mL penicillin, 100 g/mL streptomycin) either supplemented with 40-45% human serum or 10% fetal bovine serum (as reference). Fresh Huh-7 cells were seeded similarly into column 1 for the luminescence background control. Plates were incubated at 37° C./5% CO$_2$ for 4 hours. Drug solutions were made up freshly in assay media as 2× stocks. Eight serial three-fold dilutions were prepared in assay medium containing 40-45% human serum or 10% fetal bovine serum. Diluted drug (50 L) was added into 96-well plates, for a total volume of 100 μL per well. Final concentrations of drug typically ranged from 10 μM to 1 nM. PBS was added in 200 μL aliquots to the outside wells in order to decrease evaporation. Plates were incubated at 37° C., 5% CO$_2$ for three days. Then, the inhibition of HCV replication was measured by quantification of photons emitted after mono-oxygenation of 5'-fluoroluciferin to oxyfluoroluciferin by firefly luciferase. For this, media was removed from the plates via gentle tapping. Fifty microliters of ONE-glo luciferase assay reagent was added to each well. The plates were shaken gently for 3 minutes at room temperature and luminescence was measured on a Victor³ V 1420 multilabel counter (PERKIN ELMER) with a 1 second read time using a 700 nm cut-off filter. The EC$_{50}$ values were calculated from dose response curves from the resulting best-fit equations determined by MICROSOFT EXCEL and XLfit 4.1 software.

For cytotoxicity evaluation, Zluc cells were treated in assay media containing either 40-45% human serum or 10% FBS with compound as described above, and cell viability was monitored using the CELLTTITER96® Aqueous One Solution cell proliferation assay by adding 20 μL of MTS solution to each well. The plates were then incubated at 37° C./5% CO$_2$ for at least 3 hours. Plates were read at A$_{490}$ nm in a Victor³ V 1420 multilabel counter (PERKIN ELMER) and CC$_{50}$ concentrations were determined using MICROSOFT EXCEL and XLfit 4.1 software.

The EC$_{50}$ results using 40-45% human serum are summarized in Table 4, wherein "A" represents a value smaller than 0.1 μM, "B" represents a value between 0.1 μM to 8.3 μM, and C represents a value greater than 8.3 μM.

TABLE 4

| Compound | EC$_{50}$ (μM)* |
|---|---|
| 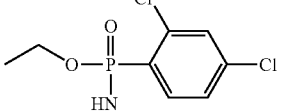 11 | B |
| 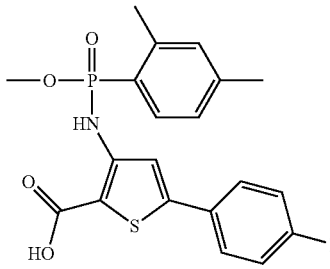 21 | C |

TABLE 4-continued
| Compound | EC$_{50}$ (μM)* |
|---|---|
| 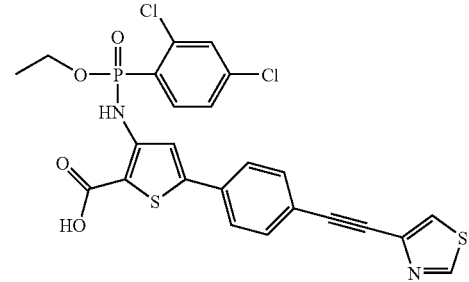 24 | B |
| 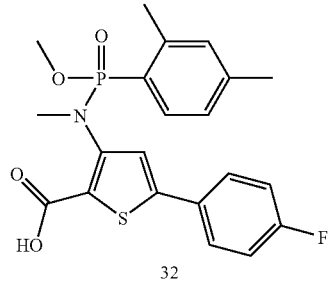 32 | C |
| 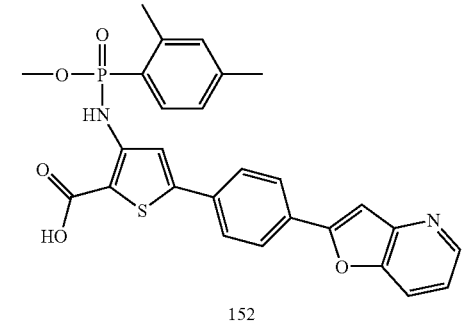 152 | A |
| 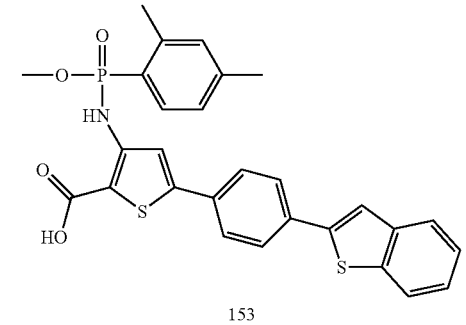 153 | B |
| 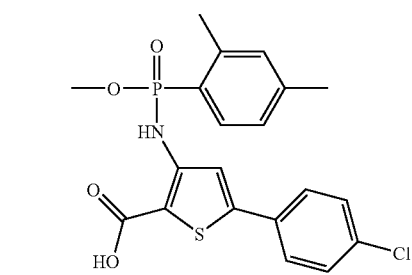 155 | C |
| 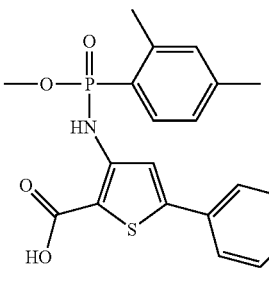 156 | C |
| 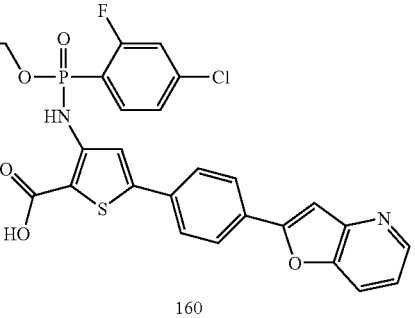 160 | B |
| 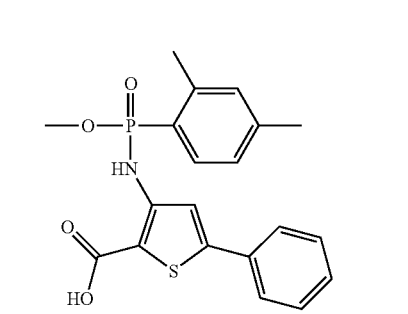 162 | C |
| 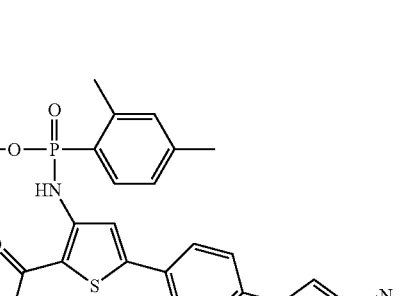 169 | A |
For reference, the EC$_{50}$ results using 10% fetal bovine serum are summarized in Table 5, wherein "A" represents a value smaller than 0.1 μM and "B" represents a value between 0.1 μM to 8.3 μM.

TABLE 5

| Compound | EC$_{50}$ (μM)* |
|---|---|
| 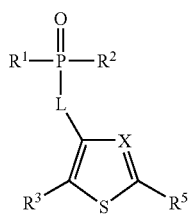 186 | A |
| 189 | A |

*Note:
The number of tests performed for determining EC$_{50}$ values for the compounds in Table 4 and Table 5 is 2 or 3.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula I:

(I)

or a single enantiomer, a mixture of an enantiomeric pair, an individual diastereomer, a mixture of diastereomers, or a tautomeric form thereof; or a pharmaceutically acceptable salt or an isotopically enriched form thereof;
wherein each of $R^1$ and $R^2$ is independently —OR$^6$, alkyl, alkenyl, alkynyl, aryl, aralkyl, alkaryl, cycloalkyl, heterocyclyl or heteroaryl;

$R^3$ is —C(O)R$^7$, —C(O)OR$^8$, —C(O)NR$^9$R$^{10}$, —C(=NR$^{11}$)R$^{12}$, —P(O)(OR$^6$)$_2$ or —C(O)NHSO$_2$R$^{21}$;

X is CR$^4$;

each of $R^4$ and $R^5$ is independently H, halogen, cyano, azido, alkyl, alkenyl, alkynyl, aryl, aralkyl, alkaryl, cycloalkyl, heterocyclyl, heteroaryl, —OR$^6$, —C(O)R$^7$, —C(O)OR$^8$, —C(O)NR$^9$R$^{10}$, —C(=NR$^{11}$)R$^{12}$, —NHSO$_2$R$^{13}$, —NR$^{14}$R$^{15}$, —SO$_3$R$^{17}$ or —SO$_2$R$^{18}$, or $R^4$ and $R^5$ together with the two carbon atoms to which they are attached form a ring;

L is NR$^{16}$; and each of $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{21}$ is independently hydrogen, alkyl, alkenyl, alkynyl, cycloalkyl, aryl, heteroaryl, heterocyclyl, alkyl-cycloalkylene or cycloalkyl-alkylene, wherein each alkyl, aryl, arylalkyl, alkaryl, heteroaryl, alkenyl, alkynyl, cycloalkyl, heterocyclyl or alkyl-cycloalkyl is optionally substituted.

2. The compound of claim 1 according to Formula IIA, IIIA, VA, or VIA:

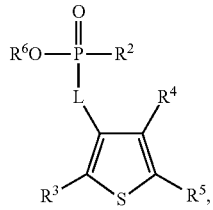

(IIA)

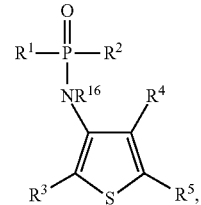

(IIIA)

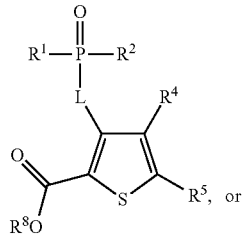

(VA)

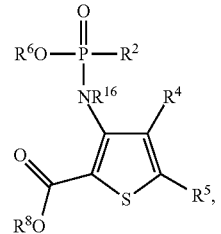

(VIA)

or a single enantiomer, a mixture of an enantiomeric pair, an individual diastereomer, a mixture of diastereomers, or a tautomeric form thereof; or a pharmaceutically acceptable salt thereof;
wherein each of $R^1$ and $R^2$ is independently —OR$^6$, alkyl, alkenyl, alkynyl, aryl, aralkyl, alkaryl, cycloalkyl, heterocyclyl or heteroaryl;

each R³ is —C(O)R⁷, —C(O)OR⁸, —C(O)NR⁹R¹⁰, —C(=NR¹¹)R¹², —P(O)(OR⁶)₂, or —C(O)NHSO₂R²¹;

each of R⁴ and R⁵ is independently H, halogen, cyano, azido, alkyl, alkenyl, alkynyl, aryl, aralkyl, alkaryl, cycloalkyl, heterocyclyl, heteroaryl, —OR⁶, —C(O)R⁷, —C(O)OR⁸, —C(O)NR⁹R¹⁰, —C(=NR¹¹)R¹², —NHSO₂R¹³, —NR¹⁴R¹⁵, —SO₃R¹⁷ or —SO₂R¹⁸, or R⁴ and R⁵ together with the two carbon atoms to which they are attached form a ring;

each L is NR¹⁶; and each of R⁶, R⁷, R⁸, R⁹, R¹⁰, R¹¹, R¹², R¹³, R¹⁴, R¹⁵, R¹⁶, R¹⁷, R¹⁸, and R²¹ is independently hydrogen, alkyl, alkenyl, alkynyl, cycloalkyl, aryl, heteroaryl, heterocyclyl, alkyl-cycloalkylene or cycloalkyl-alkylene, wherein each alkyl, aryl, arylalkyl, alkaryl, heteroaryl, alkenyl, alkynyl, cycloalkyl, heterocyclyl, or alkyl-cycloalkyl is optionally substituted.

3. The compound of claim 2 having Formula IIA.
4. The compound of claim 2 having Formula IIIA.
5. The compound of claim 2 having Formula VA.
6. The compound of claim 2 having Formula VIA.
7. The compound of claim 1, wherein each alkyl, aryl, arylalkyl, alkaryl, heteroaryl, alkenyl, alkynyl, cycloalkyl, heterocyclyl, or alkyl-cycloalkyl is unsubstituted.
8. The compound of claim 1, wherein each R¹ is alkyl, alkoxy, hydroxy or aryl.
9. The compound of claim 1, wherein each R¹ is methyl, ethyl, methoxy, ethoxy or hydroxy.
10. The compound of claim 1, wherein each R² is cycloalkyl, aryl or heteroaryl and wherein each cycloalkyl, aryl or heteroaryl is optionally substituted.
11. The compound of claim 1, wherein each R³ is —C(O)OH or —C(O)OCH₃.
12. The compound of claim 1, wherein each R⁴ is H, alkenyl, alkynyl, halogen, aryl, heteroaryl.
13. The compound of claim 1, wherein each R⁵ is alkyl, alkenyl, alkynyl, aryl, heteroaryl.
14. The compound of claim 1, wherein each R⁶ is H, methyl, ethyl, n-propyl, iso-propyl, n-butyl, iso-butyl or tert-butyl.
15. The compound of claim 1, wherein each R⁸ is H, methyl, ethyl, n-propyl, iso-propyl, n-butyl, iso-butyl or tert-butyl.
16. The compound of claim 1, wherein each R¹⁶ is H, methyl, ethyl, n-propyl, iso-propyl, n-butyl, iso-butyl, tert-butyl, cycloalkyl or heterocyclyl.
17. The compound of claim 1 according to the following structure:

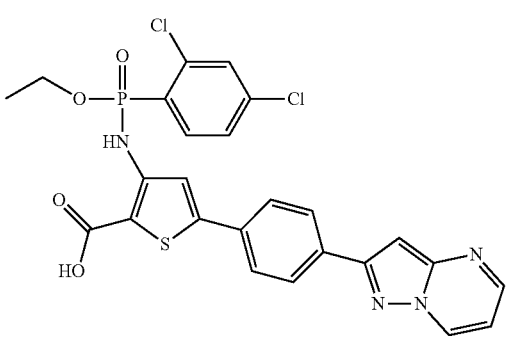

or a single enantiomer, a mixture of an enantiomeric pair, an individual diastereomer, a mixture of diastereomers, or a tautomeric form thereof; or a pharmaceutically acceptable salt thereof.

18. The compound of claim 1 according to the following structure:

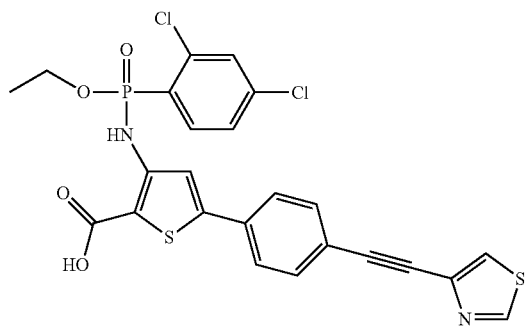

or a single enantiomer, a mixture of an enantiomeric pair, an individual diastereomer, a mixture of diastereomers, or a tautomeric form thereof; or a pharmaceutically acceptable salt thereof.

19. The compound of claim 1 according to the following structure:

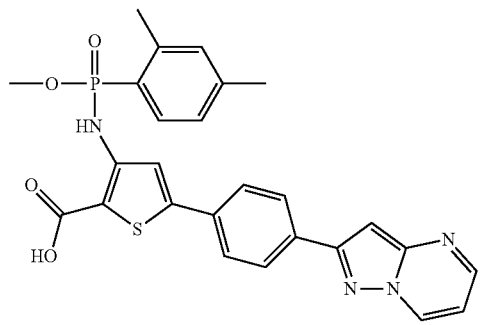

or a single enantiomer, a mixture of an enantiomeric pair, an individual diastereomer, a mixture of diastereomers, or a tautomeric form thereof; or a pharmaceutically acceptable salt thereof.

20. The compound of claim 1, wherein the compound is isotopically enriched.
21. A pharmaceutical composition comprising the compound of claim 1 and one or more pharmaceutically acceptable diluents, excipients, or carriers.
22. The pharmaceutical composition of claim 21, further comprising a second antiviral agent.
23. The pharmaceutical composition of claim 22, wherein the second antiviral agent is selected from the group consisting of an interferon, ribavirin, an interleukin, an NS3 protease inhibitor, a cysteine protease inhibitor, a phenathrenequinone, a thiazolidine, a benzanilide, a helicase inhibitor, a polymerase inhibitor, a nucleotide analogue, a liotoxin, acerulenin, an antisense phosphorothioate oligodeoxynucleotide, an inhibitor of IRES-dependent translation, a ribozyme and combinations thereof.
24. The pharmaceutical composition of claim 22, wherein the second antiviral agent is an interferon.
25. The pharmaceutical composition of claim 24, wherein the interferon is selected from the group consisting of pegylated interferon alpha 2a, interferon alphcon-1, natural interferon, albuferon, interferon beta-1a, omega interferon, interferon alpha, interferon gamma, interferon tau, interferon delta, interferon gamma-1 b and combinations thereof.
26. The pharmaceutical composition of claim 21, wherein the composition is formulated for single dose administration.

27. The pharmaceutical composition of claim 21, wherein the composition is formulated as an oral, parenteral, or intravenous dosage form.

28. The pharmaceutical composition of claim 27, wherein the oral dosage form is a tablet or capsule.

29. The pharmaceutical composition of claim 21, wherein the compound is administered in a dose from about 0.5 milligram to about 1,000 milligram daily.

* * * * *